United States Patent
Martinez Botella et al.

(10) Patent No.: US 11,261,211 B2
(45) Date of Patent: *Mar. 1, 2022

(54) 19-NOR NEUROACTIVE STEROIDS AND METHODS OF USE THEREOF

(71) Applicant: Sage Therapeutics, Inc., Cambridge, MA (US)

(72) Inventors: Gabriel Martinez Botella, Wayland, MA (US); Boyd L. Harrison, Princeton Junction, NJ (US); Albert Jean Robichaud, Boston, MA (US); Francesco G. Salituro, Marlborough, MA (US); Richard Thomas Beresis, Shanghai (CN)

(73) Assignee: Sage Therapeutics, Inc., Cambridge, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/440,527

(22) Filed: Jun. 13, 2019

(65) Prior Publication Data

US 2020/0048300 A1    Feb. 13, 2020

Related U.S. Application Data

(63) Continuation of application No. 15/143,312, filed on Apr. 29, 2016, now Pat. No. 10,377,790, which is a continuation of application No. 14/785,192, filed as application No. PCT/CN2014/075593 on Apr. 17, 2014, now Pat. No. 9,365,611.

(30) Foreign Application Priority Data

Apr. 17, 2013    (WO) ................ PCT/CN2013/074312

(51) Int. Cl.
| | | |
|---|---|---|
| *C07J 43/00* | (2006.01) | |
| *C07J 21/00* | (2006.01) | |
| *C07J 3/00* | (2006.01) | |
| *C07J 7/00* | (2006.01) | |
| *C07J 13/00* | (2006.01) | |
| *C07J 31/00* | (2006.01) | |

(52) U.S. Cl.
CPC .............. *C07J 43/003* (2013.01); *C07J 3/00* (2013.01); *C07J 7/002* (2013.01); *C07J 7/007* (2013.01); *C07J 7/0085* (2013.01); *C07J 13/007* (2013.01); *C07J 21/00* (2013.01); *C07J 31/006* (2013.01)

(58) Field of Classification Search
CPC ... C07J 43/003; C07J 3/00; C07J 7/002; C07J 7/007; C07J 7/0085; C07J 13/007; C07J 21/00; C07J 31/006
USPC ....................................................... 514/176
See application file for complete search history.

(56) References Cited

U.S. PATENT DOCUMENTS

| | | |
|---|---|---|
| 2,856,415 A | 10/1958 | Mihina |
| 3,169,134 A | 2/1965 | Klimstra et al. |
| 3,206,459 A | 9/1965 | Cross |
| 3,580,937 A | 5/1971 | Campbell et al. |
| 3,943,124 A | 3/1976 | Phillipps et al. |
| 3,983,111 A | 9/1976 | Phillipps et al. |
| 3,998,829 A | 12/1976 | Phillips et al. |
| 4,029,777 A | 6/1977 | Engelfried et al. |
| 4,071,625 A | 1/1978 | Grunwell et al. |
| 4,179,336 A | 12/1979 | Weber et al. |

(Continued)

FOREIGN PATENT DOCUMENTS

| | | |
|---|---|---|
| CA | 2831054 A1 | 12/2013 |
| CN | 1190404 A | 8/1998 |

(Continued)

OTHER PUBLICATIONS

Steiner et al Neuropsychopharmacology, 2011, 36, 848-856 (Year: 2011).*

(Continued)

*Primary Examiner* — Yevgeny Valenrod

(74) *Attorney, Agent, or Firm* — Honigman LLP; Kathryn D. Doyle; Jonathan P. O'Brien

(57) ABSTRACT

Provided herein are 3,3-disubstituted 19-nor-steroidal compounds according to Formula (1): and pharmaceutical compositions thereof. Such compounds are contemplated useful for the prevention and treatment of a variety of CNS-related conditions, for example, treatment of sleep disorders, mood disorders, schizophrenia spectrum disorders, disorders of memory and/or cognition, movement disorders, personality disorders, autism spectrum disorders, pain, traumatic brain injury, vascular diseases, substance abuse disorders and/or withdrawal syndromes, tinnitus, and status epilepticus.

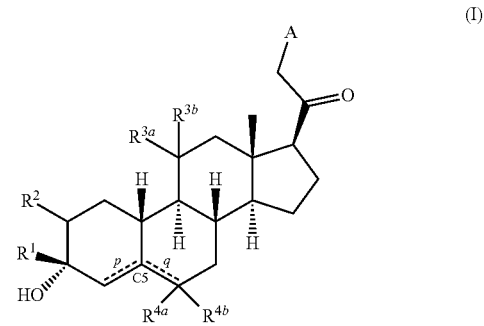

24 Claims, 7 Drawing Sheets

(56) References Cited

U.S. PATENT DOCUMENTS

| | | |
|---|---|---|
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0249120 A1 | 9/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0233433 A1 | 8/2017 | Martinez Botella et al. |
| 2017/0246191 A1 | 8/2017 | Martinez Botella et al. |
| 2018/0071315 A1 | 3/2018 | Cashman et al. |
| 2019/0160078 A1 | 5/2019 | Masuoka et al. |

FOREIGN PATENT DOCUMENTS

| | | | |
|---|---|---|---|
| CN | 101412742 A | 4/2009 | |
| CN | 101624414 A | 1/2010 | |
| CN | 104136452 A | 11/2014 | |
| CN | 108727453 A | 11/2018 | |
| DE | 2330342 A1 | 1/1974 | |
| DE | 2526373 A1 | 12/1976 | |
| DE | 2700267 A1 | 7/1977 | |
| DE | 2632677 A1 | 1/1978 | |
| EP | 0104489 A1 | 4/1984 | |
| EP | 0554436 A1 | 8/1993 | |
| EP | 0656365 A1 | 6/1995 | |
| EP | 0701444 A1 | 3/1996 | |
| EP | 1038880 A2 | 9/2000 | |
| FR | 1994 M | 9/1963 | |
| GB | 1380246 A | 1/1975 | |
| GB | 1430942 A | 4/1976 | |
| GB | 1494097 A | 12/1977 | |
| GB | 1538869 A | 1/1979 | |
| GB | 1570394 A | 7/1980 | |
| GB | 1581234 A | 12/1980 | |
| GB | 1581235 A | 12/1980 | |
| RU | 2194712 C2 | 12/2002 | |
| RU | 2243232 C2 | 12/2004 | |
| RU | 2010100334 A | 7/2011 | |
| RU | 2675855 C2 | 12/2018 | |
| WO | 1991016897 A1 | 11/1991 | |
| WO | 9303732 A1 | 3/1993 | |
| WO | 9305786 A1 | 4/1993 | |
| WO | 9318053 A1 | 9/1993 | |
| WO | 9427608 A1 | 12/1994 | |
| WO | 1995021617 A1 | 8/1995 | |
| WO | 1996003421 A1 | 2/1996 | |
| WO | 1996016076 A1 | 5/1996 | |
| WO | 9640043 A2 | 12/1996 | |
| WO | 9805337 A1 | 2/1998 | |
| WO | 0066614 A1 | 11/2000 | |
| WO | 2005051972 A1 | 6/2005 | |
| WO | 2005105822 A2 | 11/2005 | |
| WO | 2006037016 A2 | 4/2006 | |
| WO | 2006131392 A1 | 12/2006 | |
| WO | 2008151745 A1 | 12/2008 | |
| WO | 2008157460 A1 | 12/2008 | |
| WO | 2010003391 A2 | 1/2010 | |
| WO | 2010054158 A2 | 5/2010 | |
| WO | 2010107815 A1 | 9/2010 | |
| WO | 2012013816 A1 | 2/2012 | |
| WO | 2012083090 A2 | 6/2012 | |
| WO | 2012109752 A1 | 8/2012 | |
| WO | 2012110010 A1 | 8/2012 | |
| WO | 2012116290 A2 | 8/2012 | |
| WO | 2013019711 A2 | 2/2013 | |
| WO | 2013036835 A1 | 3/2013 | |
| WO | 2013056181 A1 | 4/2013 | |
| WO | 2013188792 A2 | 12/2013 | |
| WO | 2013192097 A1 | 12/2013 | |
| WO | 2014058736 A1 | 4/2014 | |
| WO | 2014071449 A1 | 5/2014 | |
| WO | 2014100228 A1 | 6/2014 | |
| WO | 2014108808 A2 | 7/2014 | |
| WO | 2014122480 A1 | 8/2014 | |
| WO | 2014169831 A1 | 10/2014 | |
| WO | 2014169832 A1 | 10/2014 | |
| WO | 2014169833 A1 | 10/2014 | |
| WO | 2014169836 A1 | 10/2014 | |
| WO | 2015010054 A2 | 1/2015 | |
| WO | 2015027227 A1 | 2/2015 | |
| WO | 2015180679 A1 | 12/2015 | |
| WO | 2015195962 A1 | 12/2015 | |
| WO | 2016036724 A1 | 3/2016 | |
| WO | 2016061527 A1 | 4/2016 | |
| WO | 2016061537 A1 | 4/2016 | |
| WO | 2016082789 A1 | 6/2016 | |
| WO | 2016123056 A1 | 8/2016 | |
| WO | 2016131414 A1 | 8/2016 | |
| WO | 2016134301 A2 | 8/2016 | |
| WO | 2016209847 A1 | 12/2016 | |
| WO | 2017044659 A1 | 3/2017 | |
| WO | 2017066626 A1 | 4/2017 | |
| WO | 2017087864 A1 | 5/2017 | |
| WO | 2017156103 A1 | 9/2017 | |
| WO | 2017156418 A1 | 9/2017 | |
| WO | 2018013613 A1 | 1/2018 | |
| WO | 2018013615 A1 | 1/2018 | |
| WO | 2018039378 A1 | 3/2018 | |
| WO | 2019018119 A1 | 1/2019 | |
| WO | 2019045121 A1 | 3/2019 | |
| WO | 2019051264 A1 | 3/2019 | |
| WO | 2019094724 A1 | 5/2019 | |

OTHER PUBLICATIONS

Mohler Neuropharmacology, 2012, 62, 42-53 (Year: 2012).*
Hawkinson et al., "3a-Hydroxy-3b-trifluoromethyl-5a-pregnan-20-one (Co 2-1970): A Partial Agonist at the Neuroactive Steroid Site of the y-Aminobutyric acidA Receptor" Molecular Pharmacology (1996) vol. 49, pp. 897-906.

(56) References Cited

OTHER PUBLICATIONS

Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.
Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids. VII. Preparation of of androstan-3(b)-ol-7-one from from dehydroisoandrosterone", Journal of Biological Chemistry, 1946, vol. 165, pp. 677-685.
Hewett et al., "Amino steroids Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten und bela,gamma-ngesalligten, homoallylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/018748 dated Aug. 29, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for Corresponding International Application No. PCT/US2018/050012 dated Dec. 7, 2018.
International Search Report and Written Opinion for Corresponding International Application No. PCT/US2018/051048 dated Jan. 11, 2019.
International Search Report and Written Opinion for Corresponding International Application No. PCT/US2018/064546 dated Apr. 9, 2019.
International Search Report and Written Opinion for Corresponding International Application No. PCT/US2019/036848 dated Aug. 22, 2019.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 1, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report and Written Opinion for International Application No. PCT/US2018/067277 dated May 24, 2019.
International Search Report and Written Opinion for International Application No. PCT/US2018/067306 dated May 28, 2019.
International Search Report and Written Opinion for International Application No. PCT/US2019/013315 dated Jun. 14, 2019.
International Search Report for International Application No. PCT/US2012/060136 dated Mar. 27, 2013.
Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Jungmann et al., "7-Keto-5b-ätiansäure-Derivate. über Gallensäuren und verwandte Stoffe, 51. Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7-dideoxyxestobergsterol A", Chem. & Pharm. Bulletin, 2000, vol. 48, No. 10, pp. 1480-1483.
Kanes et al., "A multiple-ascending dose study of the neuroactive steroid Sage-217", Biological Psychiatry, vol. 81, No. 10, 2017, pp. S347.
Kanes et al., "A single-ascending dose study of the neuroactive steroid Sage-217", Biological Psychiatry, vol. 81, No. 10, 2017, pp. S31.

(56) References Cited

OTHER PUBLICATIONS

Kasal et al., "Neurosteroid analogues: synthesis of 6-aza-allopregnanolone", Tetrahedron, Elsevier Science Publishers, 2005, vol. 61, No. 9, pp. 2269-2278.
Katona et al., "Neurosteroid analogues. 12. Potent enhancement of GABA-mediated chloride currents at GABAA receptors by ent-androgens", European Journal of Medicinal Chemistry, 2008, vol. 43, No. 1, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lehmann et al., "Schweinegallensäuren Der Abbau von Hyocholsäure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Mariangela et al., "The influence of neuroactive steroid lipophilicity on gabaa receptor modulation: Evidence for a low-affinity interaction", Journal of Neurophysiology, 2009, vol. 102, No. 2, pp. 1254-1264.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Möhler, "The GABA system in anxiety and depression and its therapeutic potential", Neuropharmacology, (2012) 62; pp. 42-53.
Nicoletti et al., "Synthesis and GABAA receptor activity of 6-oxa-analogs of neurosteroids", Steroids, Elsevier Science Publishers 2000, vol. 65, No. 6, pp. 349-356.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.

Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem CID: 70249446, [database online], created Dec. 1, 2012 [retrieved on Mar. 21, 2018]. Retrieved from the National Center for Biotechnology Information, PubChem Compound Database, using internet URL: <https://pubchem.ncbi.nlm.nih.gov/compound/70249446>.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.
Rogawski et al., "Neuroactive Steroids for the Treatment of Status Epilepticus", Epilepsia (2013), vol. 54, No. 6, pp. 93-98.
Rongone et al., "In vivo metabolism of d-homotestosterone", Steroids, vol. 1, No. 6, 1963, pp. 664-669.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.
Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fflf35-fc4c-4eb2-9456-3228ec891a59; [retrieved on Dec. 21, 2018].
Santaniello & Caspi, "Reduction of certain steroidal 19-sulfonic esters with metal hydrides", J. of Ster. Biochem, 1976, vol. 7, No. 3, pp. 223-227.
Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.
Sarett., "A new method for the preparation of 17(alpha)-hydroxy-20-ketopregnanes", J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.
Shen et al., "Microbial aromatization of 19-hydroxymethylepidehydroandrosterone acetate by Corynebacterium simplex", Huaxue Xuebao, 1983, vol. 41, No. 5, pp. 473-474.
Shu et al., "Characteristics of concatemeric GABM receptors containing alpha4/d subunits expressed in Xenopus oocytes" British Journal of Pharmacology (2012) 165, 2228-2243.
Shu et al., "Photodynamic effects of steroid-conjugated fluorophores on gabaa receptors", Molecular Pharmacology, 2009, vol. 76, No. 4, pp. 754-765.

(56) References Cited

OTHER PUBLICATIONS

Slavíková et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16-Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Stastna et al., "The use of symmetry in enantioselective synthesis: Four pairs of chrysene enantiomers prepared from 19-nortestosterone", Org. Biomol. Chem., 2011, vol. 9, pp. 4685-4694.
Sunöl et al., "Activity of b-nor analogues of neurosteroids on the gabaa receptor in primary neuronal cultures", Journal of Medicinal Chemistry, 2006, vol. 49, No. 11, pp. 3225-3234.
Supplemental European Search Report, European Patent Application No. 14826212.4, dated Feb. 16, 2017.
Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.
Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.
Upasani et al., "3a-Hydroxy-3ß-(phenylethynyl)-5ß-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Veleiro et al., "Structure-activity relationships of neuroactive steroids acting on the gabaa receptor", Current Medicinal Chemistry, 2009, vol. 16, No. 4, pp. 455-472.
Veleiro et al., "Synthesis and GABAA Receptor Acitivity of a6, 19-Oxido Analogue of Pregnanolone", Bioorganic & Medicinal Chemistry Letters, (2003), vol. 13, pp. 343-345.
Welling, "Interactions affecting drug absorption", Clinical Pharmacokinetics, vol. 9, No. 5, Sep. 1984 (Sep. 1984), pp. 404-434.
Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethyl-19ß-alcohols", Journal of the Chemical Society [Section] C: Organic, 1969, vol. 6, pp. 947-951.
Wicha et al., "Transformations of steroidal neopentyl systems. VI. Intramolecular Claisen condensation of 19R-acetoxy-19A-methyl-3-ones of the 5alpha series", Tetrahedron, 1969, vol. 25, No. 17, pp. 3961-3968.
Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs", Journal of Organic Chemistry, 1973, vol. 38 No. 7, pp. 1280-1283.
Wu, "A New Classification of Prodrugs: Regulatory Perspectives", Pharmaceuticals, 2009, vol. 2, pp. 77-81.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Zorumski et al., "Enantioselective Modulation of GABAergic Synaptic Transmission by Steroids and Benz[dindenes in Hippocampal Microcultures", Synapse, (1998), vol. 29, pp. 162-171.
Adams et al., "The estrogenic activity and enzymic oxidation of 17b-estradiol-17a-d1", Steroids, Elsevier Science Publishers, (1965), pp. 75-84.
Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Anonymous: "Archive History for NCT03000530", Aug. 4, 2017, Retrieved from the Internet: <URL:https://www.clinicaltrials.gov/ct2/his> tory/NCT03000530?V-_6=View#StudyPageTop; [retrieved on Nov. 20, 2018].
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, BE., "Rett Syndrome Medication" [online], Updated Feb. 6, 2017, [retrieved on May 3, 2018]. Retrieved from the website Medscape, using internet URL: <https://emedicine.medscape.com/article/916377-medication>.
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-yl)-19-nor-5b-pregnan-20-one(SAGE-217): A Clinical Next Generation Neuroactive Steroid Positive

(56) References Cited

OTHER PUBLICATIONS

Allosteric Modulator of the (g-Aminobutyric Acid) A Receptor" Journal of Medical Chemistry, 2017, 10 pp A-J.
CAS Registry No. 1040410-23-8 [Database Registry in STN]; STN Entry Date: Aug. 12, 2008; Chemical Name: 1-((3S,8R,9S,10S,13S,14S,17S)-3-hydroxy-10,13-dimethyl-2,3,4,5,8,9,10,11,12,13,14,15,16,17-tetradecahydro-1H-cyclopenta[a]phenanthren-17-yl)ethan-1-one.
CAS Registry No. 162882-77-1 [Database Registry in STN]; STN Entry Date: May 11, 1995; Chemical Name: (3a,5b)-3-Hydroxy-3-methyl-19-norpregnan-20-one.
CAS Registry No. 162883-68-3 [Database Registry in STN]; STN Entry Date: May 11, 1995; Chemical Name: 19-Norpregnan-20-one, 3-hydroxy-3-methyl-, (3a,5a).
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[O-(carboxymethyl) oxime] derivatives", Collection of Czechoslovak Chemical Communications, 2004, vol. 69, No. 9, pp. 1805-1817.
Chen et al., "The mechanism investigation in substitution of 21-bromo-3a-hydroxy-3b-methoxymethyl-5a-pregnan-20-one with nucleophiles", Steroids, vol. 71, (2006), pp. 942-948.
Chodounska et al., "Epalons: Synthesis of 3a, 7a-Dihydroxy-5a-Pregnan-20-One", Collection Symposium Series, vol. 63, No. 10, (1998), pp. 1543-1548.
D'hulst et al., "Expression of the GABAergic system in animal models for fragile X syndrome and fragile X associated tremor/ataxia syndrome (FXTAS)", Brain Research, 2008, vol. 1253, pp. 176-183.
Database CAPLUS in STN, Acc. No. 1995:986323, UPASANI et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Database Medline, US National Library of Medicine, Bethesda, MD, 1984, Welling: "Intentions affecting drug absorption", Database accession No. NLM6388952, abstract.
Deluca et al., "Synthesis of 3b-Hydroxy[21-14C]-5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, Pg. IX.
Durán et al., "Synthesis of 6-thia analogs of the natural neurosteroid allopregnanolone", Tetrahedron, Elsevier Science Publishers, 2006, vol. 62, No. 20, pp. 4762-4768.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Eimon et al., "Brain activity patterns in high-throughput electrophysiology screen predict both drug efficacies and side effects", Nature Communications, (2018) 9:219, pp. 1-14.
Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.

Extended European Search Report for application PCT/CN2014075593 dated Aug. 26, 2016.
Extended European Search Report for application PCT/CN2014075594 dated Aug. 26, 2016.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrance Perturbation and Anesthetic Activity", Molecular Pharmacology, 1985, vol. 27, pp. 624-629.
Galofre et al., "GABAA receptor and cell membrane potential as functional endpoints in cultured neurons to evaluate chemicals for human acute toxicity", Neurotoxicology and Teratology, (2009), vol. 32, pp. 52-61.
Gasior et al., "Neuroactive steroids: potential therapeutic use in neurological and psychiatric disorders", Trends in Pharmacological Science, (1999), vol. 20, No. 3, pp. 107-112.
Gottesmann, "GABA Mechanisms and Sleep", Neuroscience, (2002), vol. 111, No. 2, pp. 231-239.
Green et al., "The nonfeminizing enantiomer of 17b-estradiol exerts protective effects in neuronal cultures and a rat model of cerebral ischemia", Endocrinology, 2001, vol. 142, pp. 400-406.
Guardia et al., "GABAergic and Glutamatergic Modulation in Binge Eating: Therapeutic Approach", Current pharmaceutical design, 2011, vol. 17, No. 14, pp. 1396-1409.
Gunduz-Bruce et al.,"Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.
Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.
Han et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkins et al., "The synthetic neuroactive steroid SGE-516 reduces seizure burden and improves survival in a Dravet syndrome mouse model", Science Reports, (2017), pp. 1-8.

* cited by examiner

19-NOR NEUROACTIVE STEROIDS AND METHODS OF USE THEREOF

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids (Lan, N. C. et al., *Neurochem. Res.* 16:347-356 (1991).

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy,* 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet,* 1235-1237 (1956)). A more direct correlation has been observed with a reduction in progesterone metabolites (Rosciszewska et al., *J. Neurol. Neurosurg. Psych.* 49:47-51 (1986)). In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy,* 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium,* Raven Press, New York (1984), pp. 279-282, and Dalton, K., *Premenstrual Syndrome and Progesterone Therapy,* 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

The present invention is based, in part, on the desire to provide novel 19-nor (i.e., C19 desmethyl) compounds, e.g., related to progesterone, deoxycorticosterone, and their metabolites, with good potency, pharmacokinetic (PK) properties, oral bioavailability, formulatability, stability, safety, clearance and/or metabolism. One key feature of the compounds as described herein is disubstitution at the C3 position (e.g., with one substituent being a 3α hydroxy moiety. The inventors envision disubstitution at C-3 will eliminate the potential for oxidation of the hydroxy moiety to the ketone, prevent further metabolism, and reduce the potential for secondary elimination pathways, such as glucuronidation. The inventors further envision the overall effect of C3 disubstitution should be of improving the overall PK parameters and reducing potential toxicities and side effects, which may allow, in certain embodiments, administration orally and/or chronically. Another key feature of the compounds as described herein is the presence of a hydrogen at the C19 position ("19-nor") rather than a methyl group. The inventors envision 19-nor compounds, as compared to their C19-methyl counterparts, will have improved physical properties, such as improved solubility. The inventors envision further enhancement of solubility, for example, when the AB ring system is in the cis configuration.

Thus, in one aspect, provided herein are compounds of Formula (I):

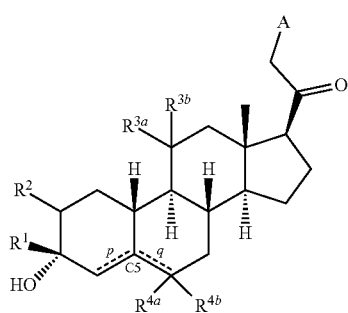

and pharmaceutically acceptable salts thereof;
wherein:
═══ represents a single or double bond;
$R^1$ substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;
$R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl;
$R^{3a}$ is hydrogen or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, and $R^{3b}$ is hydrogen; or $R^{3a}$ and $R^{3b}$ are joined to form an oxo (═O) group;
each instance of $R^{4a}$ and $R^{4b}$ is independently hydrogen, substituted or unsubstituted $C_{1-6}$ alkyl, or halogen;
provided if bond p is a double bond, then bond q is a single bond, provided if bond q is a double bond, then bond p is a single bond and $R^{4b}$ is absent; and provided if both bonds p and q are single bonds, then the hydrogen at C5 is in the alpha or beta configuration;
A is of Formula (A-1) or Formula (A-2):

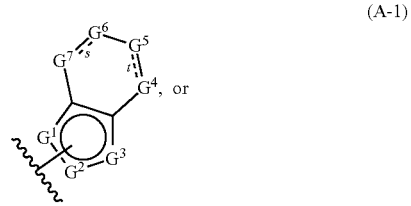

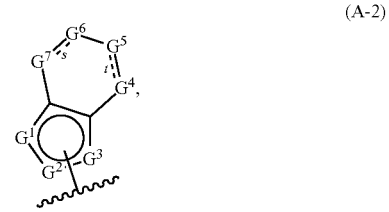

wherein the point of attachment is at $G^1$ or $G^2$ in Formula (A-1) and the point of attachment is at $G^2$ or $G^3$ in Formula (A-2)
$G^1$ is N, $NR^{N1}$, O, S, C, or C—$R^{G1}$ as valency permits;
$G^2$ is N, $NR^{N2}$, O, S, C, —C═N—, or C—$R^{G2}$ as valency permits;
$G^3$ is N, $NR^{N3}$, O, S, C, or C—$R^{G3}$ as valency permits;
$G^4$ is N, $NR^{N4}$, C—$R^{G4}$, or C—$(R^{G4})_2$ as valency permits;
$G^5$ is N, $NR^{N5}$, C—$R^{G5}$, or C—$(R^{G5})_2$ as valency permits;
$G^6$ is N, $NR^{N6}$, C—$R^{G6}$, or C—$(R^{G6})_2$ as valency permits; and
$G^7$ is N, $NR^{N7}$, C—$R^{G7}$, or C—$(R^{G7})_2$ as valency permits;
each instance of $R^{G1}$, $R^{G2}$, $R^{G3}$, $R^{G4}$, $R^{G5}$, $R^{G6}$, and $R^{G7}$ is, independently, hydrogen, halogen, —$NO_2$, —CN, —$OR^{GA}$, —$N(R^{GA})_2$, —C(═O)$R^{GA}$, —C(═O)$OR^{GA}$, —OC(═O)$R^{GA}$, —OC(═O)$OR^{GA}$, —C(═O)N($R^{GA})_2$, —N($R^{GA}$)C(═O)$R^{GA}$, —OC(═O)N($R^{GA})_2$, —N($R^{GA}$)C(═O)$OR^{GA}$, —S(═O)$_2R^{GA}$, —S(═O)$_2OR^{GA}$, —OS(═O)$_2R^{GA}$, —S(═O)$_2$N($R^{GA})_2$, —N($R^{GA}$)S(═O)$_2R^{GA}$, —S(═O)$R^{GA}$, —S(═O)$OR^{GA}$, —OS(═O)$R^{GA}$, —S(═O)N($R^{GA})_2$, —N($R^{GA}$)S(═O)$R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl;
each instance of $R^{N1}$, $R^{N2}$, $R^{N3}$, $R^{N4}$, $R^{N5}$, $R^{N6}$, and $R^{N7}$ is independently hydrogen, substituted or unsubstituted $C_{1-6}$ alkyl, or a nitrogen protecting group; and
each instance of $R^{GA}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, a nitrogen protecting group when attached to nitrogen, or two $R^{GA}$ groups are taken with the intervening atoms to form a substituted or unsubstituted carbocyclic or heterocyclic ring.

In certain embodiments, $G^4$ is N or $NR^{N4}$, and/or $G^5$ is N or $NR^{N5}$, and/or $G^6$ is N or $NR^{N6}$, and/or $G^7$ is N or $NR^{N7}$.

Compounds of Formula (I), sub-genera thereof, and pharmaceutically acceptable salts thereof are collectively referred to herein as "compounds of the present invention."

In another aspect, provided is a pharmaceutical composition comprising a compound of the present invention and a pharmaceutically acceptable excipient. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related disorder in a subject in need thereof, comprising administering to the subject an effective amount of a compound of the present invention. In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl($C_1$), ethyl ($C_2$), n-propyl($C_3$), isopropyl($C_3$), n-butyl($C_4$), tertbutyl ($C_4$), sec-butyl($C_4$), iso-butyl($C_4$), n-pentyl($C_5$), 3-pentanyl ($C_5$), amyl($C_5$), neopentyl($C_5$), 3-methyl-2-butanyl($C_5$), tertiary amyl($C_5$), and n-hexyl($C_6$). Additional examples of alkyl groups include n-heptyl($C_7$), n-octyl($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl(methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straightchain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl($C_2$), 1-propenyl($C_3$), 2-propenyl ($C_3$), 1-butenyl($C_4$), 2-butenyl($C_4$), butadienyl($C_4$), and the like. Examples of $C_{2-6}$ alkenyl groups include the aforementioned $C_{2-4}$ alkenyl groups as well as pentenyl($C_5$), pentadienyl($C_5$), hexenyl($C_6$), and the like. Additional examples of alkenyl include heptenyl($C_7$), octenyl($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl(methyl) groups, include but are not limited to, substituted ethylene (—C(CH$_3$)=CH—, —CH=C (CH$_3$)—), substituted propylene (e.g., —C(CH$_3$) =CHCH$_2$—, —CH=C(CH$_3$)CH$_2$—, —CH=CHCH (CH$_3$)—, —CH=CHC(CH$_3$)$_2$—, —CH(CH$_3$)— CH=CH—, —C(CH$_3$)$_2$—CH=CH—, —CH$_2$—C(CH$_3$) =CH—, —CH$_2$—CH=C(CH$_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl($C_2$), 1-propynyl ($C_3$), 2-propynyl($C_3$), 1-butynyl($C_4$), 2-butynyl($C_4$), and the like. Examples of $C_{2-6}$ alkynyl groups include the aforementioned $C_{2-4}$ alkynyl groups as well as pentynyl($C_5$), hexynyl ($C_6$), and the like. Additional examples of alkynyl include heptynyl($C_7$), octynyl($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and for 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and for 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and for 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

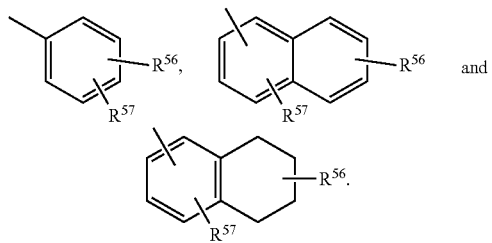

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

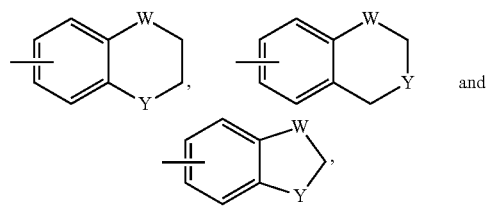

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

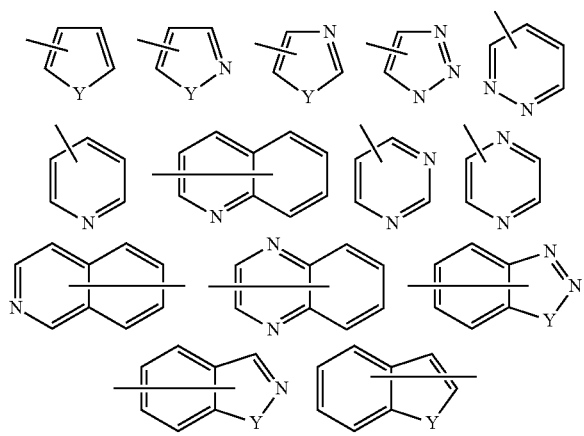

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a nonaromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl(C$_3$), cyclopropenyl(C$_3$), cyclobutyl(C$_4$), cyclobutenyl(C$_4$), cyclopentyl(C$_5$), cyclopentenyl (C5), cyclohexyl(C$_6$), cyclohexenyl(C$_6$), cyclohexadienyl(C$_6$), and the like. Exemplary C$_{3-8}$ carbocyclyl groups include, without limitation, the aforementioned C$_{3-6}$ carbocyclyl groups as well as cycloheptyl(C$_7$), cycloheptenyl(C$_7$), cycloheptadienyl(C$_7$), cycloheptatrienyl(C$_7$), cyclooctyl(C$_5$), cyclooctenyl(C$_5$), bicyclo[2.2.1]heptanyl (C$_7$), bicyclo[2.2.2]octanyl(C$_5$), and the like. Exemplary C$_{3-10}$ carbocyclyl groups include, without limitation, the aforementioned C$_{3-8}$ carbocyclyl groups as well as cyclononyl(C$_9$), cyclononenyl(C$_9$), cyclodecyl(C$_{10}$), cyclodecenyl(C$_{10}$), octahydro-1H-indenyl(C$_9$), decahydronaphthalenyl (C$_{10}$), spiro[4.5]decanyl(C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl(C$_5$) and cyclohexyl(C$_5$). Examples of C$_{3-6}$ cycloalkyl groups include the aforementioned C$_{5-6}$ cycloalkyl groups as well as cyclopropyl(C$_3$) and cyclobutyl(C$_4$). Examples of C$_{3-8}$ cycloalkyl groups include the aforementioned C$_{3-6}$ cycloalkyl groups as well as cycloheptyl(C$_7$) and cyclooctyl(C$_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3 to 10-membered nonaromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

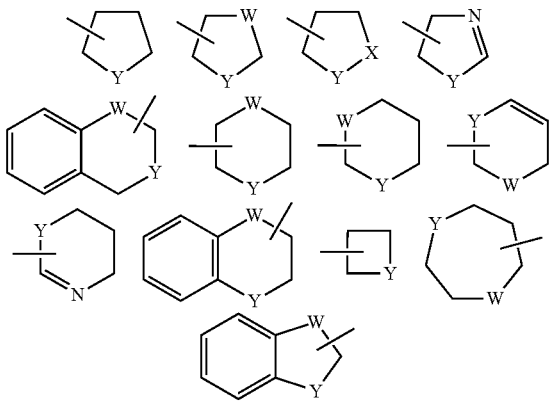

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl(carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, R$^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Acylamino" refers to a radical —$NR^{22}C(O)R^{23}$, where each instance of $R^{22}$ and R23 is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}C(O)$—$C_1$-$C_8$ alkyl, —$NR^{24}C(O)$—$(CH_2)_t(C_6$-$C_{10}$ aryl), —$NR^{24}C(O)$—$(CH_2)_t$(5-10 membered heteroaryl), —$NR^{24}C(O)$—$(CH_2)_t(C_3$-$C_{10}$ cycloalkyl), and $NR^{24}C(O)$—$(CH_2)_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided at least one of $R^{25}$ and $R^{26}$ is other than H.

"Acyloxy" refers to a radical —$OC(O)R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—$(CH_2)_t(C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2NMe_2$.

"Amino" refers to the radical —$NH_2$.

"Substituted amino" refers to an amino group of the formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —$C(O)NH_2$.

"Substituted carbamoyl" or "substituted amido" refers to the radical —$C(O)N(R^{62})_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary "substituted carbamoyl" groups include, but are not limited to, —C(O)NR$^{64}$—$C_1$-$C_8$ alkyl, —C(O)NR$^{64}$—(CH$_2$)$_t$($C_6$-$C_{10}$ aryl), —C(O)N$^{64}$—(CH$_2$)$_t$(5-10 membered heteroaryl), —C(O)NR$^{64}$—(CH$_2$)$_t$($C_3$-$C_{10}$ cycloalkyl), and —C(O)NR$^{64}$—(CH$_2$)$_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethylene" refers to substituted or unsubstituted —(C—C)—.

"Ethenyl" refers to substituted or unsubstituted —(C=C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$X$^-$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+$X$^-$, —NH($C_{1-6}$ alkyl)$_2^+$X$^-$, —NH$_2$($C_{1-6}$ alkyl)$^+$X$^-$, —NH$_3^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)SC$_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

Figure 1:
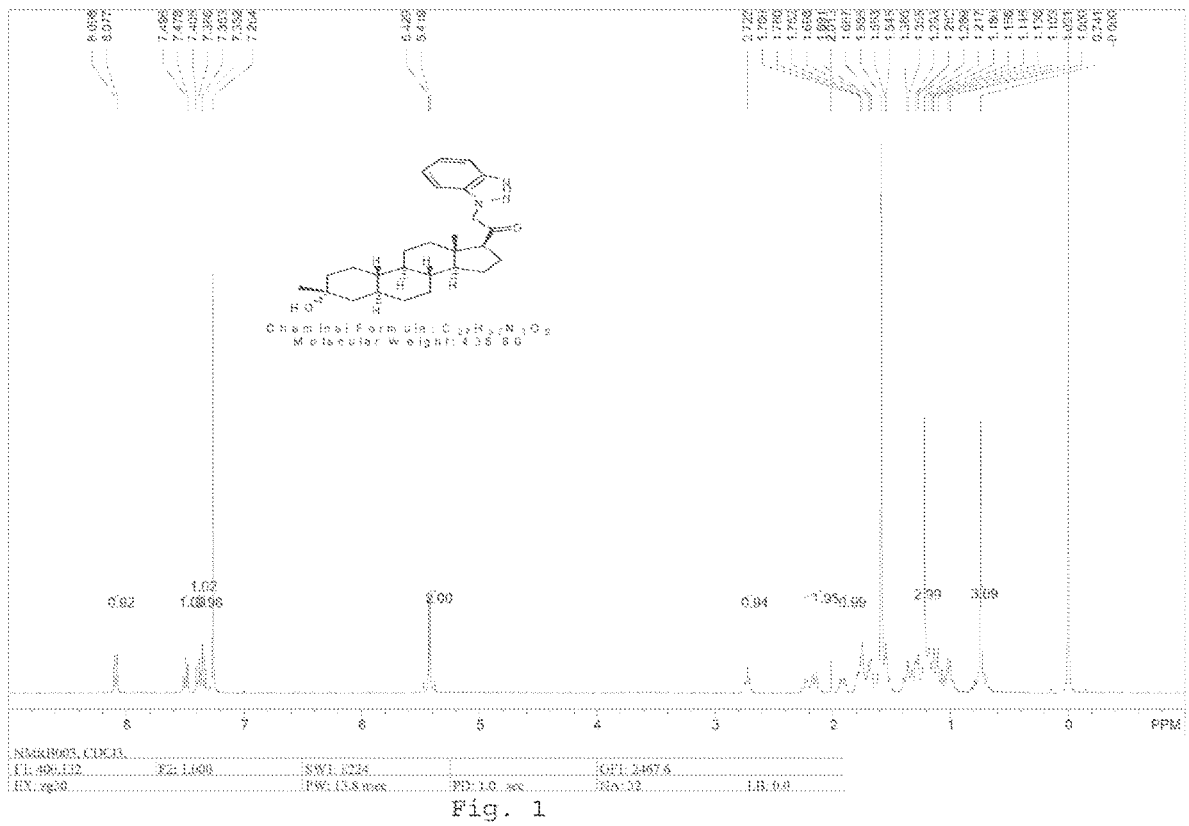
FIGS. 1-13 depict representative $^1$H NMR spectrum of exemplary compounds described herein.
Figure 2:
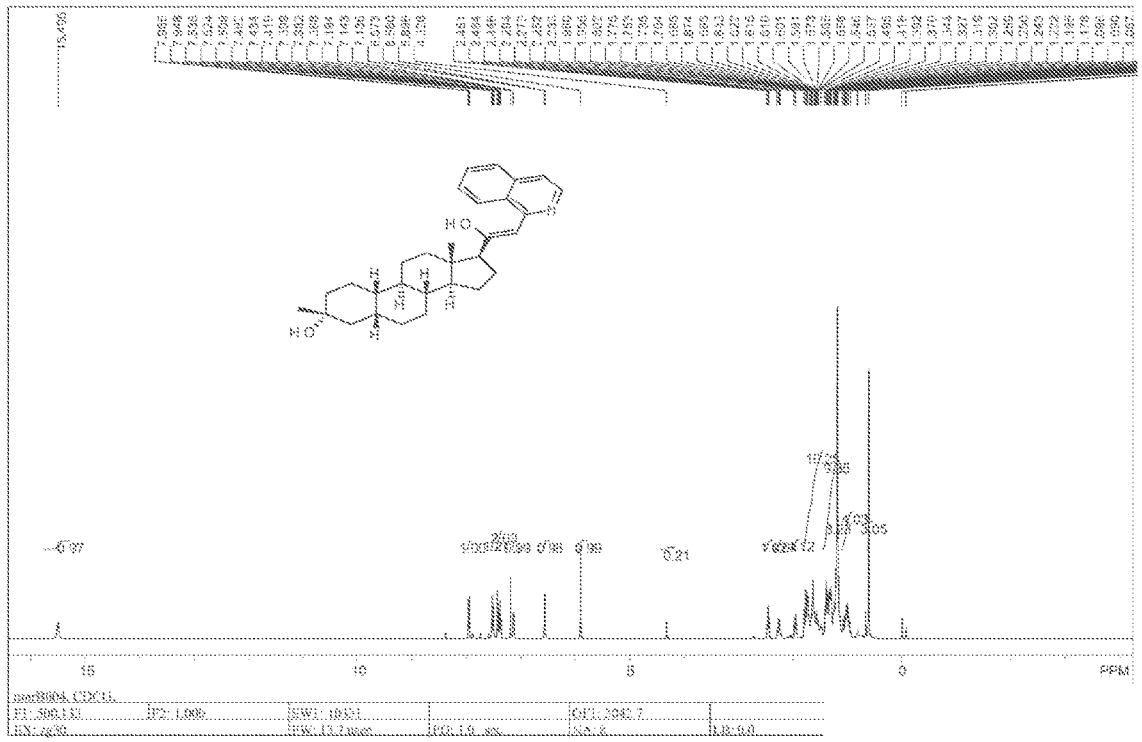
Figure 3:
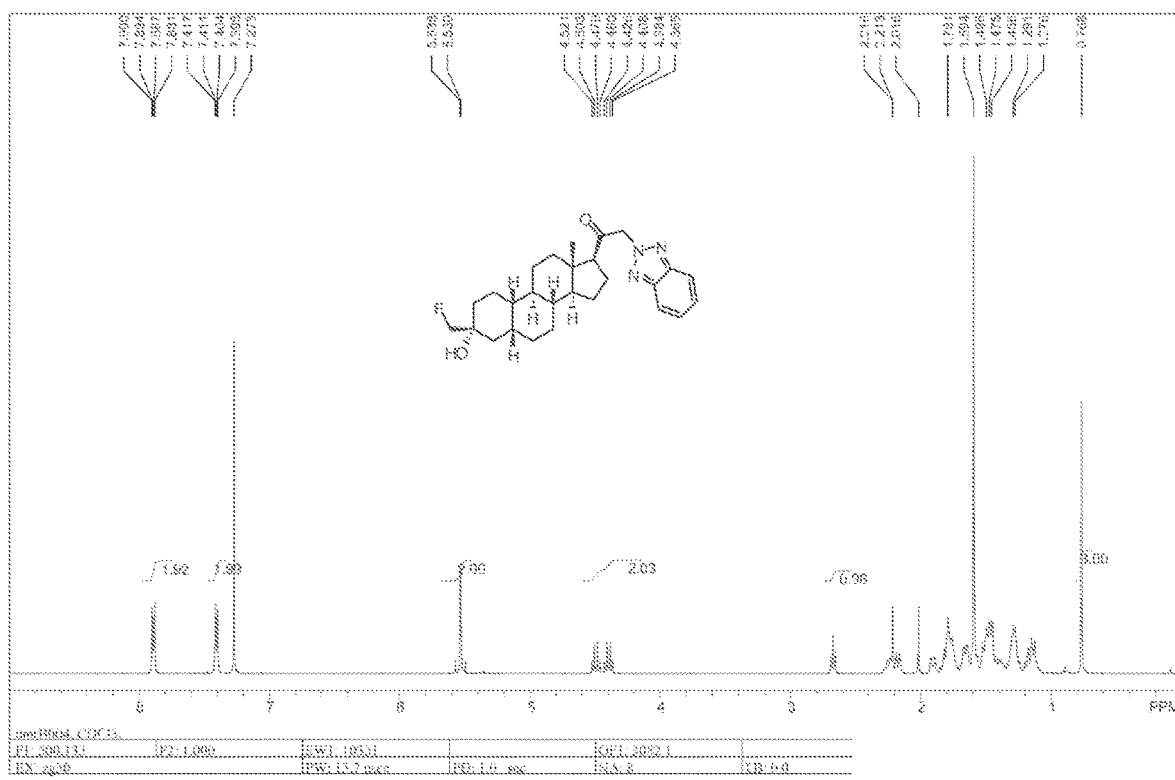
Figure 4:
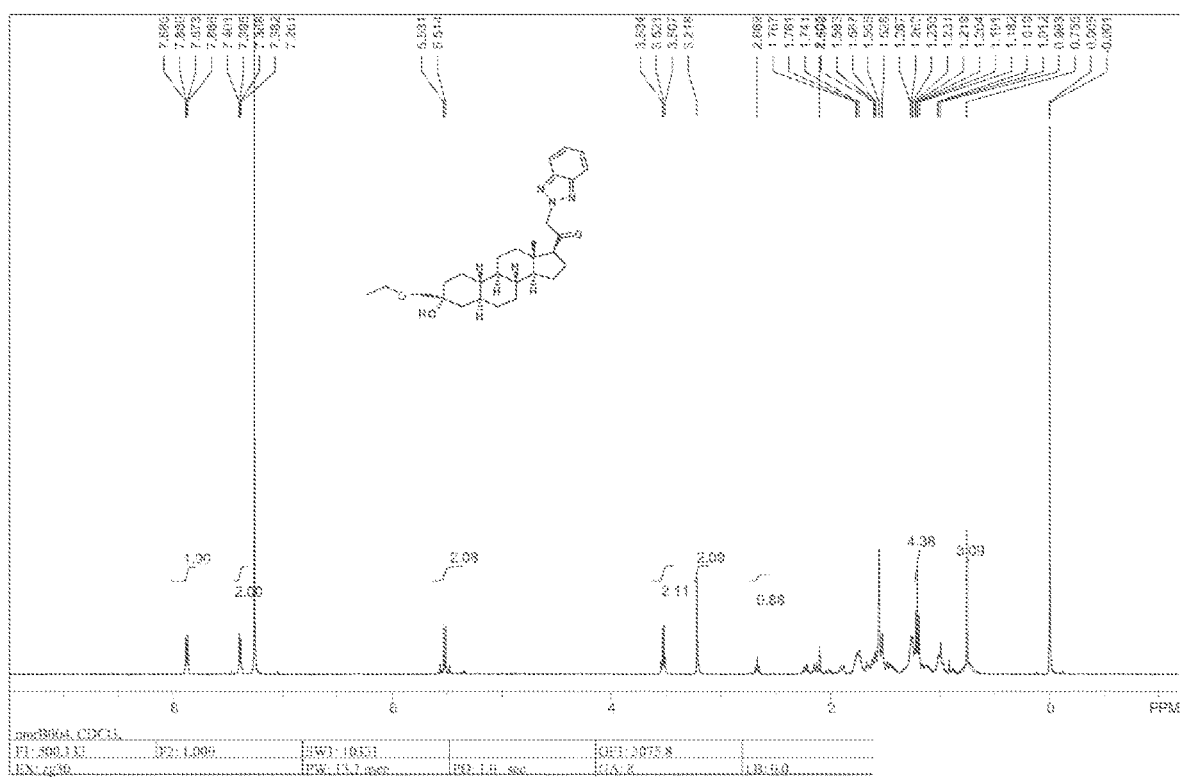
Figure 5:
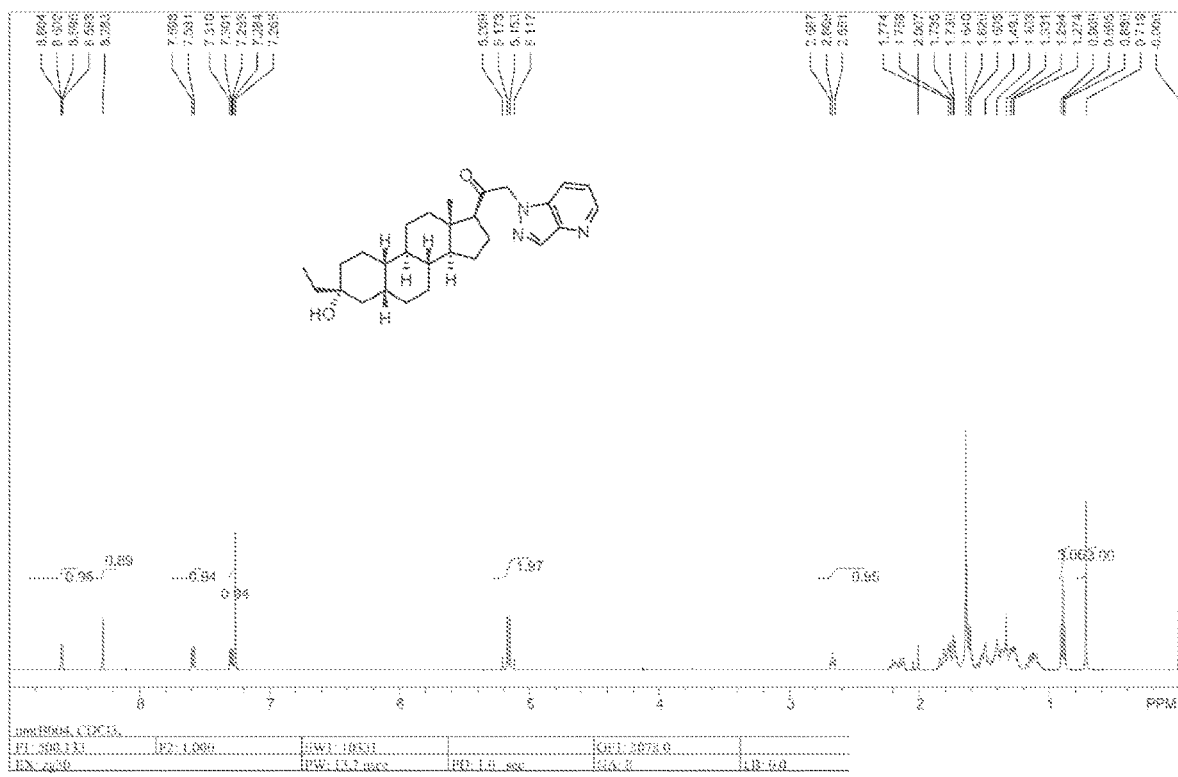
Figure 6:
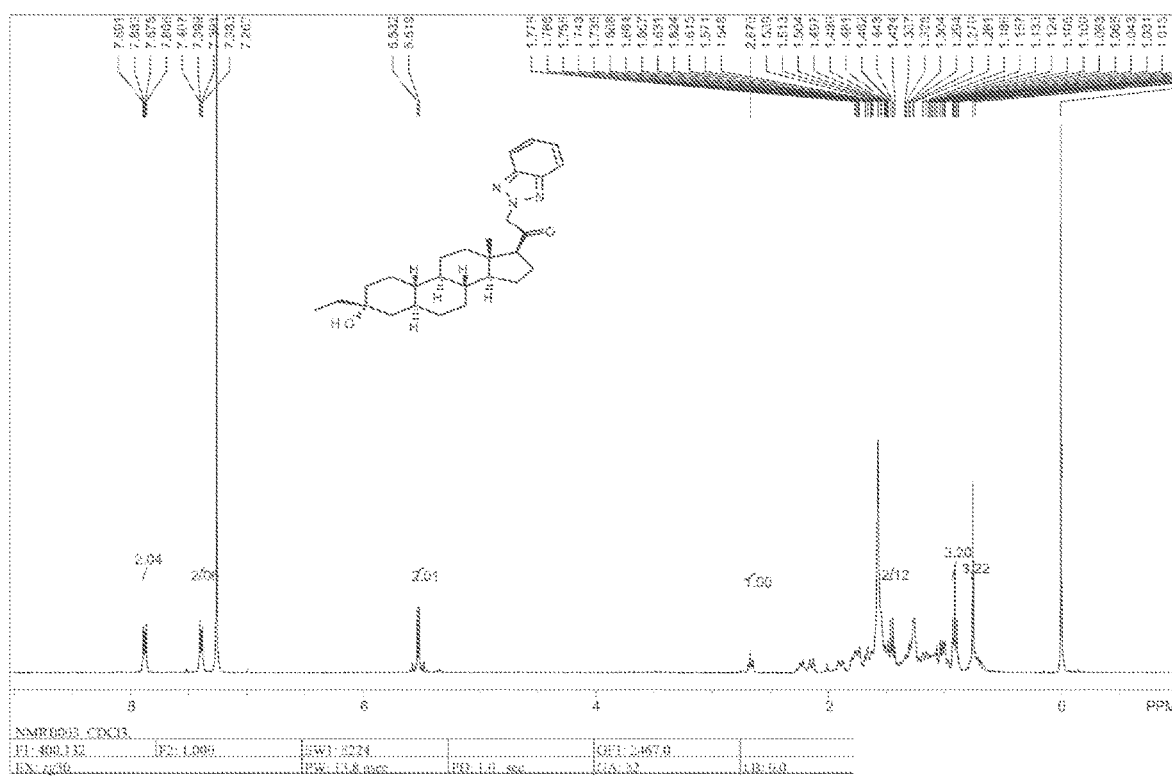
Figure 7:
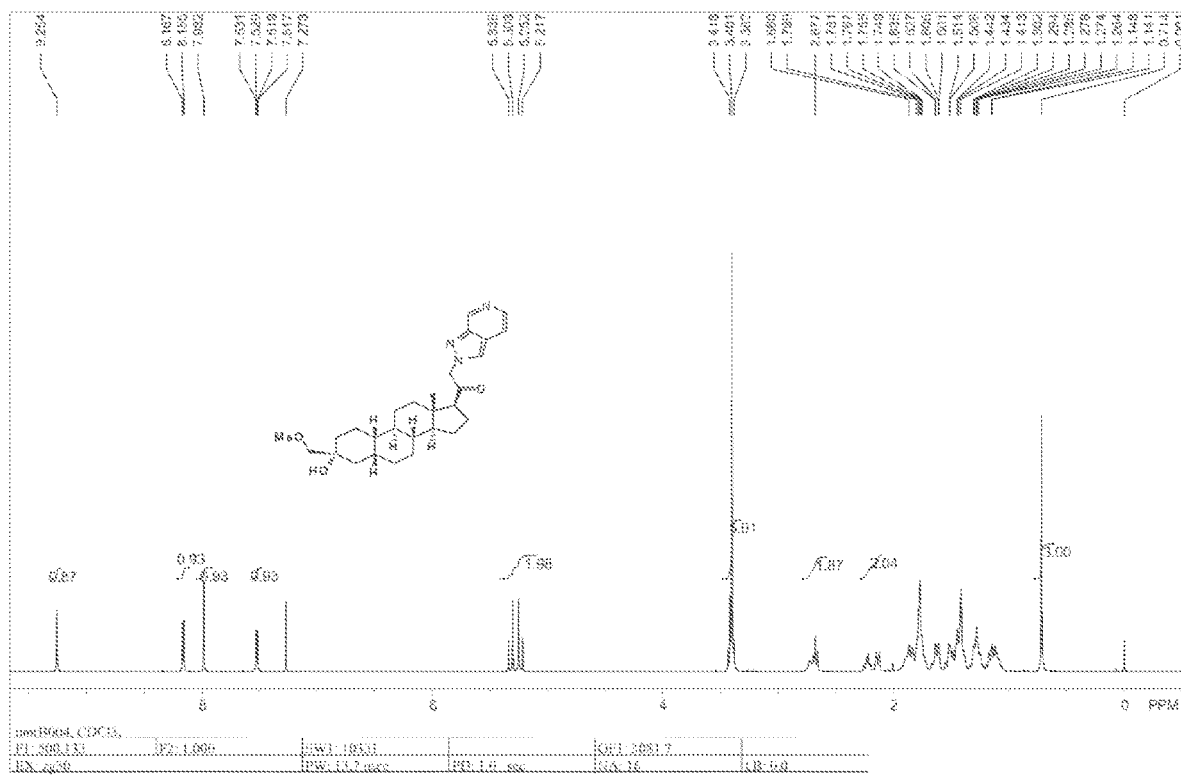
Figure 8:
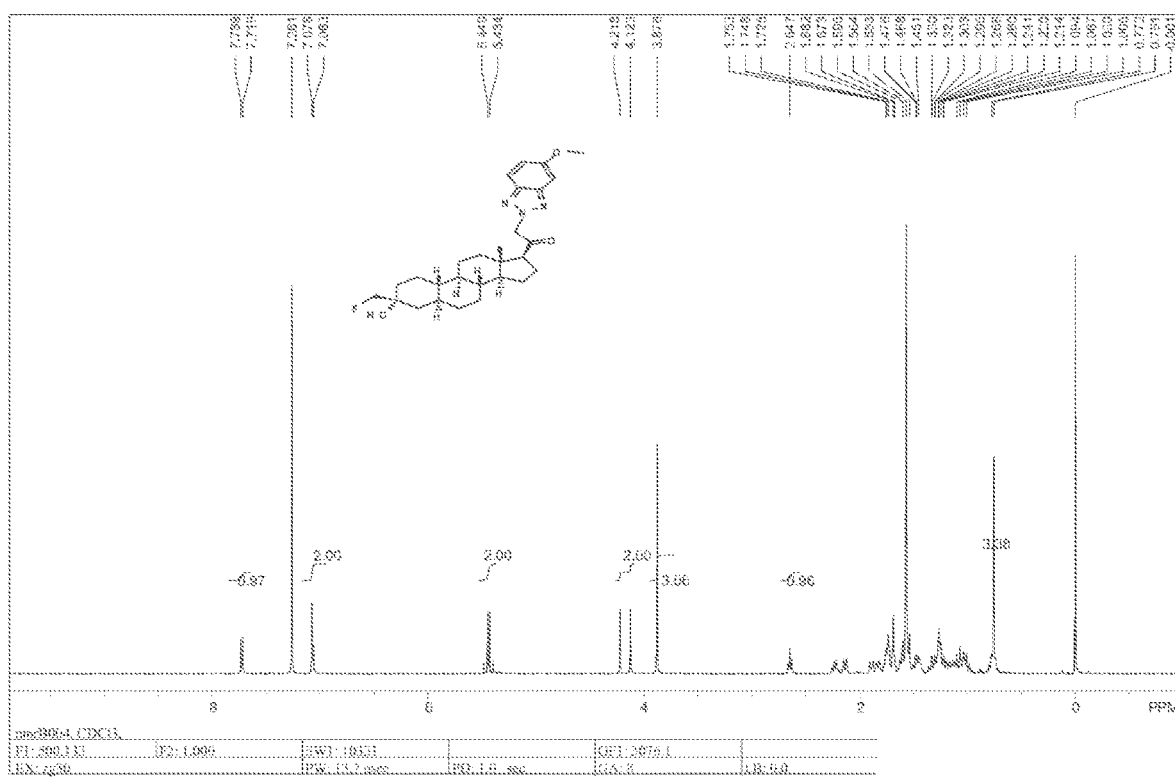
Figure 9:
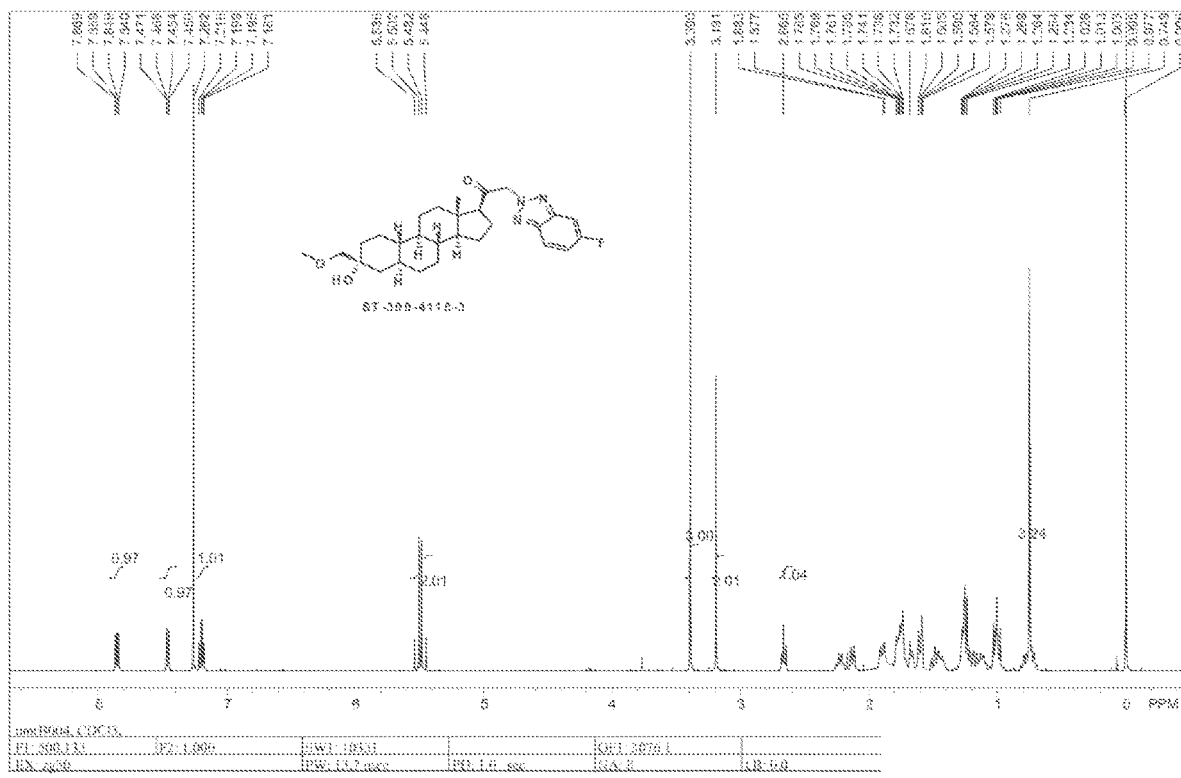
Figure 10:
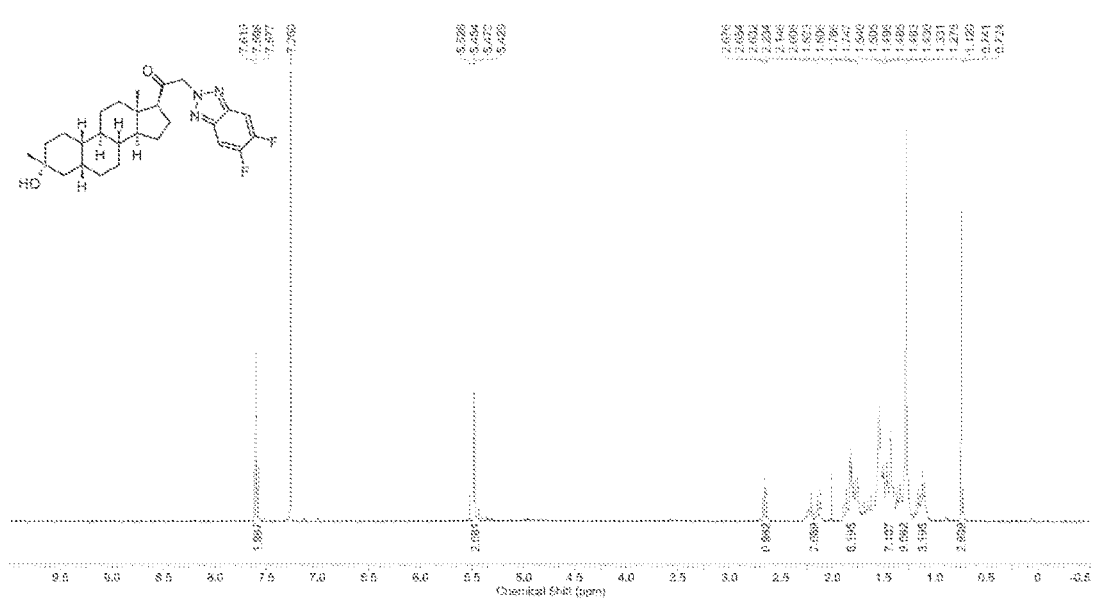
Figure 11:
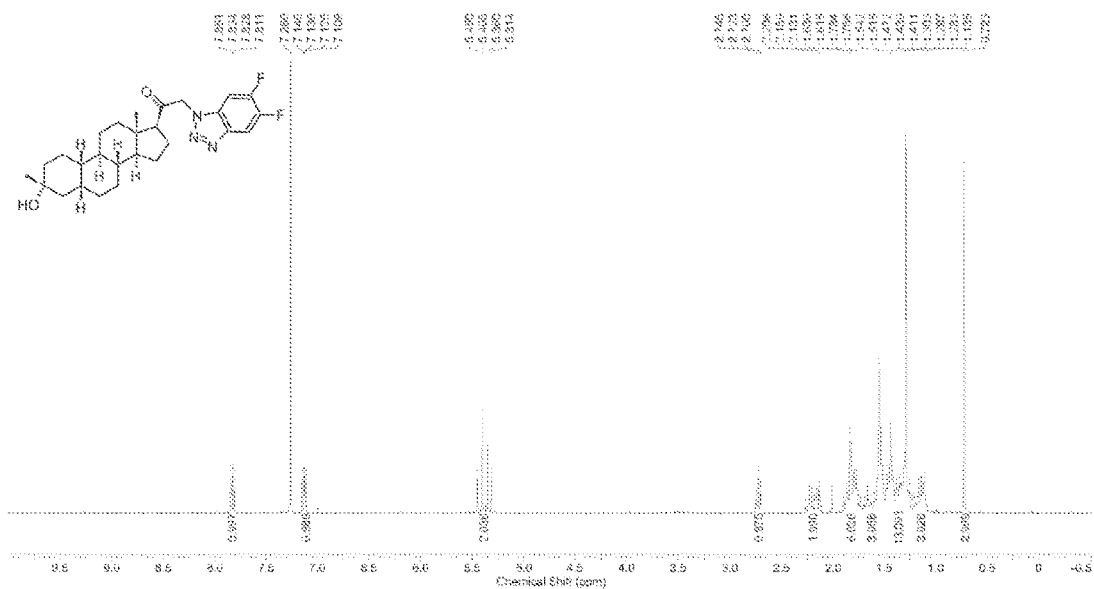
Figure 12:
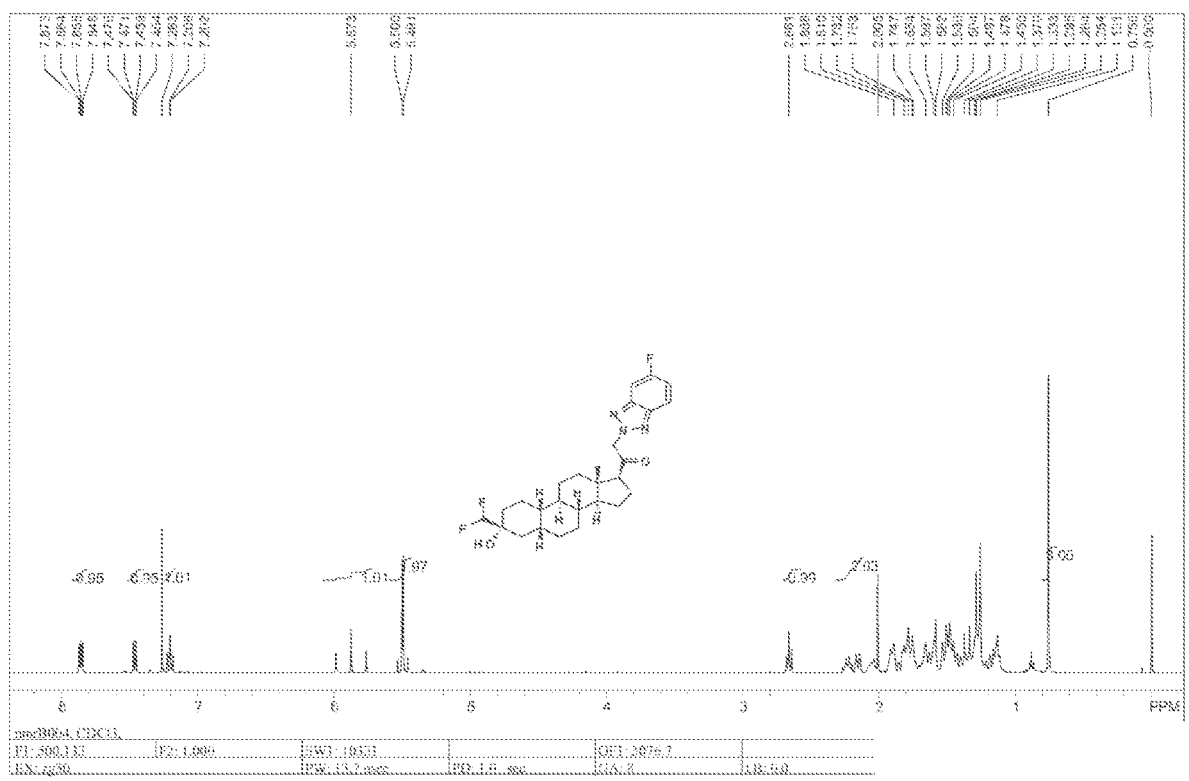
Figure 13:
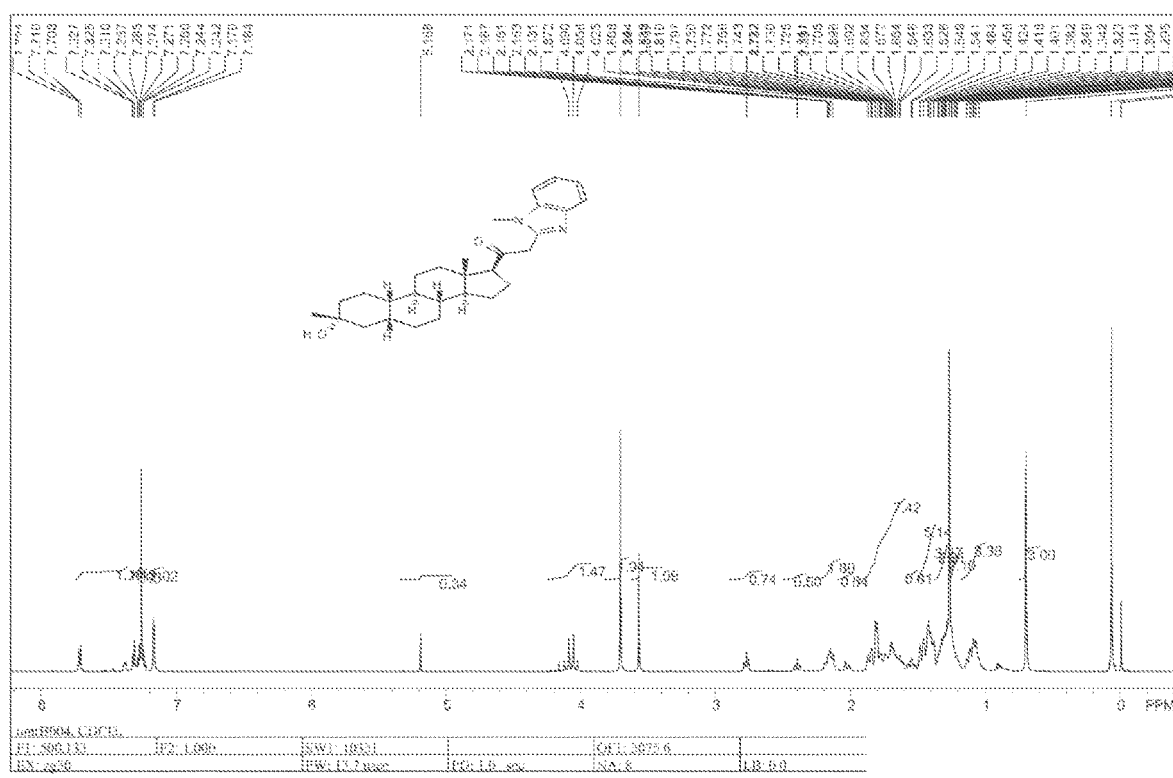

As described herein, the present invention provides 3,3-disubstituted 19-nor neuroactive steroids of Formula (I):

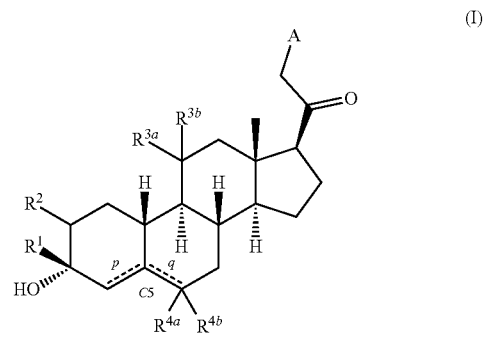

and pharmaceutically acceptable salts thereof;
wherein:
═ represents a single or double bond as valency permits;
A is of Formula (A-1) or Formula (A-2):

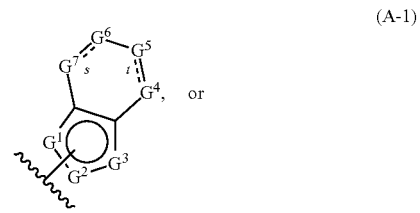

-continued

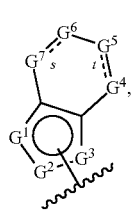
(A-2)

wherein the point of attachment is at $G^1$ or $G^2$ in Formula (A-1) and the point of attachment is at $G^2$ or $G^3$ in Formula (A-2);

$G^1$ is N, $NR^{N1}$, O, S, C, or $C-R^{G1}$ as valency permits;

$G^2$ is N, $NR^{N2}$, O, S, C, —C=N—, or $C-R^{G2}$ as valency permits;

$G^3$ is N, $NR^{N3}$, O, S, C, or $C-R^{G3}$ as valency permits;

$G^4$ is N, $NR^{N4}$, $C-R^{G4}$, or $C-(R^{G4})_2$ as valency permits;

$G^5$ is N, $NR^{N5}$, $C-R^{G5}$, or $C-(R^{G5})_2$ as valency permits;

$G^6$ is N, $NR^{N6}$, $C-R^{G6}$, or $C-(R^{G6})_2$ as valency permits; and $G^7$ is N, $NR^{N7}$, $C-R^{G7}$, or $C-(R^{G7})_2$ as valency permits;

each instance of $R^{G1}$, $R^{G2}$, $R^{G3}$, $R^{G4}$, $R^{G5}$, $R^{G6}$, and $R^{G7}$ is, independently, hydrogen, halogen, $-NO_2$, $-CN$, $-OR^{GA}$, $-N(R^{GA})_2$, $-C(=O)R^{GA}$, $-C(=O)OR^{GA}$, $-OC(=O)R^{GA}$, $-OC(=O)OR^{GA}$, $-C(=O)N(R^{GA})_2$, $-N(R^{GA})C(=O)R^{GA}$, $-OC(=O)N(R^{GA})_2$, $-N(R^{GA})C(=O)OR^{GA}$, $-S(=O)_2R^{GA}$, $-S(=O)_2OR^{GA}$, $-OS(=O)_2R^{GA}$, $-S(=O)_2N(R^{GA})_2$, $-N(R^{GA})S(=O)_2R^{GA}$, $-S(=O)R^{GA}$, $-S(=O)OR^{GA}$, $-OS(=O)R^{GA}$, $-S(=O)N(R^{GA})_2$, $-N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl;

each instance of $R^{GA}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, a nitrogen protecting group when attached to nitrogen, or two $R^{GA}$ groups are taken with the intervening atoms to form a substituted or unsubstituted carbocyclic or heterocylic ring;

$R^1$ is substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl;

$R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, or $-OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl;

$R^{3a}$ is hydrogen or $-OR^{A3}$, wherein $R^{A3}$ is hydrogen, or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group;

each of $R^{4a}$ or $R^{4b}$ is independently hydrogen, substituted or unsubstituted $C_{1-6}$ alkyl, or halogen; and provided if bond p is a double bond, then bond q is a single bond, provided if bond q is a double bond, then bond p is a single bond and $R^{4b}$ is absent; and provided if both bonds q and p are single bonds, then the hydrogen at C5 is in the alpha or beta configuration.

In certain embodiments, $G^4$ is N or $NR^{N4}$, and/or $G^5$ is N or $NR^{N5}$, and/or $G^6$ is N or $NR^{N6}$, and/or $G^7$ is N or $NR^{N7}$.

It is understood, based on the aforementioned description, that compounds of Formula (I) encompass 3,3-disubstituted 19-nor neuroactive steroids wherein the A/B ring system of the compound is cis (as provided in Formula (I-A), wherein the A/B ring system of the compound is trans (as provided in Formula (I-B), wherein the B ring of the compound comprises a C5-C6 double bond (as provided in Formula (I-C)), and wherein the A ring of the compound comprises a $C_{4-C}5$ double bond (as provided in Formula (I-D)),

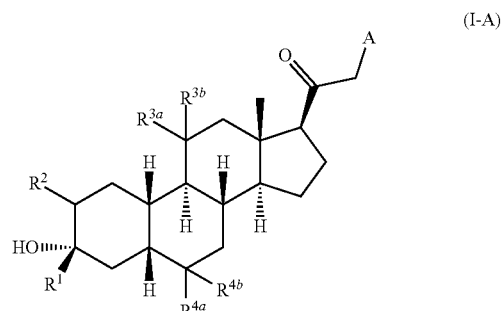
(I-A)

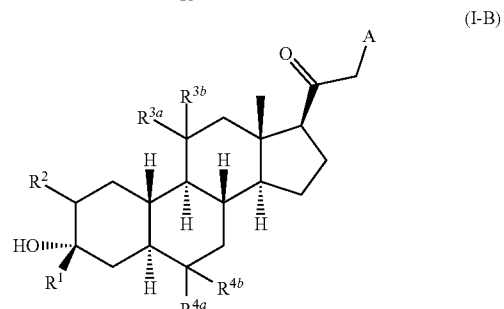
(I-B)

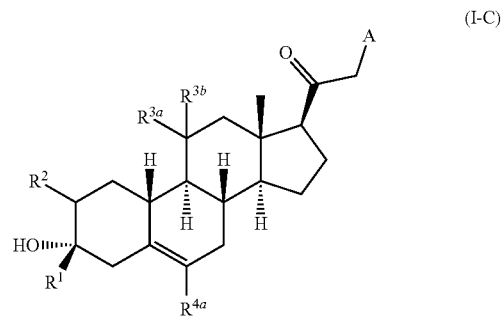
(I-C)

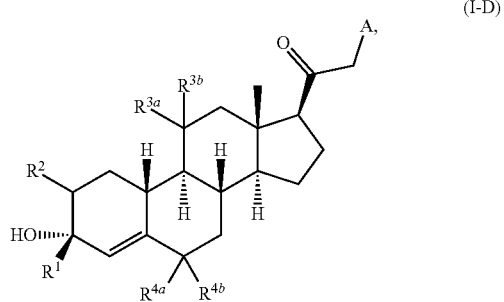
(I-D)

and pharmaceutically acceptable salts thereof.

Group $R^1$

As generally defined herein, $R^1$ is substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl.

In certain embodiments, $R^1$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^1$ $C_{1-6}$alkyl groups include, but are not limited to, substituted or unsubstituted methyl($C_1$), ethyl($C_2$), n-propyl($C_3$), isopropyl($C_3$), n-butyl($C_4$), tert-butyl($C_4$), sec-butyl($C_4$), iso-butyl ($C_4$), n-pentyl (C5), 3-pentanyl($C_5$), amyl($C_5$), neopentyl ($C_5$), 3-methyl-2-butanyl($C_5$), tertiary amyl($C_5$), n-hexyl ($C_6$), $C_{1-6}$ alkyl substituted with 1, 2, 3, 4, 5, 6, 7, 8, 9, 10, or more fluoro groups (e.g., —$CF_3$, —$CH_2F$, —$CHF_2$, difluoroethyl, and 2,2,2-trifluoro-1,1-dimethyl-ethyl), $C_{1-6}$ alkyl substituted with 1, 2, 3, 4, 5, 6, 7, 8, 9, 10, or more chloro groups (e.g., —$CH_2Cl$, —$CHCl_2$), and $C_{1-6}$ alkyl substituted with alkoxy groups (e.g., —$CH_2OCH_3$ and —$CH_2OCH_2CH_3$). In certain embodiments, $R^1$ is substituted $C_{1-6}$ alkyl, e.g., $R^1$ is haloalkyl, alkoxyalkyl, or aminoalkyl. In certain embodiments, $R^1$ is Me, Et, n-Pr, n-Bu, i-Bu, fluoromethyl, chloromethyl, difluoromethyl, trifluoromethyl, trifluoroethyl, difluoroethyl, 2,2,2-trifluoro-1,1-dimethyl-ethyl, methoxymethyl, methoxyethyl, or ethoxymethyl.

In certain embodiments, $R^1$ is unsubstituted $C_{1-3}$ alkyl, e.g., $R^1$ is —$CH_3$, —$CH_2CH_3$, or —$CH_2CH_2CH_3$.

In certain embodiments, $R^1$ is $C_{1-6}$ alkyl substituted with one or more fluorine atoms; e.g., $R^1$ is —$CH_2F$, —$CHF_2$, or —$CF_3$.

In certain embodiments, $R^1$ is $C_{1-6}$ alkyl substituted with one or more —$OR^{A1}$ groups, wherein $R^{A1}$ is hydrogen or substituted or unsubstituted alkyl. In certain embodiments, $R^1$ is —$CH_2OR^{A1}$, e.g., wherein $R^{A1}$ is hydrogen, —$CH_3$, —$CH_2CH_3$, or —$CH_2CH_2CH_3$, e.g., to provide a group $R^1$ of formula —$CH_2OH$, —$CH_2OCH_3$, —$CH_2OCH_2CH_3$, or —$CH_2OCH_2CH_3$.

In certain embodiments, $R^1$ is substituted or unsubstituted $C_{2-6}$ alkenyl, e.g., substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl. In certain embodiments, $R^1$ is ethenyl($C_2$), propenyl($C_3$), or butenyl($C_4$), unsubstituted or substituted with one or more substituents selected from the group consisting of alkyl, halo, haloalkyl, alkoxyalkyl, or hydroxyl. In certain embodiments, $R^1$ is ethenyl, propenyl, or butenyl, unsubstituted or substituted with alkyl, halo, haloalkyl, alkoxyalkyl, or hydroxy. In certain embodiments, $R^1$ is ethenyl.

In certain embodiments, $R^1$ is substituted or unsubstituted $C_{2-6}$ alkynyl, e.g., substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl. In certain embodiments, $R^1$ is ethynyl, propynyl, or butynyl, unsubstituted or substituted with alkyl, halo, haloalkyl (e.g., $CF_3$), alkoxyalkyl, cycloalkyl (e.g., cyclopropyl or cyclobutyl), or hydroxyl. In certain embodiments, $R^1$ is selected from the group consisting of trifluoroethynyl, cyclopropylethynyl, cyclobutylethynyl, and propynyl, fluoropropynyl, and chloroethynyl. In certain embodiments, $R^1$ is ethynyl($C_2$), propynyl($C_3$), or butynyl($C_4$), unsubstituted or substituted with one or more substituents selected from the group consisting of substituted or unsubstituted aryl, substituted or unsubstituted heteroaryl, substituted or unsubstituted carbocyclyl, and substituted or unsubstituted heterocyclyl. In certain embodiments, $R^1$ is ethynyl($C_2$), propynyl ($C_3$), or butynyl($C_4$) substituted with substituted phenyl. In certain embodiments, the phenyl substituent is further substituted with one or more substituents selected from the group consisting of halo, alkyl, trifluoroalkyl, alkoxy, acyl, amino or amido. In certain embodiments, $R^1$ is ethynyl($C_2$), propynyl($C_3$), or butynyl($C_4$) substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, or tetrazolyl.

In certain embodiments, $R^1$ is ethynyl, propynyl, or butynyl, unsubstituted or substituted with alkyl, halo, haloalkyl, alkoxyalkyl, or hydroxyl. In certain embodiments, $R^1$ is ethynyl or propynyl, substituted with substituted or unsubstituted aryl. In certain embodiments, $R^1$ is ethynyl or propynyl, substituted with phenyl unsubstituted or substituted with halo, alkyl, alkoxy, haloalkyl, trihaloalkyl, or acyl. In certain embodiments, $R^1$ is ethynyl or propynyl, substituted with substituted or unsubstituted carbocyclyl. In certain embodiments, $R^{3a}$ is ethynyl or propynyl, substituted with substituted or unsubstituted cyclopropyl, cyclobutyl, cyclopentyl, or cyclohexyl. In certain embodiments, $R^1$ is ethynyl or propynyl, substituted with substituted or unsubstituted heteroaryl. In certain embodiments, $R^1$ is ethynyl or propynyl, substituted with substituted or unsubstituted pyridinyl, or pyrimidinyl. In certain embodiments, $R^1$ is ethynyl or propynyl, substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl. In certain embodiments, $R^1$ is ethynyl or propynyl, substituted with substituted or unsubstituted heterocyclyl. In certain embodiments, $R^1$ is ethynyl or propynyl, substituted with substituted or unsubstituted pyrrolidinyl, piperidinyl, piperazinyl, or mopholinyl. In certain embodiments, $R^1$ is propynyl or butynyl, substituted with hydroxyl or alkoxy. In certain embodiments, $R^1$ is propynyl or butynyl, substituted with methoxy or ethoxy. In certain embodiments, $R^1$ is ethynyl or propynyl, substituted with chloro. In certain embodiments, $R^1$ is ethynyl or propynyl, substituted with trifluoromethyl.

In certain embodiments, $R^1$ is substituted or unsubstituted $C_{3-6}$ carbocyclyl, e.g., substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^1$ is substituted or unsubstituted cyclopropyl or substituted or unsubstituted cyclobutyl.

Groups ═, $R^2$, $R^{3a}$, $R^{3b}$, $R^{4a}$, and $R^{4b}$

As generally defined herein, $R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl, or —$OR^{A2}$, wherein $R^{A2}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocyclyl.

In certain embodiments, $R^2$ is hydrogen. In certain embodiments, $R^2$ is halogen, e.g., fluoro, chloro, bromo, or iodo. In certain embodiments, $R^2$ is fluoro or chloro. In certain embodiments, $R^2$ is substituted or unsubstituted $C_{1-6}$alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^2$ is substituted or unsubstituted $C_{2-6}$ alkenyl, In certain embodiments, $R^2$ is substituted or unsubstituted $C_{2-6}$ alkynyl, e.g., substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl. In certain embodiments, $R^2$ is substituted or unsubstituted $C_{3-6}$ carbocyclyl, e.g., substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^2$ is substituted or unsubstituted cyclopropyl or substituted or unsubstituted cyclobutyl. In certain embodiments, $R^2$ is —$CH_3$, —$CH_2CH_3$, —$CH_2CH_2CH_3$, or substituted or unsubstituted cyclopropyl. In certain embodiments, $R^2$ is —$OR^{A2}$. In certain embodiments, $R^{A2}$ is hydrogen. In certain embodiments, $R^{A2}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^{A2}$ is hydrogen, —$CH_3$, —$CH_2CH_3$, or —$CH_2CH_2CH_3$, i.e., to provide a group $R^2$ of formula —OH, —$OCH_3$, —$OCH_2CH_3$, or —$OCH_2CH_2CH_3$. In certain embodiments, $R^2$ is a non-hydrogen substituent in the alpha configuration. In certain embodiments, $R^2$ is a non-hydrogen substituent in the beta configuration.

As generally defined herein, $R^{3a}$ is hydrogen or —$OR^{A3}$, wherein $R^{A3}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group.

In certain embodiments, both $R^{3a}$ and $R^{3b}$ are both hydrogen.

In certain embodiments, $R^{3a}$ and $R^{3b}$ are joined to form an oxo (=O) group.

In certain embodiments, $R^{3a}$ is —$OR^{A3}$ and $R^{3b}$ is hydrogen. In certain embodiments, wherein $R^{3a}$ is —$OR^{A3}$, $R^{3a}$ is in the alpha or beta configuration (e.g., R or S configuration). In certain embodiments, wherein $R^{3a}$ is —$OR^{A3}$, $R^{3a}$ is in the alpha configuration. In certain embodiments, wherein $R^{3a}$ is —$OR^{A3}$, $R^{3a}$ is in the beta configuration. In certain embodiments, $R^{A3}$ is hydrogen. In certain embodiments, $R^{A3}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^{A3}$ is hydrogen, —$CH_3$, —$CH_2CH_3$, or —$CH_2CH_2CH_3$, i.e., to provide a group $R^{3a}$ of formula —OH, —$OCH_3$, —$OCH_2CH_3$, or —$OCH_2CH_2CH_3$.

As generally defined herein, each instance of $R^{4a}$ and $R^{4b}$ is independently hydrogen, substituted or unsubstituted $C_{1-6}$ alkyl, or halogen, provided if the === between C5 and C6 are single bonds, then the hydrogen at C5 and $R^{4a}$ are each independently provided in the alpha or beta configuration, and $R^{4b}$ is absent.

In certain embodiments, === is a single bond, at least one of $R^{4a}$ and $R^{4b}$ is hydrogen. In certain embodiments, === is a single bond, at least one of $R^{4a}$ and $R^{4b}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, === is a single bond, at least one of $R^{4a}$ and $R^{4b}$ is $C_1$ alkyl, e.g., —$CH_3$ or —$CF_3$. In certain embodiments, === is a single bond, at least one of $R^{4a}$ and $R^{4b}$ is halogen, e.g., fluoro.

In certain embodiments, === is a single bond, and both of $R^{4a}$ and $R^{4b}$ are hydrogen. In certain embodiments, === is a single bond, and both of $R^{4a}$ and $R^{4b}$ are independently substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, === is a single bond, and both of $R^{4a}$ and $R^{4b}$ are independently $C_1$ alkyl, e.g., —$CH_3$ or —$CF_3$. In certain embodiments, === is a single bond, and both of $R^{4a}$ and $R^{4b}$ are halogen, e.g., fluoro.

In certain embodiments, wherein === represents a single bond, $R^{4a}$ is a non-hydrogen substituent in the alpha configuration. In certain embodiments, wherein === represents a single bond, $R^{4a}$ is a non-hydrogen substituent in the beta configuration.

In certain embodiments, === is a double bond, and $R^{4a}$ is hydrogen. In certain embodiments, === is a double bond, and $R^{4a}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, === is a double bond, and $R^{4a}$ is $C_1$ alkyl, e.g., —$CH_3$ or —$CF_3$. In certain embodiments, === is a double bond, and $R^{4a}$ is halogen, e.g., fluoro.

Groups A

As generally defined herein, A is of Formula (A-1) or Formula (A-2)

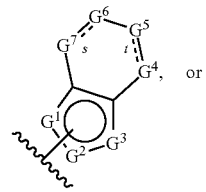

(A-1)

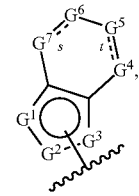

(A-2)

wherein:
the point of attachment is at $G_1$ or $G_2$ in Formula (A-1) and the point of attachment is at $G_2$ or $G_3$ in Formula (A-2);
$G^1$ is N, $NR^{N1}$, O, S, C, or C—$R^{G1}$ as valency permits;
$G^2$ is N, $NR^{N2}$, O, S, C, —C=N—, or C—$R^{G2}$ as valency permits;
$G^3$ is N, $NR^{N3}$, O, S, C, or C—$R^{G3}$ as valency permits;
$G^4$ is N, $NR^{N4}$, C—$R^{G4}$, or C—$(R^{G4})_2$ as valency permits;
$G^5$ is N, $NR^{N5}$, C—$R^{G5}$, or C—$(R^{G5})_2$ as valency permits;
$G^6$ is N, $NR^{N6}$, C—$R^{G6}$, or C—$(R^{G6})_2$ as valency permits; and
$G^7$ is N, $NR^{N7}$, C—$R^{G7}$, or C—$(R^{G7})_2$ as valency permits;
each instance of $R^{G1}$, $R^{G2}$, $R^{G3}$, $R^{G4}$, $R^{G5}$, $R^{G6}$, and $R^{G7}$ is, independently, hydrogen, halogen, —$NO_2$, —CN, —$OR^{GA}$, —$N(R^{GA})_2$, —C(=O)$R^{GA}$, —C(=O)$OR^{GA}$, —OC(=O)$R^{GA}$, —OC(=O)$OR^{GA}$, —C(=O)$N(R^{GA})_2$, —N($R^{GA}$)C(=O)$R^{GA}$, —OC(=O)$N(R^{GA})_2$, —N($R^{GA}$)C(=O)$OR^{GA}$, —S(=O)$_2R^{GA}$, —S(=O)$_2OR^{GA}$, —OS(=O)$_2R^{GA}$, —S(=O)$_2N(R^{GA})_2$, —N($R^{GA}$)S(=O)$_2R^{GA}$, —S(=O)$R^{GA}$, —S(=O)$OR^{GA}$, —OS(=O)

$R^{GA}$, —S(=O)N($R^{GA}$)$_2$, —N($R^{GA}$)S(=O)$R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl;

each instance of $R^{N2}$, $R^{N4}$, $R^{N5}$, $R^{N6}$, and $R^{N7}$ is independently hydrogen, substituted or unsubstituted $C_{1-6}$ alkyl, or a nitrogen protecting group; and each instance of $R^{GA}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, a nitrogen protecting group when attached to nitrogen, or two $R^{GA}$ groups are taken with the intervening atoms to form a substituted or unsubstituted carbocyclic or heterocylic ring.

In certain embodiments, $G^4$ is N or $NR^{N4}$, and/or $G^5$ is N or $NR^{N5}$, and/or $G^6$ is N or $NR^{N6}$, and/or $G^7$ is N or $NR^{N7}$;

In certain embodiments, A is of Formula (A-1)

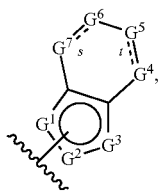

(A-1)

wherein the point of attachment is at $G^1$ or $G^2$. In certain embodiments, A is of Formula (A-1)

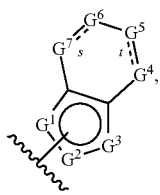

(A-1)

wherein the point of attachment is at $G^1$. In certain embodiments, A is of Formula (A-1)

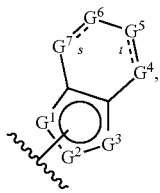

(A-1)

wherein the point of attachment is at $G^2$. In certain embodiments, A is of Formula (A-2)

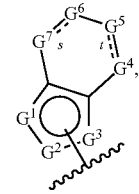

(A-2)

wherein the point of attachment is at $G^2$ or $G^3$. In certain embodiments, A is of Formula (A-2)

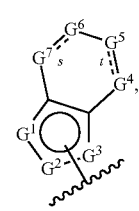

(A-2)

wherein the point of attachment is at $G^2$. In certain embodiments, A is of Formula (A-2)

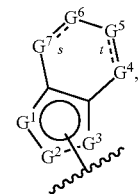

(A-2)

wherein the point of attachment is at $G^3$. In certain embodiments, A is one of the following formulae:

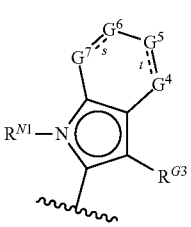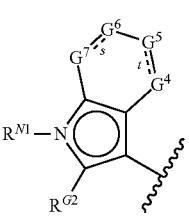

In certain embodiments, A is one of the following formulae:

-continued

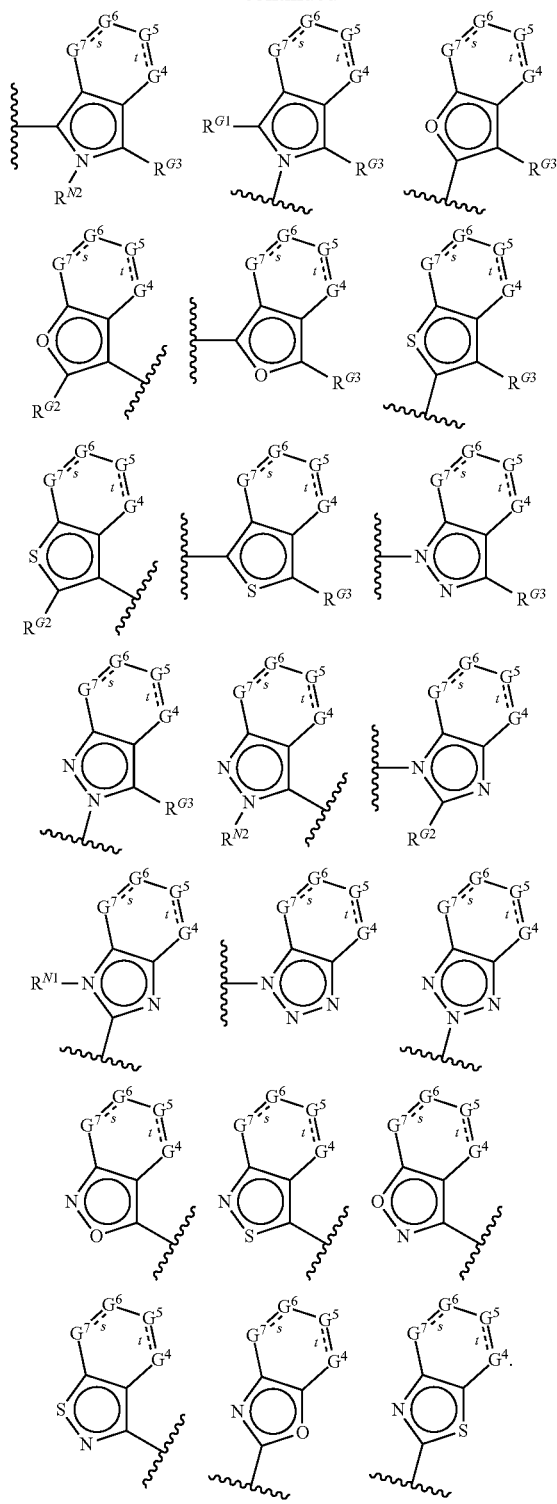

As used herein, ═ represents a single or double bond as valency permits. In certain embodiments, bond s is a double bond. In certain embodiments, bond s is a single bond. In certain embodiments, bond t is a double bond. In certain embodiments, bond t is a single bond.

In certain embodiments, A is one of the following formulae:

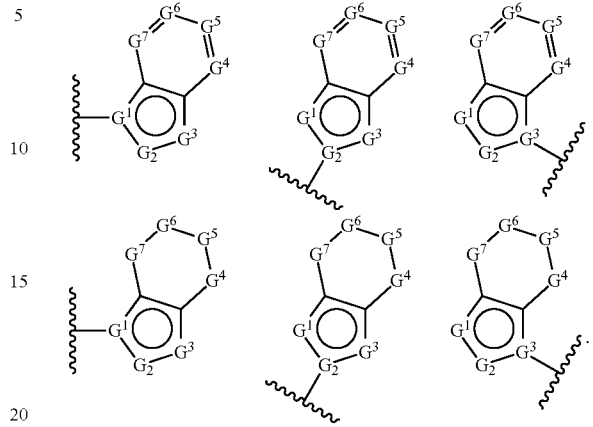

As generally defined herein, each instance of $R^{G1}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, —$S(=O)R^{GA}$, —$S(=O)OR^{GA}$, —$OS(=O)R^{GA}$, —$S(=O)N(R^{GA})_2$, —$N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl. In some embodiments, $R^{G1}$ is hydrogen. In some embodiments, $R^{G1}$ is halogen. In certain embodiments, $R^{G1}$ is F. In certain embodiments, $R^{G1}$ is Cl. In certain embodiments, $R^{G1}$ is Br. In certain embodiments, $R^{G1}$ is I. In certain embodiments, $R^{G1}$ is substituted or unsubstituted $C_{1-6}$ alkyl. In certain embodiments, $R^{G1}$ is substituted $C_{1-6}$ alkyl. In certain embodiments, $R^{G1}$ is —$CH_2F$, —$CHF_2$, or —$CF_3$. In certain embodiments, $R^{G1}$ is unsubstituted $C_{1-6}$ alkyl. In certain embodiments, $R^{G1}$ is methyl, ethyl, propyl, butyl, pentyl, or hexyl. In some embodiments, $R^{G1}$ is —CN. In some embodiments, $R^{G1}$ is —$NO_2$. In some embodiments, $R^{G1}$ is substituted or unsubstituted carbocyclyl, substituted or unsubstituted phenyl, substituted or unsubstituted heterocyclyl, or substituted or unsubstituted heteroaryl. In some embodiments, $R^{G1}$ is cyclopropyl or cyclobutyl. In certain embodiments, $R^{G1}$ is —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, or —$N(R^{GA})S(=O)_2R^{GA}$. In certain embodiments, $R^{G1}$ is —$NHR^{GA}$. In certain embodiments, $R^{G1}$ is —$NH_2$. In certain embodiments, $R^{G1}$ is —$NHR^{GA}$, wherein $R^{GA}$ is substituted or unsubstituted $C_{1-6}$ alkyl. In certain embodiments, $R^{G1}$ is —$NHR^{GA}$, wherein $R^{GA}$ is methyl, ethyl, or propyl. In certain embodiments, $R^{G1}$ is —$N(R^{GA})_2$, wherein each $R^{GA}$ is independently substituted or unsubstituted $C_{1-6}$ alkyl. In certain embodiments, $R^{G1}$ is —$N(CH_3)R^{GA}$, wherein each $R^{GA}$ is independently unsubstituted $C_{1-6}$ alkyl. In certain embodiments, $R^{G1}$ is —$N(CH_2CH_3)R^{GA}$, wherein each $R^{GA}$ is independently substituted or unsubstituted $C_{1-6}$ alkyl. In certain embodiments, $R^{G1}$ is —$OR^{GA}$. In certain embodiments, $R^{G1}$ is —OH. In certain embodiments, $R^{G1}$ is —$OR^{GA}$, wherein $R^{GA}$ is substituted or unsubstituted $C_{1-6}$ alkyl. In certain embodiments, $R^{G1}$ is —O-methyl, —O-ethyl, or —O-propyl. In certain embodiments, $R^{G1}$ is —$OR^{GA}$, wherein $R^{GA}$ is substituted or unsubstituted aryl. In certain embodiments, $R^{G1}$ is —O-phenyl.

As generally defined herein, each instance of $R^{G2}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, —$S(=O)R^{GA}$, —$S(=O)OR^{GA}$, —$OS(=O)R^{GA}$, —$S(=O)N(R^{GA})_2$, —$N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl. In some embodiments, $R^{G2}$ is hydrogen. In some embodiments, $R^{G2}$ is halogen. In certain embodiments, $R^{G2}$ is F. In certain embodiments, $R^{G2}$ is Cl. In certain embodiments, $R^{G2}$ is Br. In certain embodiments, $R^{G2}$ is I. In certain embodiments, $R^{G2}$ is substituted or unsubstituted $C_{1-6}$ alkyl. In certain embodiments, $R^{G2}$ is substituted $C_{1-6}$ alkyl. In certain embodiments, $R^{G2}$ is —$CH_2F$, —$CHF_2$, or —$CF_3$. In certain embodiments, $R^{G2}$ is unsubstituted $C_{1-6}$ alkyl. In certain embodiments, $R^{G2}$ is methyl, ethyl, propyl, butyl, pentyl, or hexyl. In some embodiments, $R^{G2}$ is —CN. In some embodiments, $R^{G2}$ is —$NO_2$. In some embodiments, $R^{G2}$ is substituted or unsubstituted carbocyclyl, substituted or unsubstituted phenyl, substituted or unsubstituted heterocyclyl, or substituted or unsubstituted heteroaryl. In some embodiments, $R^{G2}$ is cyclopropyl or cyclobutyl. In certain embodiments, $R^{G2}$ is —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, or —$N(R^{GA})S(=O)_2R^{GA}$. In certain embodiments, $R^{G2}$ is —$NHR^{GA}$. In certain embodiments, $R^{G2}$ is —$NH_2$. In certain embodiments, $R^{G2}$ is —$NHR^{GA}$, wherein $R^{GA}$ is substituted or unsubstituted $C_{1-6}$ alkyl. In certain embodiments, $R^{G2}$ is —$NHR^{GA}$, wherein $R^{GA}$ is methyl, ethyl, or propyl. In certain embodiments, $R^{G2}$ is —$N(R^{GA})_2$, wherein each $R^{GA}$ is independently substituted or unsubstituted $C_{1-6}$ alkyl. In certain embodiments, $R^{G2}$ is —$N(CH_3)R^{GA}$, wherein each $R^{GA}$ is independently unsubstituted $C_{1-6}$ alkyl. In certain embodiments, $R^{G2}$ is —$N(CH_2CH_3)R^{GA}$, wherein each $R^{GA}$ is independently substituted or unsubstituted $C_{1-6}$ alkyl. In certain embodiments, $R^{G2}$ is —$OR^{GA}$. In certain embodiments, $R^{G2}$ is —OH. In certain embodiments, $R^{G2}$ is —$OR^{GA}$, wherein $R^{GA}$ is substituted or unsubstituted $C_{1-6}$ alkyl. In certain embodiments, $R^{G2}$ is —O-methyl, —O-ethyl, or —O-propyl. In certain embodiments, $R^{G2}$ is —$OR^{GA}$, wherein $R^{GA}$ is substituted or unsubstituted aryl. In certain embodiments, $R^{G2}$ is —O-phenyl.

As generally defined herein, each instance of $R^{G3}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, —$S(=O)R^{GA}$, —$S(=O)OR^{GA}$, —$OS(=O)R^{GA}$, —$S(=O)N(R^{GA})_2$, —$N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl. In some embodiments, $R^{G3}$ is hydrogen. In some embodiments, $R^{G3}$ is halogen. In certain embodiments, $R^{G3}$ is F. In certain embodiments, $R^{G3}$ is Cl. In certain embodiments, $R^{G3}$ is Br. In certain embodiments, $R^{G3}$ is I. In certain embodiments, $R^{G3}$ is substituted or unsubstituted $C_{1-6}$ alkyl. In certain embodiments, $R^{G3}$ is substituted $C_{1-6}$ alkyl. In certain embodiments, $R^{G3}$ is —$CH_2F$, —$CHF_2$, or —$CF_3$. In certain embodiments, $R^{G3}$ is unsubstituted $C_{1-6}$ alkyl. In certain embodiments, $R^{G3}$ is methyl, ethyl, propyl, butyl, pentyl, or hexyl. In some embodiments, $R^{G3}$ is —CN. In some embodiments, $R^{G3}$ is —$NO_2$. In some embodiments, $R^{G3}$ is substituted or unsubstituted carbocyclyl, substituted or unsubstituted phenyl, substituted or unsubstituted heterocyclyl, or substituted or unsubstituted heteroaryl. In some embodiments, $R^{G3}$ is cyclopropyl or cyclobutyl. In certain embodiments, $R^{G3}$ is —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, or —$N(R^{GA})S(=O)_2R^{GA}$. In certain embodiments, $R^{G3}$ is —$NHR^{GA}$. In certain embodiments, $R^{G3}$ is —$NH_2$. In certain embodiments, $R^{G3}$ is —$NHR^{GA}$, wherein $R^{GA}$ is substituted or unsubstituted $C_{1-6}$ alkyl. In certain embodiments, $R^{G3}$ is —$NHR^{GA}$, wherein $R^{GA}$ is methyl, ethyl, or propyl. In certain embodiments, $R^{G3}$ is —$N(R^{GA})_2$, wherein each $R^{GA}$ is independently substituted or unsubstituted $C_{1-6}$ alkyl. In certain embodiments, $R^{G3}$ is —$N(CH_3)R^{GA}$, wherein each $R^{GA}$ is independently unsubstituted $C_{1-6}$ alkyl. In certain embodiments, $R^{G3}$ is —$N(CH_2CH_3)R^{GA}$, wherein each $R^{GA}$ is independently substituted or unsubstituted $C_{1-6}$ alkyl. In certain embodiments, $R^{G3}$ is —$OR^{GA}$. In certain embodiments, $R^{G3}$ is —OH. In certain embodiments, $R^{G3}$ is —$OR^{GA}$, wherein $R^{GA}$ is substituted or unsubstituted $C_{1-6}$ alkyl. In certain embodiments, $R^{G3}$ is —O-methyl, —O-ethyl, or —O-propyl. In certain embodiments, $R^{G3}$ is —$OR^{GA}$, wherein $R^{GA}$ is substituted or unsubstituted aryl. In certain embodiments, $R^{G3}$ is —O-phenyl.

As generally defined herein, each instance of $R^{G4}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, —$S(=O)R^{GA}$, —$S(=O)OR^{GA}$, —$OS(=O)R^{GA}$, —$S(=O)N(R^{GA})_2$, —$N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl. In some embodiments, $R^{G4}$ is hydrogen. In some embodiments, $R^{G4}$ is halogen. In certain embodiments, $R^{G4}$ is F. In certain embodiments, $R^{G4}$ is Cl. In certain embodiments, $R^{G4}$ is Br. In certain embodiments, $R^{G4}$ is I. In certain embodiments, $R^{G4}$ is substituted or unsubstituted $C_{1-6}$ alkyl. In certain embodiments, $R^{G4}$ is substituted $C_{1-6}$ alkyl. In certain embodiments, $R^5$ is —$CH_2F$, —$CHF_2$, or —$CF_3$. In certain embodiments, $R^{G4}$ is unsubstituted $C_{1-6}$ alkyl. In certain embodiments, $R^{G4}$ is methyl, ethyl, propyl, butyl, pentyl, or hexyl. In some embodiments, $R^{G4}$ is —CN. In some embodiments, $R^{G4}$ is —$NO_2$. In some embodiments, $R^{G4}$ is substituted or unsubstituted carbocyclyl, substituted or unsubstituted phenyl, substituted or unsubstituted heterocyclyl, or substituted or unsubstituted heteroaryl. In some embodiments, $R^{G4}$ is cyclopropyl or cyclobutyl. In certain embodiments, $R^{G4}$ is —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, or —$N(R^{GA})S(=O)_2R^{GA}$. In certain embodiments, $R^{G4}$ is —$NHR^{GA}$. In certain embodiments, $R^{G4}$ is —$NH_2$. In certain embodiments, $R^{G4}$ is —$NHR^{GA}$, wherein $R^{GA}$ is substituted or unsubstituted $C_{1-6}$ alkyl. In certain embodiments, $R^{G4}$ is —$NHR^{GA}$, wherein $R^{GA}$ is methyl, ethyl, or propyl. In certain embodiments, $R^{G4}$ is —$N(R^{GA})_2$, wherein each $R^{GA}$ is independently substituted or unsubstituted $C_{1-6}$ alkyl. In certain embodiments, $R^{G4}$ is —$N(CH_3)R^{GA}$, wherein each $R^{GA}$ is independently unsubstituted $C_{1-6}$ alkyl. In certain embodiments, $R^{G4}$ is —$N(CH_2CH_3)R^{GA}$, wherein each $R^{GA}$ is independently substituted or unsubstituted $C_{1-6}$ alkyl. In certain embodiments, $R^{G4}$ is —$OR^{GA}$. In certain embodiments, $R^{G4}$ is —OH. In certain embodiments, $R^{G4}$ is —$OR^{GA}$, wherein $R^{GA}$ is substituted or unsubstituted $C_{1-6}$ alkyl. In certain embodiments, $R^{G4}$ is —O-methyl, —O-ethyl, or —O-propyl. In certain embodiments, $R^{G4}$ is —$OR^{GA}$, wherein $R^{GA}$ is substituted or unsubstituted aryl. In certain embodiments, $R^{G4}$ is —O-phenyl.

As generally defined herein, each instance of $R^{G5}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, —$S(=O)R^{GA}$, —$S(=O)OR^{GA}$, —$OS(=O)R^{GA}$, —$S(=O)N(R^{GA})_2$, —$N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl. In some embodiments, $R^{G5}$ is hydrogen. In some embodiments, $R^{G5}$ is halogen. In certain embodiments, $R^{G5}$ is F. In certain embodiments, $R^{G5}$ is Cl. In certain embodiments, $R^{G5}$ is Br. In certain embodiments, $R^{G5}$ is I. In certain embodiments, $R^{G5}$ is substituted or unsubstituted $C_{1-6}$ alkyl. In certain embodiments, $R^{G5}$ is substituted $C_{1-6}$ alkyl. In certain embodiments, $R^5$ is —$CH_2F$, —$CHF_2$, or —$CF_3$. In certain embodiments, $R^{G5}$ is unsubstituted $C_{1-6}$ alkyl. In certain embodiments, $R^{G5}$ is methyl, ethyl, propyl, butyl, pentyl, or hexyl. In some embodiments, $R^{G5}$ is —CN. In some embodiments, $R^{G5}$ is —$NO_2$. In some embodiments, $R^{G5}$ is substituted or unsubstituted carbocylyl, substituted or unsubstituted phenyl, substituted or unsubstituted heterocyclyl, or substituted or unsubstituted heteroaryl. In some embodiments, $R^{G5}$ is cyclopropyl or cyclobutyl. In certain embodiments, $R^{G5}$ is —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, or —$N(R^{GA})S(=O)_2R^{GA}$. In certain embodiments, $R^{G5}$ is —$NHR^{GA}$. In certain embodiments, $R^{G5}$ is —$NH_2$. In certain embodiments, $R^{G5}$ is —$NHR^{GA}$, wherein $R^{GA}$ is substituted or unsubstituted $C_{1-6}$ alkyl. In certain embodiments, $R^{G5}$ is —$NHR^{GA}$, wherein $R^{GA}$ is methyl, ethyl, or propyl. In certain embodiments, $R^{G5}$ is —$N(R^{GA})_2$, wherein each $R^{GA}$ is independently substituted or unsubstituted $C_{1-6}$ alkyl. In certain embodiments, $R^{G5}$ is —$N(CH_3)R^{GA}$, wherein each $R^{GA}$ is independently unsubstituted $C_{1-6}$ alkyl. In certain embodiments, $R^{G5}$ is —$N(CH_2CH_3)R^{GA}$, wherein each $R^{GA}$ is independently substituted or unsubstituted $C_{1-6}$ alkyl. In certain embodiments, $R^{G5}$ is —$OR^{GA}$. In certain embodiments, $R^{G5}$ is —OH. In certain embodiments, $R^{G5}$ is —$OR^{GA}$, wherein $R^{GA}$ is substituted or unsubstituted $C_{1-6}$ alkyl. In certain embodiments, $R^{G5}$ is —O-methyl, —O-ethyl, or —O-propyl. In certain embodiments, $R^{G5}$ is —$OR^{GA}$, wherein $R^{GA}$ is substituted or unsubstituted aryl. In certain embodiments, $R^{G5}$ is —O-phenyl.

As generally defined herein, each instance of $R^{G6}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, —$N(R^{GA})S(=O)_2R^{GA}$, —$S(=O)R^{GA}$, —$S(=O)OR^{GA}$, —$OS(=O)R^{GA}$, —$S(=O)N(R^{GA})_2$, —$N(R^{GA})S(=O)R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl. In some embodiments, $R^{G6}$ is hydrogen. In some embodiments, $R^{G6}$ is halogen. In certain embodiments, $R^{G6}$ is F. In certain embodiments, $R^{G6}$ is Cl. In certain embodiments, $R^{G6}$ is Br. In certain embodiments, $R^{G6}$ is I. In certain embodiments, $R^{G6}$ is substituted or unsubstituted $C_{1-6}$ alkyl. In certain embodiments, $R^{G6}$ is substituted $C_{1-6}$ alkyl. In certain embodiments, $R^5$ is —$CH_2F$, —$CHF_2$, or —$CF_3$. In certain embodiments, $R^{G6}$ is unsubstituted $C_{1-6}$ alkyl. In certain embodiments, $R^{G6}$ is methyl, ethyl, propyl, butyl, pentyl, or hexyl. In some embodiments, $R^{G6}$ is —CN. In some embodiments, $R^{G6}$ is —$NO_2$. In some embodiments, $R^{G6}$ is substituted or unsubstituted carbocyclyl, substituted or unsubstituted phenyl, substituted or unsubstituted heterocyclyl, or substituted or unsubstituted heteroaryl. In some embodiments, $R^{G6}$ is cyclopropyl or cyclobutyl. In certain embodiments, $R^{G6}$ is —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C(=O)R^{GA}$, —$OC(=O)N(R^{GA})_2$, —$N(R^{GA})C(=O)OR^{GA}$, —$S(=O)_2R^{GA}$, —$S(=O)_2OR^{GA}$, —$OS(=O)_2R^{GA}$, —$S(=O)_2N(R^{GA})_2$, or —$N(R^{GA})S(=O)_2R^{GA}$. In certain embodiments, $R^{G6}$ is —$NHR^{GA}$. In certain embodiments, $R^{G6}$ is —$NH_2$. In certain embodiments, $R^{G6}$ is —$NHR^{GA}$, wherein $R^{GA}$ is substituted or unsubstituted $C_{1-6}$ alkyl. In certain embodiments, $R^{G6}$ is —$NHR^{GA}$, wherein $R^{GA}$ is methyl, ethyl, or propyl. In certain embodiments, $R^{G6}$ is —$N(R^{GA})_2$, wherein each $R^{GA}$ is independently substituted or unsubstituted $C_{1-6}$ alkyl. In certain embodiments, $R^{G6}$ is —$N(CH_3)R^{GA}$, wherein each $R^{GA}$ is independently unsubstituted $C_{1-6}$ alkyl. In certain embodiments, $R^{G6}$ is —$N(CH_2CH_3)R^{GA}$, wherein each $R^{GA}$ is independently substituted or unsubstituted $C_{1-6}$ alkyl. In certain embodiments, $R^{G6}$ is —$OR^{GA}$. In certain embodiments, $R^{G6}$ is —OH. In certain embodiments, $R^{G6}$ is —$OR^{GA}$, wherein $R^{GA}$ is substituted or unsubstituted $C_{1-6}$ alkyl. In certain embodiments, $R^{G6}$ is —O-methyl, —O-ethyl, or —O-propyl. In certain embodiments, $R^{G6}$ is —$OR^{GA}$, wherein $R^{GA}$ is substituted or unsubstituted aryl. In certain embodiments, $R^{G6}$ is —O-phenyl.

As generally defined herein, each instance of $R^{G7}$ is, independently, hydrogen, halogen, —$NO_2$, —CN, —$OR^{GA}$, —$N(R^{GA})_2$, —$C(=O)R^{GA}$, —$C(=O)OR^{GA}$, —$OC(=O)R^{GA}$, —$OC(=O)OR^{GA}$, —$C(=O)N(R^{GA})_2$, —$N(R^{GA})C (=O)R$^{GA}$, —OC(=O)N(R$^{GA}$)$_2$, —N(R$^{GA}$)C(=O)OR$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, —N(R$^{GA}$)S(=O)$_2$R$^{GA}$, —S(=O)R$^{GA}$, —S(=O)OR$^{GA}$, —OS(=O)R$^{GA}$, —S(=O)N(R$^{GA}$)$_2$, —N(R$^{GA}$)S(=O)R$^{GA}$, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocylyl, substituted or unsubstituted 3- to 6-membered heterocylyl, substituted or unsubstituted aryl, or substituted or unsubstituted heteroaryl. In some embodiments, R$^{G7}$ is hydrogen. In some embodiments, R$^{G7}$ is halogen. In certain embodiments, R$^{G7}$ is F. In certain embodiments, R$^{G7}$ is Cl. In certain embodiments, R$^{G7}$ is Br. In certain embodiments, R$^{G7}$ is I. In certain embodiments, R$^{G7}$ is substituted or unsubstituted C$_{1-6}$ alkyl. In certain embodiments, R$^{G7}$ is substituted C$_{1-6}$ alkyl. In certain embodiments, R$^5$ is —CH$_2$F, —CHF$_2$, or —CF$_3$. In certain embodiments, R$^{G7}$ is unsubstituted C$_{1-6}$ alkyl. In certain embodiments, R$^{G7}$ is methyl, ethyl, propyl, butyl, pentyl, or hexyl. In some embodiments, R$^{G7}$ is CN. In some embodiments, R$^{G7}$ is NO$_2$. In some embodiments, R$^{G7}$ is substituted or unsubstituted carbocyclyl, substituted or unsubstituted phenyl, substituted or unsubstituted heterocyclyl, or substituted or unsubstituted heteroaryl. In some embodiments, R$^{G7}$ is cyclopropyl or cyclobutyl. In certain embodiments, R$^{G7}$ is —OR$^{GA}$, —N(R$^{GA}$)$_2$, —C(=O)R$^{GA}$, —C(=O)OR$^{GA}$, —OC(=O)R$^{GA}$, —OC(=O)OR$^{GA}$, —C(=O)N(R$^{GA}$)$_2$, —N(R$^{GA}$)C(=O)R$^{GA}$, —OC(=O)N(R$^{GA}$)$_2$, —N(R$^{GA}$)C(=O)OR$^{GA}$, —S(=O)$_2$R$^{GA}$, —S(=O)$_2$OR$^{GA}$, —OS(=O)$_2$R$^{GA}$, —S(=O)$_2$N(R$^{GA}$)$_2$, or —N(R$^{GA}$)S(=O)$_2$R$^{GA}$. In certain embodiments, R$^{G7}$ is —NHR$^{GA}$. In certain embodiments, R$^{G7}$ is —NH$_2$. In certain embodiments, R$^{G7}$ is —NHR$^{GA}$, wherein R$^{GA}$ is substituted or unsubstituted C$_{1-6}$ alkyl. In certain embodiments, R$^{G7}$ is —NHR$^{GA}$, wherein R$^{GA}$ is methyl, ethyl, or propyl. In certain embodiments, R$^{G7}$ is —N(R$^{GA}$)$_2$, wherein each R$^{GA}$ is independently substituted or unsubstituted C$_{1-6}$ alkyl. In certain embodiments, R$^{G7}$ is —N(CH$_3$)R$^{GA}$, wherein each R$^{GA}$ is independently unsubstituted C$_{1-6}$ alkyl. In certain embodiments, R$^{G7}$ is —N(CH$_2$CH$_3$)R$^{GA}$, wherein each R$^{GA}$ is independently substituted or unsubstituted C$_{1-6}$ alkyl. In certain embodiments, R$^{G7}$ is —OR$^{GA}$. In certain embodiments, R$^{G7}$ is —OH. In certain embodiments, R$^{G7}$ is —OR$^{GA}$, wherein R$^{GA}$ is substituted or unsubstituted C$_{1-6}$ alkyl. In certain embodiments, R$^{G7}$ is —O-methyl, —O-ethyl, or —O-propyl. In certain embodiments, R$^{G7}$ is —OR$^{GA}$, wherein R$^{GA}$ is substituted or unsubstituted aryl. In certain embodiments, R$^{G7}$ is —O-phenyl.

As generally defined herein, each instance of R$^{N1}$ is independently hydrogen, substituted or unsubstituted C$_{1-6}$ alkyl, or a nitrogen protecting group. In some embodiments, R$^{N2}$ is hydrogen. In some embodiments, R$^{N2}$ is substituted C$_{1-6}$ alkyl. In some embodiments, R$^{N2}$ is unsubstituted C$_{1-6}$ alkyl. In certain embodiments, R$^{N2}$ is methyl. In certain embodiments, R$^{N2}$ is ethyl. In certain embodiments, R$^{N2}$ is propyl. In certain embodiments, R$^{N2}$ is a nitrogen protecting group. In certain embodiments, R$^{N2}$ is Bn, BOC, Cbz, Fmoc, trifluoroacetyl, triphenylmethyl, or Ts.

As generally defined herein, each instance of R$^{N2}$ is independently hydrogen, substituted or unsubstituted C$_{1-6}$ alkyl, or a nitrogen protecting group. In some embodiments, R$^{N2}$ is hydrogen. In some embodiments, R$^{N2}$ is substituted C$_{1-6}$ alkyl. In some embodiments, R$^{N2}$ is unsubstituted C$_{1-6}$ alkyl. In certain embodiments, R$^{N2}$ is methyl. In certain embodiments, R$^{N2}$ is ethyl. In certain embodiments, R$^{N2}$ is propyl. In certain embodiments, R$^{N2}$ is a nitrogen protecting group. In certain embodiments, R$^{N2}$ is Bn, BOC, Cbz, Fmoc, trifluoroacetyl, triphenylmethyl, or Ts.

As generally defined herein, each instance of R$^{N3}$ is independently hydrogen, substituted or unsubstituted C$_{1-6}$ alkyl, or a nitrogen protecting group. In some embodiments, R$^{N2}$ is hydrogen. In some embodiments, R$^{N2}$ is substituted C$_{1-6}$ alkyl. In some embodiments, R$^{N2}$ is unsubstituted C$_{1-6}$ alkyl. In certain embodiments, R$^{N2}$ is methyl. In certain embodiments, R$^{N2}$ is ethyl. In certain embodiments, R$^{N2}$ is propyl. In certain embodiments, R$^{N2}$ is a nitrogen protecting group. In certain embodiments, R$^{N2}$ is Bn, BOC, Cbz, Fmoc, trifluoroacetyl, triphenylmethyl, or Ts.

As generally defined herein, each instance of R$^{N4}$ is independently hydrogen, substituted or unsubstituted C$_{1-6}$ alkyl, or a nitrogen protecting group. In some embodiments, R$^{N4}$ is hydrogen. In some embodiments, R$^{N4}$ is substituted C$_{1-6}$ alkyl. In some embodiments, R$^{N4}$ is unsubstituted C$_{1-6}$ alkyl. In certain embodiments, R$^{N4}$ is methyl. In certain embodiments, R$^{N4}$ is ethyl. In certain embodiments, R$^{N4}$ is propyl. In certain embodiments, R$^{N4}$ is a nitrogen protecting group. In certain embodiments, R$^{N4}$ is Bn, BOC, Cbz, Fmoc, trifluoroacetyl, triphenylmethyl, or Ts.

As generally defined herein, each instance of R$^{N5}$ is independently hydrogen, substituted or unsubstituted C$_{1-6}$ alkyl, or a nitrogen protecting group. In some embodiments, R$^{N5}$ is hydrogen. In some embodiments, R$^{N5}$ is substituted C$_{1-6}$ alkyl. In some embodiments, R$^{N5}$ is unsubstituted C$_{1-6}$ alkyl. In certain embodiments, R$^{N5}$ is methyl. In certain embodiments, R$^{N5}$ is ethyl. In certain embodiments, R$^{N5}$ is propyl. In certain embodiments, R$^{N5}$ is a nitrogen protecting group. In certain embodiments, R$^{N5}$ is Bn, BOC, Cbz, Fmoc, trifluoroacetyl, triphenylmethyl, or Ts.

As generally defined herein, each instance of R$^{N6}$ is independently hydrogen, substituted or unsubstituted C$_{1-6}$ alkyl, or a nitrogen protecting group. In some embodiments, R$^{N6}$ is hydrogen. In some embodiments, R$^{N6}$ is substituted C$_{1-6}$ alkyl. In some embodiments, R$^{N6}$ is unsubstituted C$_{1-6}$ alkyl. In certain embodiments, R$^{N6}$ is methyl. In certain embodiments, R$^{N6}$ is ethyl. In certain embodiments, R$^{N6}$ is propyl. In certain embodiments, R$^{N6}$ is a nitrogen protecting group. In certain embodiments, R$^{N6}$ is Bn, BOC, Cbz, Fmoc, trifluoroacetyl, triphenylmethyl, or Ts.

As generally defined herein, each instance of R$^{N7}$ is independently hydrogen, substituted or unsubstituted C$_{1-6}$ alkyl, or a nitrogen protecting group. In some embodiments, R$^{N7}$ is hydrogen. In some embodiments, R$^{N7}$ is substituted C$_{1-6}$ alkyl. In some embodiments, R$^{N7}$ is unsubstituted C$_{1-6}$ alkyl. In certain embodiments, R$^{N7}$ is methyl. In certain embodiments, R$^{N7}$ is ethyl. In certain embodiments, R$^{N7}$ is propyl. In certain embodiments, R$^{N7}$ is a nitrogen protecting group. In certain embodiments, R$^{N7}$ is Bn, BOC, Cbz, Fmoc, trifluoroacetyl, triphenylmethyl, or Ts.

As generally defined herein, each instance of R$^{GA}$ is independently hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, a nitrogen protecting group when attached to nitrogen, or two R$^{GA}$ groups are taken with the intervening atoms to form a substituted or unsubstituted heterocylyl or heteroaryl ring. In some embodiments, R$^{GA}$ is hydrogen. In certain embodiments, R$^{GA}$ is substituted or unsubstituted C$_{1-6}$ alkyl, substituted or unsubstituted C$_{2-6}$ alkenyl, substituted or unsubstituted C$_{2-6}$ alkynyl, or substituted or unsubstituted C$_{3-6}$ carbocyclyl. In certain embodiments, $R^{GA}$ is substituted or unsubstituted $C_{1-6}$ alkyl. In certain embodiments, $R^{GA}$ is unsubstituted $C_{1-6}$ alkyl. In certain embodiments, $R^{GA}$ is methyl, ethyl, propyl, butyl, pentyl, or hexyl. In certain embodiments, $R^{GA}$ is substituted or unsubstituted heterocyclyl. In certain embodiments, $R^{GA}$ is substituted or unsubstituted aryl. In certain embodiments, $R^{GA}$ is substituted or unsubstituted phenyl. In certain embodiments, $R^{GA}$ is a nitrogen protecting group. In certain embodiments, $R^{GA}$ is an oxygen protecting group.

In certain embodiments, the compound of Formula (I) is of Formula (II),

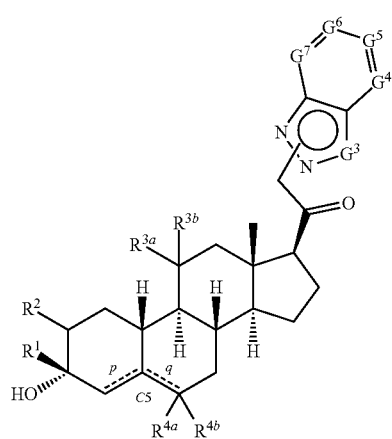

(II)

or a pharmaceutically acceptable salt thereof. In certain embodiments, the point of attachment in Formula (II) is at the nitrogen at the G1 position. In certain embodiments, the point of attachment in Formula (II) is at the nitrogen at the G2 position.

In certain embodiments, the compound of Formula (I) is of

Formula (II-a):

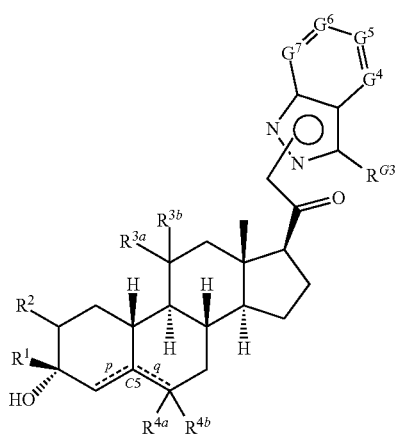

(II-a)

or a pharmaceutically acceptable salt thereof. In certain embodiments, the point of attachment in Formula (II-a) is at the nitrogen at the G1 position. In certain embodiments, the point of attachment in Formula (II-a) is at the nitrogen at the G2 position.

In certain embodiments, the compound of Formula (I) is of one of the following formulae:

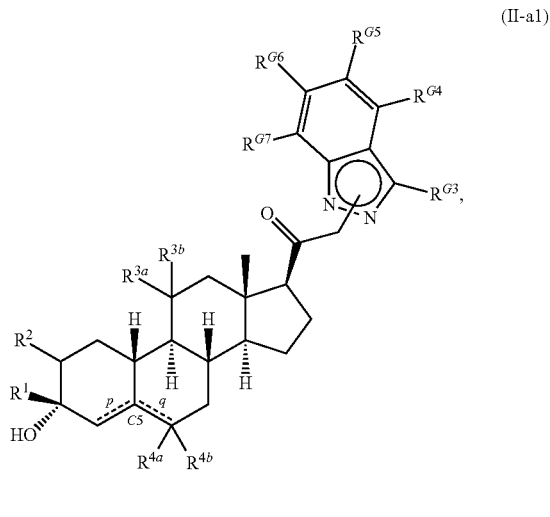

(II-a1)

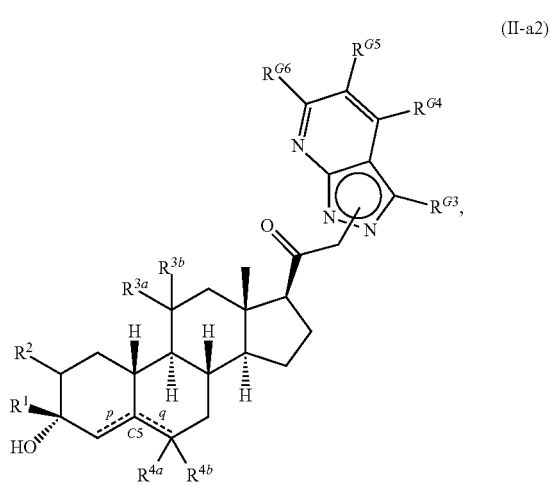

(II-a2)

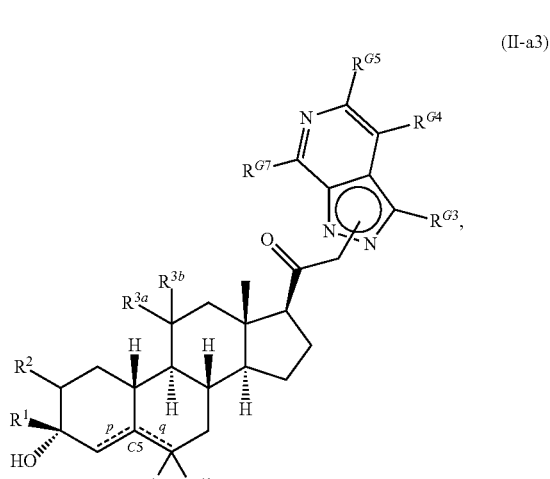

(II-a3)

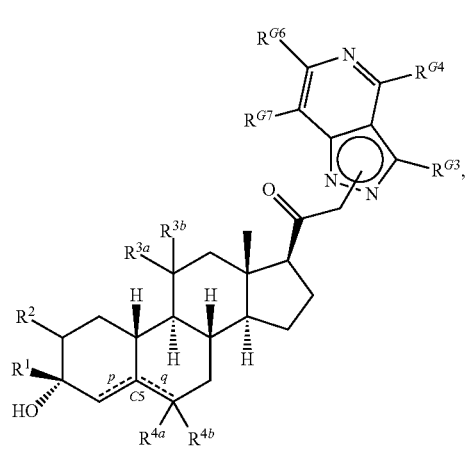
(II-a4)

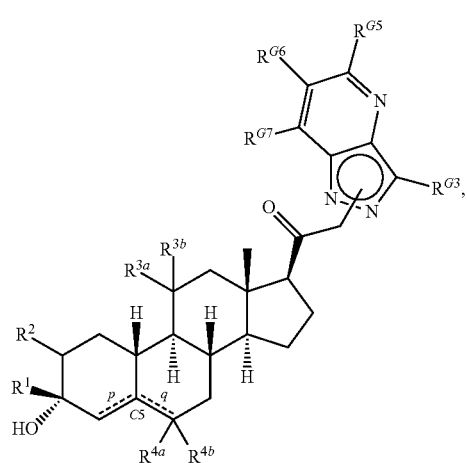
(II-a5)

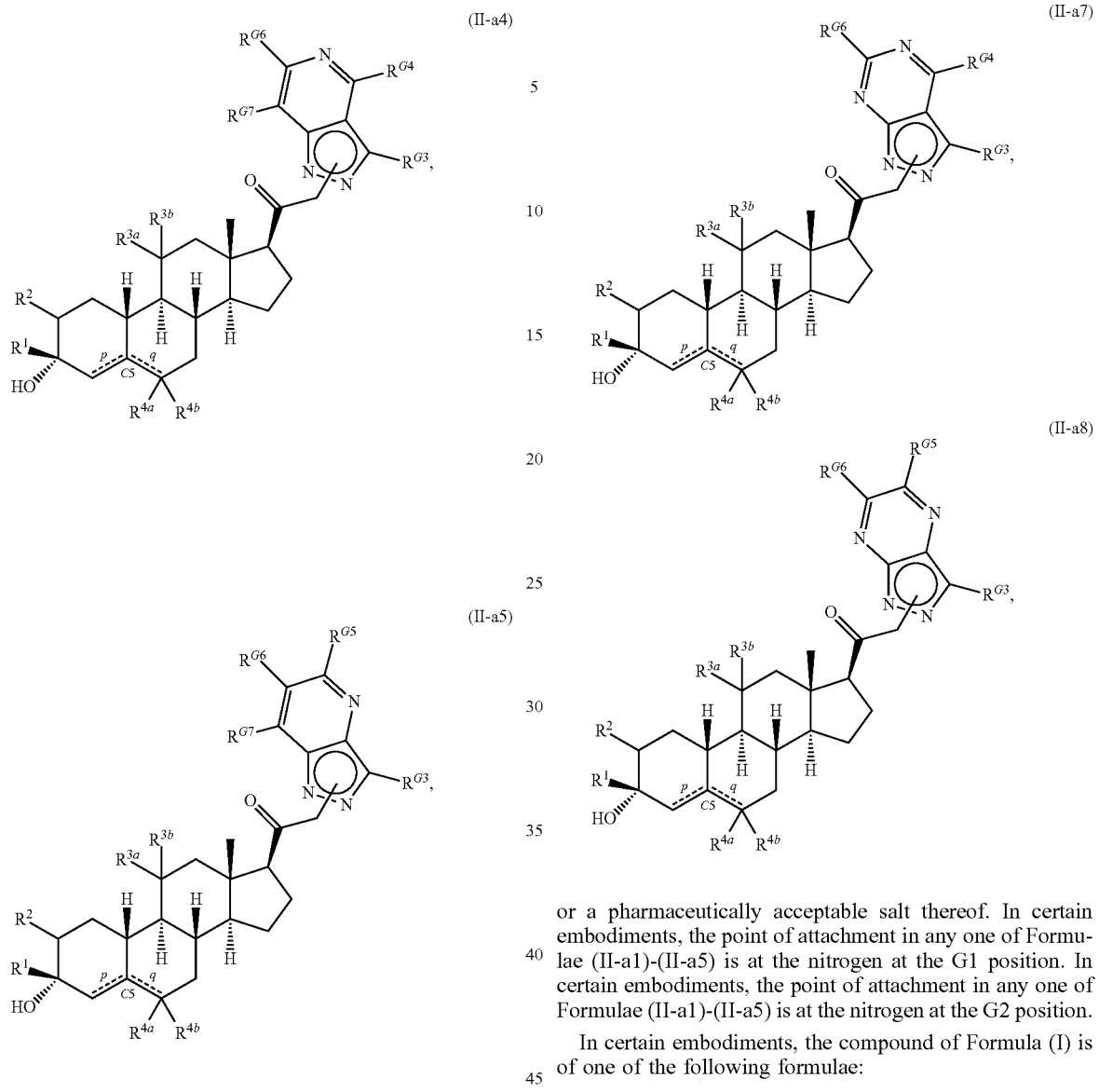

or a pharmaceutically acceptable salt thereof. In certain embodiments, the point of attachment in any one of Formulae (II-a1)-(II-a5) is at the nitrogen at the G1 position. In certain embodiments, the point of attachment in any one of Formulae (II-a1)-(II-a5) is at the nitrogen at the G2 position.

In certain embodiments, the compound of Formula (I) is of one of the following formulae:

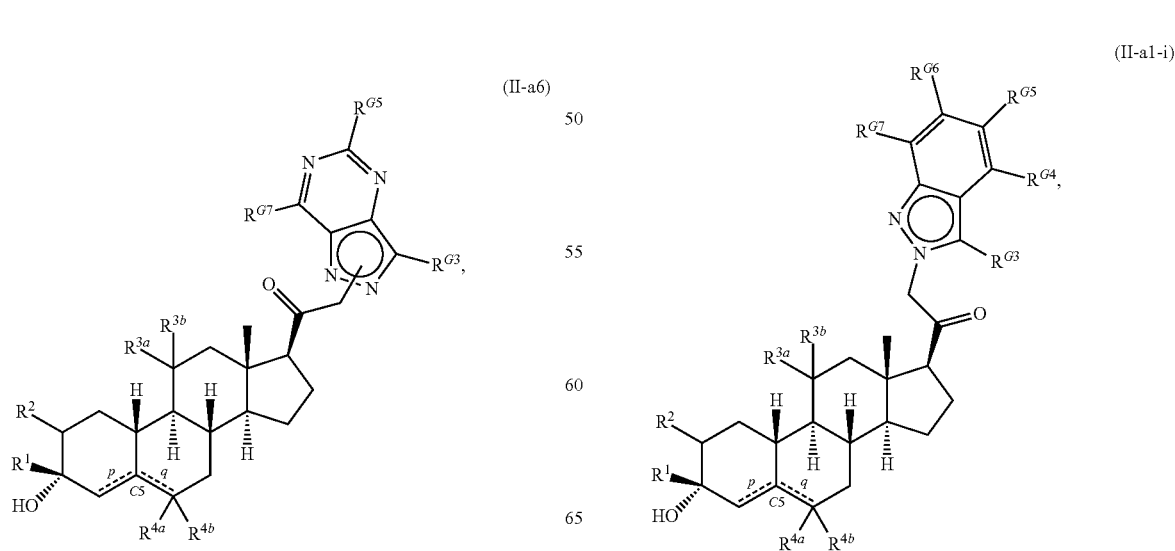

-continued
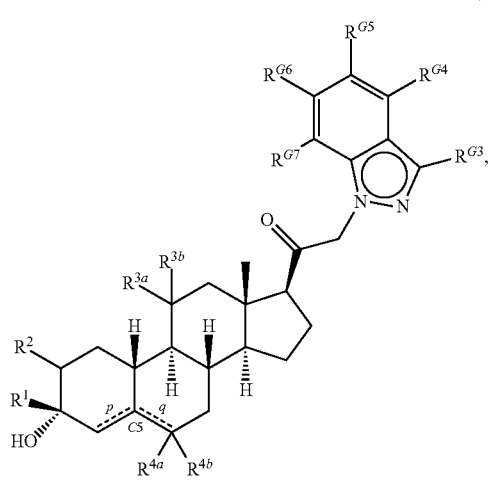
(II-a1-ii)
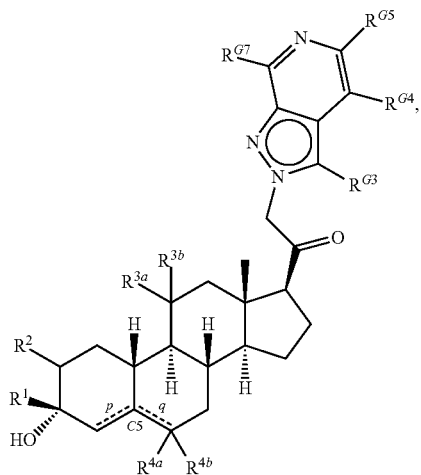
(II-a3-i)
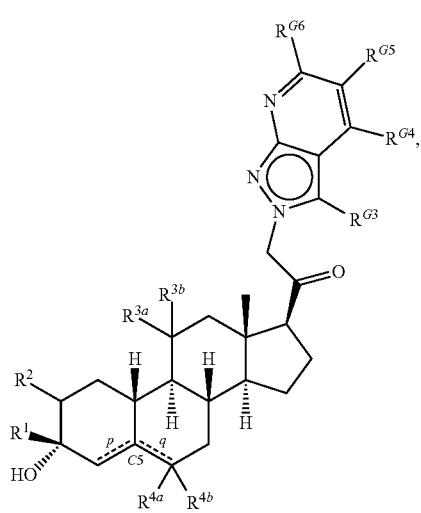
(II-a2-i)
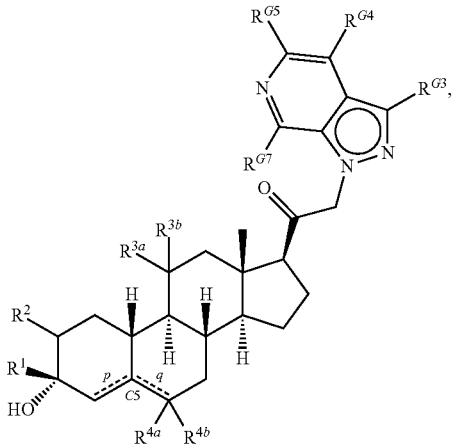
(II-a3-ii)
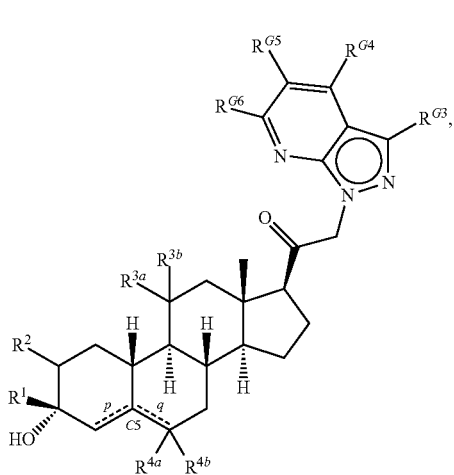
(II-a2-ii)
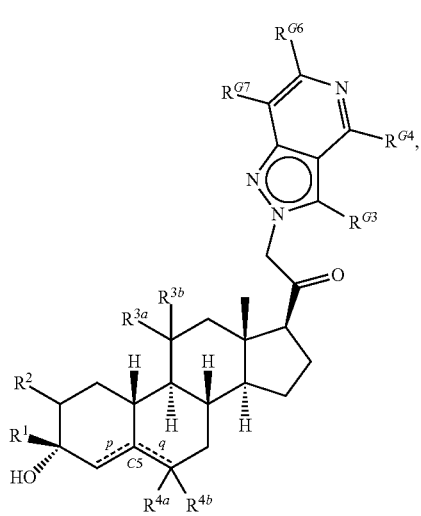
(II-a4-i)

-continued
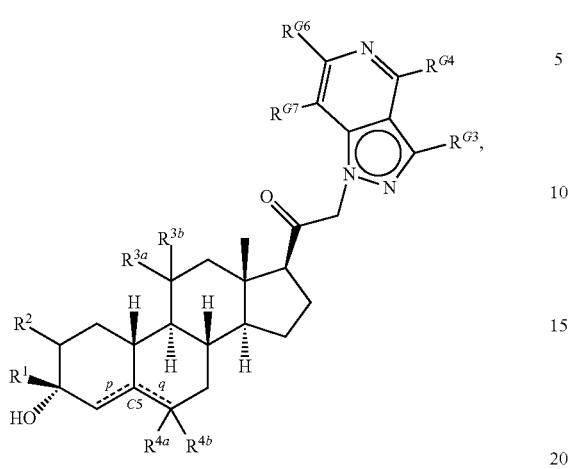
(II-a4-ii)
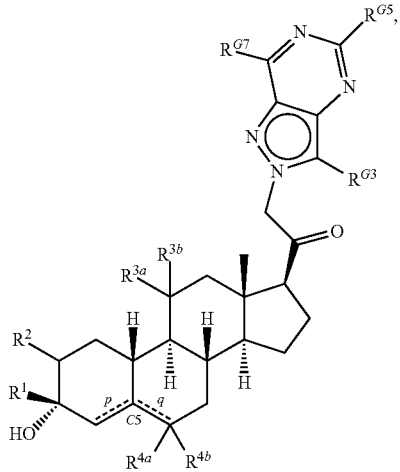
(II-a6-i)
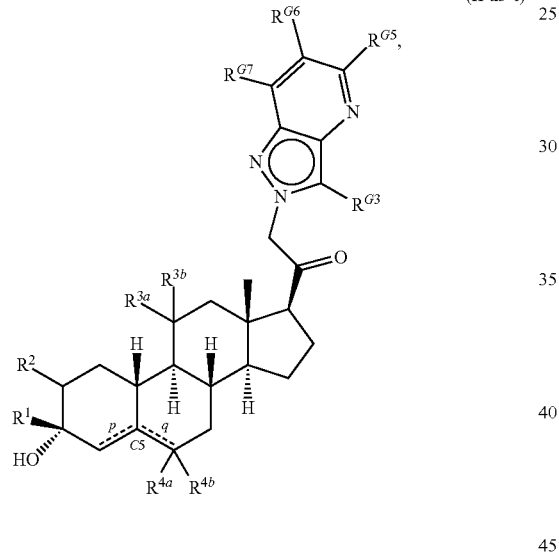
(II-a5-i)
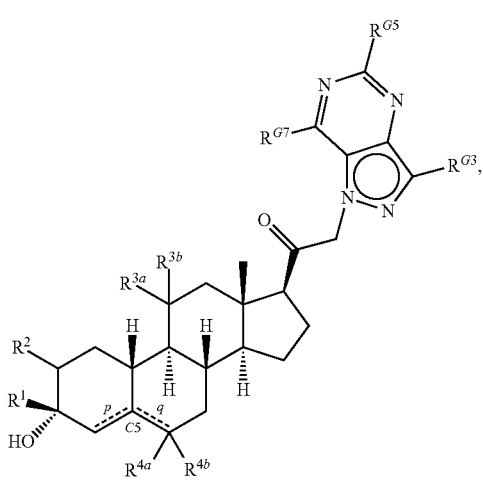
(II-a6-ii)
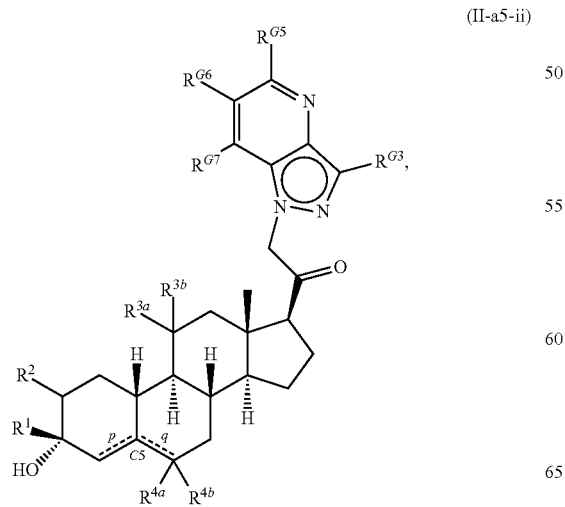
(II-a5-ii)
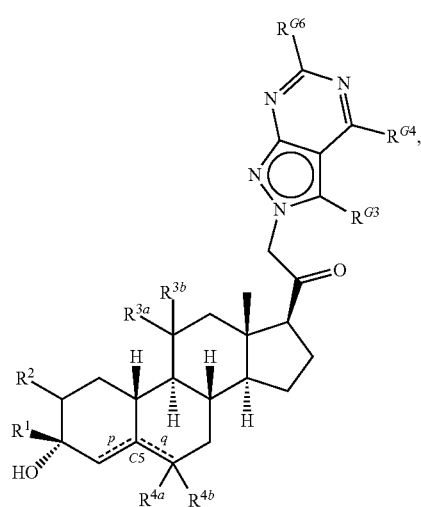
(II-a7-i)

-continued (II-a7-ii)
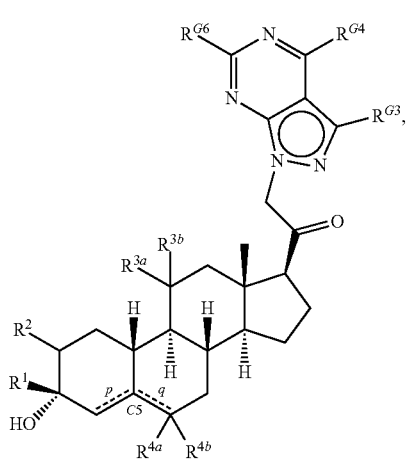

(II-a8-i)
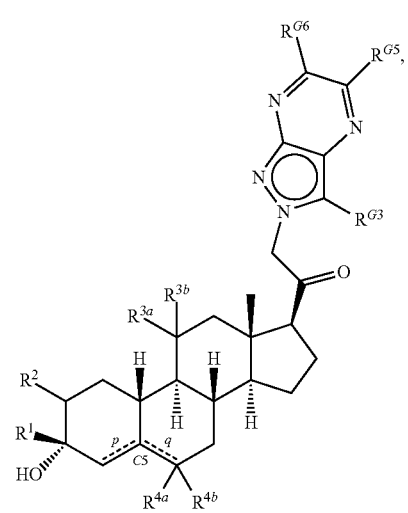

(II-a8-ii)
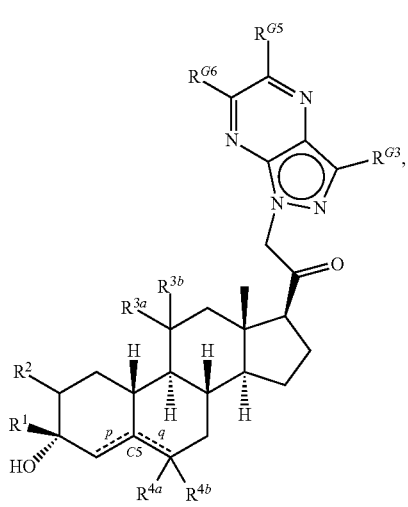

or a pharmaceutically acceptable salt thereof.

In certain embodiments, the compound of Formula (I) is of Formula (II-b):

(II-b)
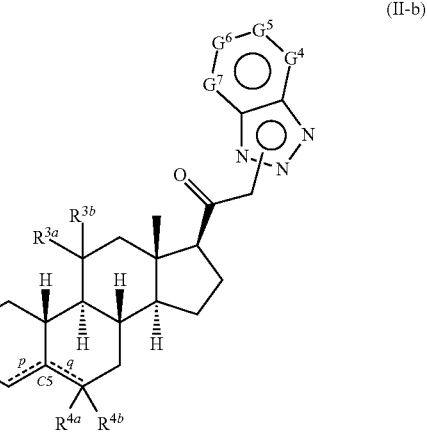

or a pharmaceutically acceptable salt thereof. In certain embodiments, the point of attachment in any one of Formula (II-b) is at the nitrogen at the G1 position. In certain embodiments, the point of attachment in any one of Formula (II-b) is at the nitrogen at the G2 position.

In certain embodiments, the compound of Formula (I) is of one of the following formulae:

(II-b1)
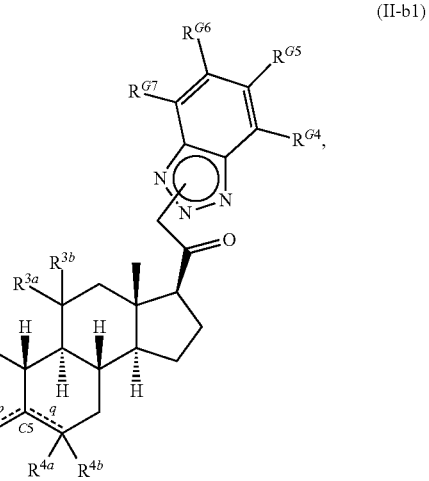

(II-b2)
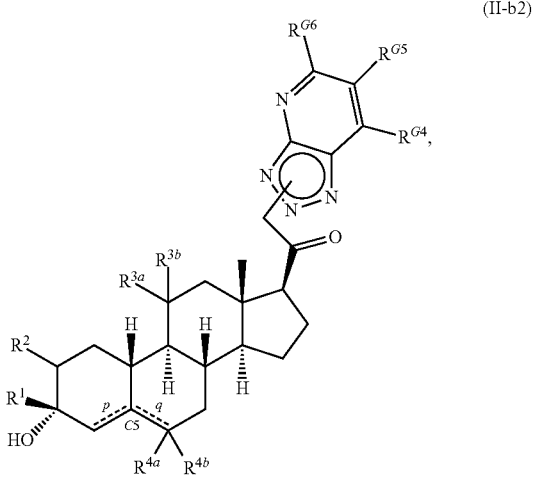

(II-b3)
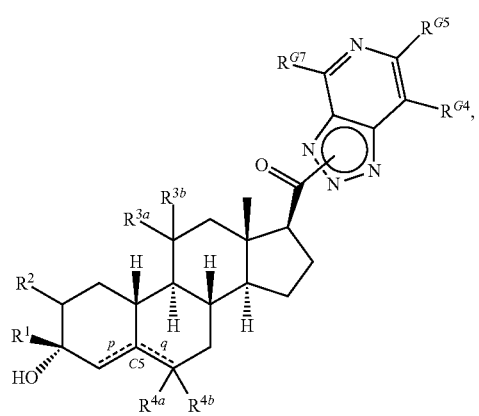

(II-b4)
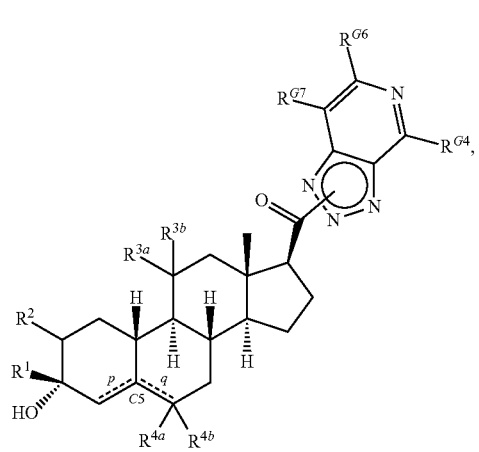

(II-b5)
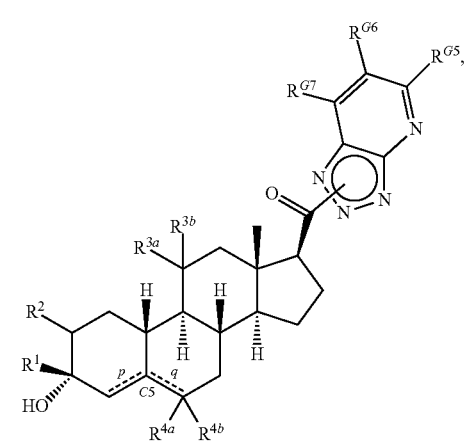

(II-b6)
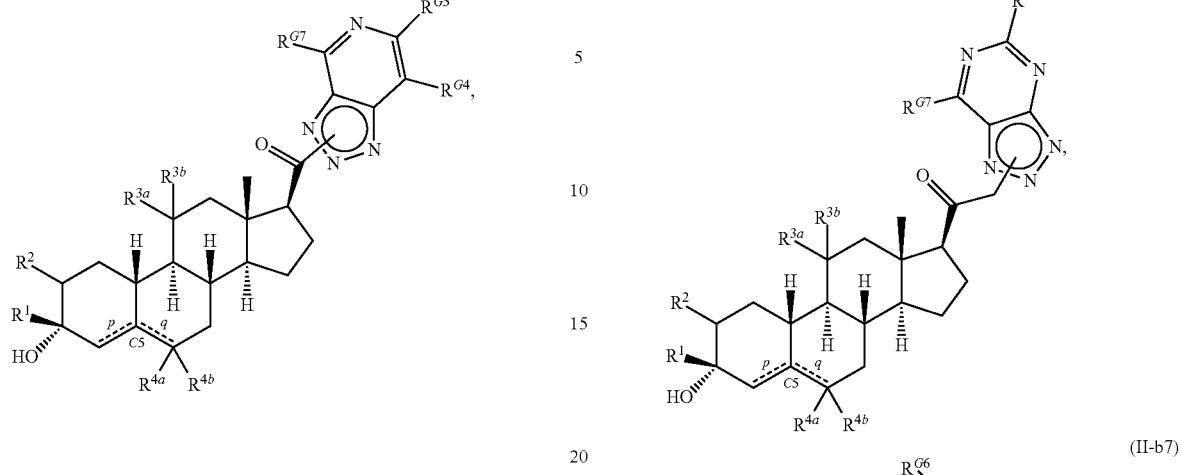

(II-b7)
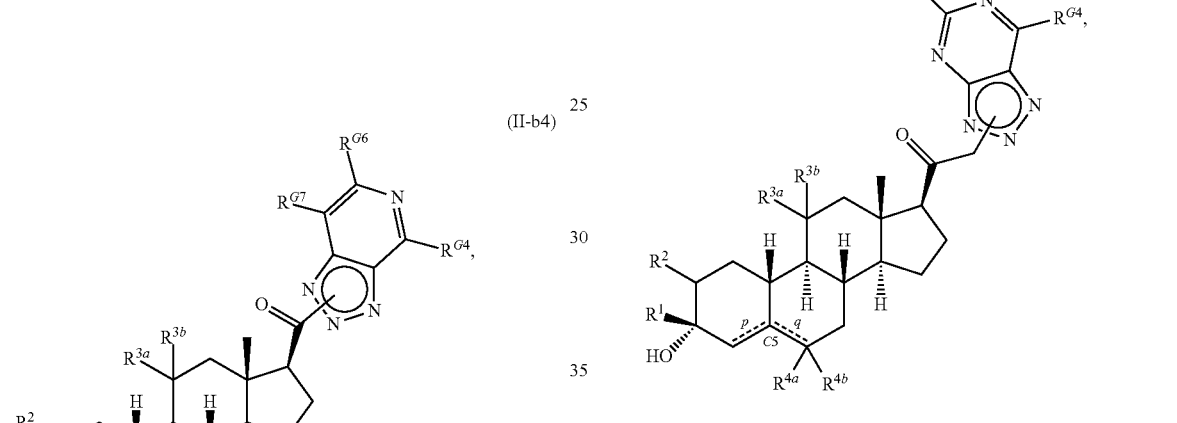

(II-b8)
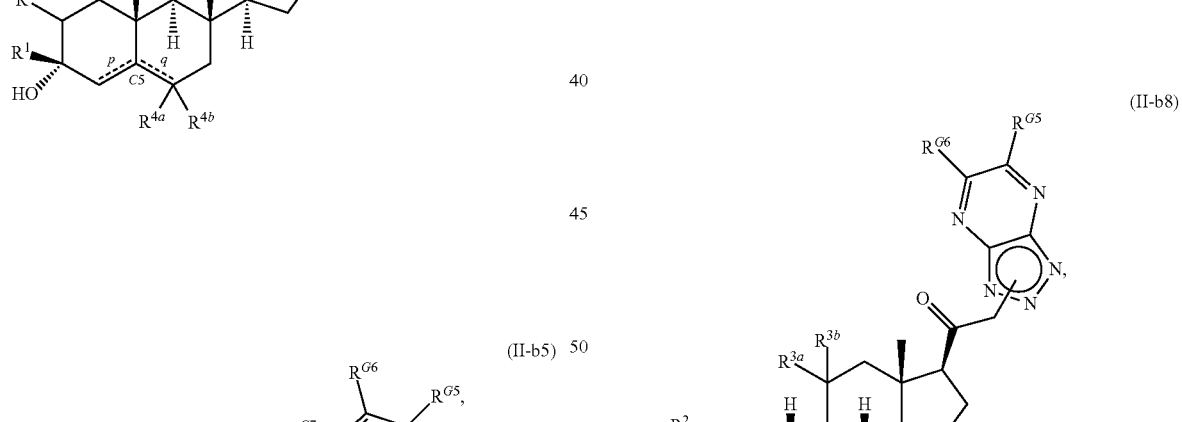

or a pharmaceutically acceptable salt thereof. In certain embodiments, the point of attachment in any one of Formulae (II-b1)-(II-b5) is at the nitrogen at the G1 position. In certain embodiments, the point of attachment in any one of Formulae (II-b1)-(II-b5) is at the nitrogen at the G2 position.

In certain embodiments, the compound of Formula (I) is of one of the following formulae:

-continued
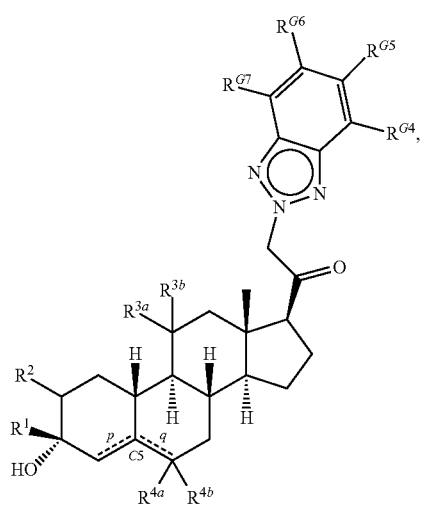
(II-b1-i)
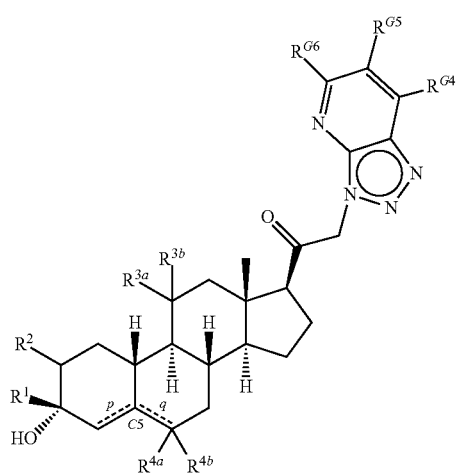
(II-b2-ii)
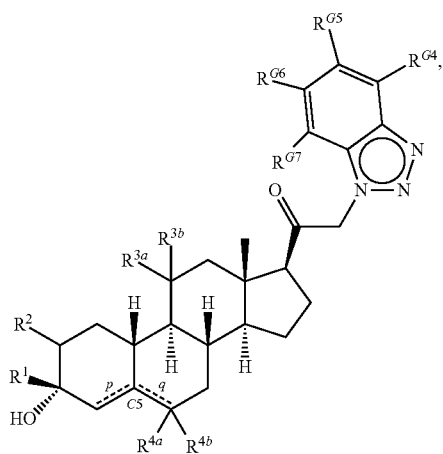
(II-b1-ii)
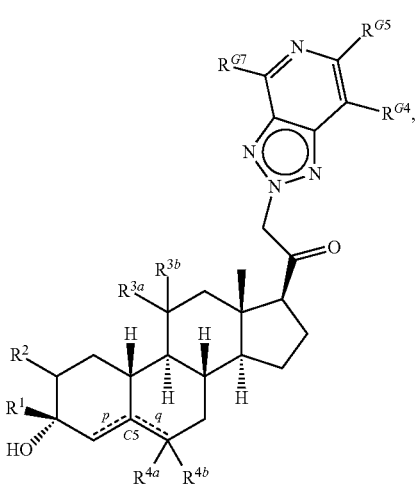
(II-b3-i)
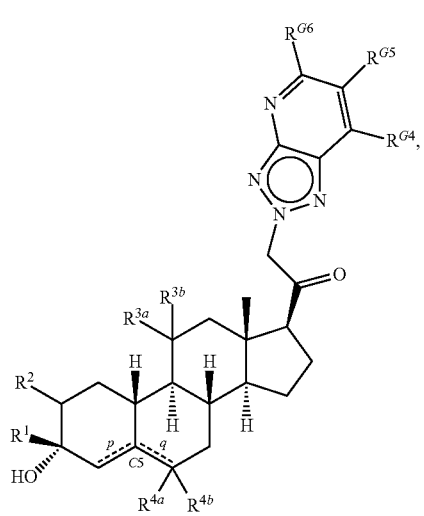
(II-b2-i)
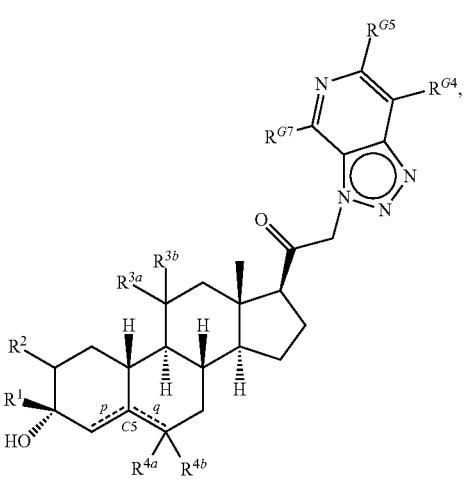
(II-b3-ii)

-continued
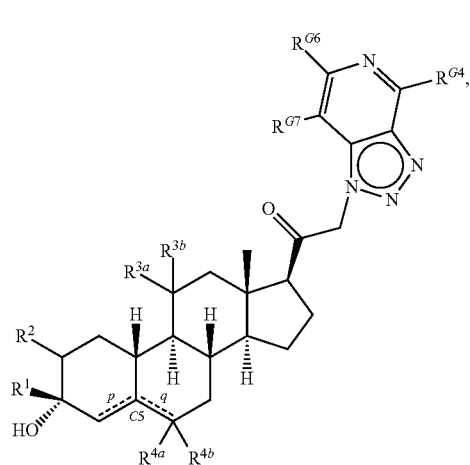
(II-b4-i)
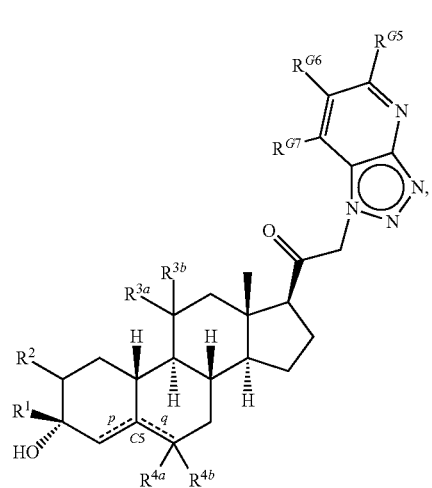
(II-b5-i)
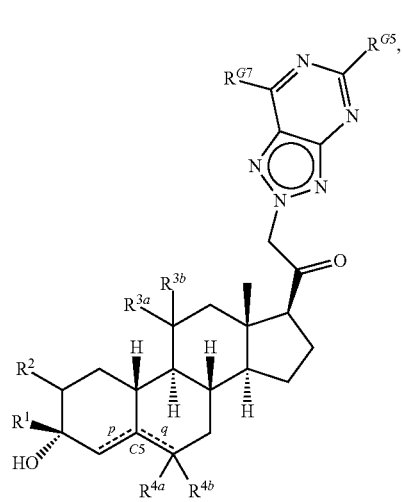
(II-b6-i)
-continued
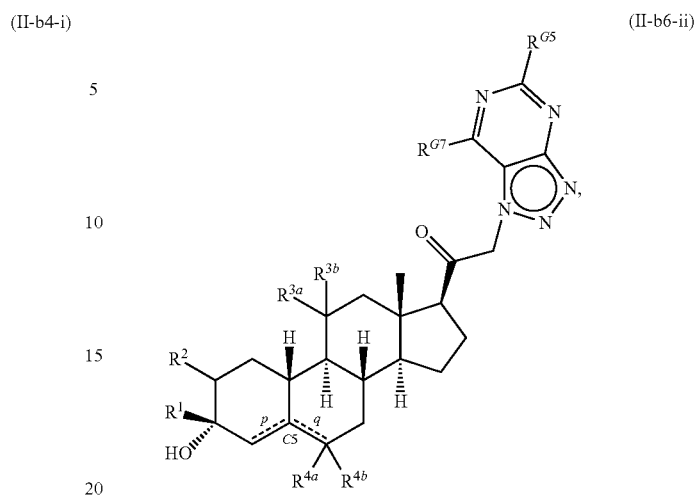
(II-b6-ii)
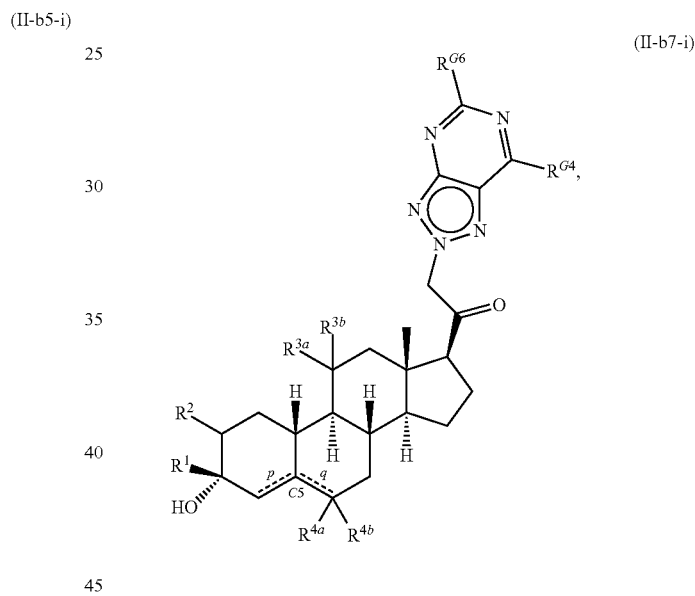
(II-b7-i)
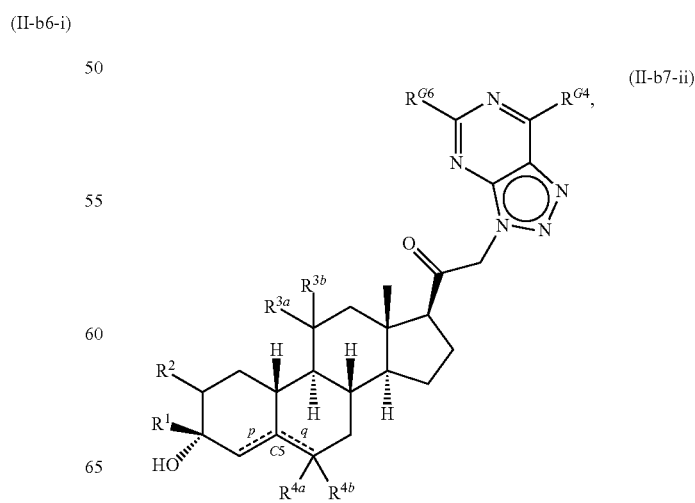
(II-b7-ii)

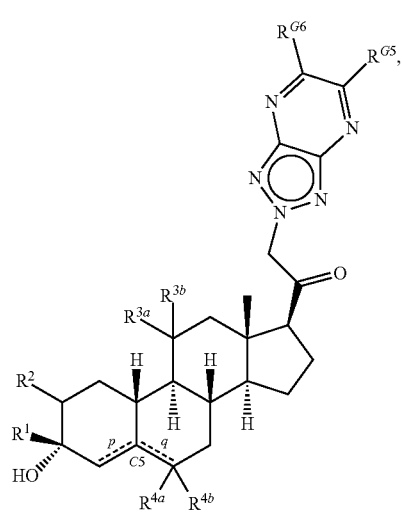
(II-b8-i)

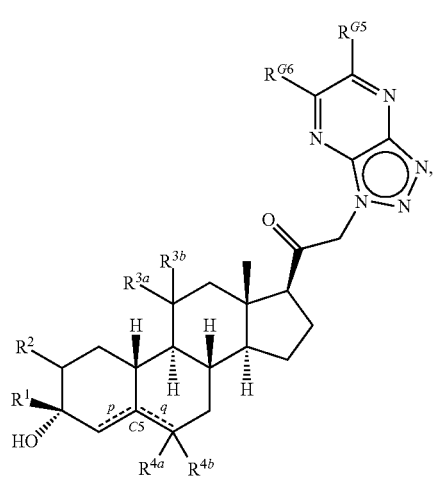
(II-b8-ii)

or a pharmaceutically acceptable salt thereof.

In certain embodiments, the compound of Formula (I) is of Formula (III):

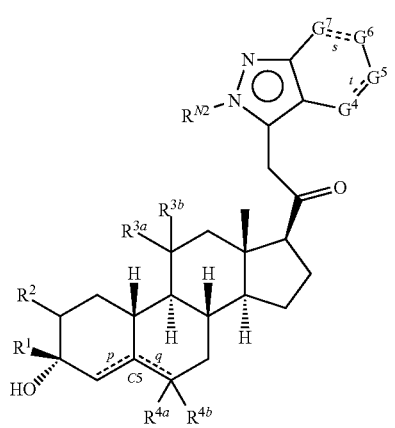
(III)

or a pharmaceutically acceptable salt thereof.

In certain embodiments, the compound of Formula (I) is of Formula (III-a):

(III-a)

or a pharmaceutically acceptable salt thereof.

In certain embodiments, the compound of Formula (I) is of Formula (III-b):

(III-b)

or a pharmaceutically acceptable salt thereof.

In certain embodiments, the compound of Formula (I) is of Formula (III-b1):

(III-b1)

or a pharmaceutically acceptable salt thereof.

In certain embodiments, the compound of Formula (I) is of Formula (IV):

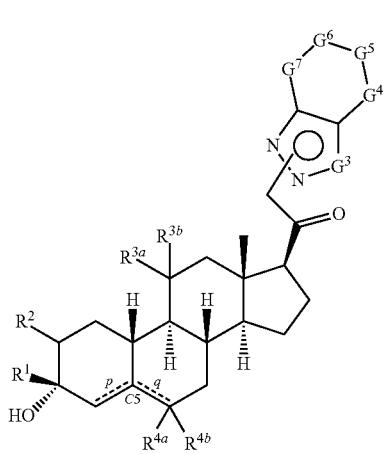

(IV)

or a pharmaceutically acceptable salt thereof. In certain embodiments, the point of attachment in Formula (IV) is at the nitrogen at the G1 position. In certain embodiments, the point of attachment in Formula (IV) is at the nitrogen at the G2 position.

In certain embodiments, the compound of Formula (I) is of Formula (IV-a):

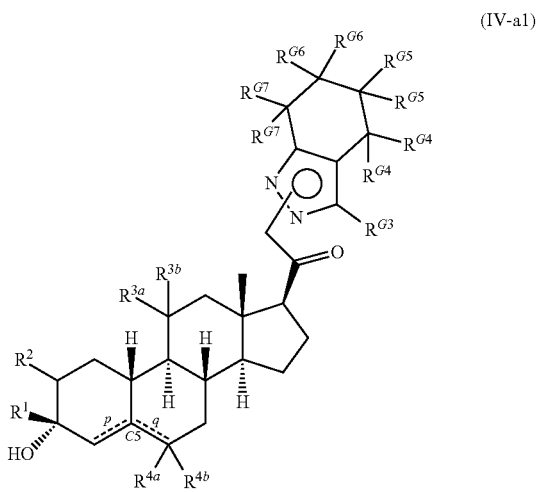

(IV-a1)

or a pharmaceutically acceptable salt thereof. In certain embodiments, the point of attachment in Formula (IV-a1) is at the nitrogen at the G1 position. In certain embodiments, the point of attachment in Formula (IV-a1) is at the nitrogen at the G2 position.

In certain embodiments, the compound of Formula (I) is of one of the following formulae:

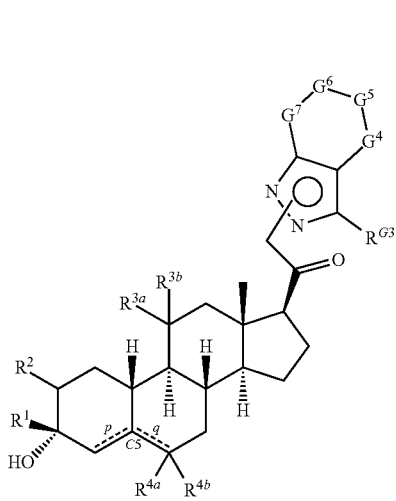

(IV-a)

or a pharmaceutically acceptable salt thereof. In certain embodiments, the point of attachment in Formula (IV-a) is at the nitrogen at the G1 position. In certain embodiments, the point of attachment in Formula (IV-a) is at the nitrogen at the G2 position.

In certain embodiments, the compound of Formula (I) is of Formula (IV-a1):

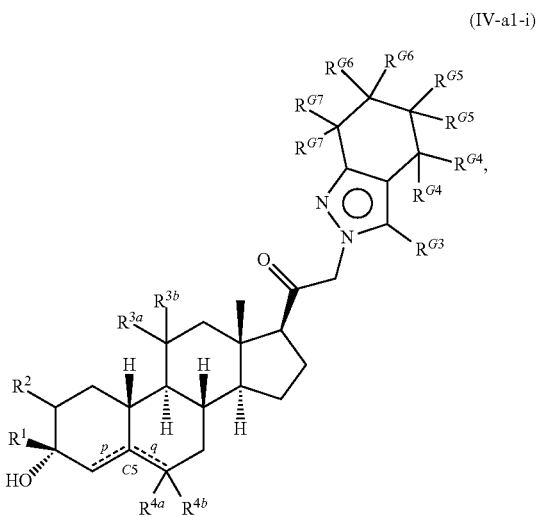

(IV-a1-i)

-continued
(IV-a1-ii)
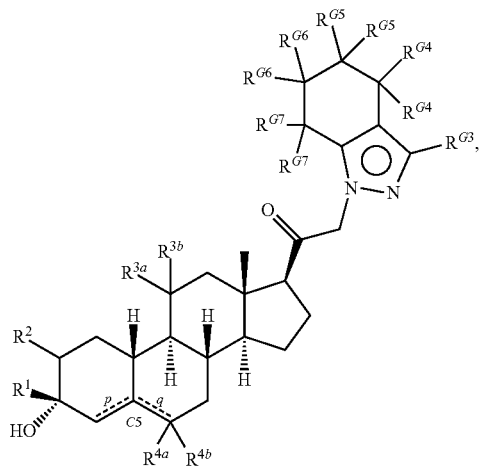
or a pharmaceutically acceptable salt thereof.
In certain embodiments, the compound of Formula (I) is of one of the following formulae:
(V)
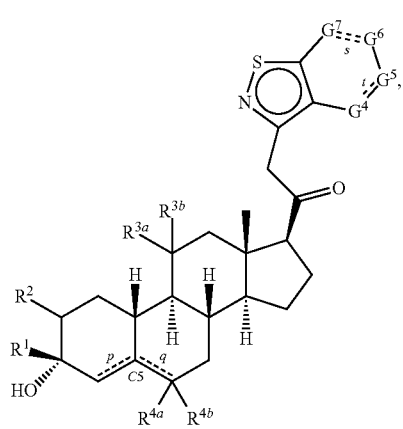
(VI)
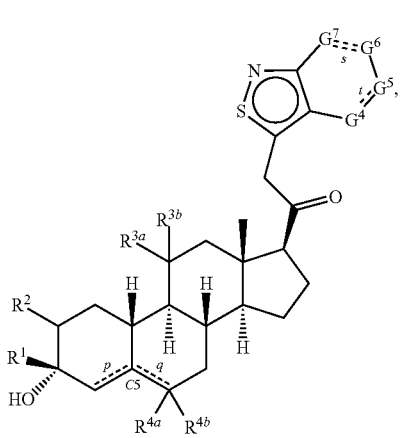
(VII)
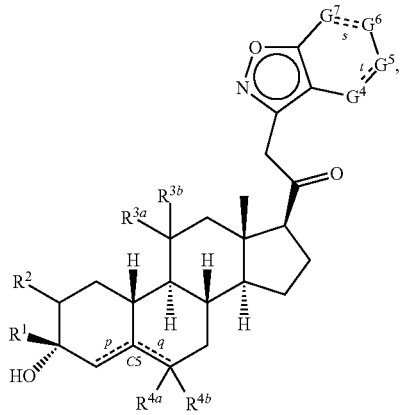
(VIII)
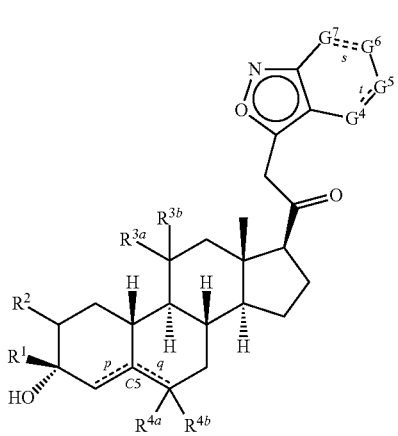
(IX)
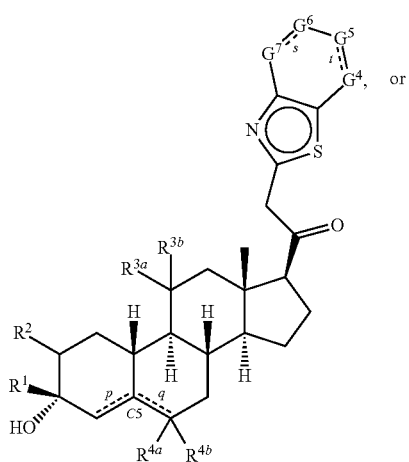
or -continued (X)

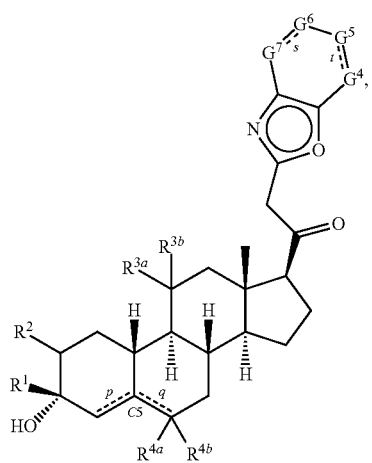

or a pharmaceutically acceptable salt thereof.

Various Combinations of Certain Embodiments

Various combinations of certain embodiments are further contemplated herein.

For example, in certain embodiments, wherein $R^2$ is hydrogen or a non-hydrogen alpha substituent, provided is a compound of Formula (I-A1), (I-B1), (I-C1), or (I-D1):

(I-A1)

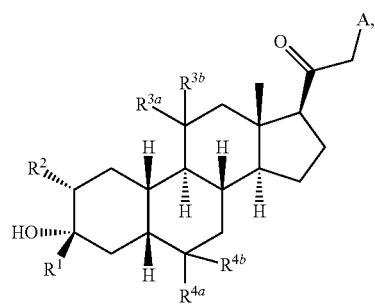

(I-B1)

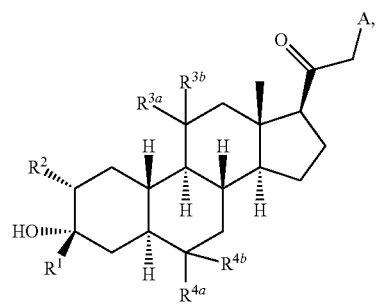

(I-C1)

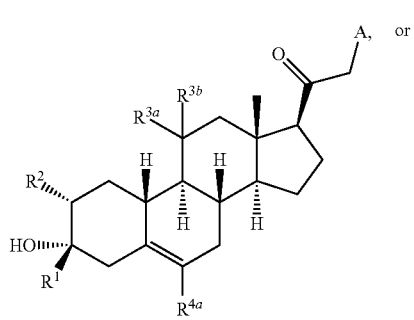

or (I-D1)

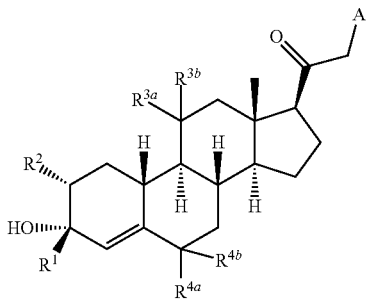

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^{3a}$ and $R^{3b}$ are both hydrogen. In certain embodiments, $R^{3a}$ and $R^{3b}$ are joined to form =O (oxo). In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen.

In certain embodiments, wherein $R^2$ is hydrogen or a non-hydrogen beta substituent, provided is a compound of Formula (I-A2), (I-B2), (I-C2), or (I-D2):

(I-A2)

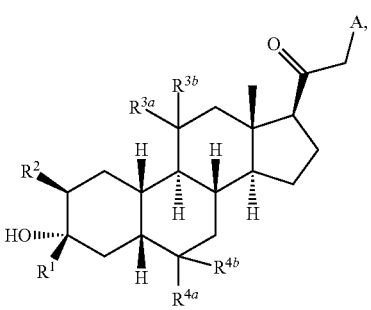

(I-B2)

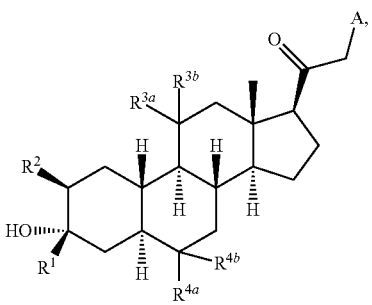

-continued

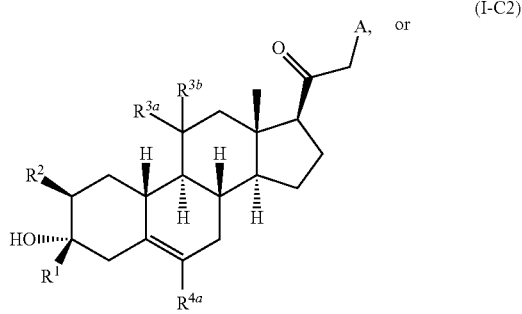

(I-C2)

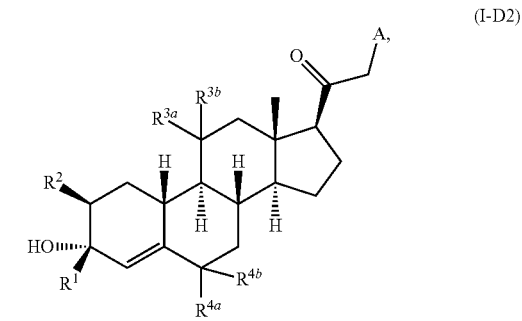

(I-D2)

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^{3a}$ and $R^{3b}$ are both hydrogen. In certain embodiments, $R^{3a}$ and $R^{3b}$ are joined to form =O (oxo). In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen.

In certain embodiments, wherein $R^{3a}$ is hydrogen or a non-hydrogen alpha substituent, and $R^{3b}$ is hydrogen, provided is a compound of Formula (I-A3), (I-B3), (I-C3), or (I-D3):

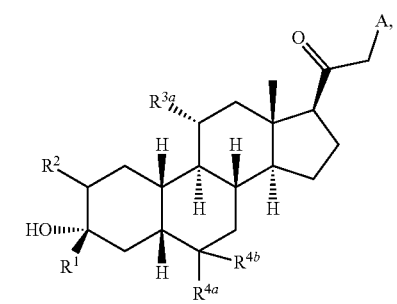

(I-A3)

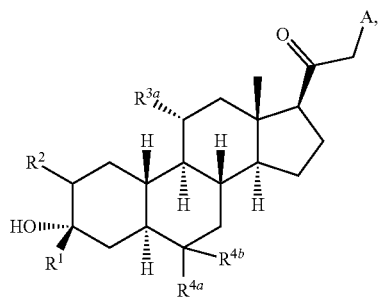

(I-B3)

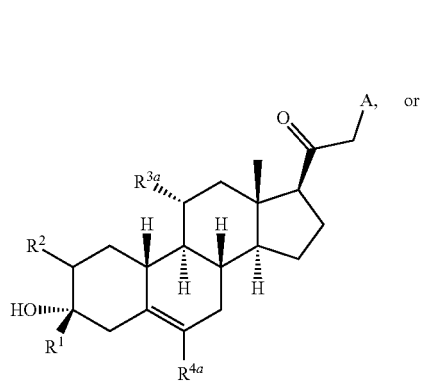

(I-C3)

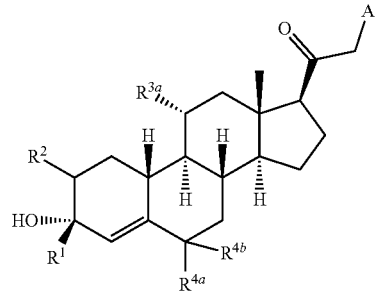

(I-D3)

or a pharmaceutically acceptable salt thereof. In certain embodiments, $R^1$ is —$CH_3$, —$CH_2CH_3$, —$CH_2F$, —$CHF_2$, —$CF_3$, —$CH_2OCH_3$, or substituted or unsubstituted cyclopropyl. In certain embodiments, $R^2$ is —OH, —$OCH_3$, —$OCH_2CH_3$, —$OCH_2CH_2CH_3$, —$CH_3$, —$CH_2CH_3$, —$CH_2CH_2CH_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, wherein Ring B comprises a C5-C6 double bond, $R^{4a}$ is hydrogen, fluoro, —$CH_3$, or —$CF_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —$CH_3$ or —$CF_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen.

In certain embodiments, wherein $R^{3a}$ is hydrogen or a non-hydrogen beta substituent, and $R^{3b}$ is hydrogen, provided is a compound of Formula (I-A4), (I-B4), (I-C4), or (I-D4):

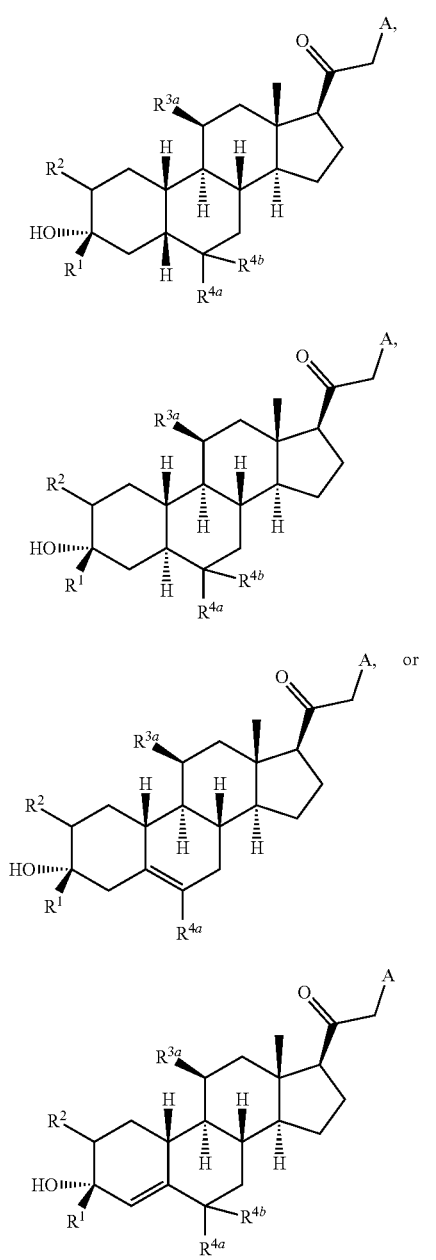

(I-A4)

(I-B4)

(I-C4)

(I-D4)

or a pharmaceutically acceptable salt thereof. In certain embodiments, $R^1$ is —CH$_3$, —CH$_2$CH$_3$, —CH$_2$F, —CHF$_2$, —CF$_3$, —CH$_2$OCH$_3$, or substituted or unsubstituted cyclopropyl. In certain embodiments, $R^2$ is —OH, —OCH$_3$, —OCH$_2$CH$_3$, —OCH$_2$CH$_2$CH$_3$, —CH$_3$, —CH$_2$CH$_3$, —CH$_2$CH$_2$CH$_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, wherein Ring B comprises a C5-C6 double bond, $R^{4a}$ is hydrogen, fluoro, —CH$_3$, or —CF$_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —CH$_3$ or —CF$_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen.

In certain embodiments, wherein $R^{3a}$ and $R^{3b}$ are joined to form an oxo group, provided is a compound of Formula (I-A5), (I-B5), (I-C5), (I-D5):

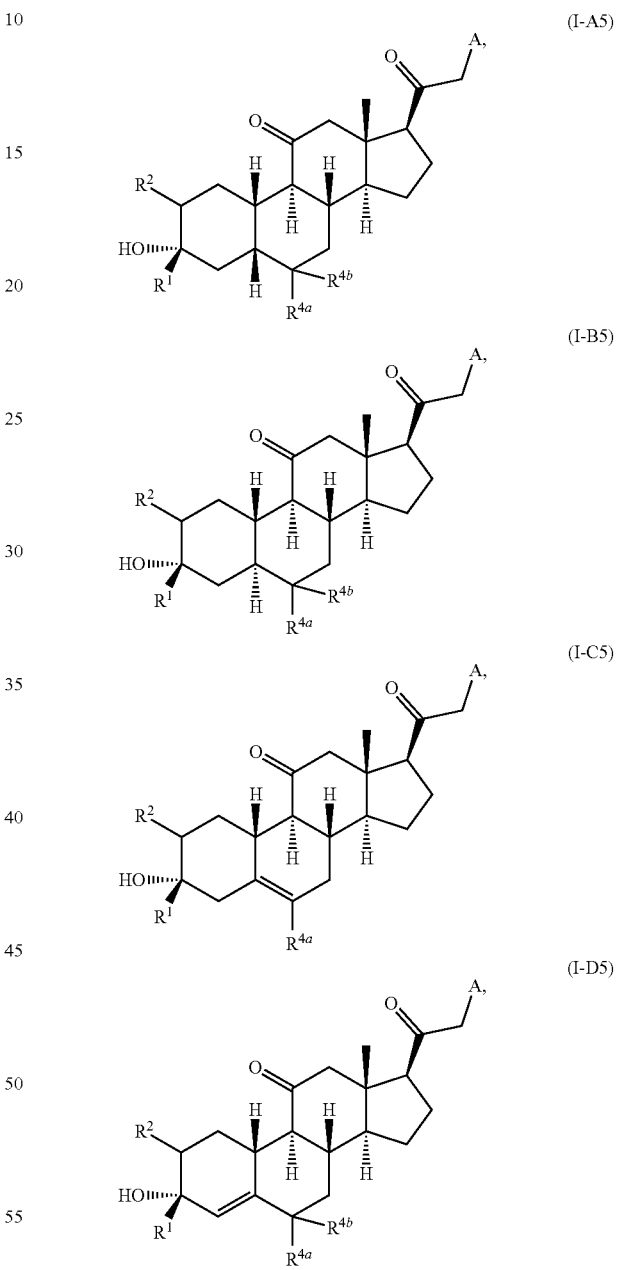

(I-A5)

(I-B5)

(I-C5)

(I-D5)

or a pharmaceutically acceptable salt thereof. In certain embodiments, $R^1$ is —CH$_3$, —CH$_2$CH$_3$, —CH$_2$F, —CHF$_2$, —CF$_3$, —CH$_2$OCH$_3$, or substituted or unsubstituted cyclopropyl. In certain embodiments, $R^2$ is —OH, —OCH$_3$, —OCH$_2$CH$_3$, —OCH$_2$CH$_2$CH$_3$, —CH$_3$, —CH$_2$CH$_3$, —CH$_2$CH$_2$CH$_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, wherein Ring B comprises a C5-C6 double bond, $R^{4a}$ is hydrogen, fluoro, —CH$_3$, or —CF$_3$. In certain embodiments, wherein Ring B does not comprises a C5-C6 double bond, both of $R^{4a}$ and $R^{4b}$ are hydrogen. In certain embodiments, wherein Ring B does not comprises a C5-C6 double bond, both of $R^{4a}$ and $R^{4b}$ are —CH$_3$ or —CF$_3$. In certain embodiments, wherein Ring B does not comprises a C5-C6 double bond, both of $R^{4a}$ and $R^{4b}$ are fluoro. In certain embodiments, wherein Ring B does not comprises a C5-C6 double bond, $R^{4a}$ is a non-hydrogen substituent and $R^{4b}$ is hydrogen.

In certain embodiments, wherein $R^{4a}$ is a non-hydrogen substituent, provided is a compound of Formula (I-A6) or (I-B6):

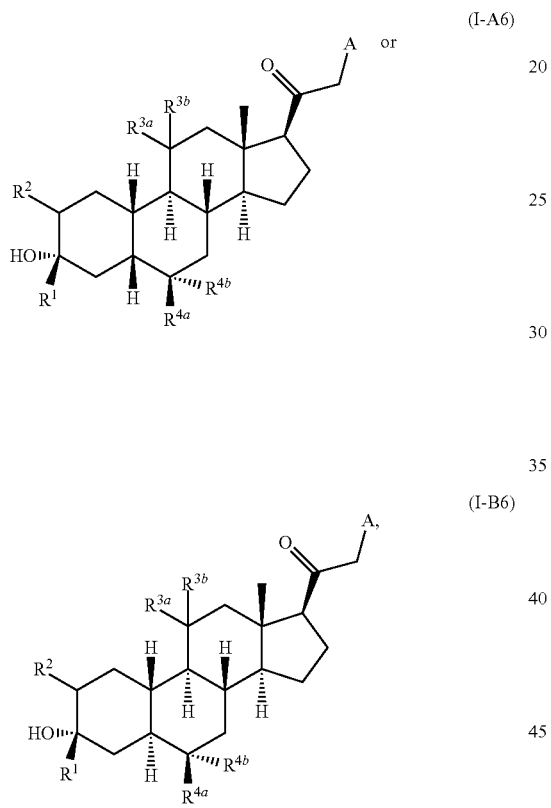

or a pharmaceutically acceptable salt thereof. In certain embodiments, $R^1$ is —CH$_3$, —CH$_2$CH$_3$, —CH$_2$F, —CHF$_2$, —CF$_3$, —CH$_2$OCH$_3$, or substituted or unsubstituted cyclopropyl. In certain embodiments, $R^2$ is —OH, —OCH$_3$, —OCH$_2$CH$_3$, —OCH$_2$CH$_2$CH$_3$, —CH$_3$, —CH$_2$CH$_3$, —CH$_2$CH$_2$CH$_3$, substituted or unsubstituted cyclopropyl, fluoro, or chloro. In certain embodiments, $R^2$ is a non-hydrogen substituent in the alpha configuration. In certain embodiments, $R^2$ is a non-hydrogen substituent in the beta configuration. In certain embodiments, $R^{3a}$ and $R^{3b}$ are both hydrogen. In certain embodiments, $R^{3a}$ and $R^{3b}$ are joined to form =O (oxo). In certain embodiments, $R^{4a}$ is fluoro, —CH$_3$, or —CF$_3$ and $R^{4b}$ is hydrogen. In certain embodiments, $R^{4b}$ is fluoro, —CH$_3$, or —CF$_3$ and $R^{4a}$ is hydrogen. In certain embodiments, both of $R^{4a}$ and $R^{4b}$ are —CH$_3$ or —CF$_3$. In certain embodiments, both of $R^{4a}$ and $R^{4b}$ are fluoro.

In certain embodiments, a compound of Formula (I) is selected from the group consisting of

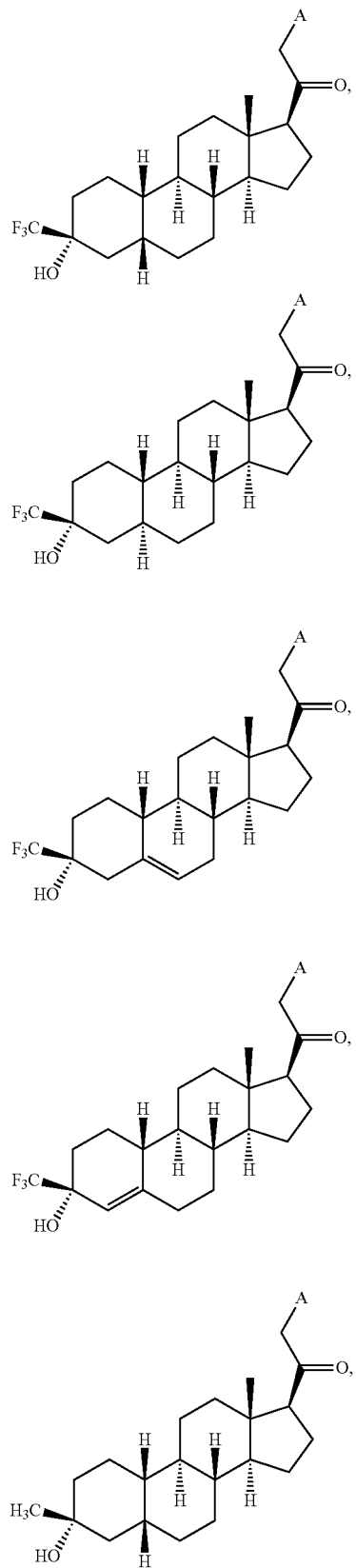

71
-continued
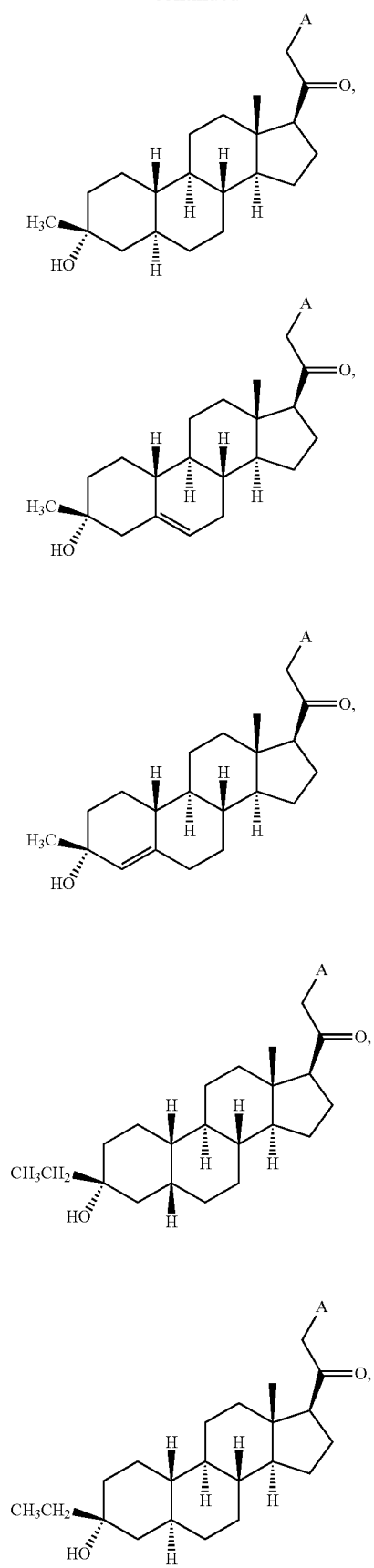
72
-continued
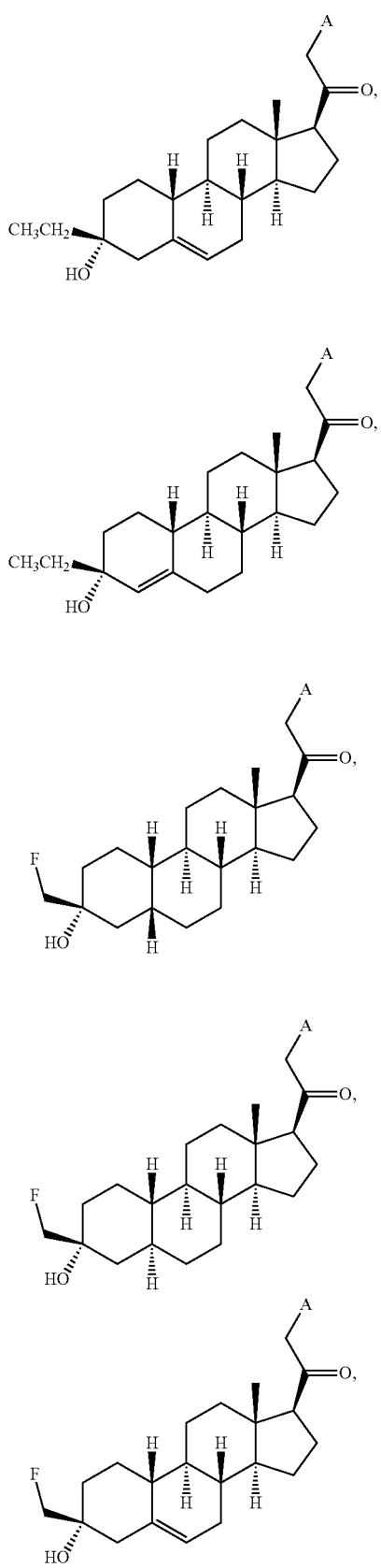

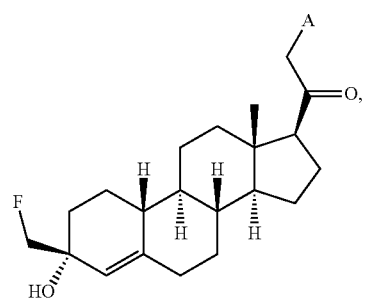
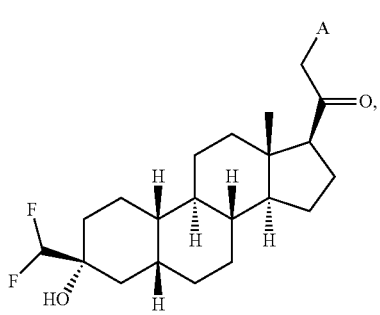
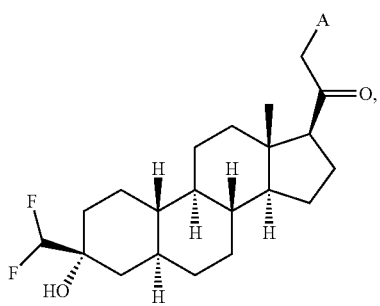
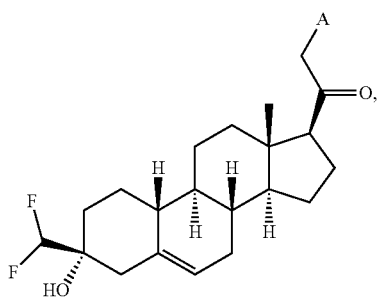
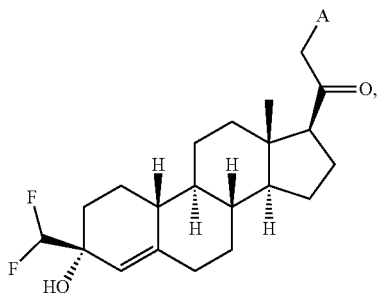
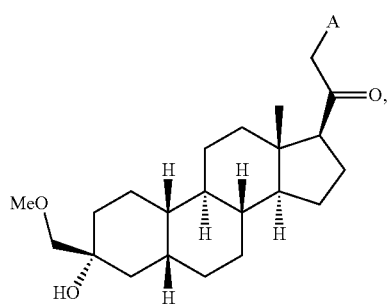
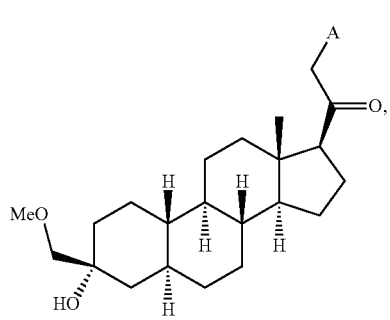
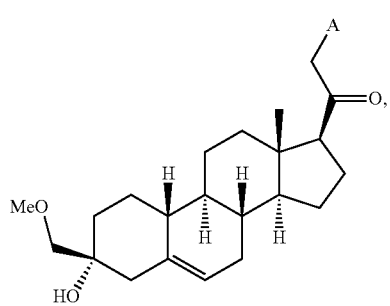
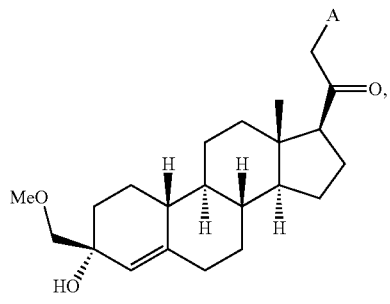
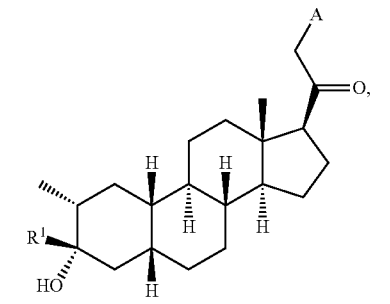

75
-continued
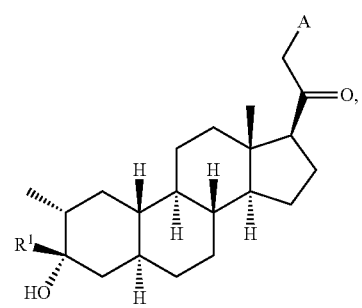
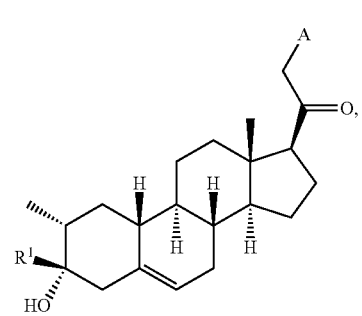
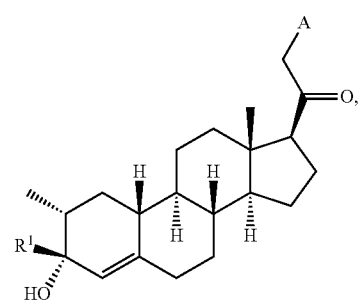
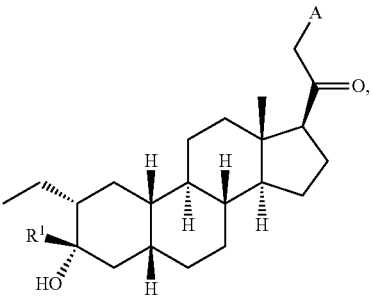
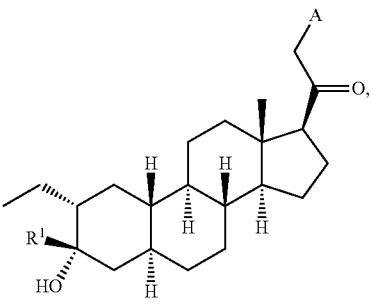
76
-continued
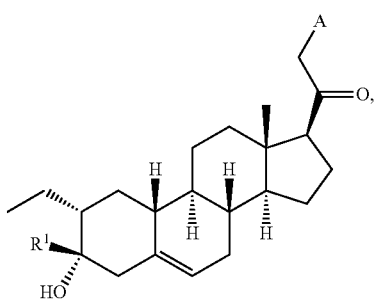
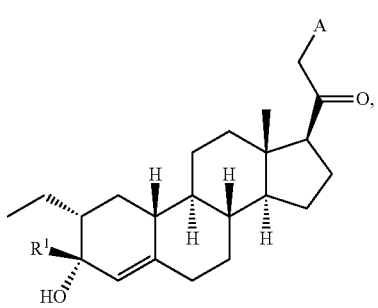
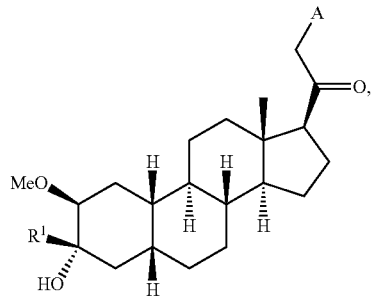
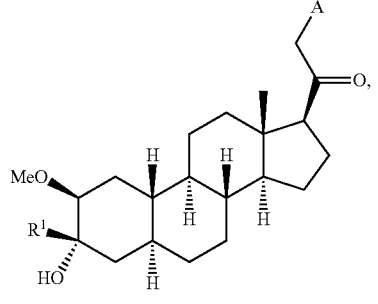
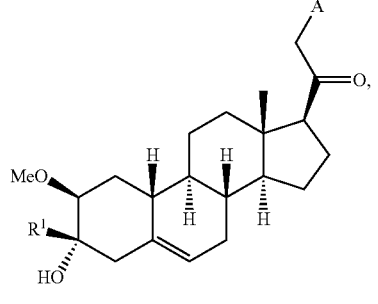

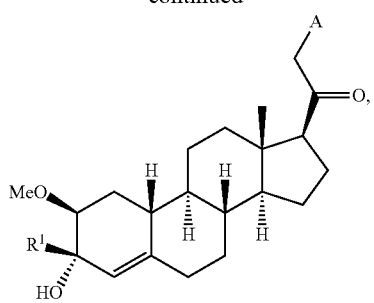
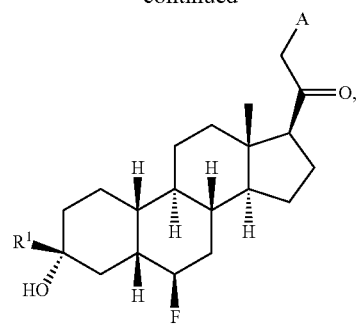
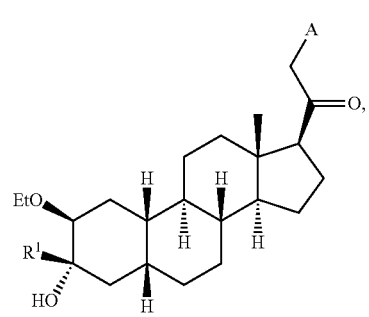
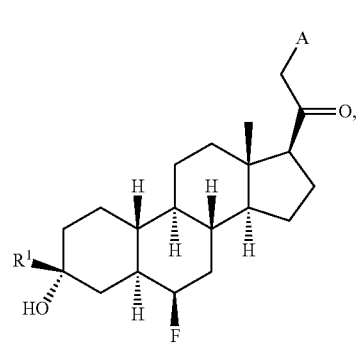
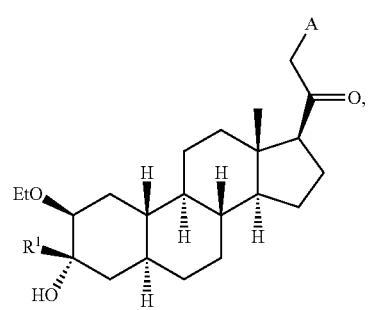
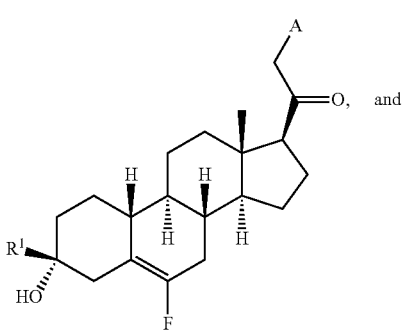
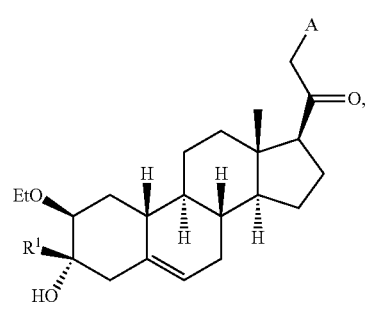
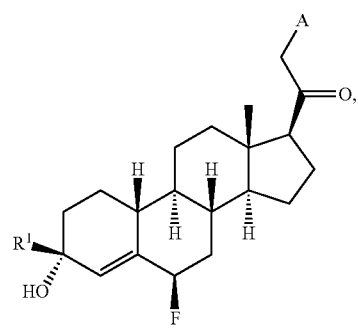
or pharmaceutically acceptable salts thereof.
In certain embodiments, a compound of Formula (I) is selected from the group consisting of:

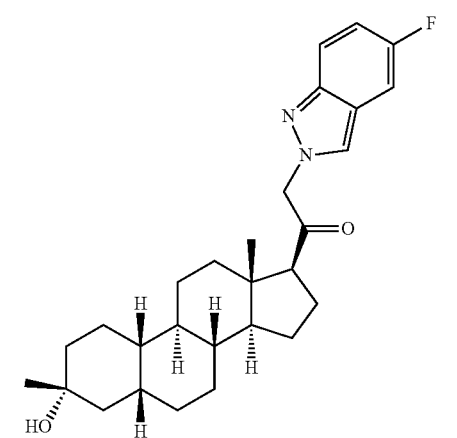
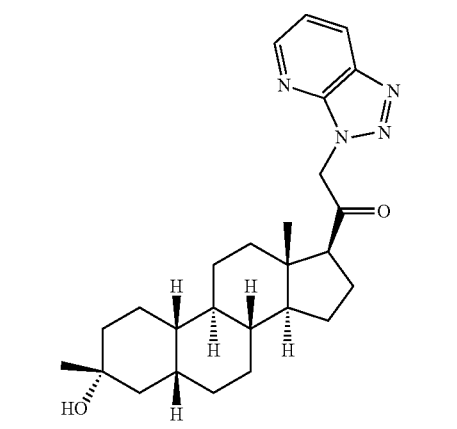
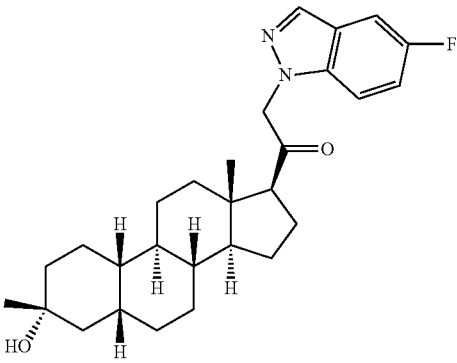
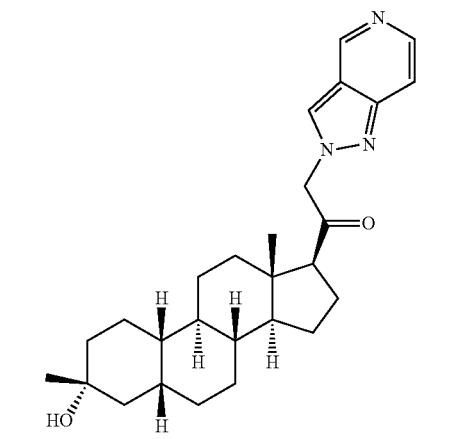
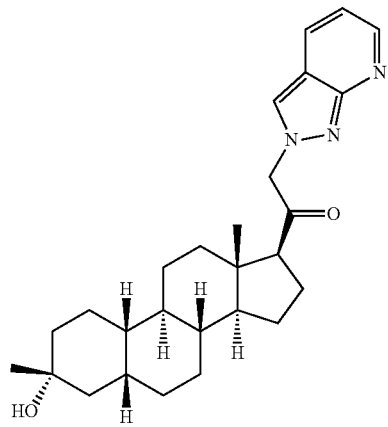
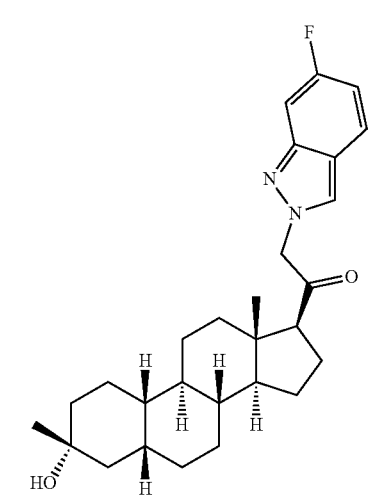
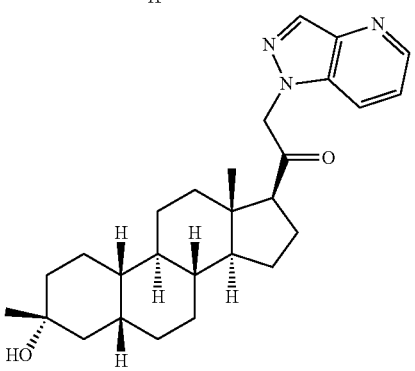
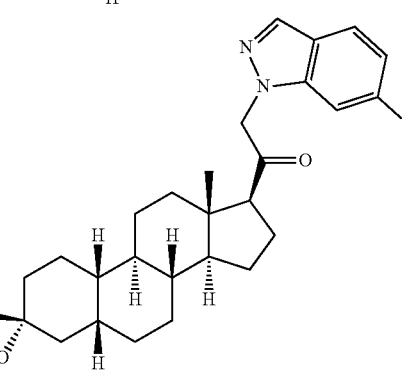

81
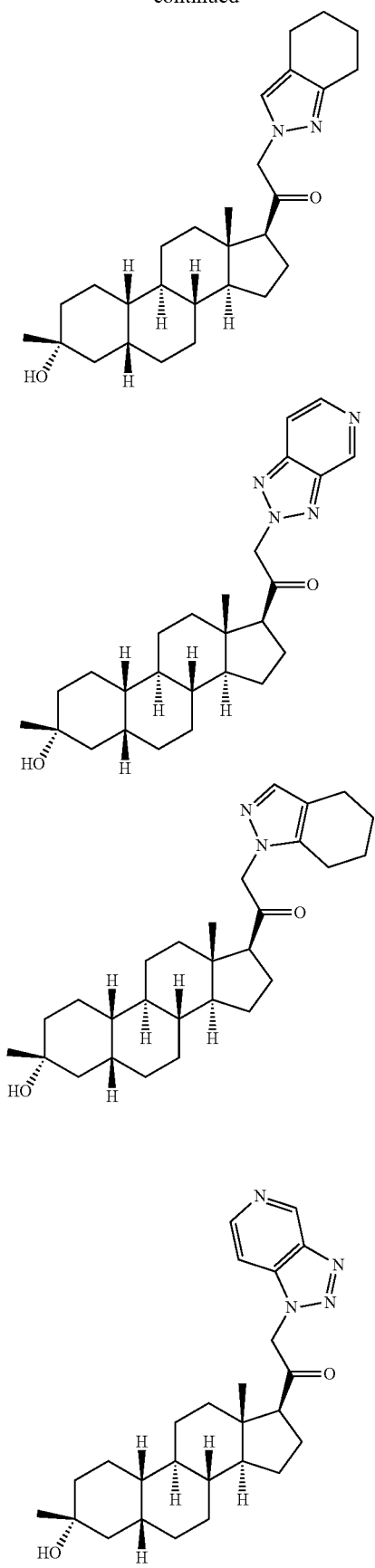
82
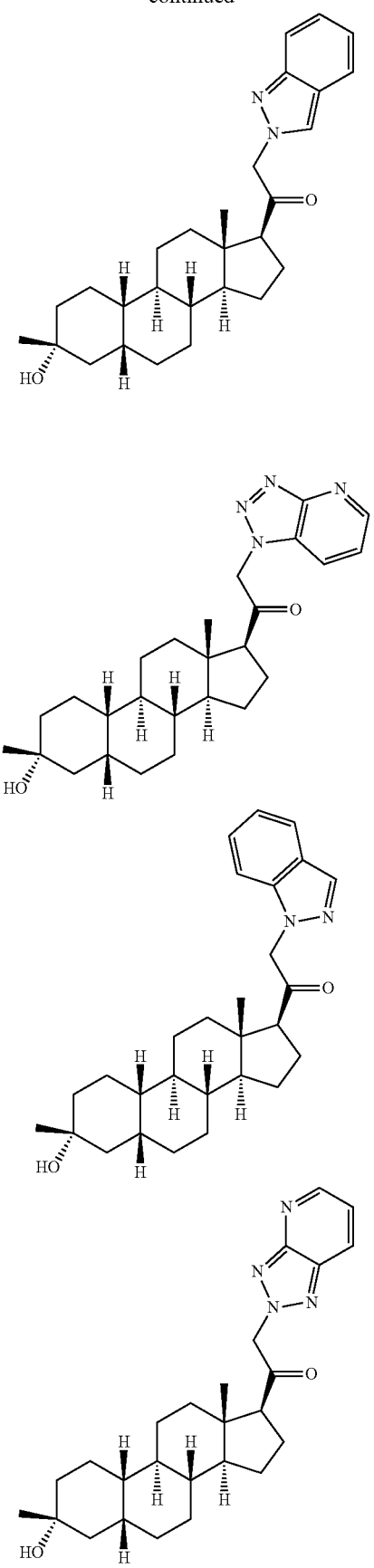

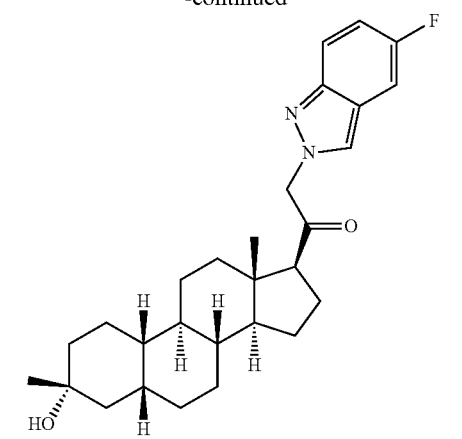
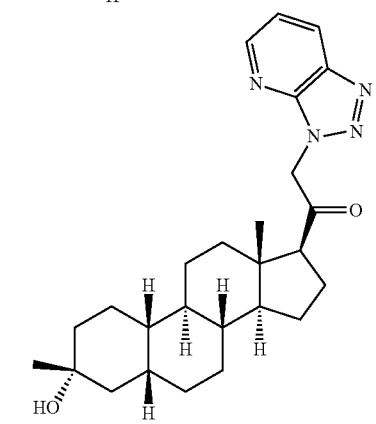
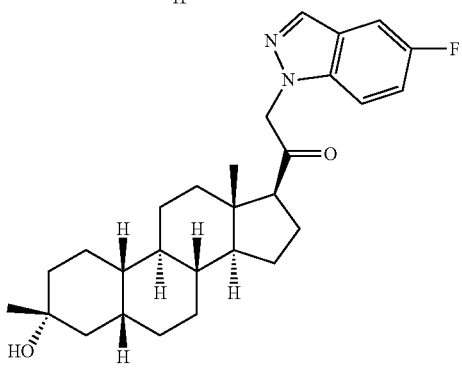
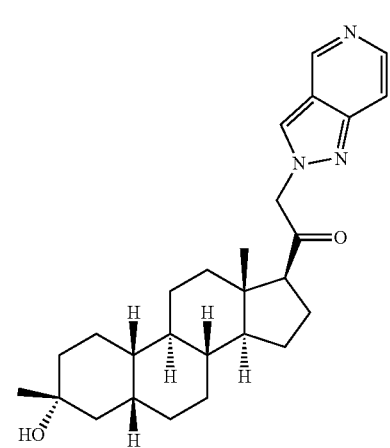
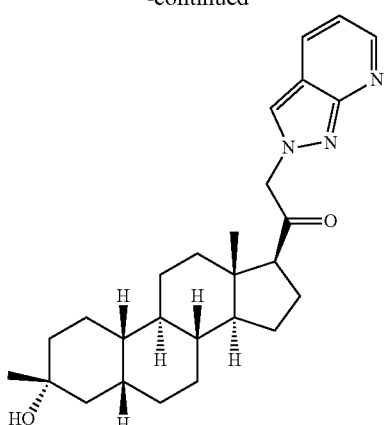
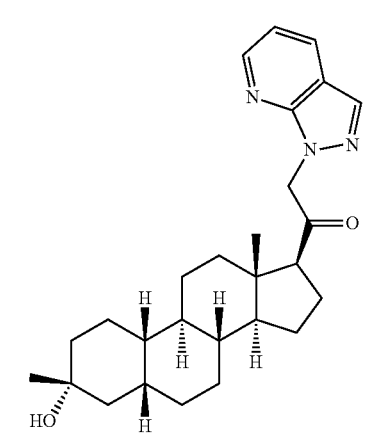
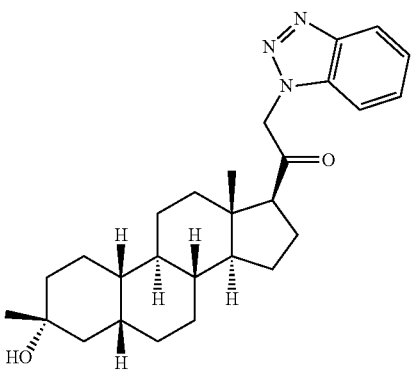
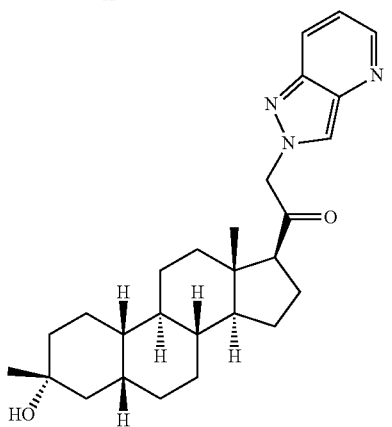

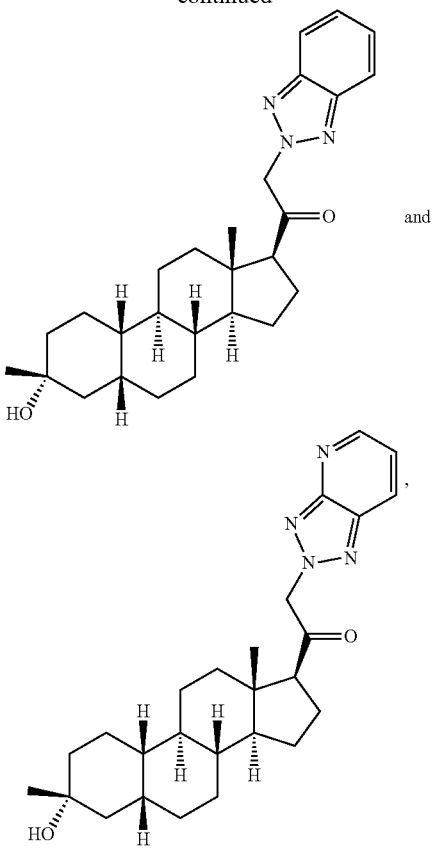

or pharmaceutically acceptable salts thereof.

Pharmaceutical Compositions

In another aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable formulations of a compound of the present invention. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol☐. See, e.g., U.S. Pat. No. 5,376,645. In certain embodiments, the formulation comprises hexapropyl-β-cyclodextrin (e.g., 10-50% in water).

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of the present invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of the present invention may be admixed as a dry powder with a starch diluent in an approximate 1:1 weight ratio. The mixture is filled into 250 mg capsules (125 mg of active compound per capsule).

Exemplary Formulation 3—Liquid: A compound of the present invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of the present invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of the present invention may be dissolved or suspended in a buffered sterile saline injectable aqueous medium to a concentration of approximately 5 mg/mL.

Exemplary Formulation 6—Tablets: A compound of the present invention may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of the present invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of the present invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of the present invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10 Tablets: A compound of the present invention may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Methods of Use and Treatment

As generally described herein, the present invention is directed to C21-substituted neuroactive steroids designed, for example, to act as GABA modulators. In certain embodiments, such compounds are envisioned to be useful as therapeutic agents for the inducement of anesthesia and/or sedation in a subject. In some embodiments, such compounds are envisioned to be useful as therapeutic agents for treating a CNS-related disorder (e.g., sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome).

Thus, in one aspect, the present invention provides a method of inducing sedation and/or anesthesia in a subject, comprising administering to the subject an effective amount of a compound of the present invention or a composition thereof. In certain embodiments, the compound is administered by intravenous administration.

Earlier studies (see, e.g., Gee et al., *European Journal of Pharmacology,* 136:419-423 (1987)) demonstrated that certain 3α-hydroxylated steroids are orders of magnitude more potent as modulators of the GABA receptor complex (GRC) than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology,* 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology,* 136:419-423 (1987). These compounds are desirable for their duration, potency, and oral activity (along with other forms of administration).

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

Exemplary CNS conditions related to GABA-modulation include, but are not limited to, sleep disorders[e.g., insomnia], mood disorders[e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders[e.g., epilepsy (e.g., status epilepticus (SE)), seizures], disorders of memory and/or cognition[e.g., attention disorders (e.g., attention deficit hyperactivity disorder (ADHD)), dementia (e.g., Alzheimer's type dementia, Lewis body type dementia, vascular type dementia], movement disorders[e.g., Huntington's disease, Parkinson's disease], personality disorders[e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain[e.g., neuropathic pain, injury related pain syndromes, acute pain, chronic pain], traumatic brain injury (TBI), vascular diseases[e.g., stroke, ischemia, vascular malformations], substance abuse disorders and/or withdrawal syndromes[e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing seizure activity in a subject, comprising administering to the subject in need of such treatment an effective amount of a compound of the present invention.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of inducing anesthesia in a subject, comprising administering to the subject an effective amount of a compound of the present invention.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

Anxiety Disorders

Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Compositions described herein can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative substituted biarylamides that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

General method for supercritical fluid chromatography (SFC): SFC purification was carried out using a Thar 200 preparative SFC instrument equipped with a ChiralPak AD-10 µM, 200×50 mm ID. The compounds were separated eluting with mixtures of carbon dioxide and methanol or ethanol (e.g., 20-35% methanol or ethanol and 0.1% ammonium hydroxide) at a flow rate of 55-200 mL/min and monitored at 220 nm wavelength.

$^1$H-NMR reported herein may be a partial representation of the full NMR spectrum of a compound, e.g., a compound described herein. For example, the reported $^1$H NMR may exclude the region between δ (ppm) of about 1 to about 2.5 ppm. Copies of full $^1$H-NMR spectrum for representative examples are provided in the Figures.

Exemplary general method for preparative HPLC: Column: Waters RBridge prep 10 µm C18, 19*250 mm. Mobile phase: aectonitrile, water (NH$_4$HCO$_3$) (30 L water, 24 g NH$_4$HCO$_3$, 30 mL NH$_3$.H$_2$O). Flow rate: 25 mL/min Exemplary general method for analytical HPLC: Mobile phase: A: water (10 mM $NH_4HCO_3$), B: acetonitrileGradient: 5%-95% B in 1.6 or 2 min Flow rate: 1.8 or 2 mL/min; Column: XBridge C18, 4.6*50 mm, 3.5 μm at 45 C.

Synthetic Procedures

The compounds of the invention can be prepared in accordance with methods described in the art (Upasani et al., *J. Med. Chem.* 1997, 40:73-84; and Hogenkamp et al., *J. Med. Chem.* 1997, 40:61-72) and using the appropriate reagents, starting materials, and purification methods known to those skilled in the art. In some embodiments, compounds described herein can be prepared using methods shown in general Schemes 1-4, comprising a nucleophilic substitution of 19-nor pregnane bromide with a neucleophile. In certain embodiments, the nucleophile reacts with the 19-nor pregnane bromide in the presence of $K_2CO_3$ in THF.

Scheme 1

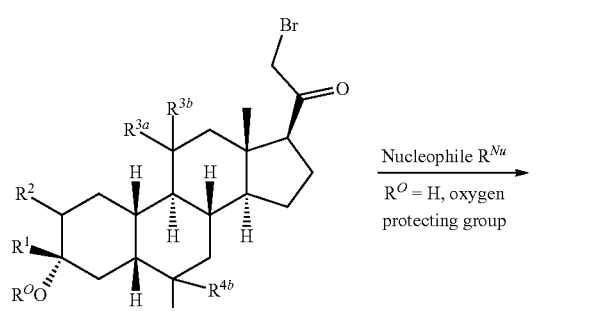

Scheme 2

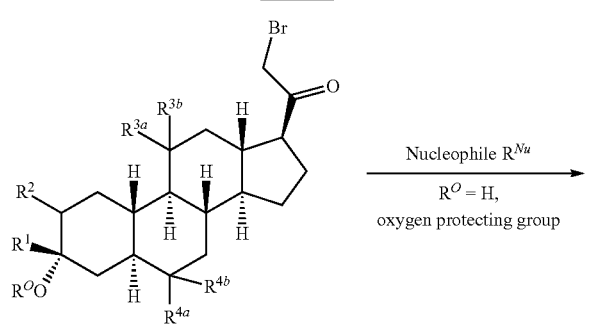

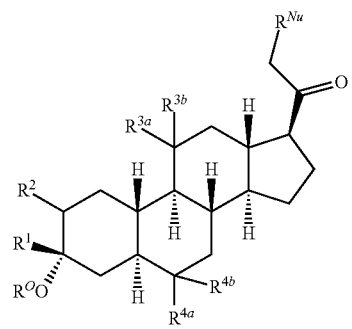

Scheme 3

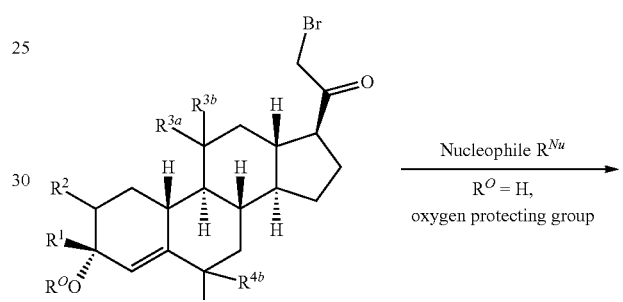

Scheme 4

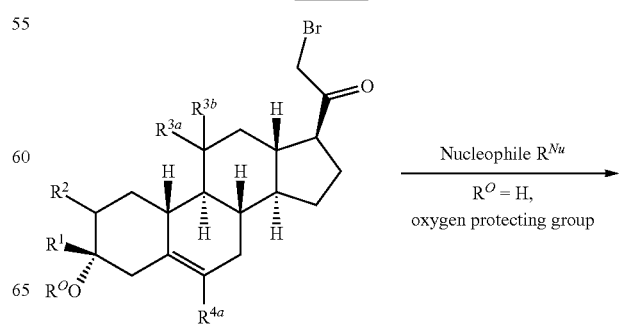

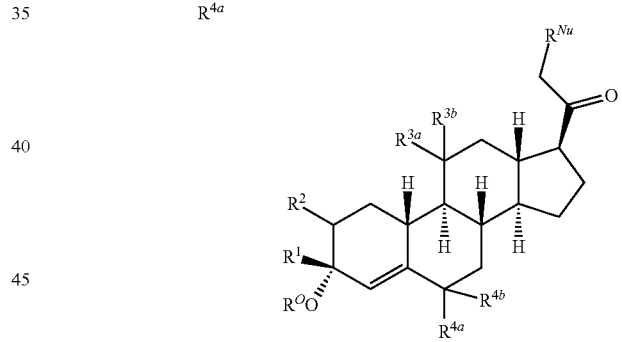

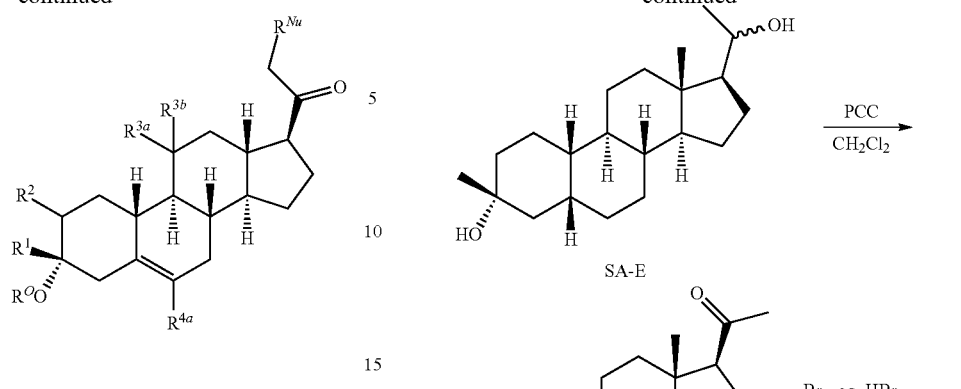

Example 1

Synthesis of SA and SA Intermediates

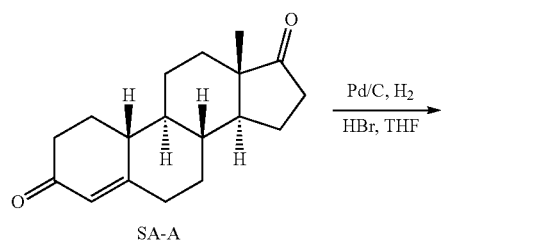

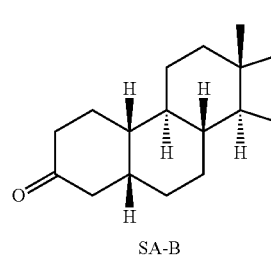

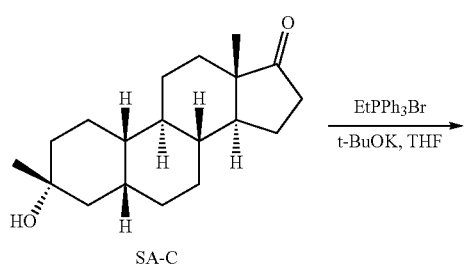

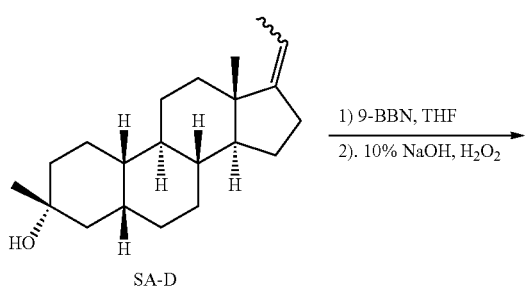

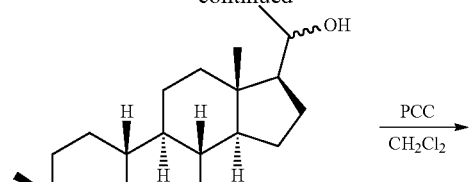

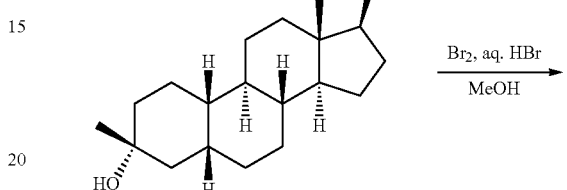

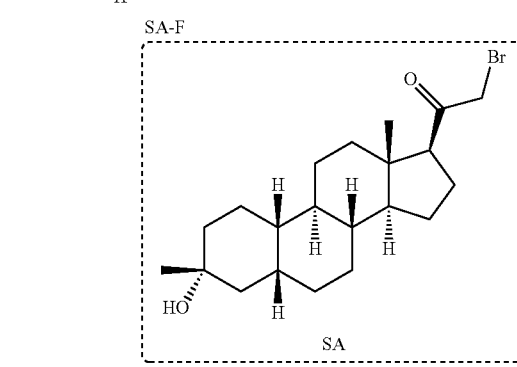

Synthesis of compound SA-B. Compound SA (50 g, 184 mmol) and palladium black (2.5 g) in tetrahydrofuran (300 mL) and concentrated hydrobromic acid (1.0 mL) was hydrogenated with 10 atm hydrogen. After stirring at room temperature for 24 h, the mixture was filtered through a pad of celite and the filtrate was concentrated in vacuo to afford the crude compound. Recrystallization from acetone gave compound SA-B (42.0 g, yield: 83.4%) as white powder.

$^1$H NMR: (400 MHz, CDCl3) δ 2.45-2.41 (m, 1H), 2.11-3.44 (m, 2H), 3.24 (s, 3H), 2.18-2.15 (m, 1H), 2.01-1.95 (m, 1H), 1.81-1.57 (m, 7H), 1.53-1.37 (m, 7H), 1.29-1.13 (m, 3H), 1.13-0.90 (m, 2H), 0.89 (s, 3H).

Synthesis of compound SA-C. A solution of SA-B (42.0 g, 153.06 mmol) in 600 mL anhydrous toluene was added dropwise to the MAD (459.19 mmol, 3.0 eq, freshly prepared) solution under N$_2$ at −78° C. After the addition was completed, the reaction mixture was stirred for 1 hr at −78° C. Then 3.0 M MeMgBr (153.06 mL, 459.19 mmol) was slowly added dropwise to the above mixture under N$_2$ at −78° C. Then the reaction mixture was stirred for 3 hr at this temperature. TLC (PE:EtOAc=3:1) showed the reaction was completed. Then saturated aqueous NH$_4$Cl was slowly added dropwise to the above mixture at −78° C. After the addition was completed, the mixture was filtered, the filter cake was washed with EtOAc, the organic layer was washed with water and brine, dried over anhydrous Na$_2$SO$_4$, filtered and concentrated, purified by flash Chromatography on silica gel (Petroleum ether/ethyl acetate 20:1 to 3:1) to afford compound SA-C (40.2 g, yield: 90.4%) as white powder. $^1$H NMR: (400 MHz, CDCl3) δ 2.47-2.41 (m, 1H), 2.13-2.03

(m, 1H), 1.96-1.74 (m, 6H), 1.70-1.62 (m, 1H), 1.54-1.47 (m, 3H), 1.45-1.37 (m, 4H), 1.35-1.23 (m, 8H), 1.22-1.10 (m, 2H), 1.10-1.01 (m, 1H), 0.87 (s, 3H).

Synthesis of compound SA-D. To a solution of PPh₃EtBr (204.52 g, 550.89 mmol) in THF (500 mL) was added a solution of t-BuOK (61.82 g, 550.89 mmol) in THF (300 mL) at 0° C. After the addition was completed, the reaction mixture was stirred for 1 h 60° C., then SA-C (40.0 g, 137.72 mmol) dissolved in THF (300 mL) was added dropwise at 60° C. The reaction mixture was heated to 60° C. for 18 h. The reaction mixture was cooled to room temperature and quenched with Sat. NH₄Cl, extracted with EtOAc (3*500 mL). The combined organic layers were washed with brine, dried and concentrated to give the crude product, which was purified by a flash column chromatography (Petroleum ether/ethyl acetate 50:1 to 10:1) to afford compound SA-D (38.4 g, yield: 92%) as a white powder. ¹H NMR: (400 MHz, CDCl3) δ 5.17-5.06 (m, 1H), 2.42-2.30 (m, 1H), 2.27-2.13 (m, 2H), 1.89-1.80 (m, 3H), 1.76-1.61 (m, 6H), 1.55-1.43 (m, 4H), 1.42-1.34 (m, 3H), 1.33-1.26 (m, 6H), 1.22-1.05 (m, 5H), 0.87 (s, 3H).

Synthesis of compound SA-E. To a solution of SA-D (38.0 g, 125.62 mmol) in dry THF (800 mL) was added dropwise a solution of BH₃.Me₂S (126 mL, 1.26 mol) under ice-bath. After the addition was completed, the reaction mixture was stirred for 3 h at room temperature (14-20° C.). TLC (Petroleum ether/ethyl acetate 3:1) showed the reaction was completed. The mixture was cooled to 0° C. and 3.0 M aqueous NaOH solution (400 mL) followed by 30% aqueous H₂O₂ (30%, 300 mL) was added. The mixture was stirred for 2 h at room temperature (14-20° C.), and then filtered, extracted with EtOAc (3*500 mL). The combined organic layers were washed with saturated aqueous Na₂S₂O₃, brine, dried over Na₂SO₄ and concentrated in vacuum to give the crude product (43 g, crude) as colorless oil. The crude product was used in the next step without further purification.

Synthesis of compound SA-F. To a solution of SA-E (43.0 g, 134.16 mmol) in dichloromethane (800 mL) at 0° C. and PCC (53.8 g, 268.32 mmol) was added portion wise. Then the reaction mixture was stirred at room temperature (16-22° C.) for 3 h. TLC (Petroleum ether/ethyl acetate 3:1) showed the reaction was completed, then the reaction mixture was filtered, washed with DCM. The organic phase was washed with saturated aqueous Na₂S₂O₃, brine, dried over Na₂SO₄ and concentrated in vacuum to give the crude product. The crude product was purified by a flash column chromatography (Petroleum ether/ethyl acetate 50:1 to 8:1) to afford compound SA-F (25.0 g, yield: 62.5%, over two steps) as a white powder. ¹H NMR (SA-F): (400 MHz, CDCl3) δ 2.57-2.50 (m, 1H), 2.19-2.11 (m, 4H), 2.03-1.97 (m, 1H), 1.89-1.80 (m, 3H), 1.76-1.58 (m, 5H), 1.47-1.42 (m, 3H), 1.35-1.19 (m, 10H), 1.13-1.04 (m, 3H), 0.88-0.84 (m, 1H), 0.61 (s, 3H).

Synthesis of compound SA. To a solution of SA-F (10 g, 31.4 mmol) and aq. HBr (5 drops, 48% in water) in 200 mL of MeOH was added dropwise bromine (5.52 g, 34.54 mmol). The reaction mixture was stirred at 17° C. for 1.5 h. The resulting solution was quenched with saturated aqueous NaHCO₃ at 0° C. and extracted with EtOAc (150 mL×2). The combined organic layers were dried and concentrated. The residue was purified by column chromatography on silica gel eluted with (PE:EA=15:1 to 6:1) to afford compound SA (9.5 g, yield: 76.14%) as a white solid. LC/MS: rt 5.4 min; m/z 379.0, 381.1, 396.1.

Example 2

Synthesis of Compounds SA-1 and SA-2

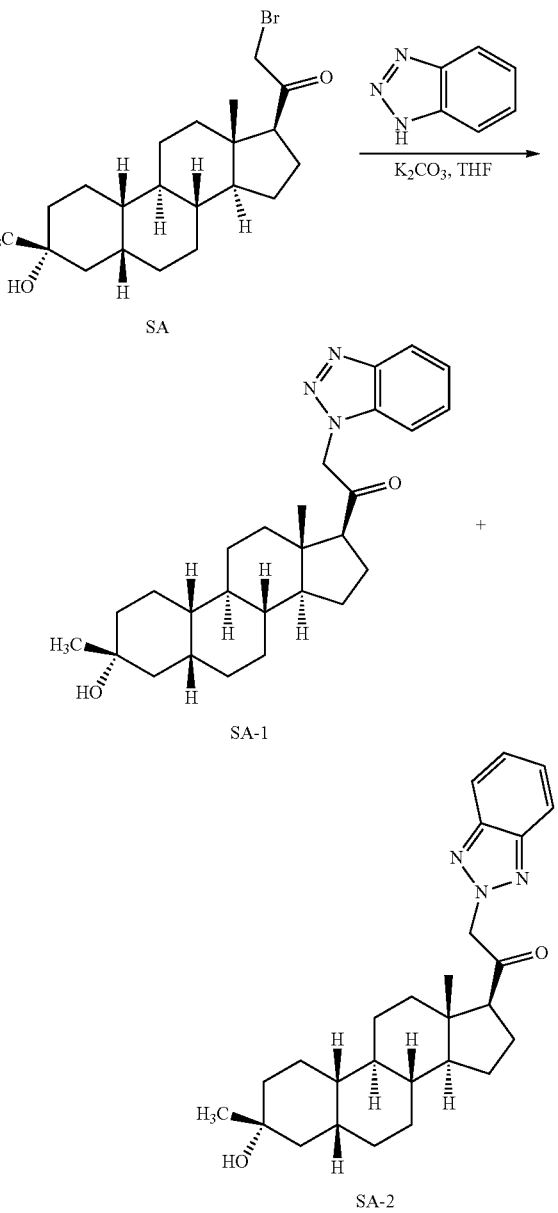

To a suspension of K₂CO₃ (50 mg, 0.36 mmol) in THF (5 mL) was added 1H-benzo[d][1,2,3]triazolel (80 mg, 0.67 mmol) and compound SA (100 mg, 0.25 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residue was purified with by reverse-phase prep-HPLC to afford the title compound as a white solid compound SA-1 (15 mg, 13.7%) and compound SA-2 (10 mg, 9.2%). Compound SA-1: ¹HNMR (500 MHz, CDCl3), δ (ppm), 8.08(d, 1H), 7.49 (t, 1H), 7.38 (t, 1H), 7.33 (d, 1H), 5.44 (1H, AB), 5.40 (1H, AB), 2.70(t, 1H), 0.73(s, 3H). Compound SA-2:

¹HNMR (500 MHz, CDCl3), δ (ppm), 7.88(d, 2H), 7.39(d, 2H), 5.53-5.52(m, 2H), 2.65(t, 1H), 0.75(s, 3H).

Example 3

Synthesis of Compounds SA-3 and SA-4

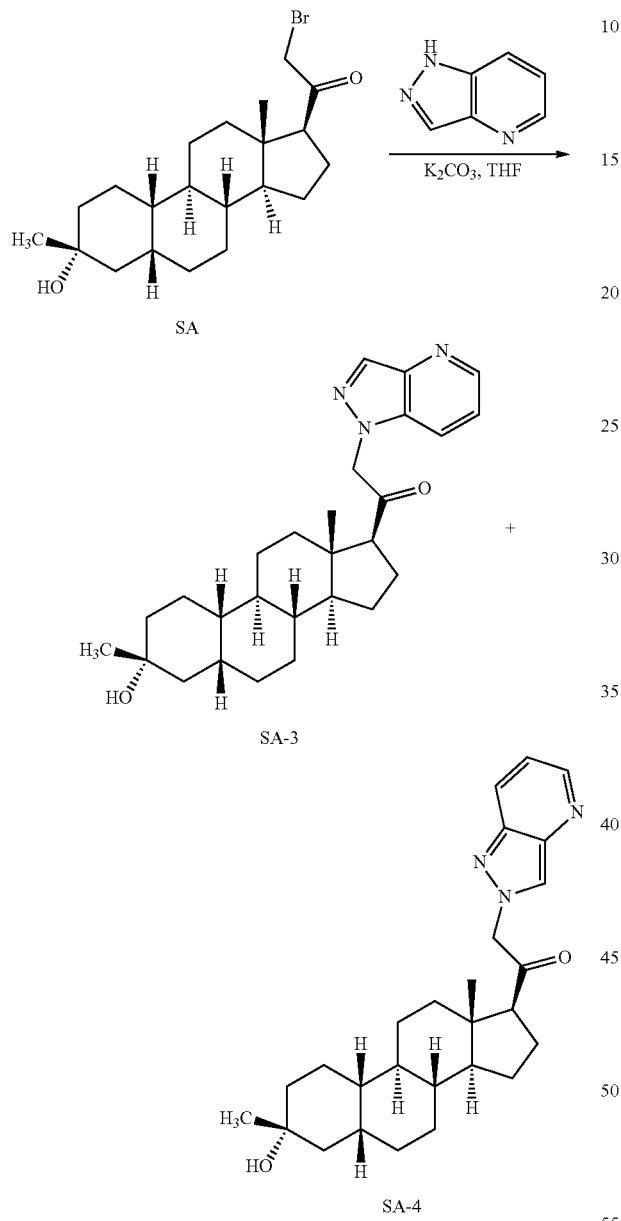

To a suspension of K₂CO₃ (50 mg, 0.36 mmol) in THF (5 mL) was added 1H-pyrazolo[4,3-b]pyridine (80 mg, 0.67 mmol) and compound SA (100 mg, 0.25 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residue was purified with by reverse-phase prep-HPLC to afford the title compound as a white solid compound SA-3 (17 mg, 15.5%) and compound SA-4 (10 mg, 9.2%). Compound SA-3: ¹HNMR(400 MHz, CDCl₃), δ (ppm), 8.59(d, 1H), 8.28(s, 1H), 7.59(d, 1H), 7.29(dd, 1H), 5.20 (1H, AB), 5.13 (1H, AB) 2.67(t, 1H), 0.71 (s, 3H). Compound SA-4: ¹HNMR (400 MHz, CDCl₃), δ (ppm), 8.58(d, 1H), 8.22 (s, 1H), 8.04 (d, 1H), 7.25(dd, 1H), 5.28 (1H, AB), 5.19 (1H, AB), 2.67 (t, 1H) 0.72(s, 3H).

Example 4

Synthesis of Compounds SA-5 and SA-6

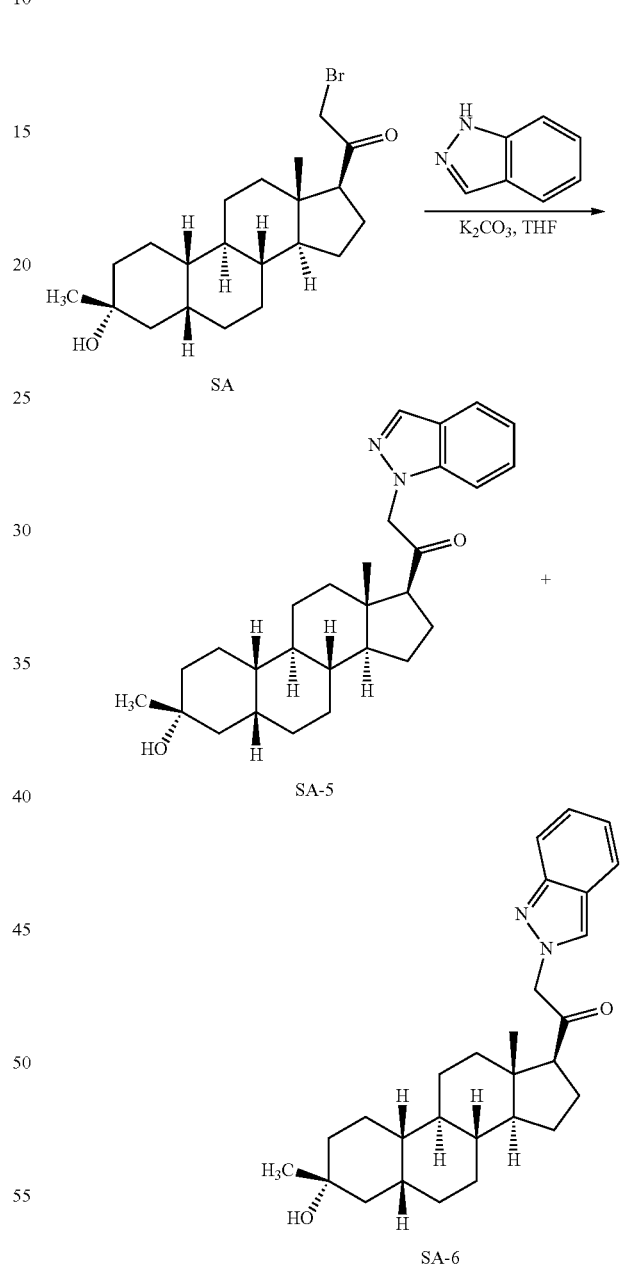

To a suspension of K₂CO₃ (50 mg, 0.36 mmol) in THF (5 mL) was added 1H-indazole (80 mg, 0.67 mmol) and compound SA (100 mg, 0.25 mmol). The mixture was stirred at rt for 15 h. The reaction mixture was poured in to 5 mL H₂O and extracted with EtOAc (2×10 mL). The combined organic layers were washed with brine, dried over sodium sulfate, filtered and concentrated. The residure mixture was purified with by reverse-phase prep-HPLC to afford the title compound as a white solid of Compound S5 (29 mg, 24.7%) and compound S6 (12 mg, 11%). Compound SA-5: ¹HNMR(500 MHz, CDCl₃), δ (ppm), 8.05(s, 1H), 7.76-7.74 (d, 1H), 7.41-7.37(t, 1H), 7.22-7.16(d and t, 2H), 5.15 (1H, AB), 5.09(1H, AB), 2.66 (t, 1H) 0.72(s, 3H). Compound SA-6: ¹HNMR(500 MHz, CDCl₃), δ (ppm), 7.93(s, 1H), 7.70-7.66(m, 2H), 7.28-7.26(m, 1H), 7.08-7.07(m, 1H), 5.25 (1H, AB), 5.15(1H, AB), 2.64 (t, 1H), 0.72 (s, 3H).

Example 5

Synthesis of Compounds SA-7 and SA-8

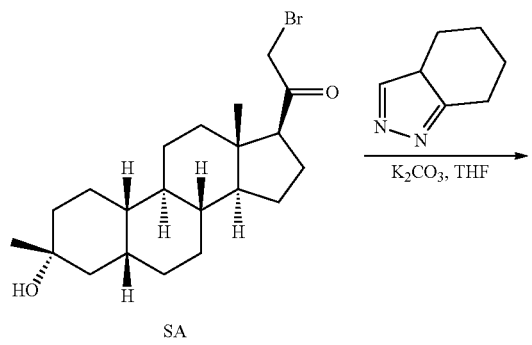

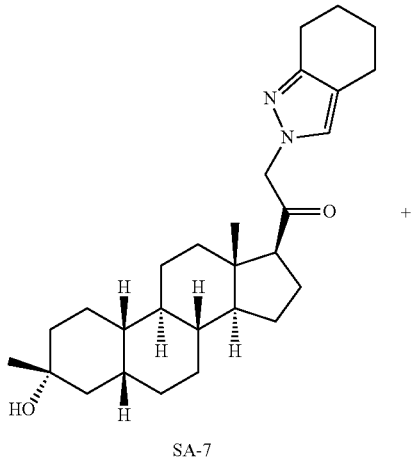

To a suspension of K₂CO₃ (55 mg, 0.4 mmol) in THF (5 mL) was added 4,5,6,7-tetrahydro-3aH-indazole (33 mg, 0.4 mmol) and compound SA (79 mg, 0.2 mmol). The mixture was stirred at RT for 15 h. The residue mixture was poured in to 5 mL H₂O and extracted with EtOAc (2×10 mL). The combined organic layers were washed with brine, dried over sodium sulfate, filtered and concentrated. The residue mixture was purified with by reverse-phase prep-HPLC to afford compound SA-7 as a white solid (9 mg, 10%) and compound SA-8 as a white solid (12 mg, 14%). Compound SA-7: ¹HNMR (400 MHz, CDCl₃), δ (ppm) (400 MHz, CD3OD) δ 7.74 (s, 1H), 5.34-5.19 (m, 2H), 2.80-2.74 (m, 3H), 2.65-2.62 (m, 2H), 2.22-2.11 (m, 2H), 1.92-1.70 (m, 11H), 1.53-1.39 (m, 9H), 1.30-1.15 (m, 8H), 0.92-0.84 (m, 1H), 0.73 (s, 3H). LC/MS: rt=1.33 min; m/z=439.3 [M+H]. Compound SA-8: ¹HNMR (400 MHz, CDCl₃), δ (ppm) (400 MHz, CD3OD) δ 7.57 (s, 1H), 5.14-4.99 (m, 2H), 2.80-2.75 (m, 1H), 2.60-2.48 (m, 4H), 2.22-2.09 (m, 2H), 1.91-1.72 (m, 11H), 1.58-1.39 (m, 9H), 1.32-1.26 (m, 5H), 1.22-1.12 (m, 3H), 0.72 (s, 3H). LC/MS: rt=1.37 min; m/z=439.3 [M+H].

Example 6

Synthesis of Compounds SA-9 and SA-10

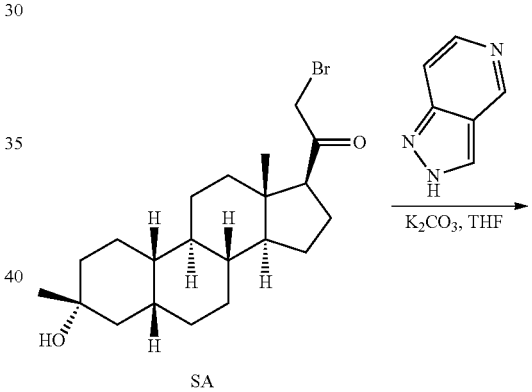

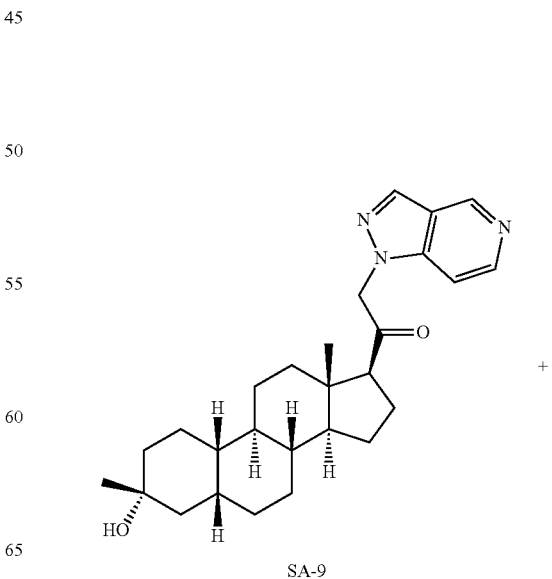

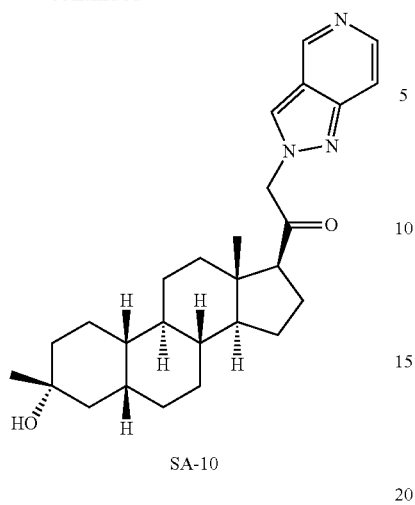

SA-10

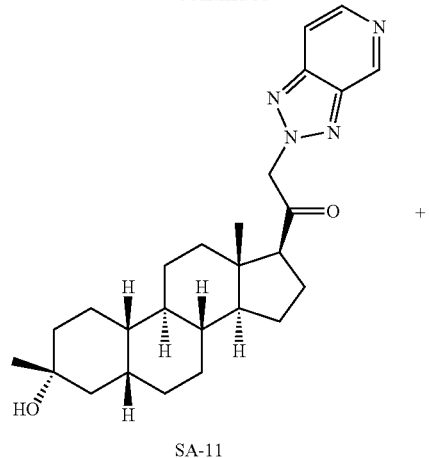

SA-11

To a suspension of $K_2CO_3$ (25 mg, 0.18 mmol) in THF (5 mL) was added 2H-pyrazolo[4,3-c]pyridine (23 mg, 0.18 mmol) and SA (36 mg, 0.09 mmol). The mixture was stirred at RT for 15 h. The residual mixture was poured into 5 mL $H_2O$ and extracted with EtOAc (2×10 mL). The combined organic layers were washed with brine, dried over sodium sulfate, filtered and concentrated. The residual mixture was purified with by reverse-phase prep-HPLC to afford the title compound SA-9 as a white solid (9 mg, 23%) and SA-10 as a white solid (5 mg, 13%). Compound SA-9 $^1$HNMR (400 MHz, CDCl3), δ (ppm), 9.14 (s, 1H), 8.45 (s, 1H), 8.19 (s, 1H), 7.13 (d, 1H), 5.18 (AB, 1H), 5.12 (AB, 1H), 2.67 (t, 1H) 0.72 (s, 3H). LC-MS: rt=2.21 min, m/z=436.3 [M+H]$^+$. Compound SA-10 $^1$HNMR (400 MHz, CDCl$_3$), δ (ppm), 9.19 (s, 1H), 8.28 (d, 1H), 8.15 (s, 1H), 7.53 (d, 1H), 5.29 (AB, 1H), 5.21 (AB, 1H), 2.68 (t, 1H 0.72 (s, 3H). LC-MS: rt=2.16 min, m/z=436.3 [M+H]$^+$ Example 7

Synthesis of Compounds SA-11 and SA-12

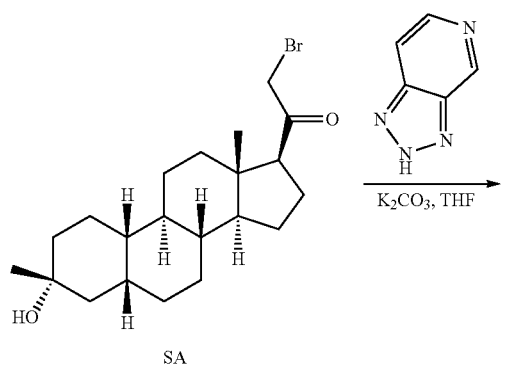

SA-12

To a suspension of $K_2CO_3$ (50 mg, 0.36 mmol) in THF (5 mL) was added 2H-[1,2,3]triazolo[4,5-c]pyridine (46 mg, 0.36 mmol) and SA (72 mg, 0.18 mmol). The mixture was stirred at RT for 15 h. The residual mixture was poured into 5 mL $H_2O$ and extracted with EtOAc (2×10 mL). The combined organic layers were washed with brine, dried over sodium sulfate, filtered and concentrated. The residual mixture was purified with by reverse-phase prep-HPLC to afford the title compound SA-11 as a white solid (23 mg, 29%) and SA-12 as a white solid (15 mg, 19%). Compound SA-11 $^1$HNMR (400 MHz, CDCl$_3$), δ (ppm), 9.46 (s, 1H), 8.47 (d, 1H), 7.76 (dd, 1H), 5.62 (AB, 1H), 5.56 (AB, 1H), 2.69 (t, 1H)0.76 (s, 3H). LC-MS: rt=2.31 min, m/z=437.3 [M+H]$^+$. Compound SA-12 $^1$HNMR (400 MHz, CDCl$_3$), δ (ppm), 9.50 (s, 1H), 8.58 (d, 1H), 7.30 (d, 1H), 5.49 (AB, 1H), 5.41 (AB, 1H), 2.75 (t, 1H) 0.73 (s, 3H). LC-MS: rt=2.24 min, m/z=437.3 [M+H]$^+$.

Example 8

Synthesis of Compounds SA-13, SA-14, and SA-15

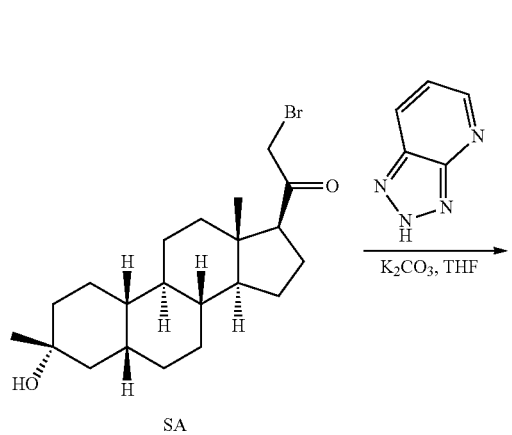

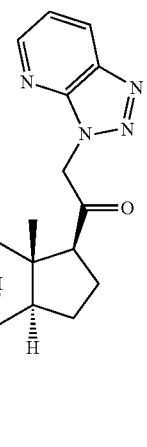

SA-15

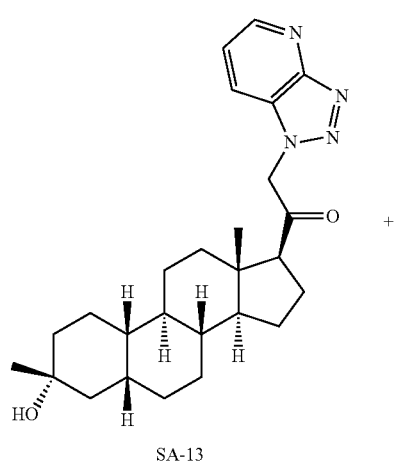

SA-13

To a suspension of K₂CO₃ (50 mg, 0.36 mmol) in THF (5 mL) was added 2H-[1,2,3]triazolo[4,5-b]pyridine (46 mg, 0.36 mmol) and SA (72 mg, 0.18 mmol). The mixture was stirred at RT for 15 h. The residual mixture was poured into 5 mL H₂O and extracted with EtOAc (2×10 mL). The combined organic layers were washed with brine, dried over sodium sulfate, filtered and concentrated. The residual mixture was purified with by reverse-phase prep-HPLC to afford the title compound SA-13 as a white solid (22 mg, 28%) and SA-14 as a white solid (6 mg, 7%) and SA-15 as a white solid (22 mg, 28%). Compound SA-13 $^1$HNMR (400 MHz, CDCl₃), δ (ppm), 8.78 (d, 1H), 7.78 (d, 1H), 7.46 (m, 1H), 5.51 (AB, 1H), 5.42 (AB, 1H), 2.75 (t, 1H) 0.72 (s, 3H). LC-MS: rt=2.21 min, m/z=437.5 [M+H]⁺. Compound SA-14 $^1$HNMR (400 MHz, CDCl₃), δ (ppm), 8.83 (s, 1H), 8.26 (dd, 1H), 7.38 (dd, 1H), 5.60 (AB, 1H), 5.54 (AB, 1H), 2.69 (t, 1H), 0.76 (s, 3H). LC-MS: rt=2.29 min, m/z=437.5 [M+H]⁺. Compound SA-15 $^1$HNMR (400 MHz, CDCl₃), δ (ppm), 8.65 (dd, 1H), 8.41 (dd, 1H), 7.37 (dd, 1H), 5.56 (AB, 1H), 5.50 (AB, 1H), 2.77 (t, 1H) 0.75 (s, 3H). LC-MS: rt=2.32 min, m/z=437.5 [M+H]⁺.

Example 9

Synthesis of Compounds SA-16 and SA-17

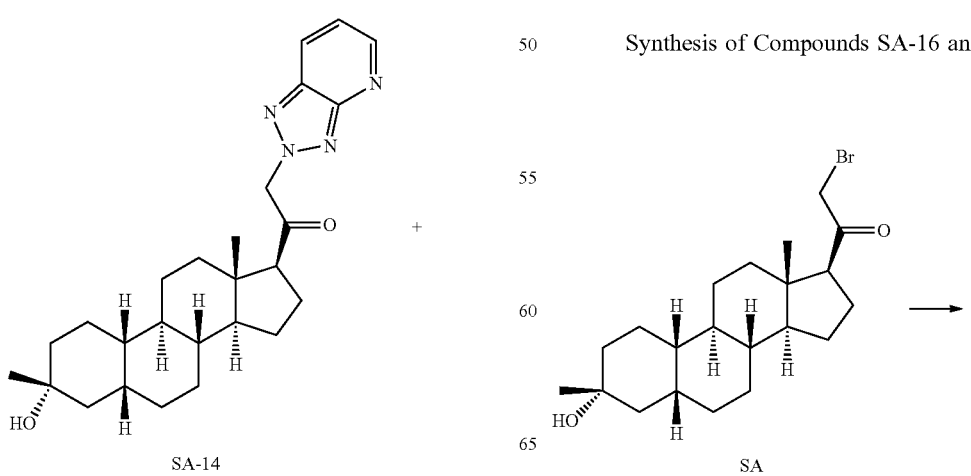

-continued

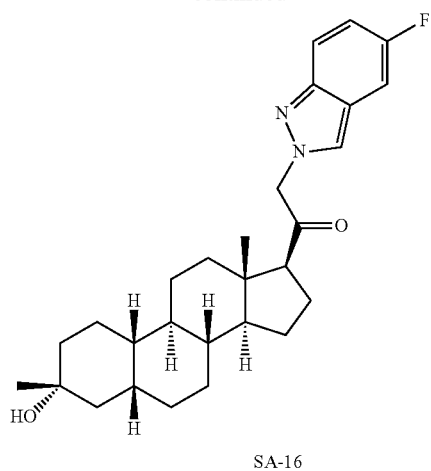

SA-16

SA-17

Example 10

Synthesis of Compounds SA-18 and SA-19

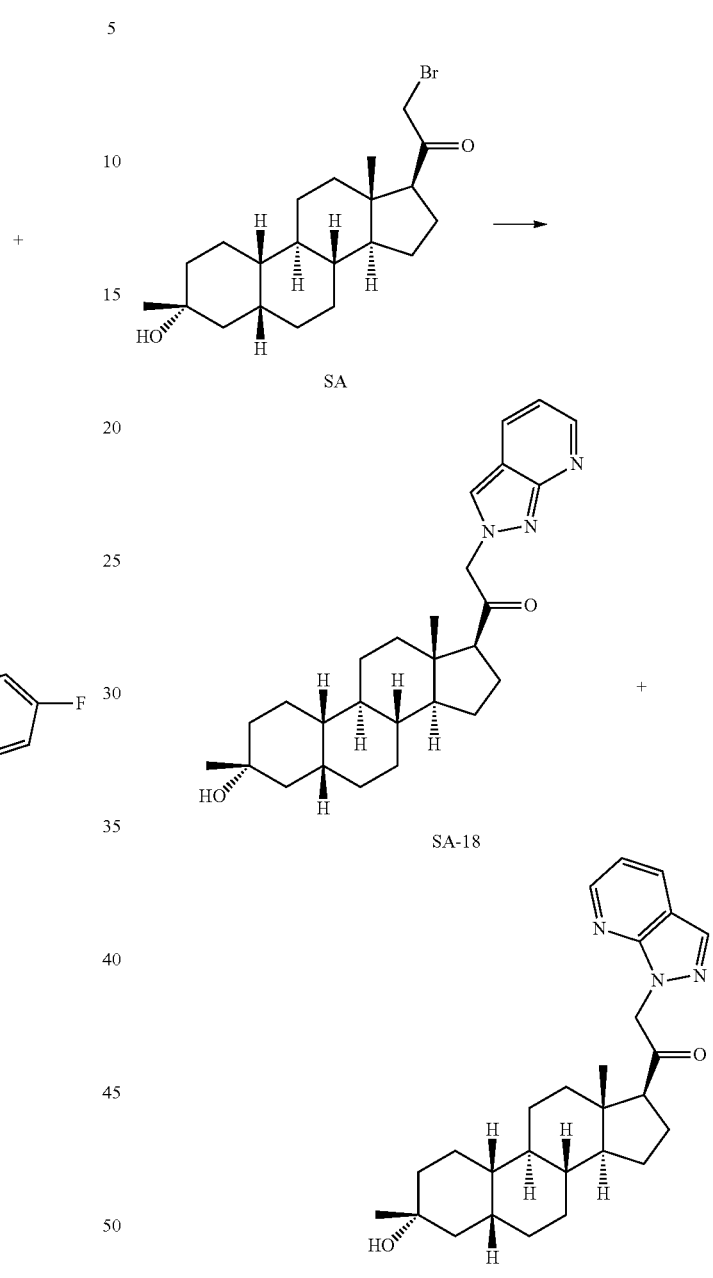

SA-18

SA-19

To a suspension of $K_2CO_3$ (50 mg, 0.36 mmol) in THF (5 mL) was added 5-fluoro-1H-indazole (41 mg, 0.3 mmol) and SA (100 mg, 0.252 mmol). The mixture was stirred at rt for 15 h. The reaction mixture was poured into 5 mL $H_2O$ and extracted with EtOAc (2×10 mL). The combined organic layers were washed with brine, dried over sodium sulfate, filtered and concentrated. The residue was purified with by reverse-phase prep-HPLC to afford the title compound as a white solid SA-16 (8.2 mg, 7.2%), SA-17 (11 mg, 9.6%) SA-16: $^1$HNMR (400 MHz, $CDCl_3$), δ (ppm), 7.89 (s, 1H), 7.63(1H, dd), 7.25(1H, dd), 7.08(1H, td), 5.22(AB1H), 5.15(AB, 1H), 2.64(1H, t)0.71 (s, 3H). SA-17: $^1$HNMR (400 MHz, $CDCl_3$), δ (ppm), 8.00 (s, 1H), 7.37 (d, 1H), 7.16 (d, 2H), 5.15(AB, 1H), 5.10(AB, 1H), 2.63(1H, t)0.71 (s, 3H).

To a suspension of $K_2CO_3$ (50 mg, 0.36 mmol) in THF (6 mL) was added 1H-pyrazolo[3,4-b]pyridine (36 mg, 0.3 mmol) and SA (100 mg, 0.252 mmol). The mixture was stirred at RT for 15 h. The reaction mixture was poured into 5 mL $H_2O$ and extracted with EtOAc (2×10 mL). The combined organic layers were washed with brine, dried over sodium sulfate, filtered and concentrated. The residue was purified with by reverse-phase prep-HPLC to afford the title compound as a white solid SA-18 (30 mg, 25.8%), SA-19 (27 mg, 24.5%). SA-18: $^1$HNMR (400 MHz, $CDCl_3$), δ (ppm), 8.69 (s, 1H), 8.05 (1H, d), 7.97(s, 1H), 7.03 (1H, dd), 5.30 (AB, 1H), 5.19 (AB, 1H), 2.67 (1H, t)0.70 (s, 3H). LC-MS: rt=2.19 min, m/z=436.1 ($M^+$+1). SA-19: $^1$HNMR (400 MHz, CDCl$_3$), δ (ppm) 8.50(1H, dd), 8.08(s, 1H), 8.06 (1H, d), 7.13(1H, dd), 5.32(AB, 1H), 5.29(AB1H), 2.70(1H, t), 0.73 (s, 3H). LC-MS: rt=2.26 min, m/z=436.1 (M$^+$+1).

Example 11

Synthesis of Compounds SA-20 and SA-21

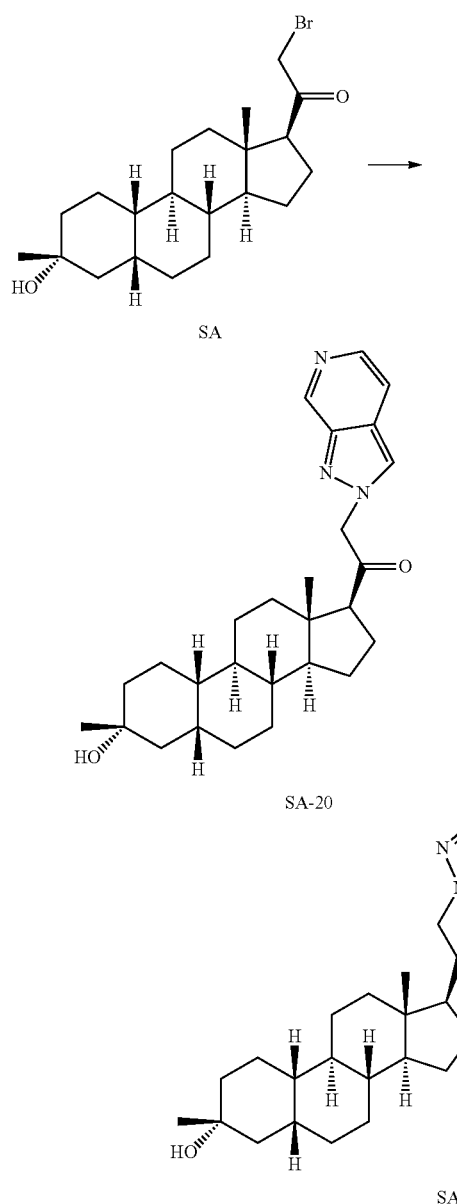

To a suspension of K$_2$CO$_3$ (50 mg, 0.36 mmol) in THF (5 mL) was added 1H-pyrazolo[3,4-c]pyridine (36 mg, 0.3 mmol) and SA (100 mg, 0.25 mmol). The mixture was stirred at rt for 24 h. The reaction mixture was poured in to 5 mL H$_2$O and extracted with EtOAc (2×10 mL). The combined organic layers were washed with brine, dried over sodium sulfate, filtered and concentrated. The residure was purified with by reverse-phase prep-HPLC to afford the title compound as a white solid, SA-20 (10 mg, 9.1%), SA-21 (12 mg, 10.9%), SA-20: $^1$HNMR (400 MHz, CDCl$_3$), δ (ppm),
9.26 (s, 1H), 8.17 (1H, d), 7.98(s, 1H), 7.53(1H, d), 5.29 (AB, 1H), 5.20(AB, 1H), 2.67(1H, t)0.72 (s, 3H). LC-MS: rt=2.19 min, m/z=436.1 (M$^+$+1). SA-21: $^1$HNMR (400 MHz, CDCl$_3$), δ (ppm), 8.80 (s, 1H), 8.33(1H, d), 8.10(s, 1H), 7.65(1H, dd), 5.26(AB, 1H), 5.24(AB, 1H), 2.68(1H, t), 0.72 (s, 3H). LC-MS: rt=2.29 min, m/z=436.2 (M$^+$+1).

Example 12

Synthesis of Compounds SA-22 and SA-23

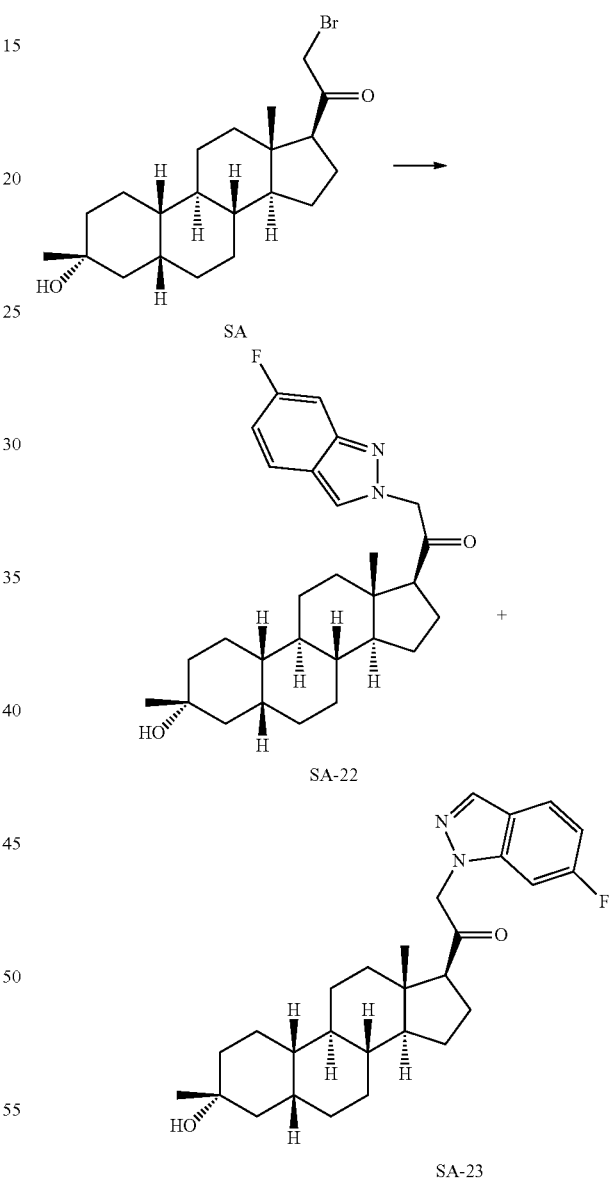

To a suspension of K$_2$CO$_3$ (50 mg, 0.36 mmol) in THF (5 mL) was added 6-fluoro-1H-indazole (41 mg, 0.3 mmol) and 9b (100 mg, 0.09 mmol). The mixture was stirred at rt for 15 h. The reaction mixture was poured into 5 mL H$_2$O and extracted with EtOAc (2×10 mL). The combined organic layers were washed with brine, dried over sodium sulfate, filtered and concentrated. The residue was purified with by reverse-phase prep-HPLC to afford the title compound as a white solid, SA-22 (19 mg, 16.7%) and SA-23 (36 mg, 31.5%). SA-22: ¹HNMR (400 MHz, CDCl₃), δ (ppm), 7.93 (s, 1H), 7.63 (1H, dd), 7.27(1H, d), 6.90(1H, t), 5.20(AB, 1H), 5.15(AB, 1H), 2.20 (1H, t), 1.27(s, 3H), 0.70 (s, 3H). LC-MS: rt=2.42 min, m/z=453.1 (M⁺+1). SA-23: ¹HNMR (400 MHz, CDCl₃), δ (ppm), 8.01 (s, 1H), 7.68(1H, t), 6.93 (1H, t), 6.85 (1H, d), 5.10(AB, 1H), 5.05(AB, 1H), 2.63(1H, t), 0.71 (s, 3H). LC-MS: rt=2.47 min, m/z=453.1 (M⁺+1).

Example 13

Synthesis of Compound SA-24 and SA-25

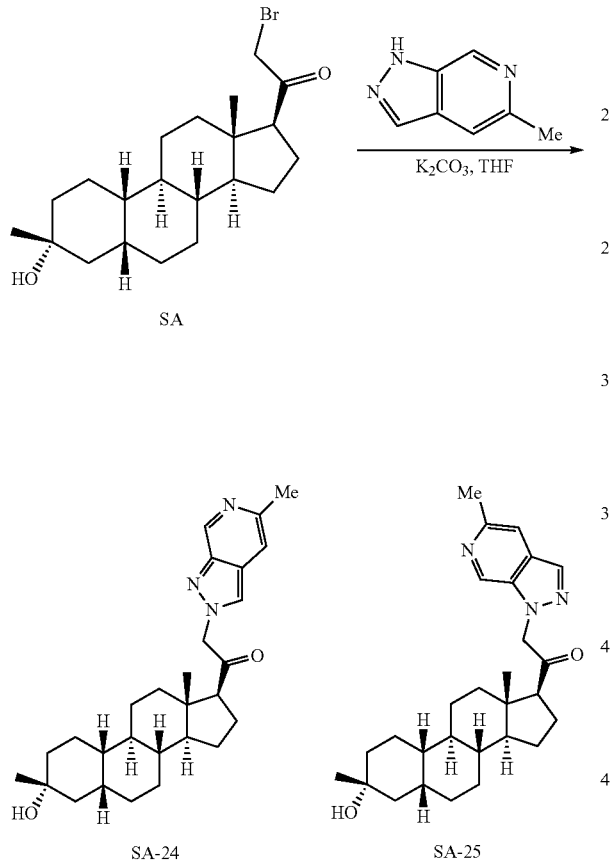

To a solution of the crude reactant SA (249.5 mg, 0.629 mmol, theoretical amount) in anhydrous THF (5 mL) was added 5-methyl-1H-pyrazolo{3,4-c]pyridine (168 mg, 1.258 mmol) followed by potassium carbonate (174 mg, 1.258 mmol) and the solution was stirred at 25° C. overnight. Then the reaction mixture was diluted with ethyl acetate (200 mL) and the resulting solution was washed with brine (2×100 mL), dried over magnesium sulfate and concentrated in vacuo. The crude product was purified by reverse phase prep-HPLC to afford product SA-24 (5 mg, 0.0106 mmol, Yield=1.7% (2 steps)) and product SA-25 (6 mg, 0.0128 mmol, Yield=2.1% (2 steps)) as white solid. Compound SA-24: ¹H NMR (400 MHz, CDCl₃) δ (ppm): 9.19 (1H, s), 7.86 (1H, s), 7.32 (1H, s), 5.28 (1H, AB), 5.19 (1H, AB), 2.66 (1H, t), 2.61 (3H, s), 0.72 (3H, s). LCMS: rt=2.31 min, m/z=450.2 [M+H]⁺ Compound SA-25: ¹H NMR (400 MHz, CDCl₃) δ (ppm): 8.67 (1H, s), 8.00 (1H, s), 7.45 (1H, s), 5.22 (1H, AB), 5.21 (1H, AB), 2.67 (1H, t), 2.66 (3H, s) 0.72 (3H, s). LCMS: rt=2.38 min, m/z=450.2 [M+H]⁺

Example 14. Synthesis of SA-26 and SA-27

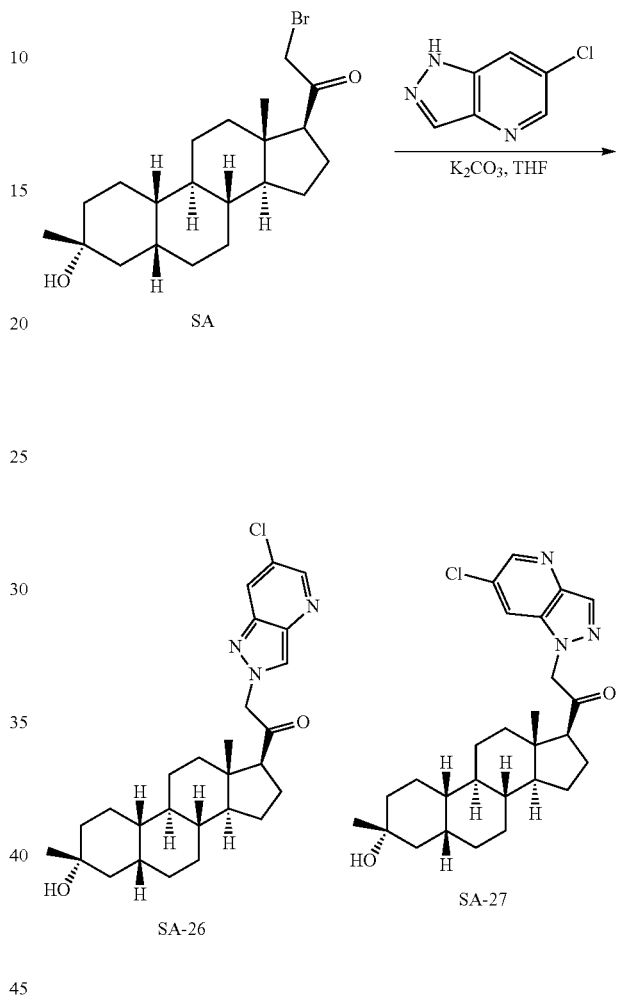

To a solution of the crude reactant SA (249.5 mg, 0.629 mmol, theoretical amount) in anhydrous THF (5 mL) was added 6-chloro-1H-pyrazolo[4,3-b]pyridine (192 mg, 1.256 mmol) followed by potassium carbonate (174 mg, 1.256 mmol) and this solution was stirred at 25° C. overnight. Then the reaction mixture was diluted with ethyl acetate (200 mL) and the resulting solution was washed with brine (2×100 mL), dried over magnesium sulfate and concentrated in vacuo. The crude product was purified by reverse phase prep-HPLC to afford product SA-26 (10 mg, 0.0213 mmol, Yield=3.4% (2 steps)) and product SA-27 (14 mg, 0.0298 mmol, Yield=4.8% (2 steps)) as white solid. Compound SA-26: ¹H NMR (400 MHz, CDCl₃) δ (ppm): 8.49 (1H, d), 8.20 (1H, s), 8.01 (1H, d), 5.26 (1H, AB), 5.17 (1H, AB), 2.66 (1H, t), 0.72 (3H, s). LCMS: rt=2.47 min, m/z=470.1 [M+H]⁺ Compound SA-27: ¹H NMR (400 MHz, CDCl₃) δ (ppm): 8.52 (1H, s), 8.24 (1H, d), 7.57 (1H, dd), 5.16 (1H, AB), 5.09 (1H, AB), 2.68 (1H, t), 0.72 (3H, s). LCMS: rt=2.50 min, m/z=470.1 [M+H]⁺

Example 15

Synthesis of Compound SA-28 and SA-29

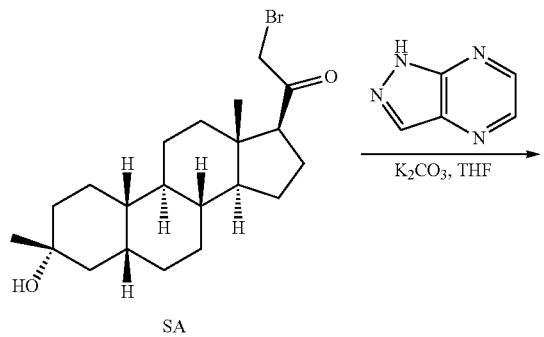
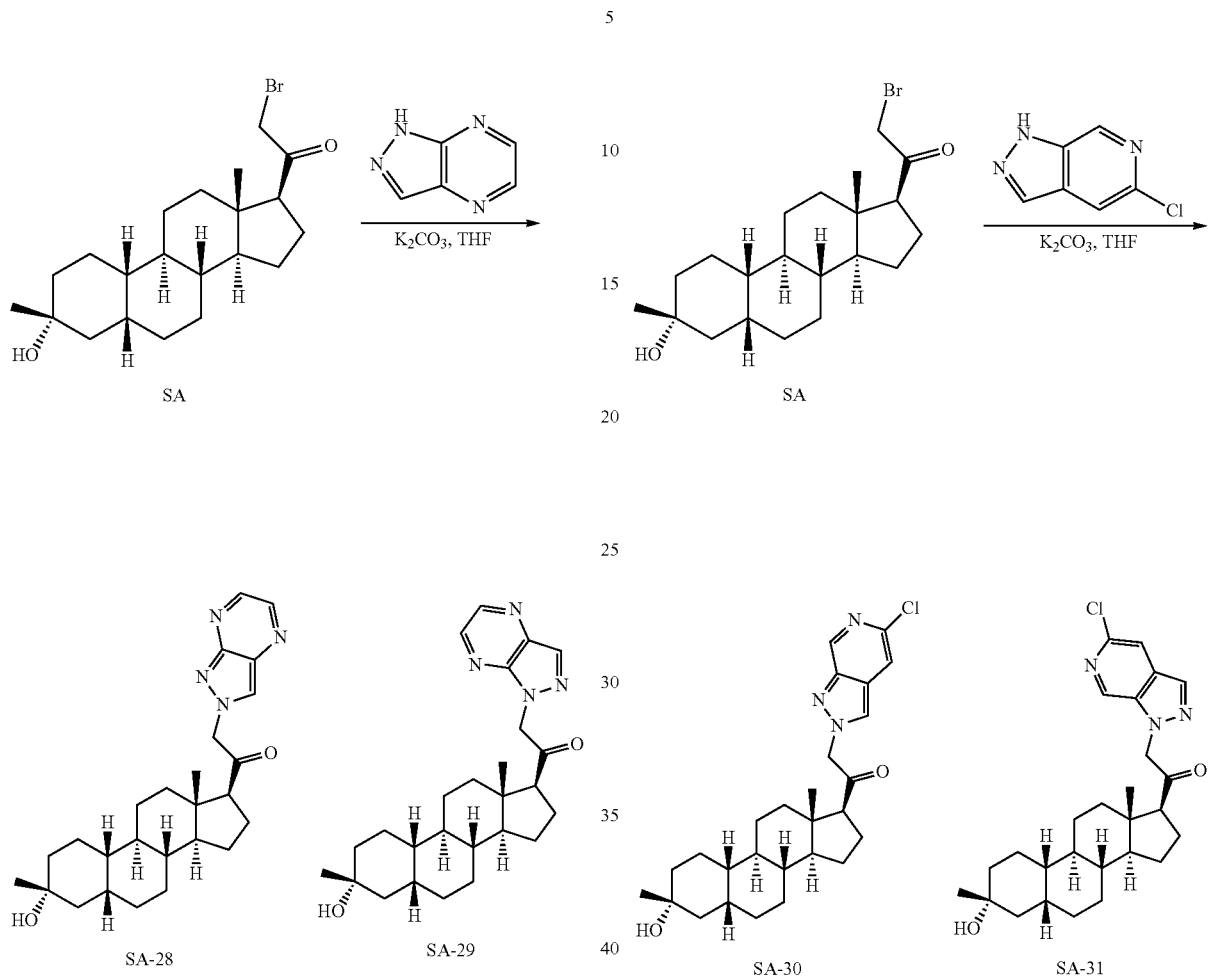

Example 16

Synthesis of Compound SA-30 and SA-31

To a solution of the crude reactant SA (249.5 mg, 0.629 mmol, theoretical amount) in anhydrous THF (5 mL) was added 1H-pyrazolo[3,4-b]pyrazine (151 mg, 1.256 mmol) followed by potassium carbonate (174 mg, 1.256 mmol) and the resulting solution was stirred at 25° C. overnight. Then the solution was diluted with ethyl acetate (200 mL) and the resulting solution was washed with brine (2×100 mL), dried over magnesium sulfate and concentrated in vacuo. The crude product was purified by reverse phase prep-HPLC to afford product SA-28 (17.3 mg, 0.0396 mmol, Yield=6.3% (2 steps)) and product SA-29 (67.5 mg, 0.155 mmol, Yield=25% (2 steps)) as white solid. Compound SA-28: $^1$H NMR (400 MHz, CDCl$_3$) δ (ppm): 8.64 (1H, d), 8.56 (1H, d), 8.27 (1H, s), 5.35 (1H, AB), 5.23 (1H, AB), 2.70 (1H, t0.72 (3H, s). LCMS: rt=2.22 min, m/z=437.2 [M+H]$^+$ Compound SA-29: $^1$H NMR (400 MHz, CDCl$_3$) δ (ppm): 8.59 (1H, d), 8.44 (1H, d), 8.34 (1H, s), 5.34 (1H, AB), 5.28 (1H, AB), 2.71 (1H, t), 0.73 (3H, s). LCMS: rt=2.37 min, m/z=437.2 [M+H]$^+$ To a solution of the crude reactant SA (249.5 mg, 0.629 mmol, theoretical amount) in anhydrous THF (5 mL) was added 5-chloro-1H-pyrazolo[3,4-c]pyridine (192 mg, 1.256 mmol) followed by potassium carbonate (174 mg, 1.256 mmol) and the resulting solution was stirred at 25° C. overnight. Then the solution was diluted with ethyl acetate (200 mL) and the resulting solution was washed with brine (2×100 mL), dried over magnesium sulfate and concentrated in vacuo. The crude product was purified by reverse phase prep-HPLC to afford fraction 1 and 2. Fraction 1 was pure product SA-30 (10.4 mg, 0.0221 mmol, Yield=3.5% (2 steps)) as white solid. Fraction 2 was not pure and had to be purified by silica gel chromatography (eluant: petroleum ether/ethyl acetate=2:3) to afford pure product SA-31 (12.2 mg, 0.026 mmol, Yield=4.1% (2 steps)) as a white solid. Compound SA-30: $^1$H NMR (400 MHz, CDCl$_3$) δ (ppm): 9.06 (1H, s), 7.95 (1H, s), 7.59 (1H, d), 5.31 (1H, AB), 5.22 (1H, AB), 2.68 (1H, t), 0.72 (3H, s). LCMS: rt=2.42 min, m/z=470.1 [M+H]$^+$ Compound SA-31: $^1$H NMR (400 MHz, CDCl$_3$) δ (ppm): 8.55 (1H, s), 8.05 (1H, d), 7.67 (1H, d), 5.24 (1H, AB), 5.22 (1H, AB), 2.68 (1H, t), 0.71 (3H, s). LCMS: rt=2.47 min, m/z=470.1 [M+H]$^+$.

Example 17

Synthesis of SA-32, SA-33, and SA-34

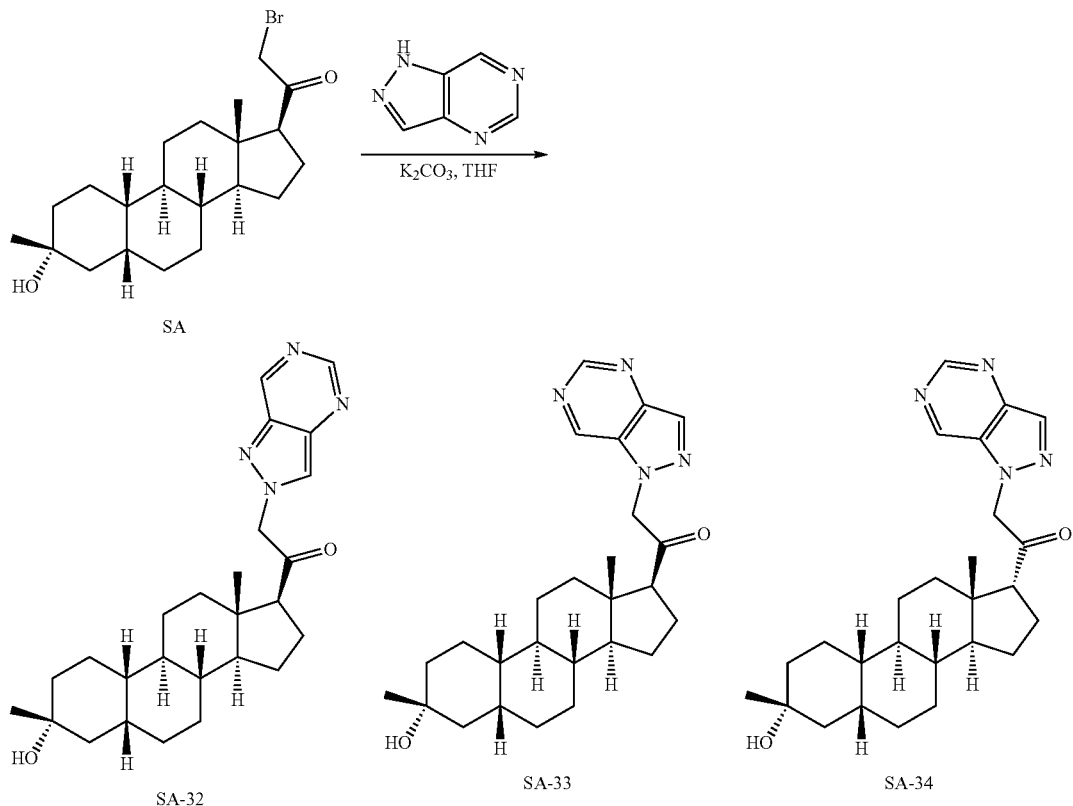

Synthesis of 1H-pyrazolo[4,3-d]pyrimidine

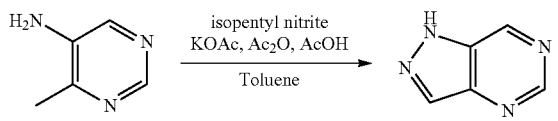

To a solution of the reactant (109 mg, 1.0 mmol) in toluene (1.5 mL) was added acetic anhydride (0.2 mL, 2.10 mmol), acetic acid (0.2 mL, 3.5 mmol) followed by potassium acetate (196 mg, 2.0 mmol). The mixture was heated to reflux and isopentyl nitrire (0.168 mL, 1.25 mmol) in toluene (0.3 mL) was added. After 2 hours, the mixture was poured into water (20 mL). The solution was made basic by addition of Na₂CO₃ solid. The solution was extracted with ethyl acetate (2×50 mL) and the combined organic extracts were washed with brine (50 mL), dried over magnesium sulfate and concentrated in vacuo. The residue was purified by silica gel chromatography (eluant: petroleum ether: ethyl acetate=1:2) to afford product product (32 mg, 0.266 mmol, Yield=27%) as yellow solid. $^1$H NMR (400 MHz, d6-DMSO) δ (ppm): 13.91 (1H, br), 9.35 (1H, s), 9.04 (1H, s), 8.45 (1H, s).

Synthesis of SA-32, SA-33, and SA-34. To a solution of the crude reactant (249.5 mg, 0.629 mmol, theoretical amount) in anhydrous THF (5 mL) was added 1H-pyrazolo [4,3-d]pyrimidine (151 mg, 1.256 mmol) followed by potassium carbonate (174 mg, 1.256 mmol) and the resulting solution was stirred at 25° C. overnight. Then the solution was diluted with ethyl acetate (200 mL) and the resulting solution was washed with brine (2×100 mL), dried over magnesium sulfate and concentrated in vacuo. The crude product was purified by reverse phase prep-HPLC to afford fraction 1, 2, and 3. Fraction 1 was not pure and had to be re-purified by silica gel chromatography (eluant: ethyl acetate) to afford product SA-32 (10.0 mg, 0.0229 mmol, Yield=3.6% (2 steps)).

Fraction was pure product SA-33 (56.8 mg, 0.130 mmol, Yield=21% (2 steps)). Fraction 3 was pure by-product SA-34 (7.3 mg, 0.0167 mmol, Yield=2.7% (2 steps)). All products was a white solid. Compound SA-32: $^1$H NMR (400 MHz, CDCl₃) δ (ppm): 9.43 (1H, s), 9.06 (1H, s), 8.22 (1H, s), 5.35 (1H, AB), 5.26 (1H, AB), 2.69 (1H, t), 0.73 (3H, s). LCMS: rt=2.10 min, m/z=437.1 [M+H]⁺ Compound SA-33: $^1$H NMR (500 MHz, CDCl₃) δ (ppm): 9.14 (1H, s), 8.96 (1H, s), 8.30 (1H, s), 5.29 (1H, AB), 5.22 (1H, AB), 2.71 (1H, t), 0.72 (3H, s). LCMS: rt=2.18 min, m/z=437.1 [M+H]⁺ Compound SA-34: $^1$H NMR (500 MHz, CDCl₃) δ (ppm): 9.15 (1H, s), 8.98 (1H, s), 8.32 (1H, s), 5.35 (1H, AB), 5.19 (1H, AB), 2.89 (1H, dd), 0.99 (3H, s). LCMS: rt=2.24 min, m/z=437.1 [M+H]⁺

Example 18

Synthesis of Compound SA-35 and SA-36

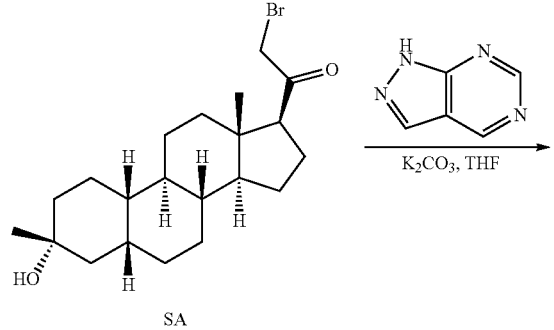

To a solution of the crude reactant SA (249.5 mg, 0.629 mmol, theoretical amount) in anhydrous THF (5 mL) was added 1H-pyrazolo[3,4-d]pyrimidine (151 mg, 1.256 mmol) followed by potassium carbonate (174 mg, 1.256 mmol) and the resulting solution was stirred at 25° C. overnight. Then the solution was diluted with ethyl acetate (200 mL) and the resulting solution was washed with brine (2×100 mL), dried over magnesium sulfate and concentrated in vacuo. The crude product was purified by reverse phase prep-HPLC to afford product SA-35 (21.7 mg, 0.0497 mmol, Yield=7.9% (2 steps)) and product SA-36 (59.4 mg, 0.136 mmol, Yield=22% (2 steps)) as white solid. Compound SA-35: $^1$H NMR (500 MHz, CDCl$_3$) δ (ppm): 9.37 (1H, s), 9.11 (1H, s), 8.17 (1H, s), 5.35 (1H, AB), 5.22 (1H, AB), 2.71 (1H, t1.28 (3H, s), 0.71 (3H, s). LCMS: rt=2.04 min, m/z=437.1 [M+H]$^+$ Compound SA-36: $^1$H NMR (500 MHz, CDCl$_3$) δ (ppm): 9.21 (1H, s), 9.00 (1H, s), 8.20 (1H, s), 5.32 (1H, AB), 5.27 (1H, AB), 2.71 (1H, t), 0.73 (3H, s). LCMS: rt=2.20 min, m/z=437.1 [M+H]$^+$

Example 19

Synthesis of Compound SA-37 and SA-38

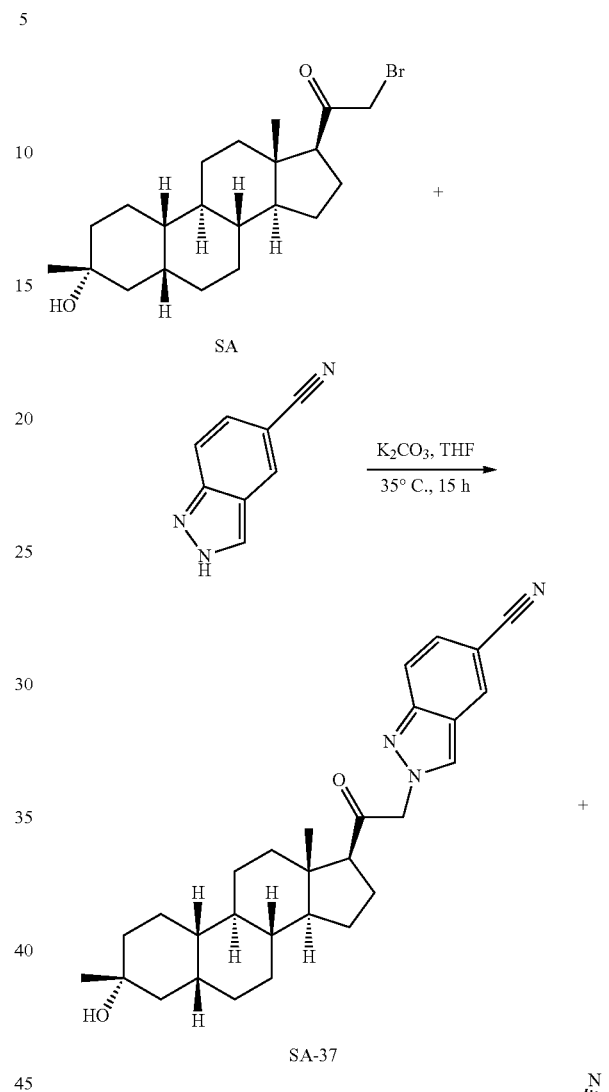

To a suspension of SA (100 mg, 0.25 mmol) in THF (25 mL) was added 2H-indazole-5-carbonitrile (107 mg, 0.75 mmol) and K₂CO₃ (103 mg, 0.75 mmol). The mixture was stirred at 35° C. for 15 h. Then the reaction mixture was was poured into ice-cold water and extracted with EtOAc (100 mL×3), washed with brine (100 mL×3), dried (MgSO₄), filtered, and evaporated in vacuo, then purified with by reverse-phase prep-HPLC to afford SA-37 as a white solid (21 mg, 17% yield) and SA-38 as a white solid (28 mg, 23% yield). SA-37: ¹H NMR (500 MHz, CDCl₃), δ (ppm), 8.14 (s, 1H), 8.11 (s, 1H), 7.75 (dd, 1H), 7.39 (d, 1H), 5.28 (1H, AB), 5.20 (1H, AB), 2.67 (t, 1H), 1.27 (s, 3H), 0.71 (s, 3H) LCMS: Rt=2,340 min, MS (ESI) m/z: 460 [M+H]⁺. SA-38: ¹H NMR (500 MHz, CDCl₃), δ (ppm), 8.14 (s, 2H), 7.57 (d, 1H), 7.28 (d, 1H), 5.21 (1H, AB), 5.15 (1H, AB), 2.67 (t, 1H), 0.71 (s, 31-1). Rt=2.372 min, MS (ESI) m/z: 460 [M+H]⁺.

Example 20

Synthesis of Compound SA-39 and SA-40 and SA-41

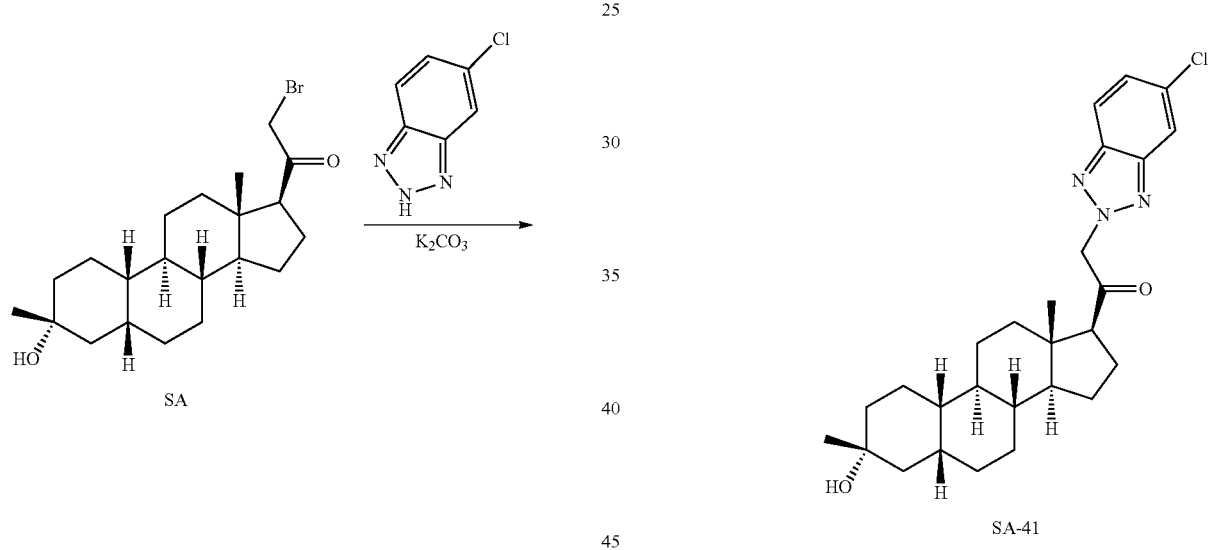

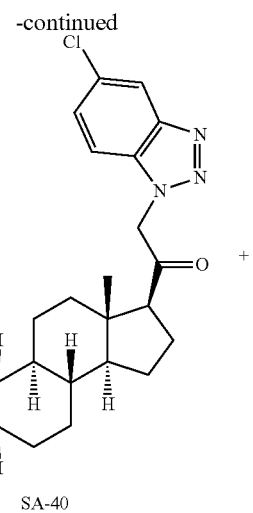

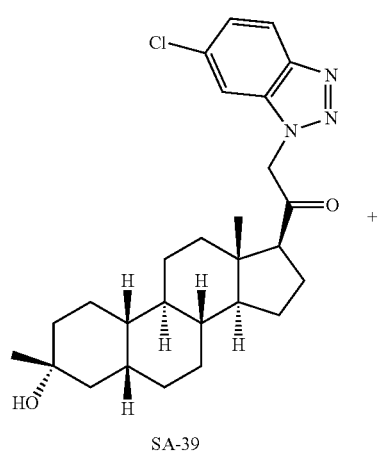

To a suspension of K₂CO₃ (55 mg, 0.4 mmol) in THF (5 mL) was added 5-chloro-2H-benzo[d][1,2,3]triazole (61 mg, 0.4 mmol) and Compound SA (85 mg, 0.2 mmol). The mixture was stirred at RT for 15 h then the residue mixture was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-39 as a white solid (8 mg, 9%) and SA-40 as a white solid (7 mg, 8%) and SA-41 as a white solid (4 mg, 5%). Compound SA-39: ¹H NMR (400 MHz, CDCl₃) δ (ppm): 8.06 (d, 1H), 7.45 (m, 2H5.44 (AB, 1H), 5.37 (AB, 1H), 2.72 (t, 1H), 0.72 (s, 3H). LC-MS: rt=2.47 min, m/z=470.4 [M+H]⁺ Compound SA-40: ¹H NMR (400 MHz, CDCl₃) δ (ppm): 8.00 (s 1H), 7.46 (d, 1H), 7.29 (d, 1H), 5.43 (AB, 1H), 5.34 (AB, 1H), 2.73 (t, 1H), 0.73 (s, 3H). LC-MS: rt=2.48 min, m/z=470.4 [M+H]⁺ Compound SA-41: ¹H NMR (500 MHz, CDCl₃) δ (ppm): 7.87 (d, 1H), 7.82 (dd, 1H), 7.35 (dd, 1H), 5.53 (AB, 1H), 5.48 (AB, 1H), 2.66 (t, 1H), 0.74 (s, 3H). LC-MS: rt=2.61 min, m/z=470.1 [M+H]⁺.

Example 21

Synthesis of Compound SA-42 and SA-43 and SA-44

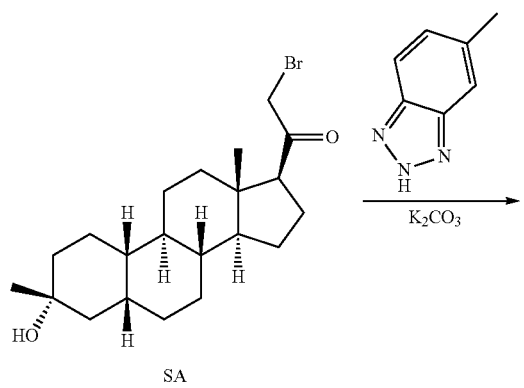

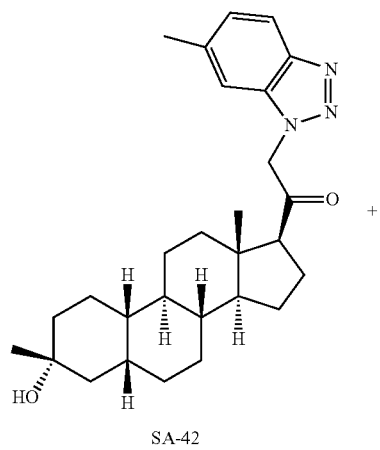

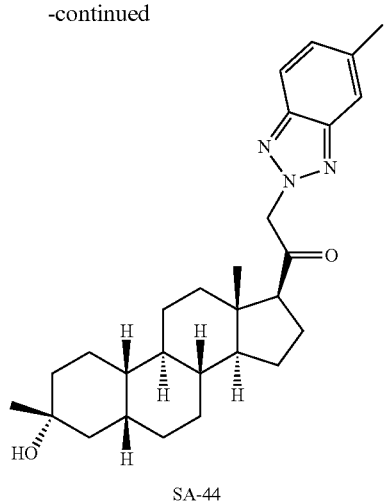

To a suspension of K$_2$CO$_3$ (83 mg, 0.6 mmol) in THF (5 mL) was added 5-methyl-2H-benzo[d][1,2,3]triazole (80 mg, 0.6 mmol) and Compound SA (118 mg, 0.3 mmol). The mixture was stirred at RT for 15 h then the residue mixture was poured into 5 mL H$_2$O and extracted with EtOAc (2×20 mL). The combined organic layers were washed with brine, dried over sodium sulfate, filtered and concentrated. The residue mixture was purified by reverse-phase prep-HPLC to afford SA-42 as a white solid (19 mg, 14%) and SA-43 as a white solid (13 mg, 10%) and SA-44 as a white solid (5 mg, 5%). Compound SA-42: $^1$H NMR (500 MHz, CDCl$_3$) δ (ppm): 7.93 (d, 1H), 7.19 (dd, 1H), 7.08 (s, 1H), 5.38 (AB, 1H), 5.33 (AB, 1H), 2.70 (t, 1H), 2.50 (s, 3H)0.73 (s, 3H). LC-MS: rt=2.39 min, m/z=450.4 [M+H]$^+$ Compound SA-43: $^1$H NMR (500 MHz, CDCl$_3$) δ (ppm): 7.82 (s, 1H), 7.31 (dd, 1H), 7.21 (d, 1H), 5.38 (AB, 1H), 5.35 (AB, 1H), 2.68 (t, 1H), 2.51 (s, 3H), 0.73 (s, 3H). LC-MS: rt=2.39 min, m/z=450.4 [M+H]$^+$ Compound SA-44: $^1$H NMR (500 MHz, CDCl$_3$) δ (ppm): 7.75 (d, 1H), 7.60(s, 1H), 7.22 (d, 1H), 5.48 (AB, 1H), 5.46 (AB, 1H), 2.63 (t, 1H), 0.74 (s, 3H). LC-MS: rt=2.51 min, m/z=450.4 [M+H].

Example 22

Synthesis of Compound SA-45 and SA-46

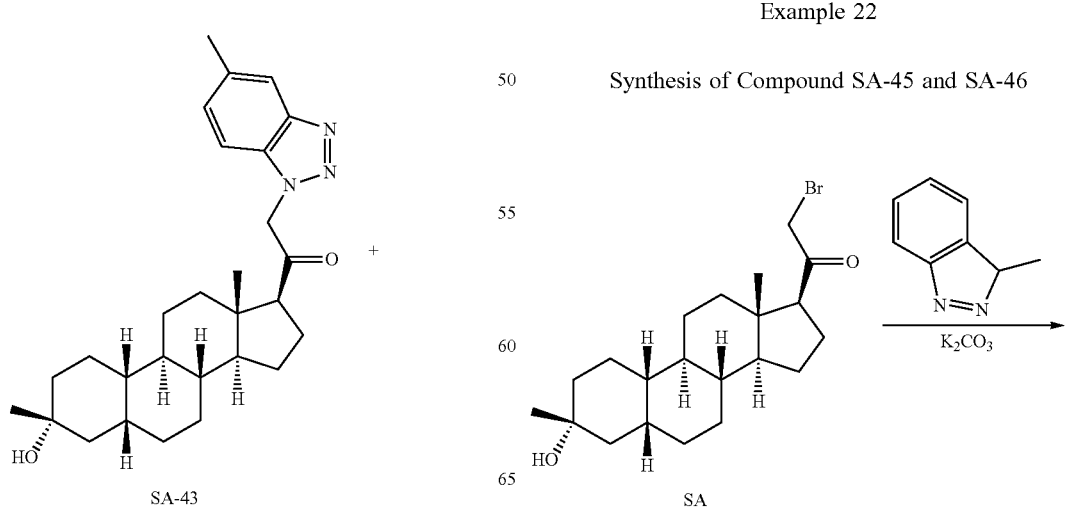

127

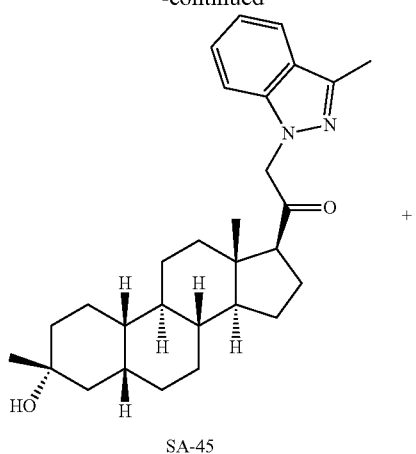

SA-45

+

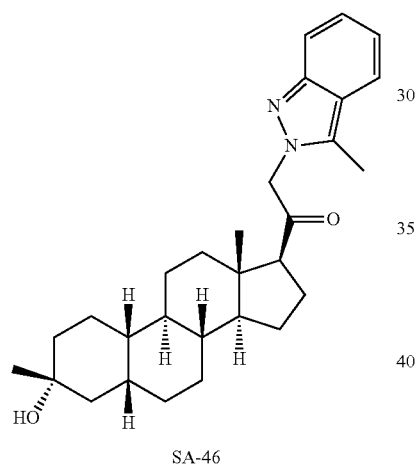

SA-46

To a suspension of $K_2CO_3$ (55 mg, 0.4 mmol) in THF (5 mL) was added 3-methyl-3H-indazole (53 mg, 0.4 mmol) and Compound SA (85 mg, 0.2 mmol). The mixture was stirred at RT for 15 h, then the residue mixture was poured into 5 mL $H_2O$ and extracted with EtOAc (2×10 mL). The combined organic layers were washed with brine, dried over sodium sulfate, filtered and concentrated. The residue mixture was purified by reverse-phase prep-HPLC to afford SA-45 as a white solid (23 mg, 26%) and SA-46 as a white solid (5 mg, 6%). Compound SA-45: $^1$H NMR (500 MHz, $CDCl_3$) δ (ppm): 7.66 (d, 1H), 7.35 (td, 1H), 7.26 (m, 1H), 7.02 (m, 1H), 5.05 (s, 2H), 2.63 (t, 1H), 2.57 (s, 3H 0.72 (s, 3H). LC-MS: rt=2.51 min, m/z=449.2 [M+H]$^+$ Compound SA-46: $^1$H NMR (500 MHz, $CDCl_3$) δ (ppm): 7.60 (d, 1H), 7.56 (d, 1H), 7.24 (dd, 1H), 7.02 (t, 1H), 5.16 (s, 2H), 2.66 (t, 1H), 2.50 (s, 3H), 0.73 (s, 3H). LC-MS: rt=2.45 min, m/z=449.3 [M+H]$^+$

128

Example 23

Synthesis of Compound SA-47, SA-48 and SA-49

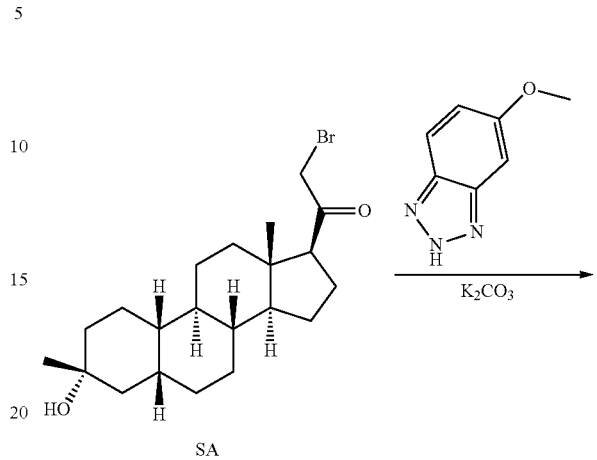

SA $\xrightarrow{K_2CO_3}$

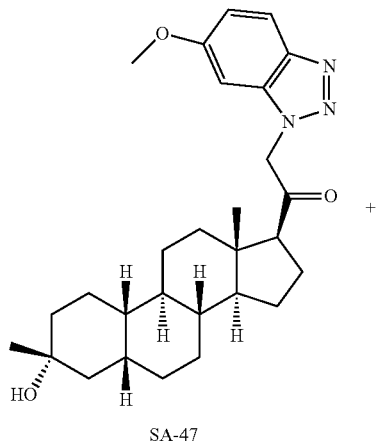

SA-47

+

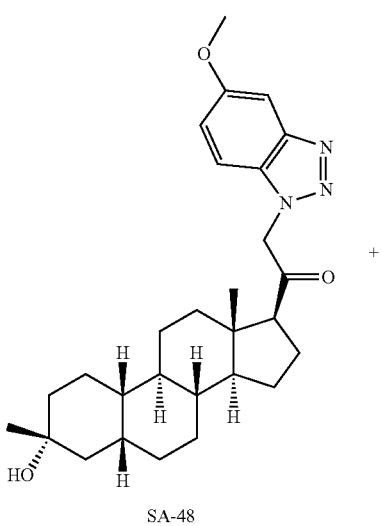

SA-48

-continued

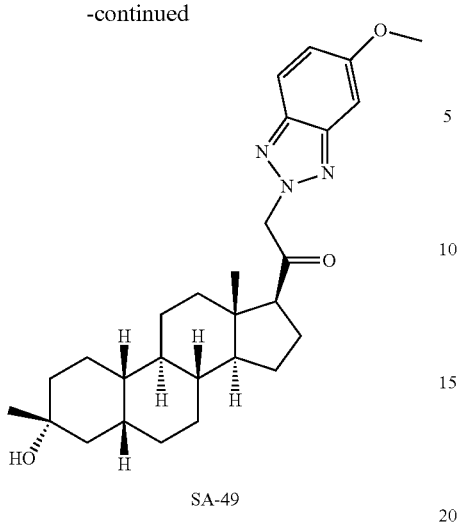

SA-49

-continued

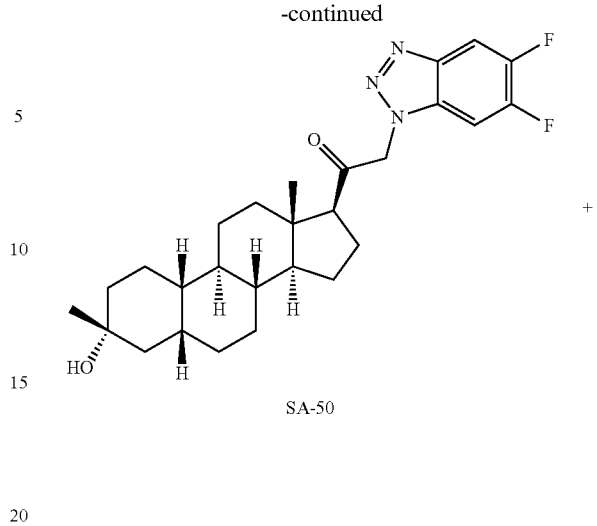

SA-50

To a suspension of $K_2CO_3$ (83 mg, 0.6 mmol) in THF (5 mL) was added 5-methoxy-2H-benzo[d][1,2,3]triazole (89 mg, 0.6 mmol) and Compound SA (118 mg, 0.3 mmol). The mixture was stirred at RT for 15 h. The residue mixture was poured into 5 mL $H_2O$ and extracted with EtOAc (2×20 mL). The combined organic layers were washed with brine, dried over sodium sulfate, filtered and concentrated. The residue mixture was purified by reverse-phase prep-HPLC to afford SA-47 as a white solid (34 mg, 24%) and SA-48 as a white solid (25 mg, 18%) and SA-49 as a white solid (22 mg, 16%). Compound SA-47: $^1H$ NMR (400 MHz, $CDCl_3$) δ (ppm): 7.88 (d, 1H), 6.98 (dd, 1H), 6.58 (d, 1H), 5.34 (AB, 1H), 5.28 (AB, 1H), 3.82 (s, 3H), 2.67 (t, 1H0.69 (s, 3H). LC-MS: rt=2.39 min, m/z=466.2 $[M+H]^+$ Compound SA-48: $^1H$ NMR (400 MHz, $CDCl_3$) δ (ppm): 7.38 (d, 1H), 7.21 (d, 1H), 7.15 (dd, 1H), 5.39 (AB, 1H), 5.34 (AB, 1H), 3.89 (s, 3H), 2.69 (t, 1H), 0.72 (s, 3H). LC-MS: rt=2.39 min, m/z=466.2 $[M+H]^+$ Compound SA-49: $^1H$ NMR (400 MHz, $CDCl_3$) δ (ppm): 7.73 (dd, 1H), 7.08-7.05 (m, 2H), 5.47 (AB, 1H), 5.42 (AB, 1H), 3.87 (s, 3H), 2.63 (t, 1H), 0.74 (s, 3H). LC-MS: rt=2.49 min, m/z=466.2 $[M+H]^+$ Example 24

Synthesis of Compound SA-50 and SA-51

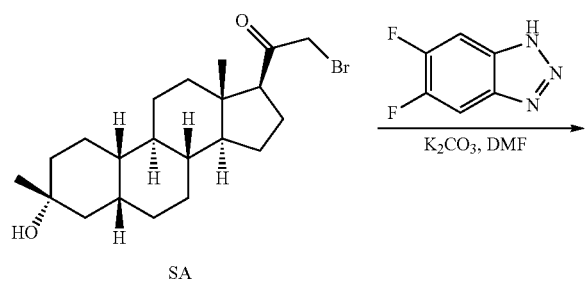

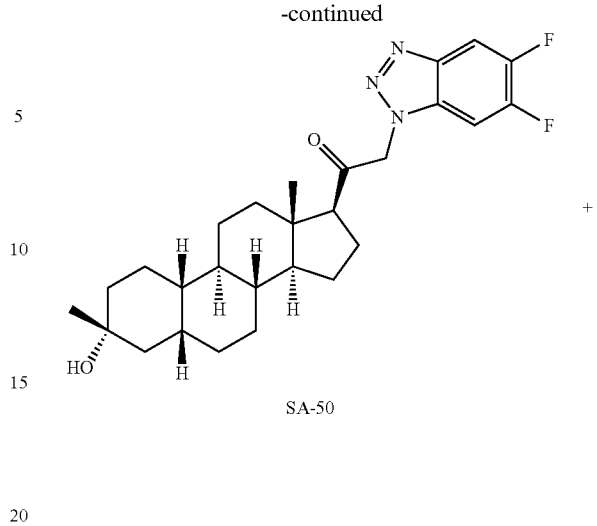

SA-51

To a solution of compound SA (100 mg, 0.252 mmol) and $K_2CO_3$ (75.6 mg, 0.504 mmol) in 10 mL dry DMF was added 5,6-difluoro-1H-benzo[d][1,2,3]triazole (78.0 mg, 0.504 mmol) under $N_2$ at room temperature (18-22° C.). The reaction mixture was stirred for 18 hr at this temperature. The reaction mixture was poured to water and extracted with EtOAc (30 mL×2). The combined organic layers were washed with brine, dried over anhydrous $Na_2SO_4$, filtered and concentrated. The residue was purified by prep-HPLC ($HCl/H_2O/CH_3CN$) to give the target compound SA-50 (25.0 mg, yield: 14%) and SA-51 (87.9 mg, yield: 49%) as off-white solid. $^1H$ NMR (SA-50): (400 MHz, $CDCl_3$) δ 7.62-7.58 (m, 2H), 5.53-5.43 (m, 2H), 2.68-2.64 (m, 1H), 2.24-2.12 (m, 2H), 1.89-1.75 (m, 6H), 1.50-1.40 (m, 7H), 1.37-1.28 (m, 9H), 1.19-1.10 (m, 3H), 0.74 (s, 3H). LC-MS: rt=1.36 min, m/z=472.2 $[M+H]^+$. $^1H$ NMR (SA-51): (400 MHz, $CDCl_3$) δ 7.85-7.81 (m, 1H), 7.15-7.11 (m, 1H), 5.45-5.32 (m, 2H), 2.75-2.70 (m, 1H), 2.24-2.13 (m, 2H), 1.89-1.75 (m, 6H), 1.69-1.57 (m, 3H), 1.48-1.25 (m, 13H), 1.21-1.10 (m, 3H), 0.73 (s, 3H). LC-MS: rt=1.42 min, m/z=472.3 $[M+H]^+$

131

Synthesis of Compound A3

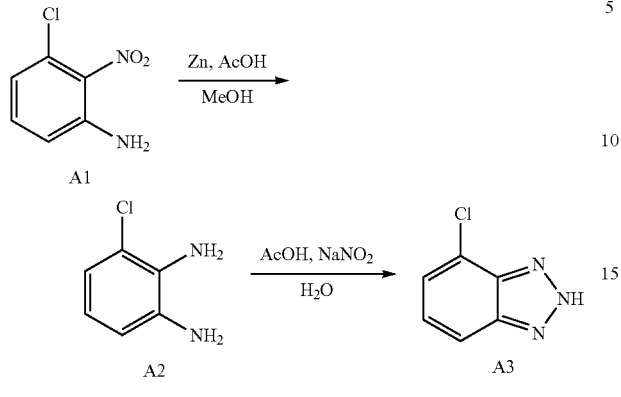

Synthesis of compound A2. To a solution of compound A1 (2.0 g, 11.6 mmol) and Zn powder (7.6 g, 116 mmol) in MeOH (40 mL) was added AcOH (10 mL) slowly at 0° C. After 5 min, the solution was stirred at room temperature for 1 h. TLC (PE/EtOAc=2/1) showed the reaction was complete. The resulting reaction mixture was filtered through a celite pad and washed with MeOH (120 mL). The filtrate was concentrated in vacuum to give the crude product A2 (1.7 g, crude) as a brown solid. The crude product was used for the next step without further purification.

Synthesis of compound A3. To a solution of compound A2 (1.7 g, 11.6 mmol, crude) in AcOH/H₂O (22 mL, 1/10) was added NaNO₂ (1.2 g, 17.4 mmol). The resulting solution was stirred at room temperature for 1 h. TLC (DCM/MeOH=15/1) showed the reaction was complete. EtOAc (100 mL) was added and the organic layer was separated. The organic layer was washed with aqueous NaHCO₃ (30 mL), 1 N HCl (30 mL) and brine. The layer was concentrated in vacuum and the residue was purified by silica gel column eluted with DCM/MeOH=100/1 to give A3 (1.0 g, 56.2%) as a brown solid. $^1$H NMR: (400 MHz, DMSO-d6) δ 16.06 (br, 1H), 7.98-7.97 (m, 1H), 7.47-7.37 (m, 2H).

Example 26

Synthesis of Compound SA-54

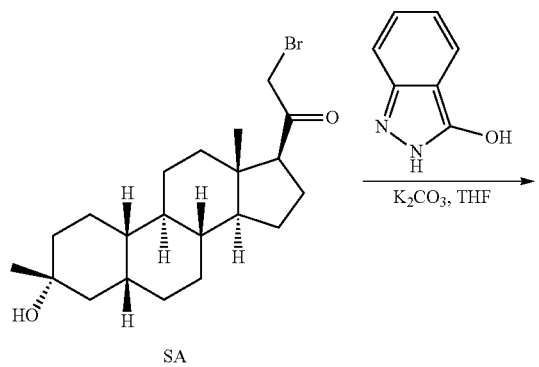

132

-continued

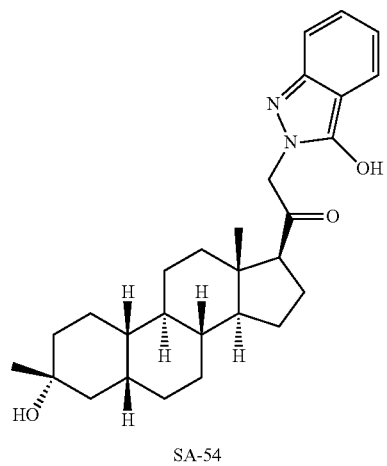

To a suspension of K₂CO₃ (50 mg, 0.36 mmol) in THF (6 mL) was added 2H-indazol-3-ol (36 mg, 0.3 mmol) and SA (100 mg, 0.268 mmol). The mixture was stirred at RT for 15 h. Then the reaction mixture was poured into 5 mL H₂O and extracted with EtOAc (2×10 mL). The combined organic layers were washed with brine, dried over sodium sulfate, filtered and concentrated. The residue was purified with by reverse-phase prep-HPLC to afford the title compound as a white solid SA-54 (5 mg, 4.42%), SA-54: $^1$H NMR (400 MHz, CDCl₃) δ (ppm): 8.87 (s, 1H), 7.76 (d, 1H), 7.38 (t, 1H), 7.30 (d, 1H), 7.12 (t, 1H), 5.00 (AB, 1H), 4.85 (AB, 1H), 2.77 (t, 1H), 0.70 (s, 3H). LC-MS: rt=2.42 min, m/z=451.1 (M⁺+1)

Example 27

Synthesis of Compound SA-55

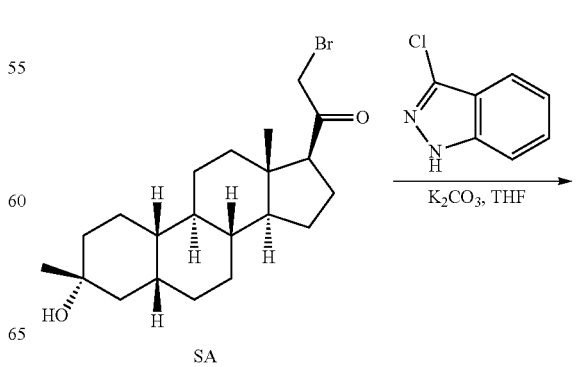

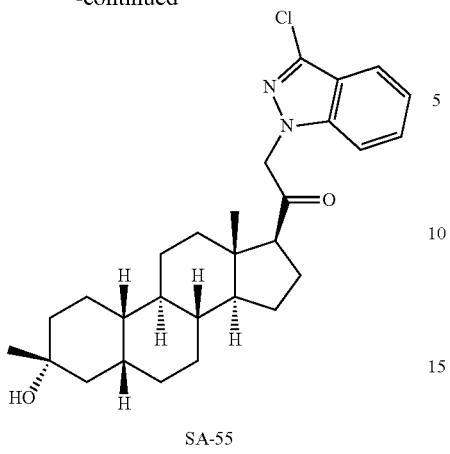

SA-55

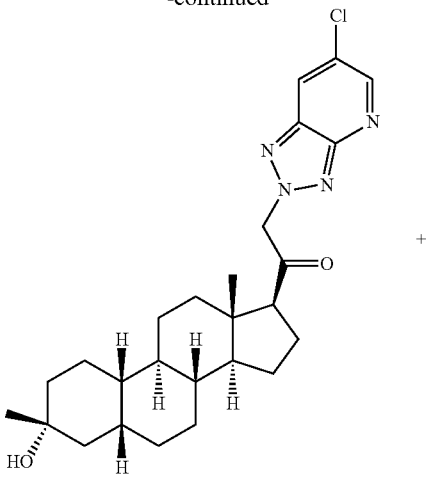

SA-57

To a suspension of K$_2$CO$_3$ (25 mg, 0.18 mmol) in THF (5 mL) was added 3-chloro-1H-indazole (20 mg, 0.13 mmol) and SA (36 mg, 0.09 mmol). The mixture was stirred at rt for 15 h. Then the reaction mixture was poured into 5 mL H$_2$O and extracted with EtOAc (2×10 mL). The combined organic layers were washed with brine, dried over sodium sulfate, filtered and concentrated. The residue was purified with by reverse-phase prep-HPLC to afford the title compound as a white solid (32 mg, 85.6%). $^1$H NMR (500 MHz, CDCl$_3$) δ (ppm): 7.68 (d, 1H), 7.42 (t, 1H) 7.21 (t, 1H) 7.16 (d, 1H), 5.08 (AB, 1H), 5.07(AB, 1H), 2.63 (1H, t), 0.71(s, 3H). LC-MS: rt=2.59 min, m/z=469.3 (M$^+$+1).

Example 28

Synthesis of Compound SA-56, SA-57, and SA-58

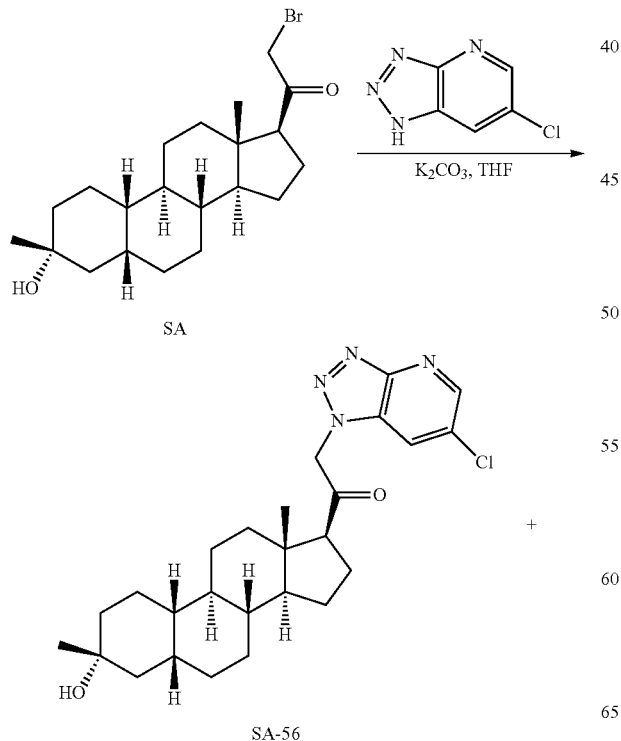

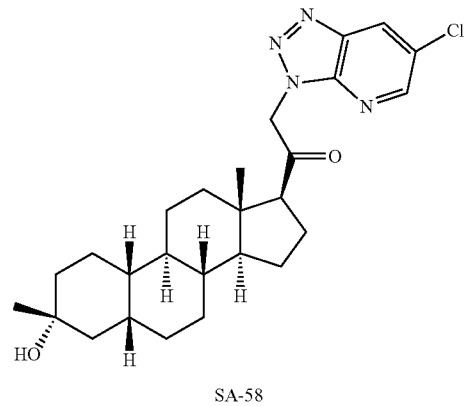

SA-58

To a suspension of K$_2$CO$_3$ (25 mg, 0.18 mmol) in THF (5 mL) was added 6-chloro-1H-[1,2,3]triazolo[4,5-b]pyridine (20 mg, 0.23 mmol) and SA (100 mg, 0.252 mmol). The mixture was stirred at rt for 15 h. Then the reaction mixture was poured into 5 mL H$_2$O and extracted with EtOAc (2×10 mL). The combined organic layers were washed with brine, dried over sodium sulfate, filtered and concentrated. The residue was purified with by reverse-phase prep-HPLC to afford the title compound as a white solid SA-56 (6.6 mg, 5.6%), SA-57 (8 mg, 6.7%), SA-58 (8.1 mg, 6.8%). SA-56 $^1$H NMR (400 MHz, CDCl$_3$) δ (ppm): 8.68 (d, 1H), 7.77 (d, 1H) 5.50 (AB, 1H), 5.37 (AB, 1H), 2.75 (1H, t), 0.72 (s, 3H). LC-MS: rt=2.37 min, m/z=471.4 (M$^+$+1). SA-57 $^1$H NMR (400 MHz, CDCl$_3$) δ (ppm): 8.74(d, 1H), 8.23(d, 1H) 5.55 (AB, 1H), 5.53 (AB, 1H), 2.68(1H, t), 0.75 (s, 3H). LC-MS: rt=2.45 min, m/z=471.4 (M$^+$+1). SA-58 $^1$H NMR (400 MHz, CDCl$_3$) δ (ppm): 8.58 (d, 1H), 8.37 (d, 1H) 5.51 (AB, 1H), 5.50 (AB, 1H), 2.75 (1H, t), 0.74 (s, 3H). LC-MS: rt=2.48 min, m/z=471.4 (M$^+$+1).

Example 30

Synthesis of Compound SA-61, SA-62 and SA-63

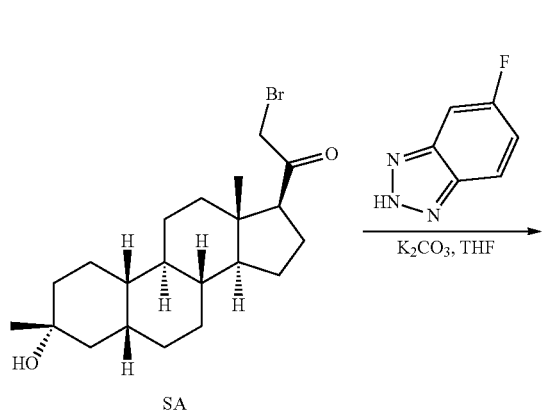

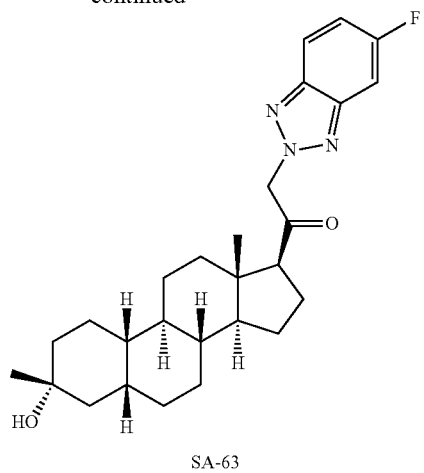

To a suspension of K₂CO₃ (50 mg, 0.36 mmol) in THF (5 mL) was added 5-fluoro-2H-benzo[d][1,2,3]triazole (49 mg, 0.36 mmol) and 9b (72 mg, 0.18 mmol). The mixture was stirred at RT for 15 h. The residual mixture was poured in to 5 mL H₂O and extracted with EtOAc (2×10 mL). The combined organic layers were washed with brine, dried over sodium sulfate, filtered and concentrated. The residual mixture was purified with by reverse-phase prep-HPLC to afford the title compound SA-61 as a white solid (7 mg, 8.6%) and SA-62 as a white solid (7 mg, 8.6%) and SA-63 as a white solid (3 mg, 3.7%). Compound SA-61 $^1$H NMR (500 MHz, CDCl₃), δ (ppm), 7.70 (dd, 1H), 7.30-7.26 (m, 2H), 5.44 (AB, 1H), 5.38 (AB, 1H), 2.71 (t, 1H), 0.72 (s, 3H). LC-MS: rt=2.34 min, m/z=454.1 [M+H]⁺ Compound SA-62 $^1$H NMR (500 MHz, CDCl₃), δ (ppm), 8.04 (dd, 1H), 7.15 (td, 1H), 6.98 (dd, 1H), 5.40 (AB, 1H), 5.34 (AB, 1H), 2.72 (t, 1H), 0.73 (s, 3H). LC-MS: rt=2.33 min, m/z=454.4 [M+H]⁺ Compound SA-63 $^1$H NMR (500 MHz, CDCl₃), δ (ppm), 7.87 (dd, 1H), 7.47 (dd, 1H), 7.20 (td, 1H), 5.52 (AB, 1H), 5.48 (AB, 1H), 2.66 (t, 1H0.75 (s, 3H). LC-MS: rt=2.41 min, m/z=454.3 [M+H]⁺

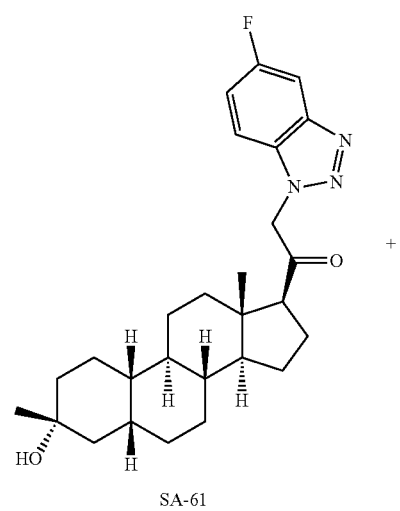

Example 31

Synthesis of Compound SA-64, SA-65 and SA-66

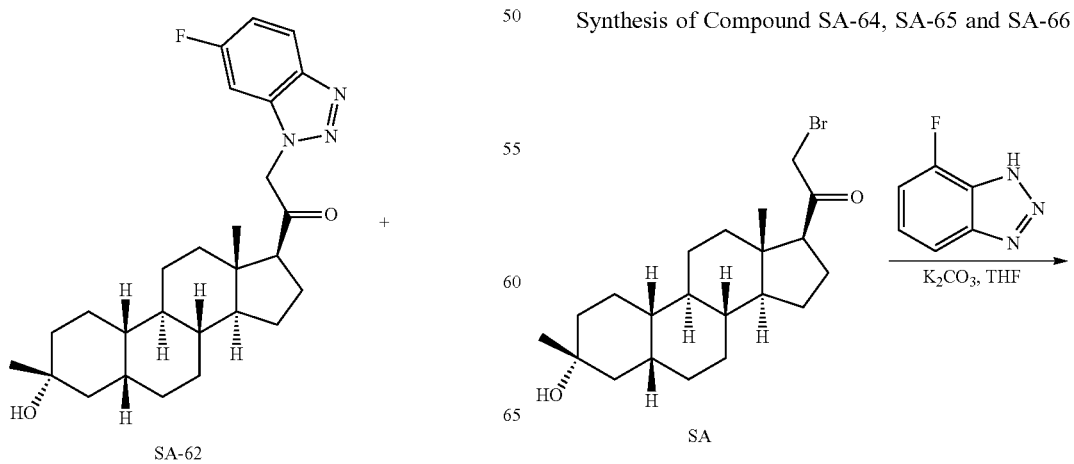

-continued

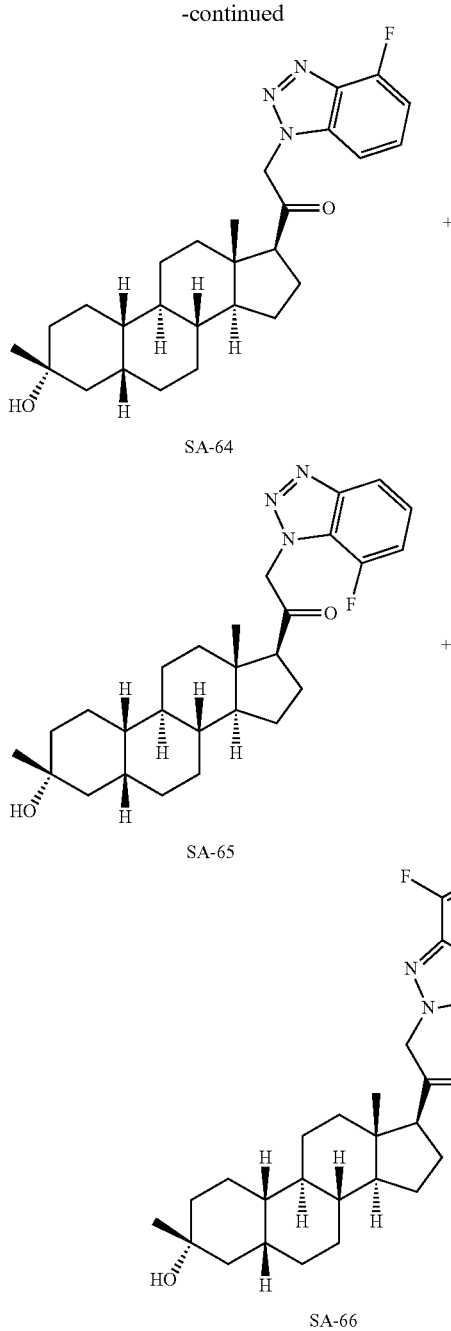

7.28 (td, 1H), 7.13 (dd, 1H), 5.54 (s, 2H), 2.71 (t, 1H), 1.28 (s, 3H), 0.73 (s, 3H). LC-MS: rt=2.39 min, m/z=454.1 [M+H]+ Compound SA-66 $^1$H NMR (500 MHz, CDCl$_3$), δ (ppm), 7.67 (d, 1H), 7.35-7.26 (m, 1H), 7.04 (dd, 1H), 5.57 (AB, 1H), 5.52 (AB, 1H), 2.67 (t, 1H), 0.75 (s, 3H). LC-MS: rt=2.45 min, m/z=454.1 [M+H]+

Example 32

Synthesis of Compound SA-67 and SA-69

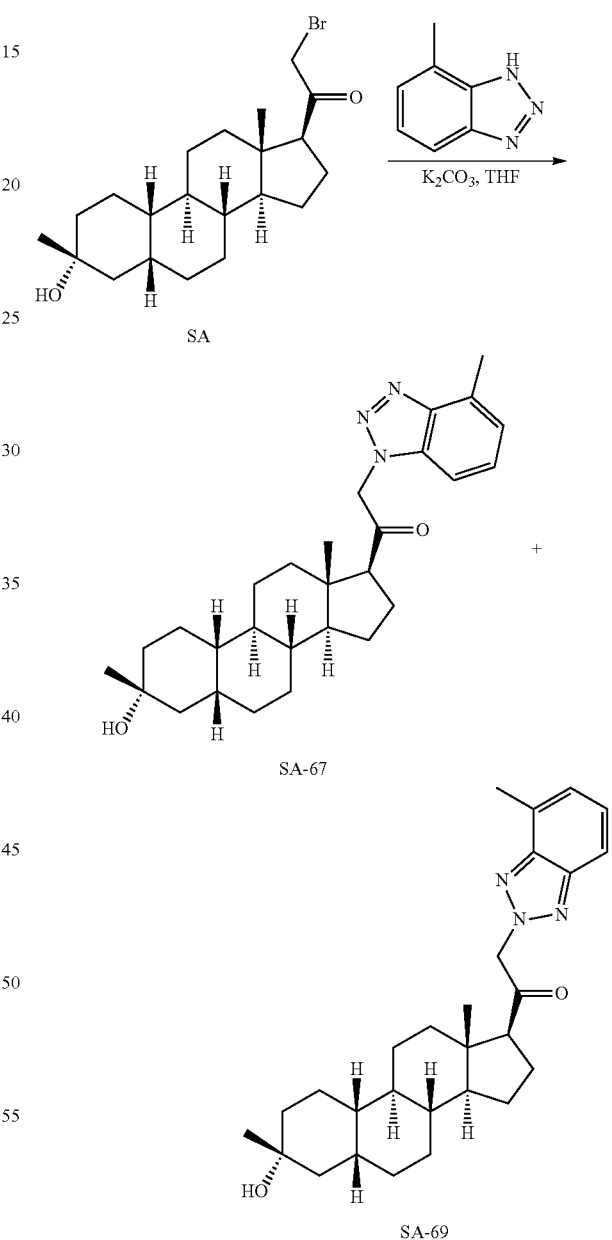

To a suspension of K$_2$CO$_3$ (50 mg, 0.36 mmol) in THF (5 mL) was added 7-fluoro-1H-benzo[d][1,2,3]triazole (50 mg, 0.36 mmol) and SA (72 mg, 0.18 mmol). The mixture was stirred at RT for 15 h. The residual mixture was poured in to 5 mL H$_2$O and extracted with EtOAc (2×10 mL). The combined organic layers were washed with brine, dried over sodium sulfate, filtered and concentrated. The residual mixture was purified with by reverse-phase prep-HPLC to afford the title compound SA-64 as a white solid (8 mg, 9.8%) and SA-65 as a white solid (9 mg, 11%) and SA-66 as a white solid (17 mg, 20.8%). Compound SA-64 $^1$H NMR (400 MHz, CDCl$_3$), δ (ppm), 7.43 (td, 1H), 7.11 (d, 1H), 7.04 (dd, 1H), 5.45 (AB, 1H), 5.40 (AB, 1H), 2.71 (t, 1H), 0.73 (s, 3H). LC-MS: rt=2.33 min, m/z=454.3 [M+H]+ Compound SA-65 $^1$H NMR (400 MHz, CDCl$_3$), δ (ppm), 7.86 (d, 1H), To a suspension of K$_2$CO$_3$ (50 mg, 0.36 mmol) in THF (5 mL) was added 7-methyl-1H-benzo[d][1,2,3]triazole (48 mg, 0.36 mmol) and SA (72 mg, 0.18 mmol). The mixture was stirred at RT for 15 h. The residual mixture was poured in to 5 mL H$_2$O and extracted with EtOAc (2×10 mL). The combined organic layers were washed with brine, dried over sodium sulfate, filtered and concentrated. The residual mixture was purified with by reverse-phase prep-HPLC to afford the title compound SA-67 as a white solid (26 mg, 32%) and SA-69 as a white solid (18 mg, 22%) and a white solid byproduct (3 mg, 3.7%). Compound SA-67 ¹H NMR (500 MHz, CDCl₃), δ (ppm), 7.36 (t, 1H), 7.14-7.12 (m, 2H), 5.39 (s, 2H), 2.81 (s, 3H), 2.68 (t, 1H), 0.73 (s, 3H). LC-MS: rt=2.38 min, m/z=450.1 [M+H]⁺ Compound SA-69 ¹H NMR (500 MHz, CDCl₃), δ (ppm), 7.68 (d, 1H), 7.28 (dd, 1H), 7.13 (d, 1H), 5.53 (AB, 1H), 5.49 (AB, 1H), 2.65 (t, 1H), 2.65 (s, 3H), 0.75 (s, 3H). LC-MS: rt=2.49 min, m/z=450.1 [M+H]⁺

Example 33

Synthesis of Compound SA-70, SA-71 and SA-72

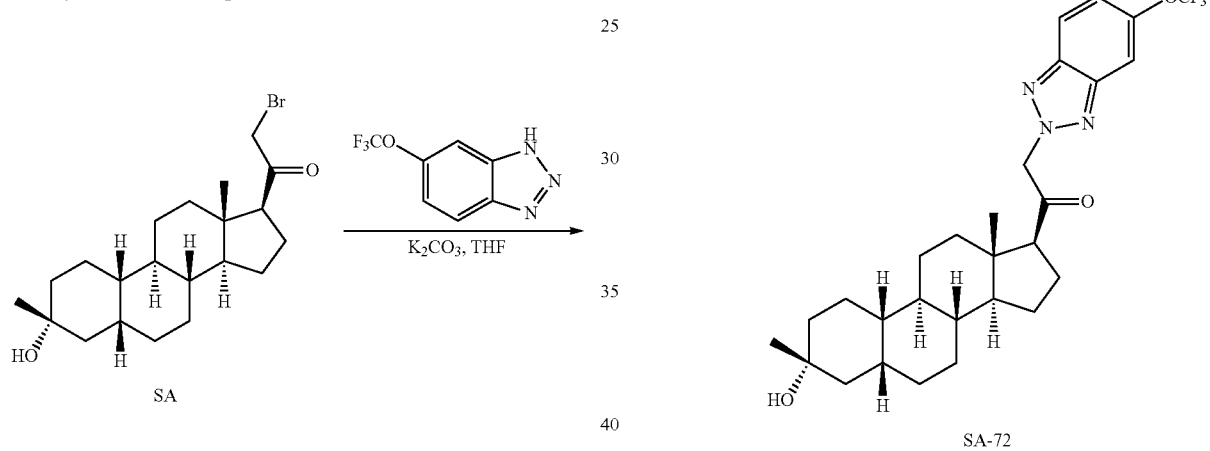

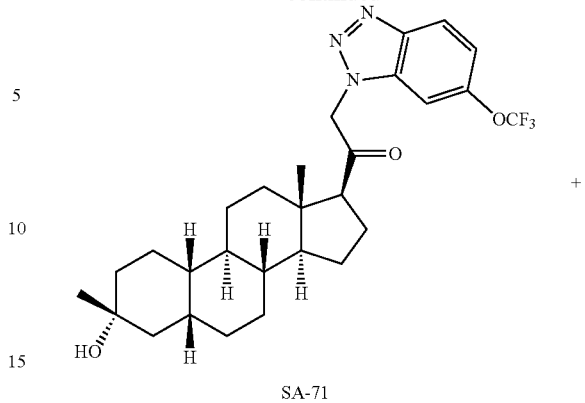

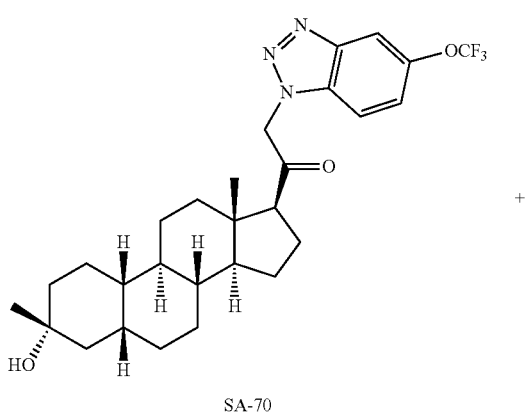

To a suspension of K₂CO₃ (100 mg, 0.72 mmol) in THF (5 mL) was added 6-(trifluoromethoxy)-1H-benzo[d][1,2,3]triazole (146 mg, 0.72 mmol) and SA (144 mg, 0.36 mmol). The mixture was stirred at RT for 15 h. The residual mixture was poured in to 5 mL H₂O and extracted with EtOAc (2×10 mL). The combined organic layers were washed with brine, dried over sodium sulfate, filtered and concentrated. The residual mixture was purified with by reverse-phase prep-HPLC to afford the title compound SA-70 as a white solid (47 mg, 25%) and SA-71 as a white solid (37 mg, 19.8%) and SA-72 as a white solid (60 mg, 32%). Compound SA-70 ¹H NMR (400 MHz, CDCl₃), δ (ppm), 7.94 (s, 1H), 7.40-7.34 (m, 2H), 5.48 (AB, 1H), 5.40 (AB, 1H), 2.73 (t, 1H 0.72 (s, 3H). LC-MS: rt=2.49 min, m/z=520.0 [M+H]⁺ Compound SA-71 ¹H NMR (500 MHz, CDCl₃), δ (ppm), 8.09 (d, 1H), 7.26 (d, 1H), 7.19 (s, 1H), 5.45 (AB, 1H), 5.38 (AB, 1H), 2.73 (t, 1H), 0.73 (s, 3H). LC-MS: rt=2.49 min, m/z=520.0 [M+H]⁺ Compound SA-72 ¹H NMR (500 MHz, CDCl₃), δ (ppm), 7.91 (d, 1H), 7.72 (s, 1H), 7.28 (d, 1H), 5.55 (AB, 1H), 5.50 (AB, 1H), 2.67 (t, 1H), 0.75 (s, 3H). LC-MS: rt=2.59 min, m/z=520.0 [M+H]⁺.

Example 34

Synthesis of Compound SA-73, SA-74 and SA-75

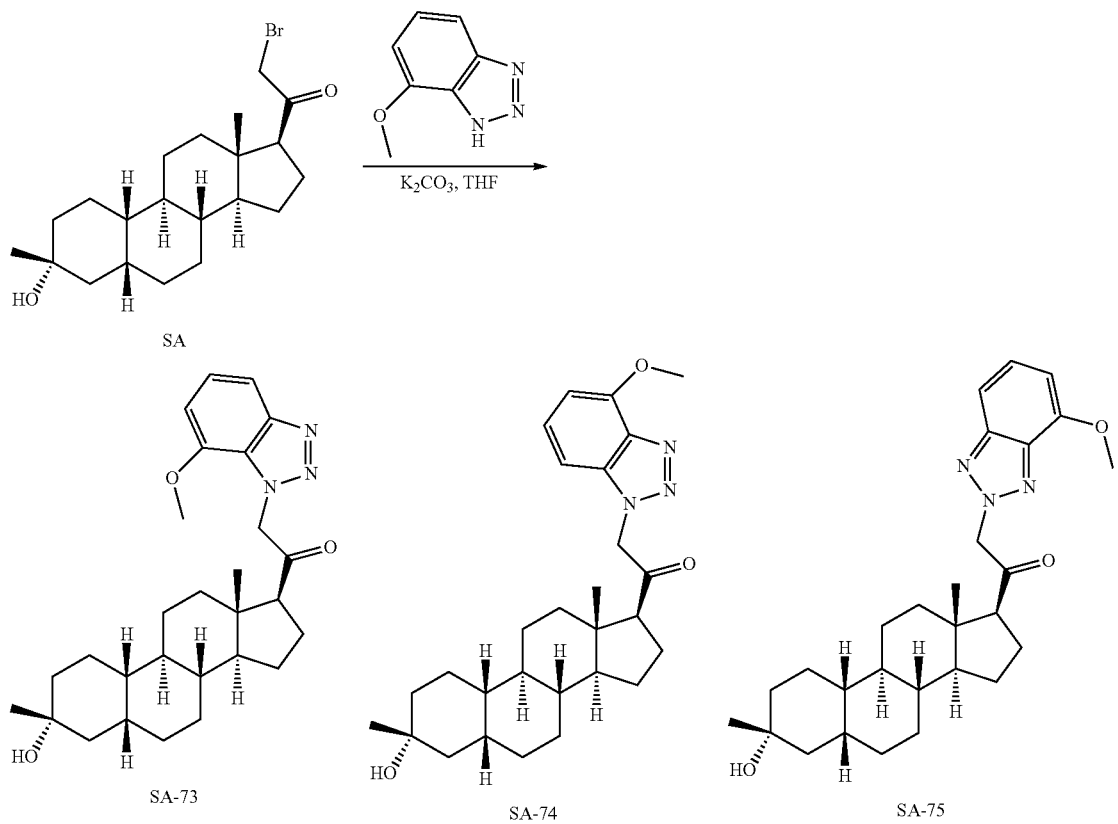

To a suspension of K$_2$CO$_3$ (67 mg, 0.50 mmol) in THF (5 mL) was added 7-methoxy-1H-benzo[d][1,2,3]triazole (74.6 mg, 0.50 mmol) and compound SA (100 mg, 0.25 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated in vacuum. The residue was purified by reverse-phase prep-HPLC to afford SA-73 as a white solid (12.8 mg, 0.027 mmol, 11.0%), SA-74 as a white solid (19.2 mg, 0.041 mmol, 16.5%) and SA-75 as a white solid (9.1 mg, 0.020 mmol, 7.8%). SA-73: $^1$H NMR (500 MHz, CDCl$_3$) δ (ppm): 7.63 (1H, d), 7.23 (1H, t), 6.76 (1H, d), 5.59 (1H, AB), 5.58 (1H, AB), 3.89 (1H, s), 2.67 (1H, t0.73 (3H, s). LCMS: Rt=2.44 min. m/z=466.2 [M+H]$^+$. SA-74: $^1$H NMR (500 MHz, CDCl$_3$) δ (ppm): 7.38 (1H, t), 6.87 (1H, d), 6.70 (1H, d), 5.37 (2H, s), 4.12 (3H, s), 2.68 (1H, t0.73 (3H, s). LCMS: Rt=2.41 min. m/z=466.2 [M+H]$^+$. SA-75: $^1$H NMR (500 MHz, CDCl$_3$) δ (ppm): 7.44 (1H, d), 7.30 (1H, t), 6.64 (1H, d), 5.50 (2H, s), 4.03 (3H, s), 2.64 (1H, t), 0.74 (3H, s). LCMS: Rt=2.50 min. m/z=466.1 [M+H]$^+$.

Example 35

Synthesis of Compound SA-76, SA-77 and SA-78

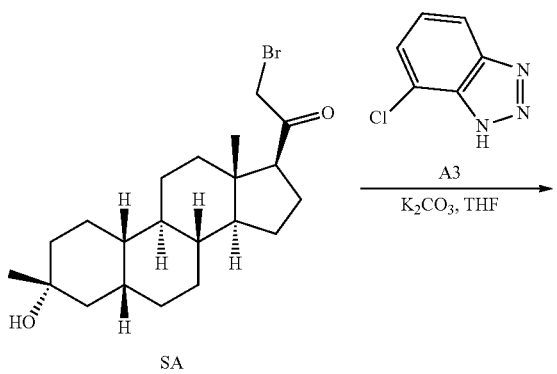

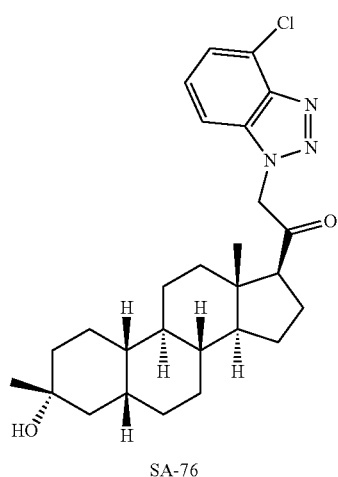

SA-76

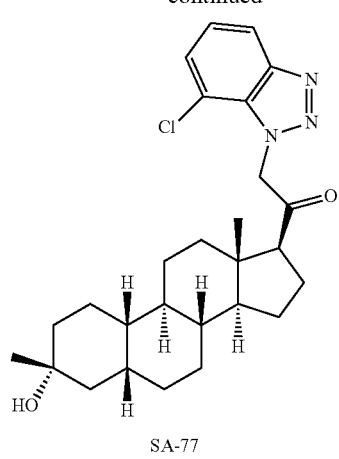

SA-77

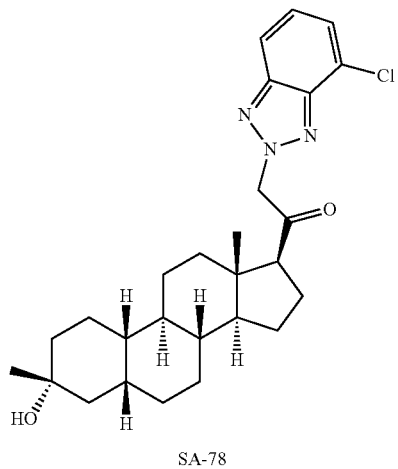

SA-78

Synthesis of Compound A3

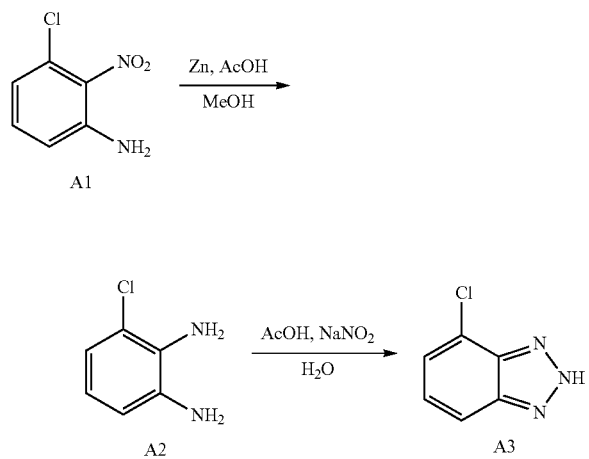

Synthesis of compound A2. To a solution of compound A1 (2.0 g, 11.6 mmol) and Zn powder (7.6 g, 116 mmol) in MeOH (40 mL) was added AcOH (10 mL) slowly at 0° C. After 5 min, the solution was stirred at room temperature for 1 h. TLC (PE/EtOAc=2/1) showed the reaction was complete. The resulting reaction mixture was filtered through a celite pad and washed with MeOH (120 mL). The filtrate was concentrated in vacuum to give the crude product A2 (1.7 g, crude) as a brown solid. The crude product was used for the next step without further purification.

Synthesis of compound A3. To a solution of compound A2 (1.7 g, 11.6 mmol, crude) in AcOH/$H_2O$ (22 mL, 1/10) was added $NaNO_2$ (1.2 g, 17.4 mmol). The resulting solution was stirred at room temperature for 1 h. TLC (DCM/MeOH=15/1) showed the reaction was complete. EtOAc (100 mL) was added and the organic layer was separated. The organic layer was washed with aqueous $NaHCO_3$ (30 mL), 1 N HCl (30 mL) and brine. The layer was concentrated in vacuum and the residue was purified by silica gel column eluted with DCM/MeOH=100/1 to give A3 (1.0 g, 56.2%) as a brown solid. $^1$H NMR: (400 MHz, DMSO-d6) δ 16.06 (br, 1H), 7.98-7.97 (m, 1H), 7.47-7.37 (m, 2H).

Synthesis of Compound SA-76, SA-77 and SA-78. To a suspension of $K_2CO_3$ (67 mg, 0.50 mmol) in THF (5 mL) was added 7-chloro-1H-benzo[d][1,2,3]triazole (76.8 mg, 0.50 mmol) and compound SA (100 mg, 0.25 mmol). After stirring at room temperature for 15 h, the reaction mixture was poured into 5 mL $H_2O$ and extracted with EtOAc (2×10 mL). The combined organic layers were washed with brine (2×10 mL), dried over sodium sulfate, filtered and concentrated in vacuum. The residue was purified by reverse-phase prep-HPLC to afford SA-76 as a white solid (19.8 mg, 0.042 mmol, 16.8%), SA-77 as a white solid (8.5 mg, 0.018 mmol, 7.2%) and SA-78 as a white solid (26.6 mg, 0.056 mmol, 22.6%). SA-76: $^1$H NMR: (400 MHz, $CDCl_3$) δ 7.43-7.38 (m, 2H), 7.25-7.23 (m, 1H), 5.43 (d, 2H), 2.73-2.69 (m, 1H), 2.26-2.14(m, 1H), 1.89-1.74 (m, 6H), 1.75-1.62 (m, 1H), 1.55-1.37 (m, 8H), 1.35-1.26 (m, 8H), 1.19-1.11 (m, 3H), 0.73 (s, 3H).LCMS: Rt=2.36 min. m/z=470.3 $[M+H]^+$. SA-77: $^1$H NMR (500 MHz, $CDCl_3$) δ (ppm): 8.00 (1H, d), 7.43 (1H, d), 7.30 (1H, t), 5.71 (2H, s), 2.72 (1H, t), 1.28 (s, 3H), 0.74 (s, 3H). LCMS: Rt=2.40 min. m/z=470.2 $[M+H]^+$. SA-78: $^1$H NMR: (400 MHz, $CDCl_3$) δ 7.79 (d, 1H), 7.41 (d, 1H), 7.34-7.30 (m, 2H), 5.56 (s, 2H), 2.69-2.64 (m, 1H), 2.27-2.13 (m, 2H), 1.82-1.75(m, 5H), 1.51-1.43 (m, 11H), 1.34-1.28 (m, 5H), 1.19-1.07 (m, 3H), 0.89-0.86 (m, 1H), 0.76 (s, 3H). LCMS: Rt=2.45 min. m/z=470.3 $[M+H]^+$.

Example 36

Synthesis of Compound SC-D2

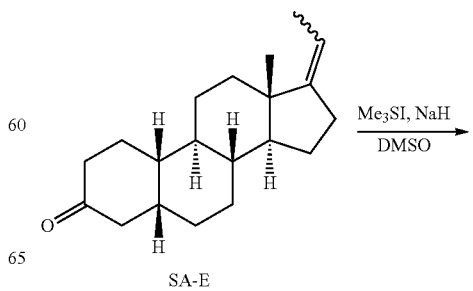

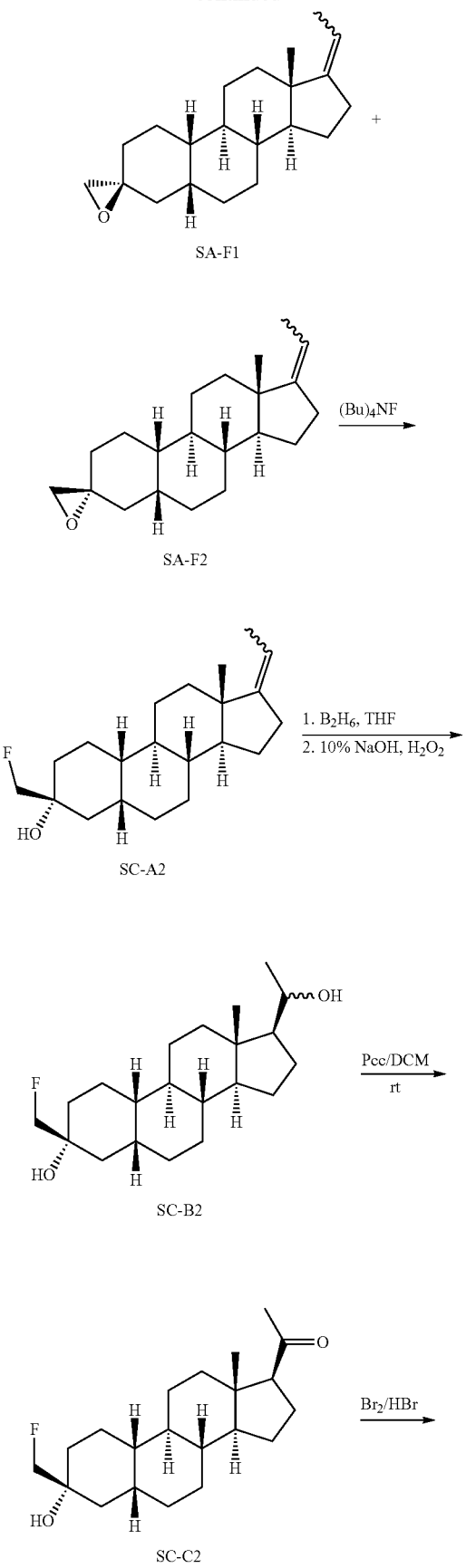

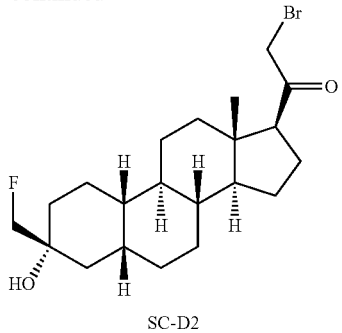

Synthesis of compounds SC-A1 and SC-A2. A mixture of reactant mixture SA-F1 and SA-F2 (3.0 g, 10.0 mmol, 1:1) was added dry (Bu)$_4$NF, then the mixture was heated 100° C. overnight. The residual mixture was poured in to 50 mL H$_2$O and extracted with EtOAc (2×50 mL). The combined organic layers were washed with brine solution, dried over sodium sulfate, filtered and concentrated. The residue was purified by flash chromatography (eluant: petroleum ether/ethyl acetate=20:1) to afford product mixture SC-A1 and SC-A2 (2.1 g, 6.5 mmol, 65%) as white solid.

Synthesis of compounds SC-B1 and SC-B2. To a solution of reactant mixture SC-A1 and SC-A2 (2.1 g, 6.5 mmol) in anhydrous THF (30 mL) was added BH$_3$. THF (1.0 M, 13.0 mL, 13.0 mmol), the solution was stirred at 25° C. overnight. Then the reaction was quenched by addition of water (5 mL). 2 M NaOH solution (20 mL) was added followed by 30% H$_2$O$_2$ (20 mL). The mixture was stirred at room temperature for 1 hour. The mixture was diluted with ethyl acetate (200 mL) and resulting solution was washed with brine (2×100 mL), dried over magnesium sulfate and concentrated in vacuo. The crude product mixture was used directly in the next step without further purification.

Synthesis of compounds SC-C1 and SC-C2. To a solution of crude reactant mixture compounds SC-B1 and SC-B2 (2.2 g, 6.5 mmol, theoretical amount) in dichloromethane (40 mL) was added Pyridinium chlorochromate (Pcc) in portions (2.8 g, 13.0 mmol). The solution was stirred at 25° C. overnight. Then the mixture was filtered through a short pad of silica gel and the silica gel was washed with dichloromethane (3×50 mL). All filtrate was combined and concentrated in vacuo. The residue was purified by flash chromatography (eluant: petroleum ether/ethyl acetate=15:1) to afford product SC-C1 (910 mg, 2.7 mmol, Yield=41% (2 steps)) as white solid and product SC-C2 (850 mg, 2.5 mmol, Yield=39% (2 steps)) as white solid. Compound SC-C1: $^1$H NMR (500 MHz, CDCl$_3$) δ (ppm): 4.17 (d, 2H), 2.53 (t, 1H), 0.62 (s, 3H). Compound SC-C2: $^1$H NMR (500 MHz, CDCl$_3$) δ (ppm): 4.45 (AB×d, 1H), 4.39 (AB×d, 1H), 2.54 (t, 1H0.62 (s, 3H).

Synthesis of compound SC-D2. To a solution of reactant SC-C2 (100 mg, 0.301 mmol) in methanol (10 mL) was added 48% hydrobromic acid (152 mg, 0.903 mmol) followed by bromine (241 mg, 0.077 mL, 1.505 mmol). The solution was heated at 25° C. for 1.5 hours. Then the mixture was poured into cooled water (50 mL). The resulting solid was extracted with ethyl acetate (2×50 mL). The combined organic extracts were washed with brine (50 mL), dried over magnesium sulfate and concentrated in vacuo. The crude product SC-D2 was used directly without further purification in the next step.

Example 37

Synthesis of Compound SA-79 and SA-80

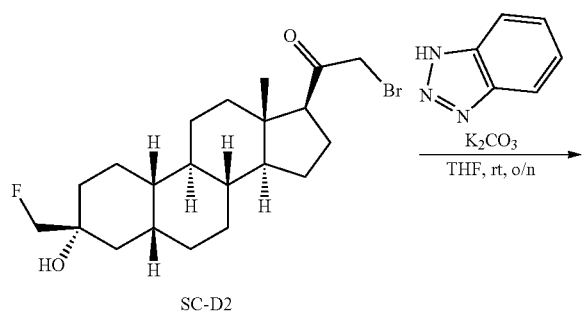
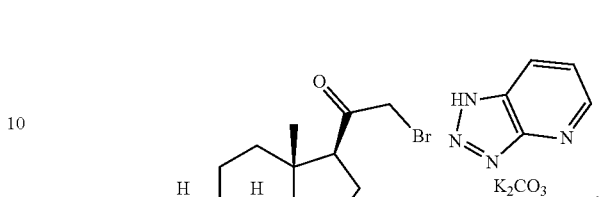

SC-D2

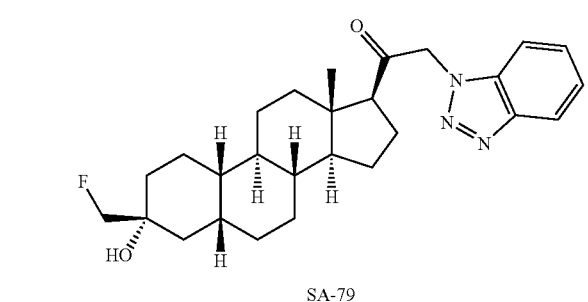

SA-79

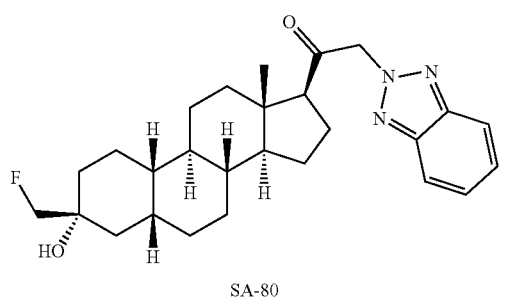

SA-80

To a solution of compound SC-D2 (120 mg, 0.29 mmol) in THF (3 mL) was added $K_2CO_3$ (200 mg, 1.45 mmol) and 2H-benzo[d][1,2,3]triazole (172 mg, 1.45 mmol). The resulting solution was stirred at room temperature overnight, then the reaction was diluted with EtOAc (20 mL). The resulting solution was washed with brine (10 mL), dried over $Na_2SO_4$ and concentrated in vacuo. The residue was purified by prep-HPLC to give SA-79 (14 mg, 25%), SA-80 (9 mg, 17%) as a white solid. SA-79: 1H NMR: (500 MHz, CDCl$_3$), δ (ppm), 8.08 (d, 2H), 7.49 (t, 1H), 7.39 (t, 1H), 7.34 (d, 1H), 5.45 (AB, 1H), 5.40 (AB, 1H), 4.49 (AB×d, 1H), 4.39 (AB×d, 1H), 2.72 (t, 1H), 0.74 (s, 3H). LC-MS: rt=2.26 min; m/z=454.4 (M+H)$^+$ SA-80: 1H NMR: (500 MHz, CDCl$_3$), δ (ppm), 7.89 (dd, 2H), 7.40 (dd, 2H), 5.54 (AB, 1H), 5.50 (AB, 1H), 4.49 (AB×d, 1H), 4.40 (AB×d, 1H), 2.67 (t, 1H), 0.77 (s, 3H). LC-MS: rt=2.38 min; m/z=454.3 (M+H)$^+$

Example 38

Synthesis of Compound SA-81 and SA-82

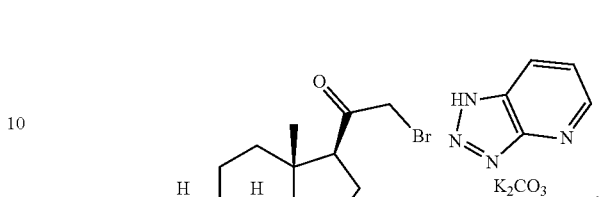

SC-D2

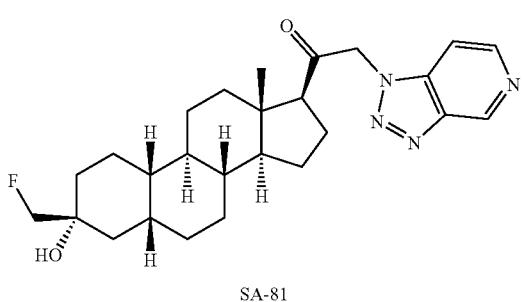

SA-81

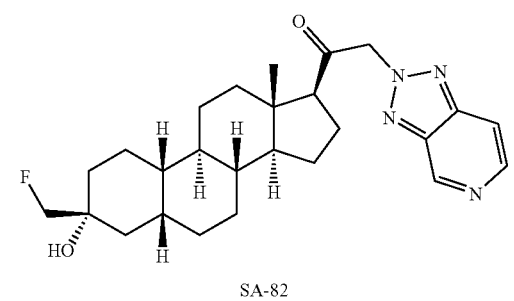

SA-82

To a solution of compound SC-D2 (120 mg, 0.29 mmol) in THF (3 mL) was added $K_2CO_3$ (200 mg, 1.45 mmol) and 1H-[1,2,3]triazolo[4,5-b]pyridine (173 mg, 1.45 mmol). The resulting solution was stirred at room temperature overnight, then the reaction was diluted with EtOAc (20 mL). The resulting solution was washed with brine (10 mL), dried over $Na_2SO_4$ and concentrated in vacuo. The residue was purified by prep-HPLC to give SA-81 (9 mg, 14%), SA-82 (10 mg, 15%) as a white solid. SA-81: 1H NMR: (500 MHz, CDCl$_3$), δ (ppm), 9.45 (s, 1H), 8.47 (d, 1H), 7.76 (dd, 1H), 5.62 (AB, 1H), 5.57 (AB, 1H), 4.48 (AB×d, 1H), 4.39 (AB×d, 1H), 2.75 (t, 1H), 0.76 (s, 3H). LC-MS: rt=2.26 min; m/z=455.3 (M+H)$^+$ SA-82: 1H NMR: (500 MHz, CDCl$_3$), δ (ppm), 9.51 (s, 1H), 8.59 (d, 1H), 7.30 (dd, 1H), 5.50 (AB, 1H), 5.41 (dd, 1H), 4.49 (AB×d, 1H), 4.39 (AB×d, 1H)), 2.76 (t, 1H), 0.74 (s, 3H). LC-MS: rt=2.19 min; m/z=455.3 (M+H)$^+$

Example 39

Synthesis of Compound SA-83 and SA-84

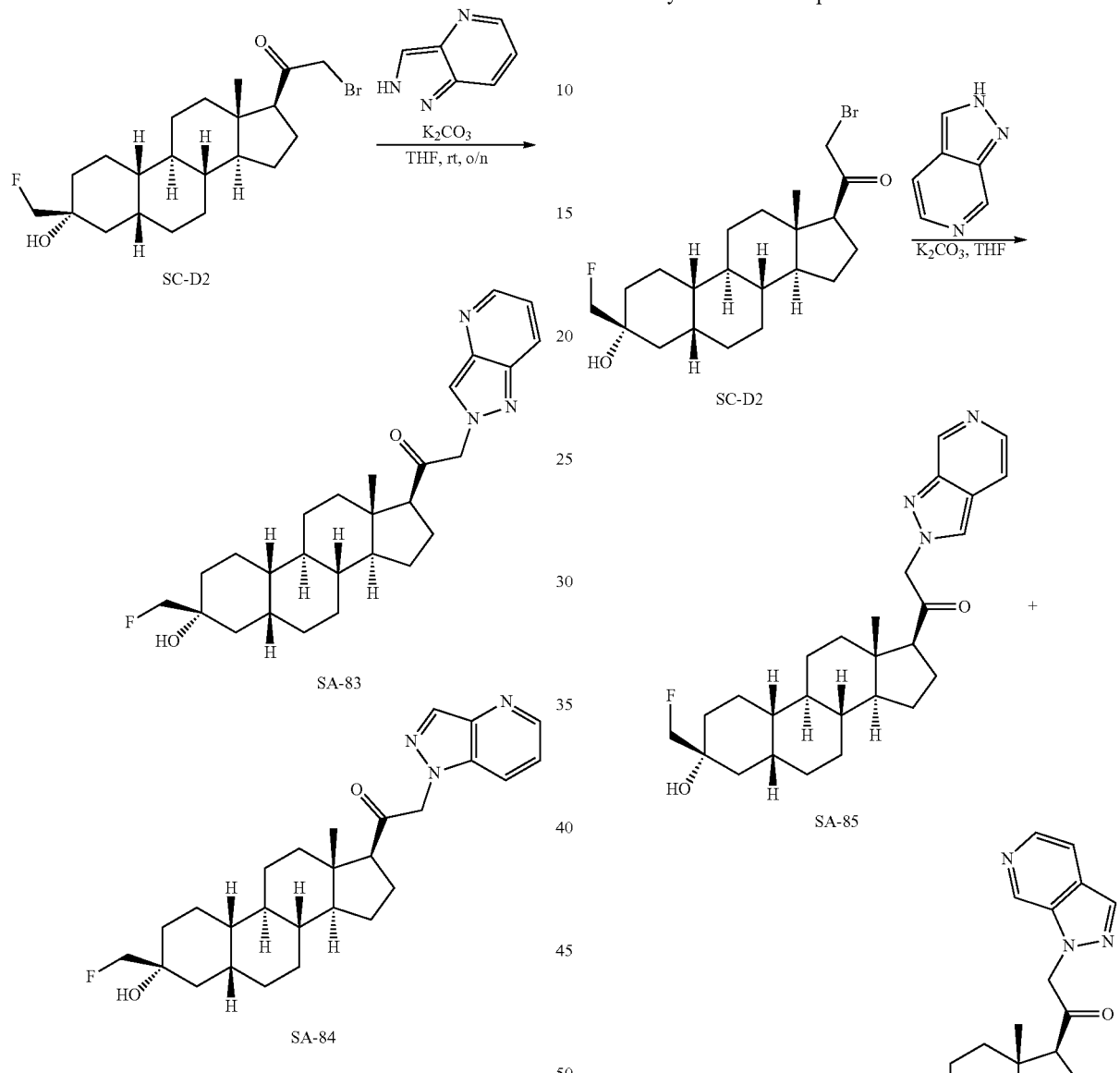

Synthesis of compounds SA-83 and SA-84. To a suspension of K₂CO₃ (55 mg, 0.4 mmol) in THF (5 mL) was added 2H-tetrazole (28 mg, 0.4 mmol) and Compound SC-D2 (83 mg, 0.2 mmol). The mixture was stirred at RT for 15 h then the residue mixture was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-83 as a white solid (10 mg, 11%) and SA-84 as a white solid (5 mg, 6%). Compound SA-83: ¹H NMR (400 MHz, CDCl₃) δ (ppm): 8.59 (d, 1H), 8.22 (s, 1H), 8.04 (d, 1H), 7.23 (dd, 1H), 5.28 (AB, 1H), 5.21 (AB, 1H), 4.50 (AB×d, 1H), 4.38 (AB×d, 1H), 2.67 (t, 1H), 0.73 (s, 3H). LC-MS: rt=2.11 min, m/z=454.4 [M+H]⁺ Compound SA-84: ¹H NMR (400 MHz, CDCl₃) δ (ppm): 8.60 (dd, 1H), 8.29 (s, 1H), 7.59 (d, 1H), 7.30 (dd, 1H), 5.20 (AB, 1H), 5.14 (AB, 1H), 4.50 (AB×d, 1H), 4.38 (AB×d, 1H), 2.68 (t, 1H), 2.29 (s, 1H), 2.24-2.12 (m, 2H), 0.72 (s, 3H). LC-MS: rt=2.15 min, m/z=454.4 [M+H]⁺

Example 40

Synthesis of Compounds SA-85 and SA-86

To a suspension of K₂CO₃ (55 mg, 0.4 mmol) in THF (5 mL) was added 2H-pyrazolo[3,4-c]pyridine (47.6 mg, 0.4 mmol) and compound SC-D2 (85 mg, 0.2 mmol) and the mixture was stirred at RT for 15 h. The residue mixture was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-85 as a white solid (5 mg, 5.5%) and SA-86 as a white solid (10 mg, 11%). Compound SA-85: $^1$H NMR (500 MHz, CDCl$_3$) δ (ppm): 9.26 (s, 1H), 8.17 (d, 1H), 7.98 (s, 1H), 7.53 (dd, 1H), 5.32 (AB, 1H), 5.23 (AB, 1H), 4.48 (AB×d, 1H), 4.39 (AB×d, 1H), 2.68 (t, 1H), 0.72 (s, 3H). LC-MS: rt=2.18 min, m/z=454.1 [M+H]$^+$ Compound SA-86: $^1$H NMR (500 MHz, CDCl$_3$) δ (ppm): 8.8 (s, 1H), 8.33 (d, 1H), 8.09 (s, 1H), 7.65 (d, 1H), 5.28 (AB, 1H), 5.23 (AB, 1H), 4.48 (AB×d, 1H), 4.39 (AB×d, 1H), 2.69 (t, 1H), 0.73 (s, 3H). LC-MS: rt=2.14 min, m/z=454.1 [M+H]$^+$ Example 41

Synthesis of Compounds SA-87, SA-88, and SA-89

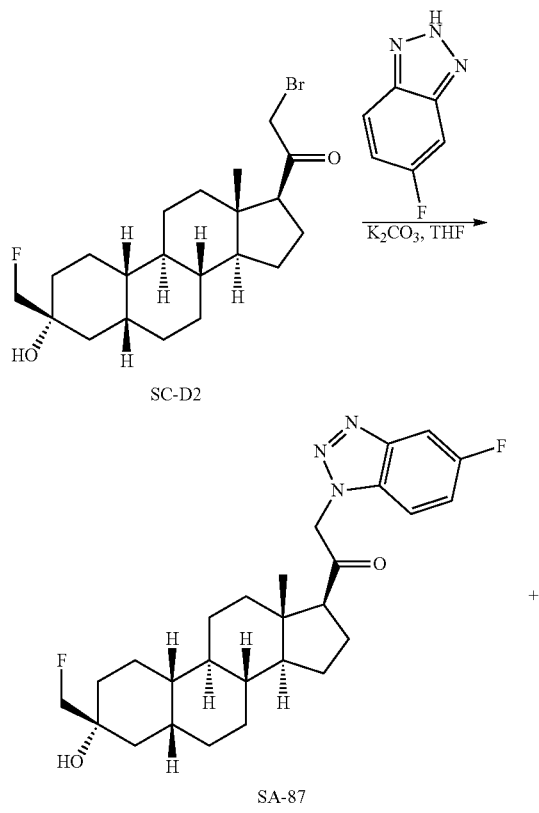

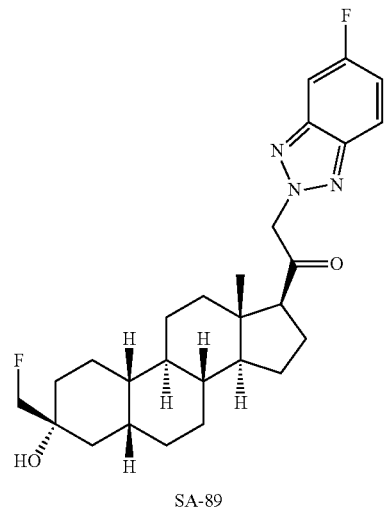

To a suspension of K$_2$CO$_3$ (55 mg, 0.4 mmol) in THF (5 mL) was added 5-fluoro-2H-benzo[d][1,2,3]triazole (55 mg, 0.4 mmol) and SC-D2 (85 mg, 0.2 mmol) and the reaction mixture was stirred at RT for 15 h. The residue mixture was poured into 5 mL H$_2$O and extracted with EtOAc (2×10 mL). The combined organic layers were washed with brine, dried over sodium sulfate, filtered and concentrated. The residue mixture was purified by reverse-phase prep-HPLC to afford SA-87 as a white solid (11.4 mg, 12%) and SA-88 as a white solid (10.2 mg, 10.8%) and SA-89 as a white solid (21.5 mg, 23.0%). Compound SA-87: $^1$H NMR (500 MHz, CDCl$_3$) δ (ppm): 7.70 (dd, 1H), 7.31-7.26 (m, 2H), 5.45 (AB, 1H), 5.38 (AB, 1H), 4.49 (AB×d, 1H), 4.38 (AB×d, 1H), 2.72 (t, 1H), 0.73 (s, 3H). LC-MS: rt=2.26 min, m/z=472.3 [M+H]$^+$ Compound SA-88: $^1$H NMR (500 MHz, CDCl$_3$) δ (ppm): 8.04 (dd, 1H), 7.15 (td, 1H), 6.98 (dd, 1H), 5.41 (AB, 1H), 5.34 (AB, 1H), 4.49 (AB×d, 1H), 4.39 (AB×d, 1H), 2.72 (t, 1H), 0.73 (s, 3H). LC-MS: rt=2.27 min, m/z=472.3 [M+H]$^+$ Compound SA-89: $^1$H NMR (500 MHz, CDCl$_3$) δ (ppm): 7.86 (dd, 1H), 7.47 (dd, 1H), 7.20 (td, 1H), 5.52 (AB, 1H), 5.48 (AB, 1H), 4.49 (AB×d, 1H), 4.39 (AB×d, 1H), 2.66 (t, 1H) 0.75 (s, 3H). LC-MS: rt=2.36 min, m/z=472.0 [M+H]$^+$ Example 42

Synthesis of Compound SC-I2

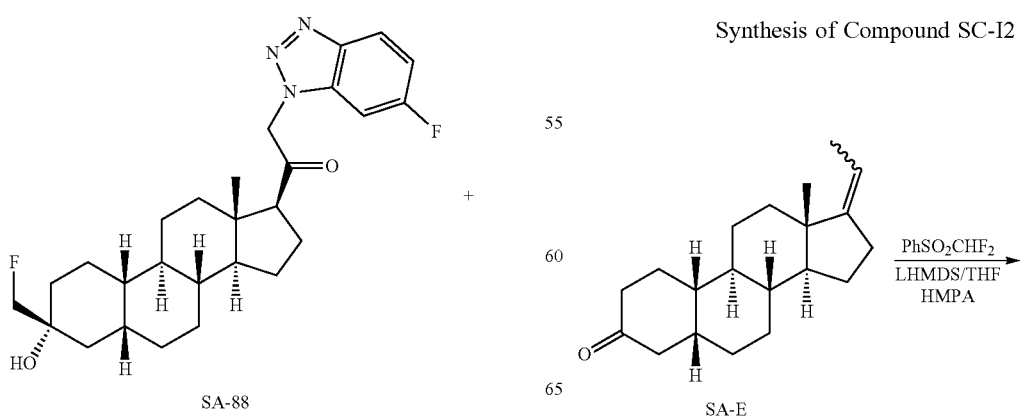

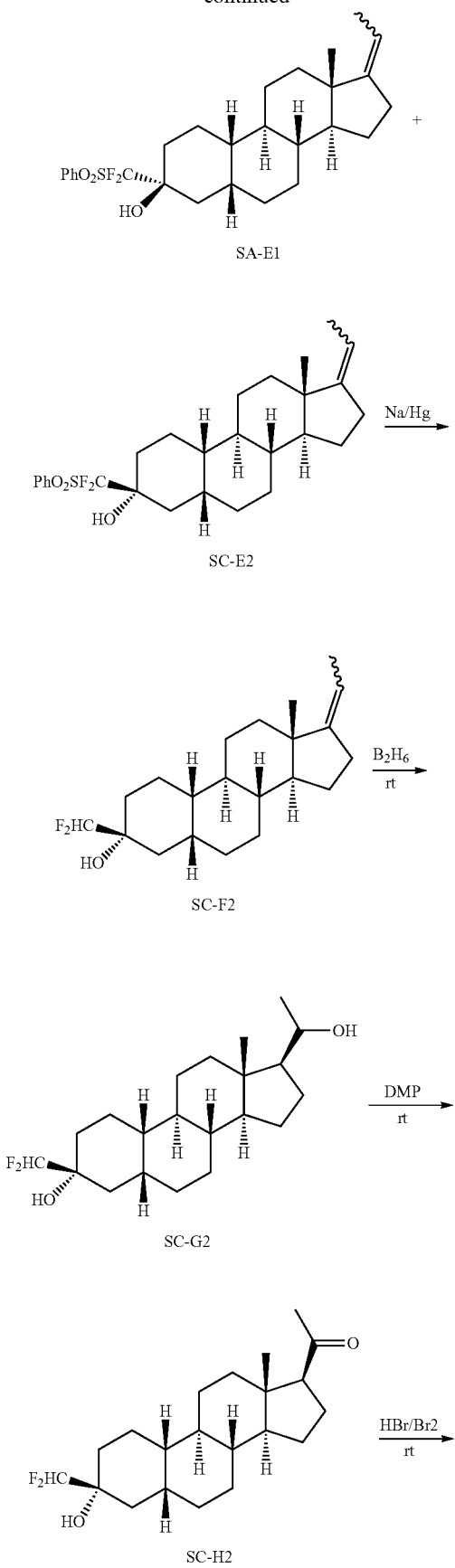

Synthesis of compound SC-E1 and SC-E2. To a solution of compound 5 (800 mg 2.79 mmol) and PhSO$_2$CF$_2$H (540 mg, 2.79 mmol) in THF (25 mL) and HMPA (0.5 mL) at −78° C. under N$_2$ was added LHMDS (4 mL, 1M in THF) dropwise. After stirring at −78° C. for 2 h, the reaction mixture was quenched with saturated aqueous NH$_4$Cl solution (10 mL) and allowed to warm to room temperature then extracted with Et$_2$O (20 mL×3). The combined organic layers were washed with brine, dried over sodium sulfate, filtered and concentrate. The residue was purified by silica gel column chromatography (pretroleum ether/ethyl acetate=10/1) to give the mixture of compound SC-E1 and SC-E2 (700 mg). The mixture was further purified by chiral-HPLC to afford compound SC-E1 (200 mg, t=4.31 min). $^1$H NMR (400 MHz, CDCl$_3$), δ (ppm), 7.99-7.97 (d, 2H), 7.77-7.75 (m, 1H), 7.64-7.60 (m, 2H), 5.14-5.08 (m, 1H), 0.88 (s, 3H); compound SC-E2 (260 mg, t=5.66 min). $^1$H NMR (400 MHz, CDCl$_3$), δ (ppm), 8.00-7.98 (d, 2H), 7.77-7.75 (m, 1H), 7.64-7.60 (m, 2H), 5.14-5.09 (m, 1H), 0.88 (s, 3H).

Synthesis of compound SF-F2. To a solution of compound SC-E2 (100 mg, 0.209 mmol) and anhydrous Na$_2$HPO$_4$ (100 mg) in anhydrous methanol (5 mL) at −20° C. under N$_2$ was added Na/Hg amalgam (500 mg). After stirring at −20° C. to 0° C. for 1 h, the methanol solution was decanted out and the solid residue was washed with Et$_2$O (5×3 mL). The combined organic layers were washed with brine (20 mL), dried over MgSO$_4$, filtered and concentrated. The residue was purified by silica gel chromatography (pretroleum ether/ ethyl acetate=10/1) to give compound SC-F2 (36 mg, 0.106 mmol, 51%). $^1$H NMR (400 MHz, CDCl$_3$), δ (ppm), 6.02-5.88 (t, 1H), 5.17-5.15 (m, 1H), 0.88 (s, 3H).

Synthesis of compound SC-G2. To a solution of compound SC-F2 (150 mg, 0.443 mmol) in dry THF (5 mL) was added borane-tetrahydrofuran complex (1.34 mL of 1.0 M solution in THF). After stirring at room temperature for 1 hour, the reaction mixture was cooled in an ice bath then quenched slowly with 10% aqueous NaOH. (1 mL) followed 30% aqueous solution of H$_2$O$_2$(1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered and concentrated to afford crude compound. SC-G2 (210 mg). The crude product was used in the next step without further purification.

Synthesis of compound SC-H2. To a solution of crude compound SC-G2 (210 mg) was dissolved in 10 mL of H$_2$O saturated dichloromethane (dichloromethane had been shaken with several milliliters of H$_2$O then separated from the water layer) was added Dess-Martin periodinate (380 mg, 0.896 mmol). After stirring at room temperature for 24 h, the reaction mixture was extracted with dichloromethane (3×10 mL). The combined organic layers were washed with 10% aqueous Na₂S₂O₃ (10 mL), brine (10 mL), dried over MgSO₄, filtered and concentrated. The residue was purified by chromatography on silica gel (pretroleum ether/ethyl acetate=5:1) to afford compound SC-H2 (90 mg, 0.254 mmol, 57%) as a white solid.

Synthesis of compound SC-I2. To a solution of compound SC-H2 (80 mg, 0.226 mmol) in MeOH (5 mL) was added 2 drops of HBr (48%) followed by bromine (100 mg, 0.63 mmol). After stirring at room temperature for 1 h, the reaction mixture was poured into ice-water then extracted with ethyl acetate (15 mL×3), The combined organic layers were washed with brine (20 mL), dried over MgSO4, filtered and concentrated to give crude compound SC-I2 (95 mg). The crude product was used in the next step without further purification.

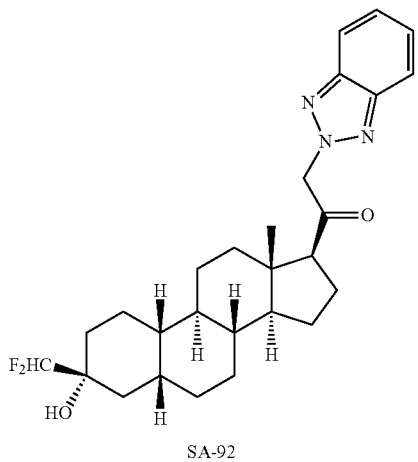

SA-92

Example 43

Synthesis of Compound SA-90 and SA-92

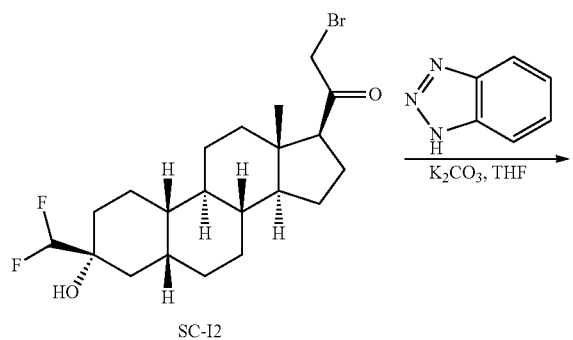

SC-I2

To a suspension of K₂CO₃ (50 mg, 0.36 mmol) in THF (5 mL) was added 1H-benzo[d][1,2,3]triazole (20 mg, 0.23 mmol) and SC-I2 (100 mg, 0.23 mmol). The mixture was stirred at rt for 15 h. The reaction mixture was poured into 5 mL H₂O and extracted with EtOAc (2×10 mL). The combined organic layers were washed with brine, dried over sodium sulfate, filtered and concentrated. The residue was purified with by reverse-phase prep-HPLC to afford the title compound as a white solid SA-90 (12.2 mg, 11%). SA-92 (6.6 mg, 6.0%). Byproduct (5 mg, 4.6%). SA-90 ¹H NMR (400 MHz, CDCl₃) δ (ppm): 8.08 (d, 1H), 7.48 (t, 1H), 7.38 (t, 1H), 7.34 (d, 1H), 5.88 (t, 1H), 5.43 (AB, 1H), 5.41(AB, 1H), 2.72 (1H, t), 0.71(s, 3H). LC-MS:rt=2.35 min, m/z=472.2 (M⁺+1). SA-92 ¹H NMR (400 MHz, CDCl₃) δ (ppm): 7.88(dd, 2H), 7.40 (dd, 2H) 6.01(t, 1H), 5.53 (AB, 1H), 5.48 (AB, 1H), 2.68 (t, 1H), 0.76 (s, 3H). LC-MS: rt=2.45 min, m/z=472.3(M⁺+1).

Example 44

Synthesis of Compound SA-93 and SA-94

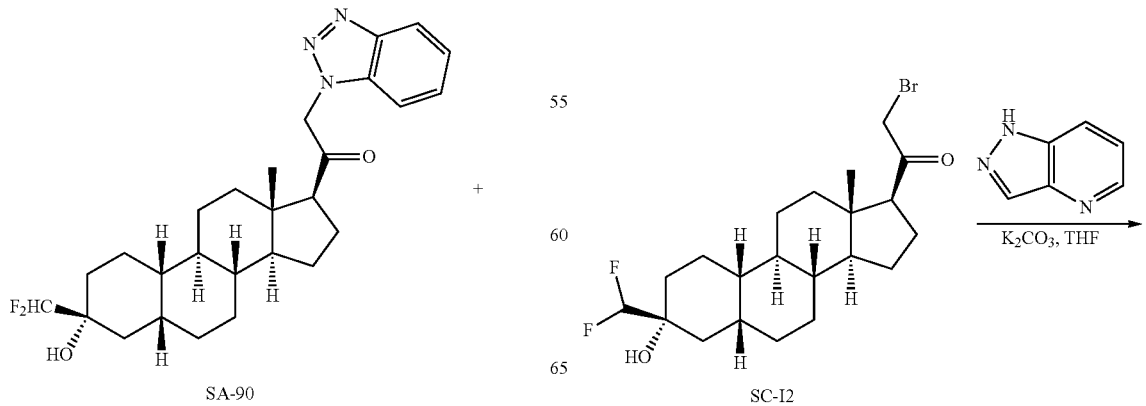

SA-90

SC-I2

Example 45

Synthesis of Compound SA-96 and SA-97

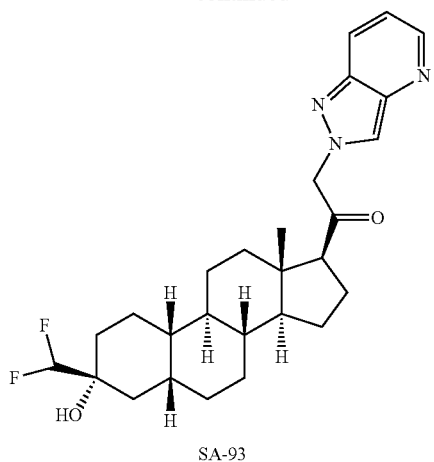

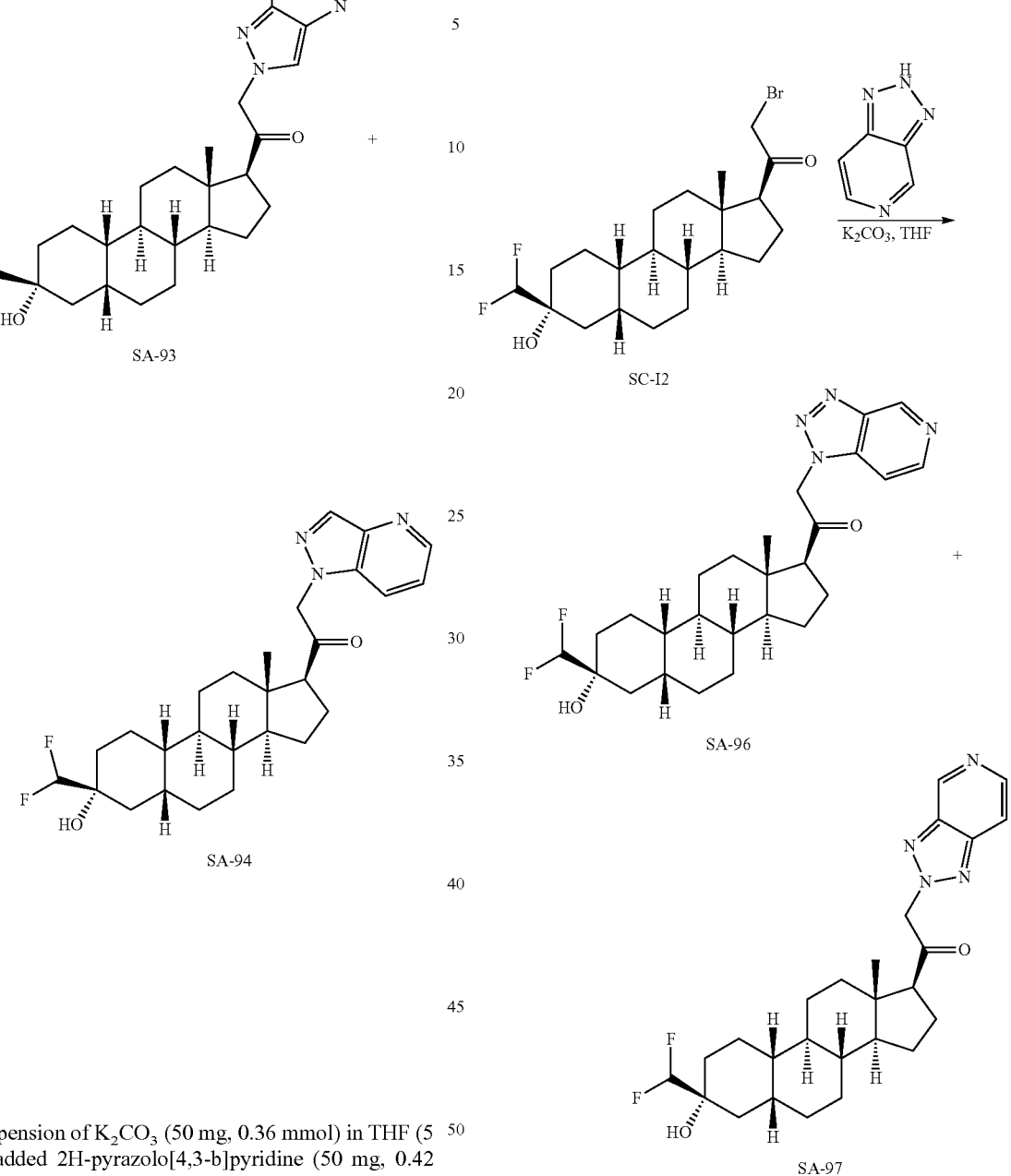

To a suspension of K₂CO₃ (50 mg, 0.36 mmol) in THF (5 mL) was added 2H-pyrazolo[4,3-b]pyridine (50 mg, 0.42 mmol) and SM (100 mg, 0.23 mmol). The mixture was stirred at rt for 15 h. The reaction mixture was poured into 5 mL H₂O and extracted with EtOAc (2×10 mL). The combined organic layers were washed with brine, dried over sodium sulfate, filtered and concentrated. The residue was purified with by reverse-phase prep-HPLC to afford the title compound as a white solid SA-93 (9.3 mg, 8.6%). SA-94 (21 mg, 19.2%). Byproduct (6 mg, 5.6%). SA-93 $^1$H NMR (400 MHz, CDCl₃) δ (ppm): 8.58(d, 1H), 8.21 (s, 1H) 8.06 (d, 1H), 7.22 (dd, 1H), 5.88(t, 1H), 5.30 (AB, 1H), 5.26 (AB, 1H), 2.69 (t, 1H), 0.71(s, 3H). LC-MS:rt=2.21 min, m/z=472.3(M⁺+1). SA-94 $^1$H NMR (400 MHz, CDCl₃) δ (ppm): 8.60 (d, 1H), 8.28 (1H, s) 7.58 (d, 1H), 7.31 (dd, 1H), 5.88(t, 1H), 5.17(AB, 1H), 5.15(AB, 1H), 2.65 (t, 1H), 0.72 (s, 3H). LC-MS: rt=2.24 min, m/z=472.2(M⁺+1).

To a suspension of K₂CO₃ (55 mg, 0.4 mmol) in THF (5 mL) was added 2H-[1,2,3]triazolo[4,5-c]pyridine (48 mg, 0.4 mmol) and 10 (86 mg, 0.2 mmol). The mixture was stirred at RT for 15 h. The residue mixture was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-96 as a white solid (30 mg, 31.8%) and SA-97 as a white solid (16 mg, 16.9%) and a white solid byproduct (2 mg, 2%). Compound SA-96: $^1$H NMR (500 MHz, CDCl₃) δ (ppm): 9.50 (s, 1H), 8.58 (d, 1H), 7.30 (d, 1H), 5.88 (t, 1H), 5.49 (AB, 1H), 5.41 (AB, 1H), 2.75 (t, 1H), 2.27-2.16 (m, 2H), 0.74 (s, 3H). LC-MS: rt=2.24 min, m/z=473.1 [M+H]⁺

Compound SA-97: $^1$H NMR (500 MHz, CDCl3) δ (ppm): 9.46 (s, 1H), 8.47 (d, 1H), 7.76 (dd, 1H), 5.87 (t, 1H), 5.62 (AB, 1H), 5.57 (AB, 1H), 2.70 (t, 1H), 2.28-2.16 (m, 2H), 0.76 (s, 3H). LC-MS: rt=2.31 min, m/z=473.1 [M+H]$^+$ Example 46

Synthesis of Compound SA-99 and SA-100

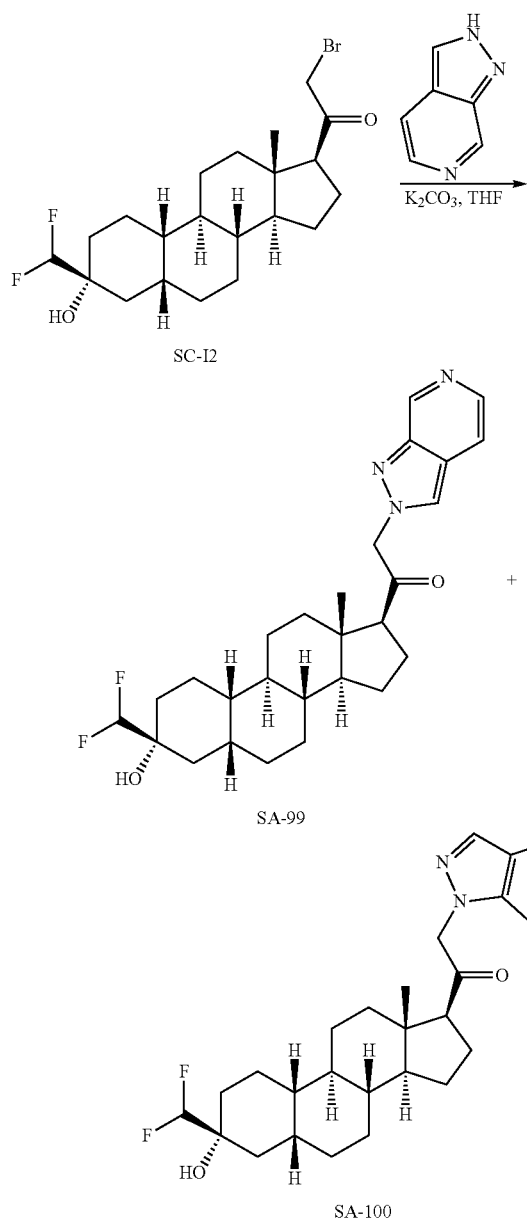

SC-I2

SA-99

SA-100

To a suspension of K$_2$CO$_3$ (55 mg, 0.4 mmol) in THF (5 mL) was added 2H-pyrazolo[3,4-c]pyridine (48 mg, 0.4 mmol) and 10 (86 mg, 0.2 mmol). The mixture was stirred at RT for 15 h. The residue mixture was poured into 5 mL H$_2$O and extracted with EtOAc (2×10 mL). The combined organic layers were washed with brine, dried over sodium sulfate, filtered and concentrated. The residue mixture was purified by reverse-phase prep-HPLC to afford SA-99 as a white solid (4 mg, 4%) and SA-100 as a white solid (19 mg, 20%) and a white solid byproduct (4 mg, 4%). Compound SA-99: $^1$H NMR (500 MHz, CDCl$_3$) δ (ppm): 9.25 (s, 1H), 8.17 (d, 1H), 7.53 (dd, 1H), 5.87 (t, 1H), 5.32 (AB, 1H), 5.23 (AB, 1H), 2.68 (t, 1H), 2.27-2.20 (m, 1H), 0.73 (s, 3H). LC-MS: rt=2.12 min, m/z=472.0 [M+H]$^+$ Compound SA-100: $^1$H NMR (500 MHz, CDCl$_3$) δ (ppm): 8.80 (s, 1H), 8.33 (d, 1H), 8.10 (s, 1H), 7.65 (dd, 1H), 5.87 (t, 1H), 5.28 (AB, 1H), 5.23 (AB, 1H), 2.69 (t, 1H), 2.24-2.13 (m, 2H), 0.73 (s, 3H). LC-MS: rt=2.18 min, m/z=472.0 [M+H]$^+$ Example 47

Synthesis of Compound SA-102, SA-103 and SA-104

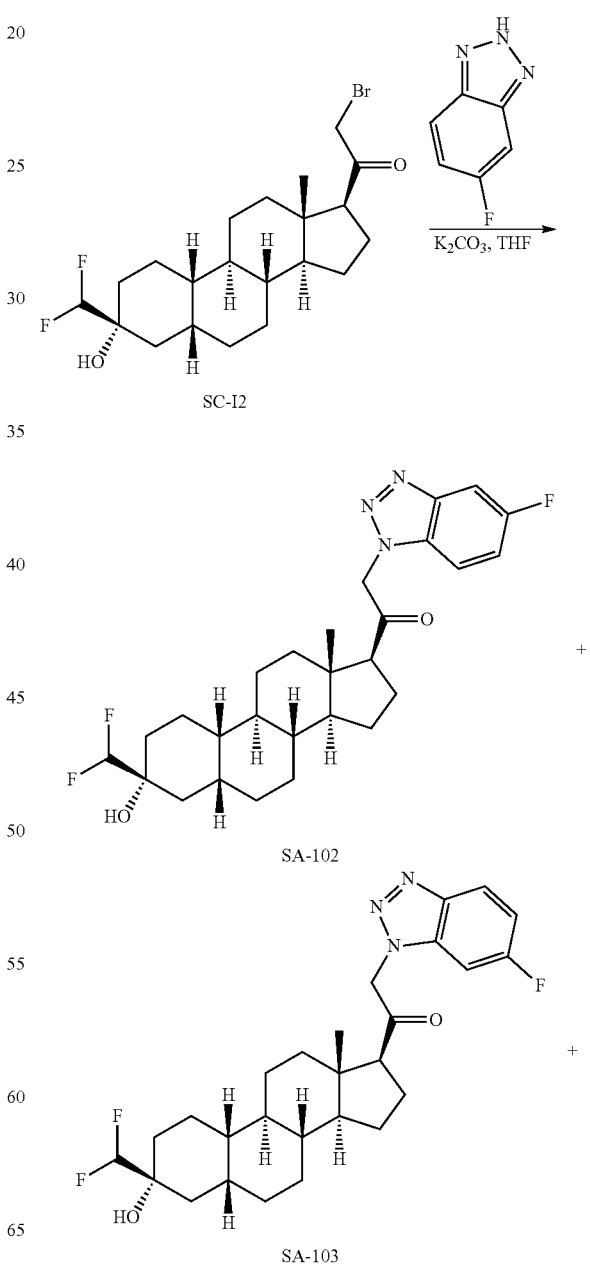

SC-I2

SA-102

SA-103

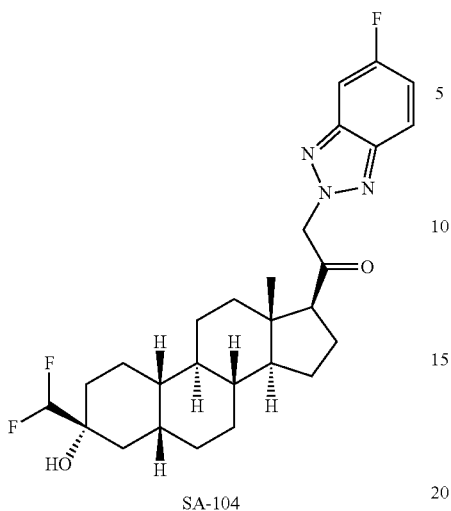

SA-104

To a suspension of K$_2$CO$_3$ (55 mg, 0.4 mmol) in THF (5 mL) was added 5-fluoro-2H-benzo[d][1,2,3]triazole (55 mg, 0.4 mmol) and 10 (86 mg, 0.2 mmol). The mixture was stirred at RT for 15 h. The residue mixture was poured into 5 mL H$_2$O and extracted with EtOAc (2×10 mL). The combined organic layers were washed with brine, dried over sodium sulfate, filtered and concentrated. The residue mixture was purified by reverse-phase prep-HPLC to afford SA-102 a white solid (15 mg, 15.3%) and SA-103 as a white solid (18.8 mg, 19%) and SA-104 as a white solid (16.3 mg, 16.5%). Compound SA-102: $^1$H NMR (400 MHz, CDCl$_3$) δ (ppm): 7.70 (dd, 1H), 7.31-7.28 (m, 2H), 5.88 (t, 1H), 5.45 (AB, 1H), 5.38 (AB, 1H), 2.72 (t, 1H), 2.27-2.13 (m, 2H), 0.73 (s, 3H). LC-MS: rt=2.38 min, m/z=490.1 [M+H]$^+$
Compound SA-103: $^1$H NMR (400 MHz, CDCl$_3$) δ (ppm): 8.04 (dd, 1H), 7.15 (td, 1H), 6.98 (dd, 1H), 5.88 (t, 1H), 5.42 (AB, 1H), 5.34 (AB, 1H), 2.72 (t, 1H), 2.23-2.14 (m, 2H), 0.73 (s, 3H). LC-MS: rt=2.39 min, m/z=490.1 [M+H]$^+$
Compound SA-104: $^1$H NMR (500 MHz, CDCl$_3$) δ (ppm): 7.86 (dd, 1H), 7.47 (dd, 1H), 7.20 (td, 1H), 5.87 (t, 1H), 5.52 (AB, 1H), 5.47 (AB, 1H), 2.66 (t, 1H), 2.24-2.13 (m, 2H), 0.75 (s, 3H). LC-MS: rt=2.48 min, m/z=490.1 [M+H]$^+$ Example 48

Synthesis of Compound SA-J

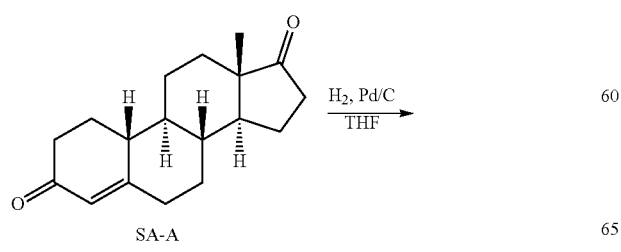

SA-A

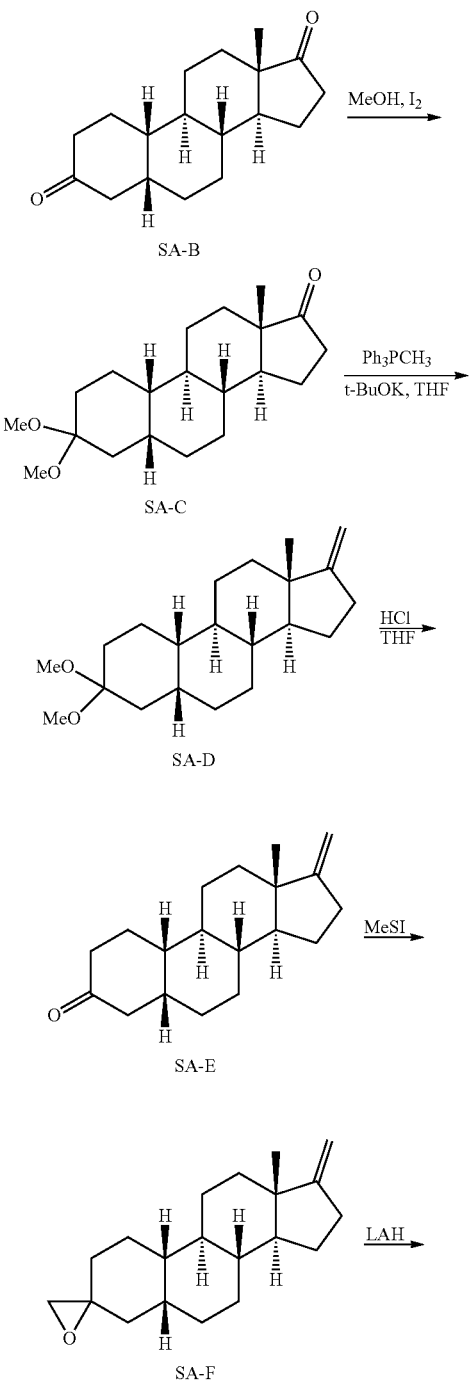

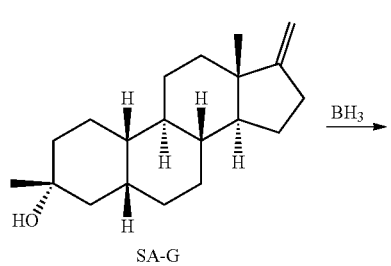

SA-G

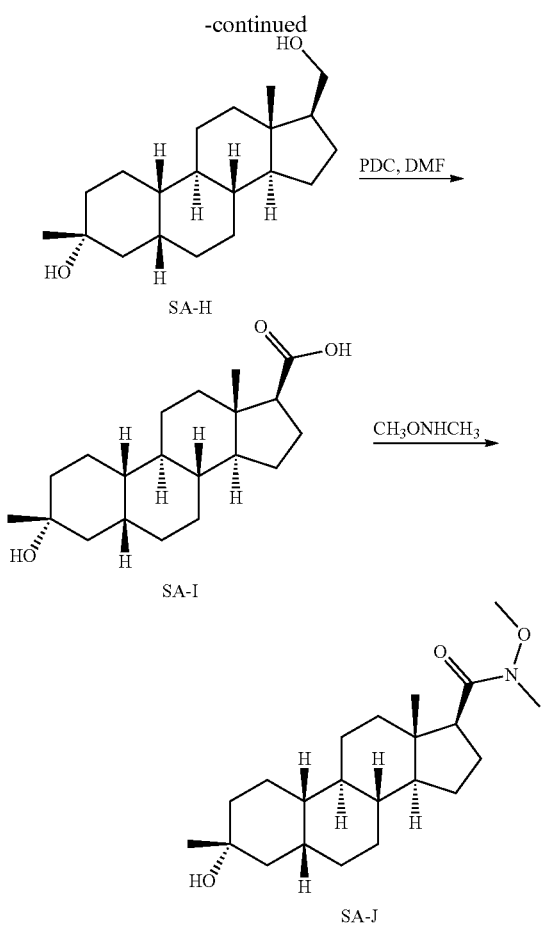

Synthesis of compound SA-B. Compound SA-A (500 mg, 1.84 mmol) and 10% Pd/black (20 mg) in tetrahydrofuran (5 mL) and concentrated hydrobromic acid (0.02 mL) was hydrogenated with a hydrogen balloon at 1 atm. After stirring at room temperature for 24 h, the mixture was filtered through a pad of celite and the filtrate was concentrated in vacuo. Recrystallization from acetone to give compound SA-B (367 mg, 1.34 mmol, 73%). $^1$H NMR (400 MHz, CDCl$_3$), δ (ppm) 2.61 (t, 1H), 2.5 (dd, 1H), 2.2 (m, 4H), 2.1 (m, 2H), 1.9 (m, 1H), 1.85 (m, 2H), 1.75 (1H), 1.65 (m, 3H), 1.55 (m, 2H), 1.45-1.1 (m, 6H), 0.98 (s, 3H).

Synthesis of compound SA-C. To a solution of compound SA-B (274 mg. 1 mmol) in methanol (4 mL) was added iodine (0.1 mmol). After stirring at 60° C. for 12 h, TLC showed no SM and the solvent was removed in vacuo. The crude product was dissolved in dichloromethane (20 mL) and washed with saturated NaHCO$_3$ (15 mL), brine, dried over Na$_2$SO$_4$, filtered and concentrated. The residue was purified by chromatography on basic alumina (pretroleum ether/ethyl acetate=9:1) to give compound SA-C (280 mg, 0.88 mmol, 88%). $^1$H NMR (400 MHz, CDCl$_3$), δ (ppm) 3.19 (s, 3H), 3.13 (s, 3H), 2.43 (dd, 1H), 2.1 (m, 1H), 1.9 (m, 2H), 1.8 (m, 4H), 1.65 (m, 2H), 1.6-1.1 (m, 13H), 0.83 (s, 3H).

Synthesis of compound SA-D. To a solution of methyl-triphenylphosphonium bromide (10.26 g, 28.84 mmol) in 30 mL THF, was added KOt-Bu (3.23 g, 28.80 mmol). The reaction was heated to 60° C. for 1 h. SA-C (3.23 g, 9.6 mmol) was added to the mixture, stirred at 60° C. for 15 h. The reaction mixture was extracted 500 ml EtOAc, washed with brine and evaporated in vacuo evaporated then purified by flash chromatographyon silica gel (petroleum ether/ethyl acetate=3:1) to afford SA-D as the white solid (2.1 g, 65% yield).

Synthesis of compound SA-E. To a solution of SA-D (1 g, 3.1 mmol) in 20 ml THF, was added 2 M HCl 2 mL, stirred at rt for 1 h. The reaction mixture was quenched with 5 mL H$_2$O and extracted with 100 mL EtOAc, washed with brine and evaporated in vacuo, then purified by chromatography (PE:EtOAc=10:1) to afford SA-E as the white solid (710 mg, 83% yield). $^1$H NMR (400 MHz, CDCl$_3$), δ (ppm) 4.65 (s, 1H), 4.63 (s, 1H), 2.6 (t, 1H), 2.5 (dd, 1H), 2.2 (m, 5H), 2.1 (m, 1H), 1.9-1.7 (mm, 4H), 1.6 (m, 3H), 1.5 (bd, 1H), 1.4-1.1 (m, 7H), 0.82 (s, 3H).

Synthesis of compound SA-F. To a stirred solution of trimethylsulfonium iodide (6.4 g, 31.5 mmol) in 10 mL of DMSO was added NaH (60%; 800 mg, 31.5 mmol).After stirring at room temperature for 1 h, a suspension of SA-E (870 mg, 3.2 mmol) in 5 mL of DMSO was added dropwise. After 15 h, the reaction mixture was poured into ice-cold water and extracted with 300 mL EtOAc, washed with 100 mL brine solution, dried and evaporated in vacuo, then purified by chromatography (PE:EtOAc=10:1) to afford SA-F as a white solid(695 mg, 76% yield).

Synthesis of compound SA-G. To a solution of SA-F and its isomer (129 mg, 0.45 mmol) in 10 mL THF, was added LiAlH$_4$ (50 mg, 1.35 mmol), stirred at rt for 1 h. The reaction mixture was quenched with 5 mL H$_2$O and extracted with 100 ml EtOAc, washed with brine solution and evaporated in vacuo then purified by chromatography (petroleum ether/ethyl acetate=3:1) to afford SA-G as a white solid (62 mg, 48% yield). $^1$H NMR (400 MHz, CDCl$_3$), δ (ppm) 4.63 (s, 1H), 4.61 (s, 1H), 2.5 (m, 1H), 2.2 (m, 1H), 1.9 (d, 1H), 1.8 (d, 3H), 1.7 (m, 3H), 1.6 (s, 3H), 1.5-1.2 (mm, 13H), 1.1 (m, 4H), 0.82 (s, 3H).

Synthesis of compound SA-H. To a solution of SA-G (86 mg, 0.3 mmol) in dry THF (5 mL) was added borane-tetrahydrofuran complex (1 mL; 1.0 M solution in THF). After stirring at room temperature for 1 hour, the reaction mixture was cooled in an ice bath then quenched slowly with 10% aqueous NaOH (1 mL) followed by 30% aqueous solution of H$_2$O$_2$ (1 mL). After stirring at room temperature for one hour, the mixture was extracted with EtOAc (3×100 mL). The combined organic layers were washed with 10% aqueous Na$_2$S$_2$O$_3$ (100 mL), brine (aq., 100 mL), dried over MgSO4, filtered and concentrated to afford SA-H as a white solid (83 mg, 91%). The crude product was used in the next step without further purification.

Synthesis of compound SA-I. To a solution of SA-H (300 mg, 0.80 mmol) in 15 mL DMF, was added PDC (2.7 g, 7.2 mmol) and 1 mL H$_2$O, stirred at rt for 15 h. The reaction mixture was extracted 100 mL EtOAc, washed with brine and evaporated in vacuo then purified by chromatography (PE:EtOAc=1:1) to afford SA-I as a white solid 128 mg, 50% yield. $^1$H NMR (400 MHz, DMSO-d6), δ (ppm), 11.90 (s, 1H), 4.22 (s, 1H), 2.28 (t, 1H), 1.9 (m, 2H), 1.6 (2×m, 7H), 1.5-0.9 (multiple m and s, 17H), 0.68 (s, 3H).

Synthesis of compound SA-J. To a solution of SA-I (200 mg, 0.61 mmol) in 5 mL DMF, was added N,O-dimethyl-hydroxylamine HCl salt (60 mg, 0.62 mmol), HATU (236 mg, 0.62 mmol), DIPEA 1 mL, and stirred at rt for 3 h, The reaction mixture was extracted 100 mL EtOAc, washed with brine solution and evaporated in vacuo then purified by chromatography (petroleum ether/ethyl acetate=1:1) to afford SA-J as a white solid 110 mg, 55% yield. $^1$H NMR (400 MHz, DMSO-d6), δ (ppm), 3.64 (s, 3H), 3.19 (s, 3H), 2.70 (bs, 1H), 2.17 (bt, 1H), 1.8-1.6 (m, 8H), 1.5-1.2 (several m and s, 14H), 1.1 (m, 3H), 0.73 (s 3H).

Example 48

Synthesis of Compound SA-105

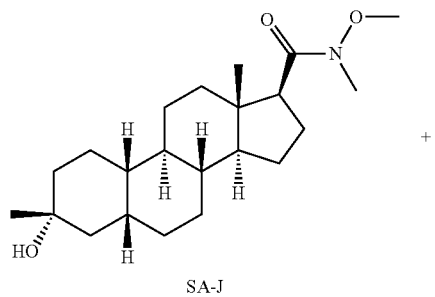
SA-J

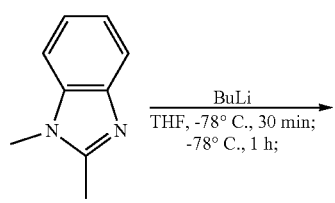
BuLi
THF, -78° C., 30 min;
-78° C., 1 h;

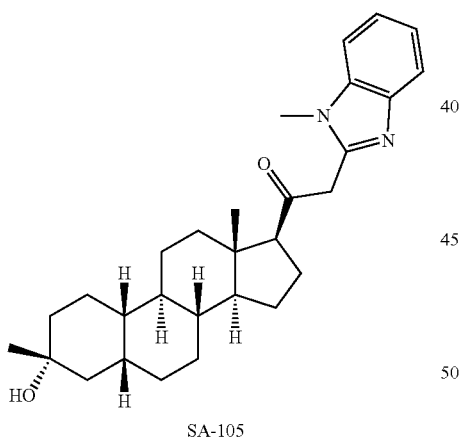
SA-105

To a stirred solution of 1,2-dimethyl-1H-benzo[d]imidazole (100 mg, 0.7 mmol) in 10 mL THF was added BuLi (2.5 M; 0.3 ml, 0.7 mmol) at −78° C. After stirring at −78° C. for 30 min, a solution of SA-J (50 mg, 0.14 mmol) in 3 mL of THF was added dropwise at −78° C. After stirring at −78° C. for 1 h, the reaction mixture was poured into ice-cold water and extracted with EtOAc (100 mL×3). The combined extracts were washed with brine (100 mL×3), dried (MgSO₄), filtered, and evaporated in vacuo, purified by prep-HPLC to afford SA-105 as the white solid 13 mg, 21.43% yield. The product exists as a mixture of C-20 ketone and enol. ¹H NMR (500 MHz, CDCL3), δ (ppm), 7.71-7.74,7.37-7.41,7.23-7.34,7.16-7.18 (m, 4H,C-20 ketone and enol), 5.20 (s, 1H,C-20 enol), 4.11(1H, AB), 4.05(1H, AB), 3.71(3H, s,C-20 ketone), 3.57(3H, C-20 enol), 2.78 (1H, t, C-20 ketone), 2.40 (1H, t, C-20 enol), 0.70 (s, 3H). LCMS:rt=2.39 min, m/z=449.3 [M+H]

Example 49

Synthesis of Compound SA-106

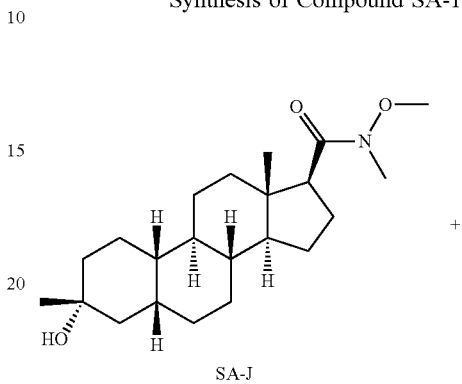
SA-J

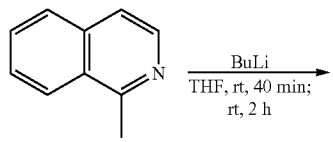
BuLi
THF, rt, 40 min;
rt, 2 h

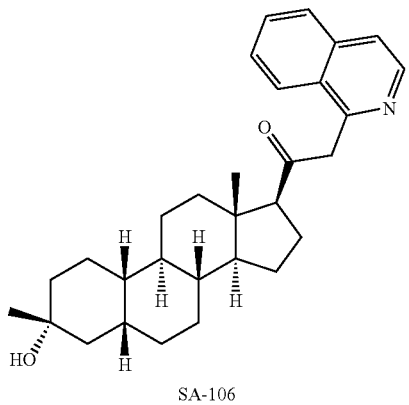
SA-106

To a stirred solution of 1-methylisoquinoline (197 mg, 1.375 mmol) in 10 mL of THF was added BuLi (2.5 M; 0.55 mL, 1.375 mmol) at rt. After stirring at rt for 40 min, a solution of SA-J (0.1 g, 0.275 mmol) in 5 mL of THF was added dropwise at 0° C. After stirring at rt for 2 h, the reaction mixture was poured into ice-cold water and extracted with EtOAc (100 mL×3), washed with brine (100 mL×3), dried (MgSO₄), filtered, and evaporated in vacuo, then purified by prep-HPLC to afford SA-106 as the yellow solid 18 mg, 15% yield. ¹H NMR (500 MHz, CDCl₃), δ (ppm), 15.49 (bs, 1H), 8.03 (d, 1H), 7.61-7.56 (m, 1H), 7.50 (d, 1H), 7.46 (t, 1H), 7.22 (d, 1H), 5.97 (s, 1H), 2.54 (t, 1H), 0.68 (s, 3H). LCMS: Rt=2.090 min, MS (ESI) m/z: 446 [M+H]⁺.

Example 50

Synthesis of Compound SD-D

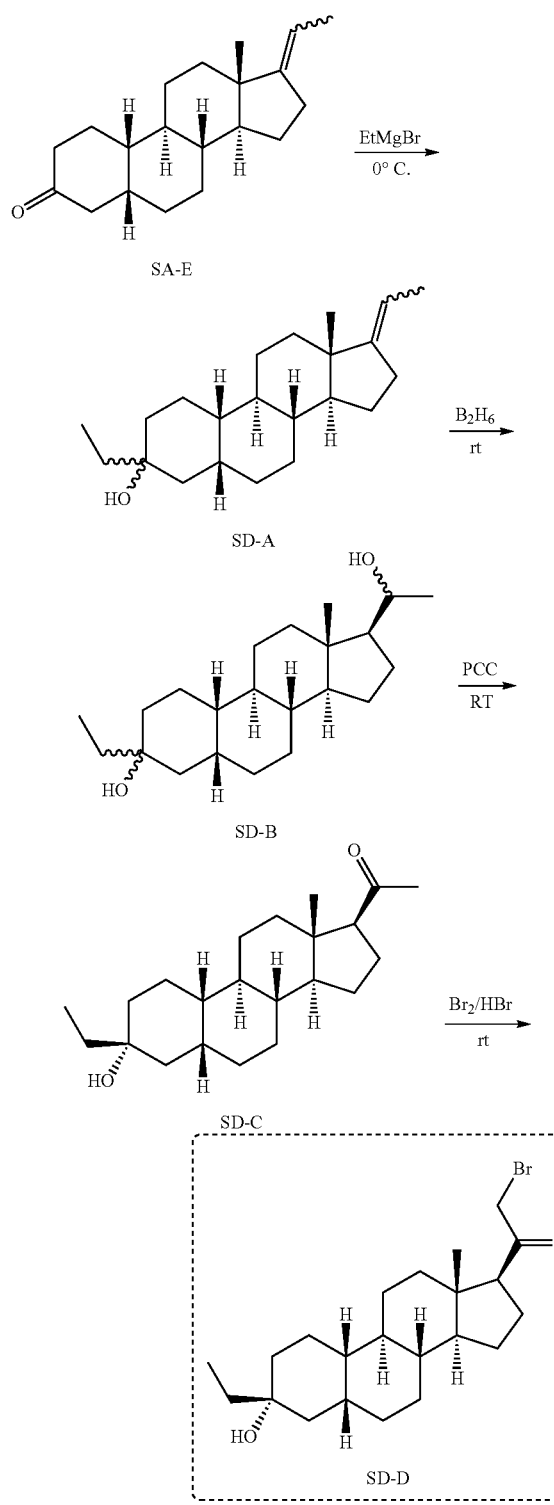

Synthesis of compound SD-A. To a solution of EtMgBr (5 mmol, 1M in THF) in THF (20 mL) at 0° C. was added a solution of compound SA-E (858 mg, 3 mmol) in dry THF (5 mL) via syringe pump over 30 min. After stirring at 0° C. for 5 h, the reaction mixture was allowed to warm up and stirred at room temperature overnight. The reaction mixture was quenched with iced-cold water and extracted with EtOAc (15 mL×3). The combined organic layers were washed with brine, dried over sodium sulfate, filtered and concentrated. The white residue was purified by flash column chromatography (petroleum ether/ethyl acetate=20:1 to 10:1) to give compound SD-A (900 mg).

Synthesis of compound SD-B. To a solution of compound SD-A (200 mg, 0.66 mmol) in dry THF (5 mL) was added borane-tetrahydrofuran complex (2 mL of 1.0 M solution in THF). After stirring at room temperature for 1 hour, the reaction mixture was cooled in an ice bath then quenched slowly with 10% aqueous NaOH (1 mL) followed by 30% aqueous solution of $H_2O_2$ (1.2 mL). The mixture was allowed to stir at room temperature for 1 hour then extracted with EtOAc (3×10 mL). The combined organic layers were washed with 10% aqueous $Na_2S_2O_3$ (10 mL), brine (10 mL), dried over $MgSO_4$, filtered and concentrated to afford compound SD-B (260 mg, crude). The crude product was used in the next step without further purification.

Synthesis of compound SD-C. To a solution of compound SD-B (260 mg, crude) was dissolved in 10 mL dichloromethane was added PCC (449 mg). After stirring at room temperature for 24 h, the reaction mixture was extracted with dichloromethane (3×10 mL). The combined organic layers were washed with 10% aqueous NaCl (10 mL), brine (10 mL), dried over $MgSO_4$, filtered and concentrated. The residue was purified by chromatography on silica gel (petroleum ether/ethyl acetate=4:1 to 2:1) to afford title SD-C (15 mg) as a white solid. $^1H$ NMR (500 MHz, $CDCl_3$), δ (ppm), 2.49(1H, t), 2.09 (s, 3H)0.84(3H, t), 0.59 (s, 3H).

Synthesis of compound SD-D. To a solution of compound SD-C (30 mg, 0.09 mmol) in MeOH (5 mL) was added 2 drops of HBr (48%) followed by bromine (100 mg, 0.62 mmol). After stirring at room temperature for 1 h, the reaction mixture was poured into ice-water then extracted with ethyl acetate (15 mL×3), The combined organic layers were washed with brine (20 mL), dried over $MgSO_4$, filtered and concentrated to give compound SD-D (36 mg crude). The crude product was used in the next step without further purification.

Example 51

Synthesis of Compound SA-107, SA-108, and SA-109

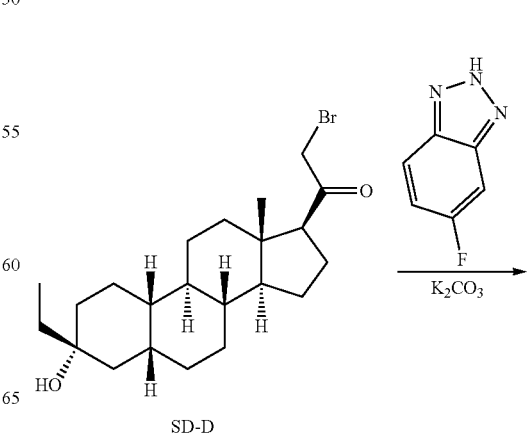

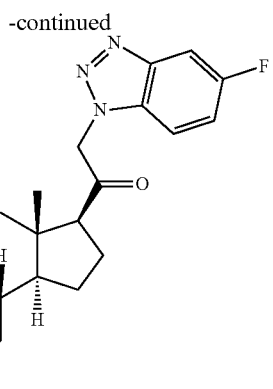

SA-107

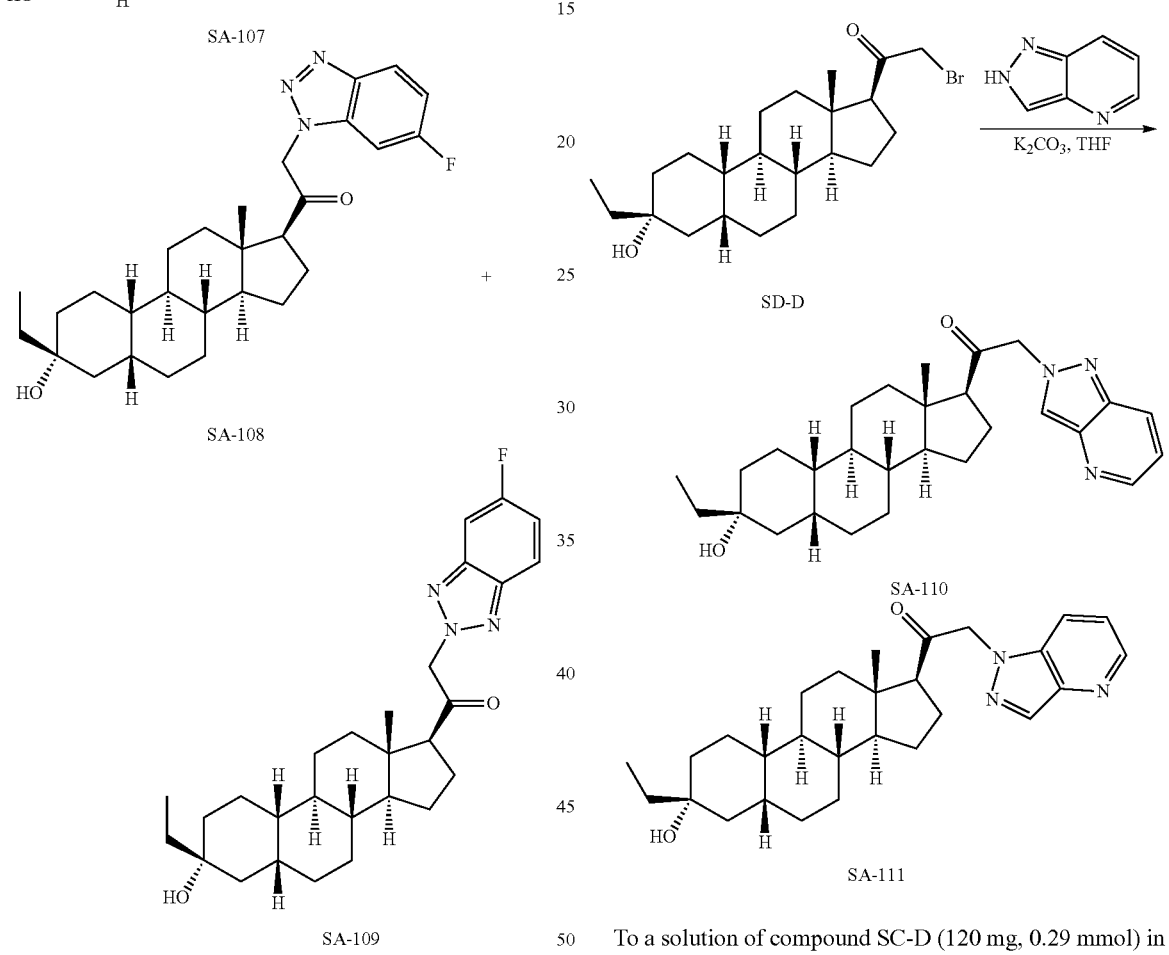

To a suspension of K₂CO₃ (55 mg, 0.4 mmol) in THF (5 mL) was added 5-fluoro-2H-benzo[d][1,2,3]triazole (55 mg, 0.4 mmol) and SD-D (85 mg, 0.2 mmol). The mixture was stirred at RT for 15 h. The residue mixture was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-107 as a white solid (5.6 mg, 5.5%) and SA-108 a white solid (8.4 mg, 8.5%) and SA-109 as a white solid (13.7 mg, 14.0%). Compound SA-107: ¹H NMR (500 MHz, CDCl₃) δ (ppm): 7.70 (d, 1H), 7.30-7.28 (m, 2H), 5.43 (AB, 1H), 5.39 (AB, 1H), 2.71 (t, 1H), 2.23-2.09 (m, 2H), 1.47 (q, 2H), 0.93 (t, 3H), 0.74 (s, 3H). LC-MS: rt=2.32 min, m/z=468.3 [M+H]⁺ Compound SA-108: ¹H NMR (500 MHz, CDCl₃) δ (ppm): 8.04 (dd, 1H), 7.15 (td, 1H), 6.98 (dd, 1H), 5.39 (AB, 1H), 5.35 (AB, 1H), 2.71 (t, 1H), 2.25-2.08 (m, 2H), 1.47 (q, 2H), 0.93 (t, 3H), 0.74 (s, 3H). LC-MS: rt=2.34 min, m/z=468.3 [M+H]⁺ Compound SA-109: ¹H NMR (500 MHz, CDCl₃) δ (ppm): 7.86 (dd, 1H), 7.47 (dd, 1H), 7.20 (td, 1H), 5.52 (AB, 1H), 5.48 (AB, 1H), 2.66 (t, 1H), 2.24-2.07 (m, 2H), 1.46 (q, 2H), 0.93 (t, 3H), 0.75 (s, 3H). LC-MS: rt=2.43 min, m/z=468.3 [M+H]⁺

Example 52

Synthesis of Compounds SA-110 and SA-111

To a solution of compound SC-D (120 mg, 0.29 mmol) in THF (3 mL) was added K₂CO₃ (210 mg, 1.5 mmol) and 2H-pyrazolo[4,3-b]pyridine (180 mg, 1.5 mmol). The resulting solution was stirred at room temperature overnight, then LCMS showed the reaction was completed. The reaction was diluted with EtOAc (20 mL) and the resulting solution was washed with brine (10 mL), dried over Na₂SO₄ and concentrated in vacuo. The residue was purified by prep-HPLC to give SA-110 (6 mg, 0.0113 mmol, Yield=5%), SA-111 (8 mg, 0.0117 mmol, Yield=6%) as a white solid. SA-110: 1H NMR: (500 MHz, CDCl₃), δ (ppm), 8.58 (t, 1H), 8.22 (s, 1H), 8.04 (d, 1H), 7.23 (dd, 1H), 5.27 (AB, 1H), 5.21 (AB, 1H), 2.67 (t, 1H), 0.89 (t, 3H), 0.72 (s, 3H). LC-MS: rt=2.276 min; m/z=450.4 (M+H)⁺ SA-111: 1H NMR: (500 MHz, CDCl₃), δ (ppm), 8.60 (dd, 1H), 8.28 (s, 1H), 7.59 (d, 1H), 7.30 (dd, 1H), 5.19 (AB, 1H), 5.13 (AB, 1H), 2.67(t, 1H), 0.90 (t, 3H), 0.72 (s, 3H). LC-MS: rt=2.389 min; m/z=450.2 (M+H)⁺

Example 53

Synthesis of Compound SA-112, SA-113 and SA-114

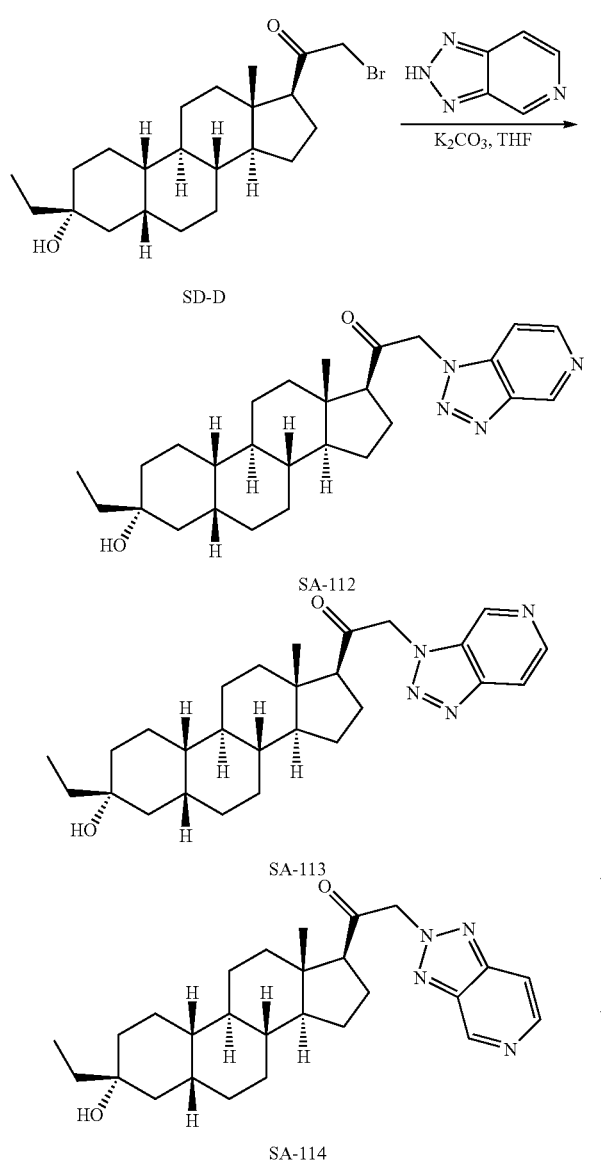

To a solution of SD-D (160 mg, 0.39 mmol) in THF (3 mL) was added 2H-[1,2,3]triazolo[4,5-c] pyridine (230 mg, 1.95 mmol) and K$_2$CO$_3$ (270 mg, 1.95 mmol). The resulting solution was stirred at room temperature overnight, then LCMS showed the reaction was completed. The reaction was diluted with EtOAc (40 mL) and washed with brine (20 mL×2), dried over Na$_2$SO$_4$ and concentrated in vacuo. The residue was purified by Prep-HPLC to give SA-112/SA-113 (mixture, 35 mg, 16%) and SA-114 (11 mg, 0.0244 mmol, Yield=5%) as a white solid. NMR showed SA-112/SA-113 is the mixture of two compounds and further purification by Chiral-HPLC to give SA-112 (9 mg, 0.02 mmol, Yield=5%), SA-113 (3 mg, 0.00666 mmol, Yield=3%) as a white solid. SA-112: 1H NMR: (500 MHz, CDCl$_3$), δ (ppm), 9.49 (d, 1H), 8.58 (d, 1H), 7.30 (dd, 1H), 5.49 (AB, 1H), 5.42 (AB, 1H), 2.75 (t, 1H), 0.90 (t, 3H), 0.76 (s, 3H). LC-MS: rt=2.291 min; m/z=451.1 (M+H)$^+$ SA-113: 1H NMR: (500 MHz, CDCl$_3$), δ (ppm), 8.97 (d, 1H), 8.55 (d, 1H), 7.98 (d, 1H), 5.57 (AB, 1H), 5.52 (AB, 1H), 2.77 (t, 1H), 0.90 (t, 3H), 0.76 (s, 3H). LC-MS: rt=2.305 min; m/z=451.1 (M+H)$^+$ SA-114: 1H NMR: (500 MHz, CDCl$_3$), δ (ppm), 9.46 (d, 1H), 8.47 (d, 1H), 7.76 (dd, 1H), 5.62 (AB, 1H), 5.57 (AB, 1H), 2.70 (t, 1H), 0.90 (t, 3H), 0.76 (s, 3H). LC-MS: rt=2.373 min; m/z=451.4 (M+H)$^+$

Example 54

Synthesis of Compound SE-D2

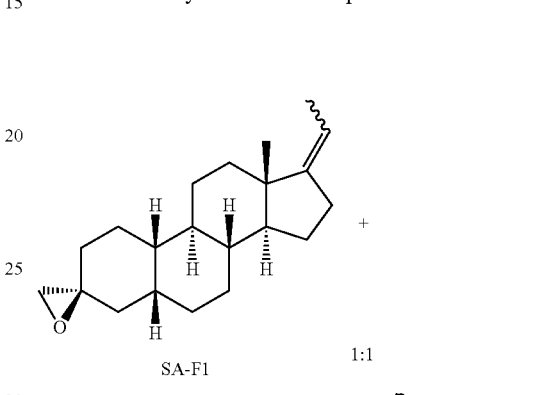

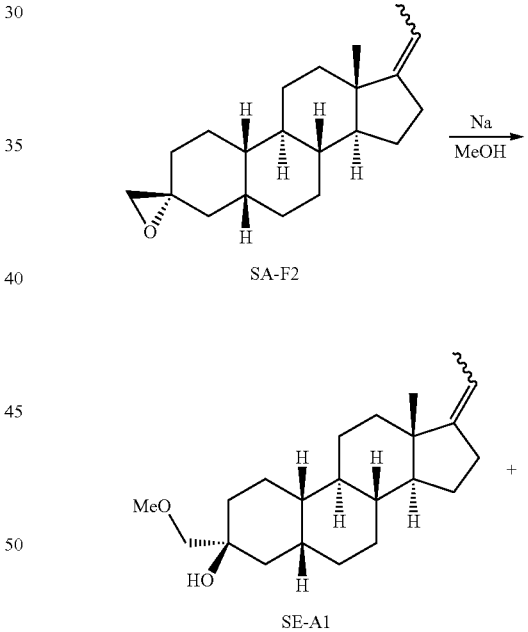

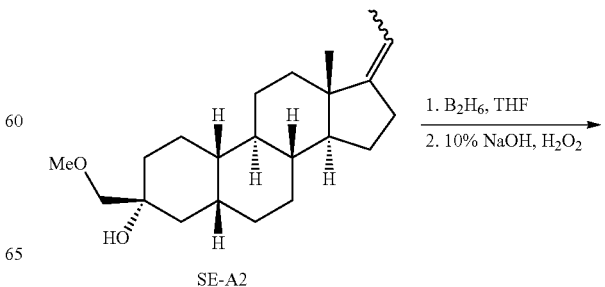

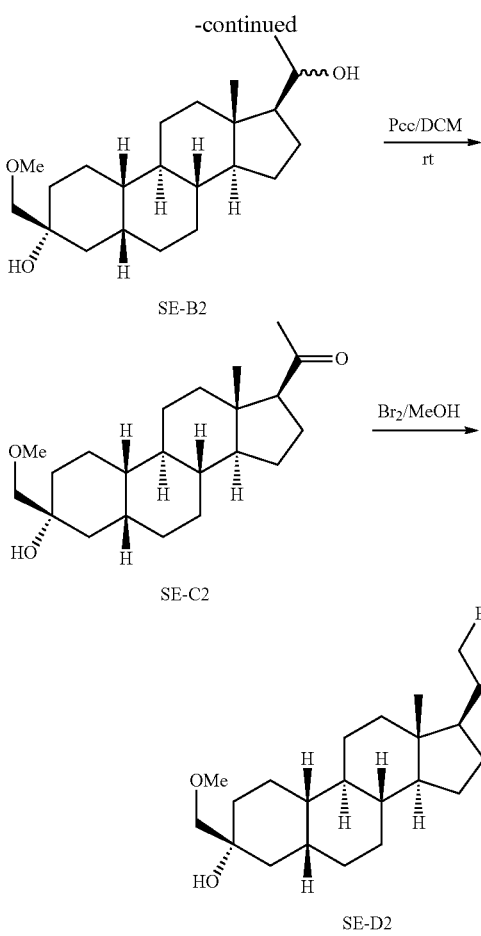

1. Synthesis of compound SE-A. Compound mixture SA-F1 and SA-F2 (5.0 g, 16.7 mmol) was dissolved in dry methanol (250 mL), and Na metal (1.2 g, 50.0 mmol) was added and the solution was refluxed for 16 h. Methanol was then evaporated off and the residue was dissolved in dichloromethane and washed with H$_2$O (3×50 mL) and brine (100 mL), dried over MgSO$_4$, filtered, and concentrated. The crude target compound was purified by via silica gel chromatography (petroleum ether/ethyl acetate=10:1 to 5:1), and concentrated to give the product mixture SE-A1 and SE-A2 (4.6 g, 83%) as a white solid.

Synthesis of compound SE-B. To a solution of reactant mixture SE-A1 and SE-A2 (4.6 g, 13.9 mmol) in anhydrous THF (30 mL) was added BH$_3$.THF (1.0 M, 27.7 mL, 27.7 mmol), the solution was stirred at 25° C. overnight, then the reaction was quenched by addition of water (5 mL). 2 M NaOH solution (30 mL) was added followed by 30% H$_2$O$_2$ (30 mL). The mixture was stirred at room temperature for 1 hour. The mixture was diluted with ethyl acetate (200 mL) and resulting solution was washed with brine (2×100 mL), dried over magnesium sulfate and concentrated in vacuo. The crude product mixture was used directly in the next step without further purification.

Synthesis of compound SE-C. To a solution of crude reactant mixture SE-B1 and SE-B2 (4.9 g, 13.9 mmol, theoretical amount) in dichloromethane (40 mL) was added Pyridinium chlorochromate (PCC) in portions (6.0 g, 27.8 mmol). The solution was stirred at 25° C. overnight then the mixture was filtered through a short pad of silica gel and the silica gel was washed with dichloromethane (3×50 mL). All filtrates were combined and concentrated in vacuo. The residue was purified by flash chromatography (eluant: petroleum ether/ethyl acetate=15:1) to afford product SE-C1 (2.1 g, 6.03 mmol, Yield=43% (2 steps)) as white solid and product SE-C2 (2.2 g, 6.32 mmol, Yield=45% (2 steps)) as white solid. Compound SE-C1: $^1$H NMR (500 MHz, CDCl$_3$) δ (ppm): 3.40 (s, 3H), 3.20 (s, 2H), 2.62-2.51 (m, 2H), 2.11 (s, 3H), 2.02-1.99 (m, 2H), 0.62 (s, 3H). Compound SE-C2: $^1$H NMR (500 MHz, CDCl$_3$) δ (ppm): 3.42 (AB, 1H), 3.38 (AB, 1H), 3.40 (s, 3H), 2.65 (s, 1H), 2.54 (t, 1H), 2.16-2.14 (m, 1H), 2.11 (s, 3H), 2.02-1.98 (m, 1H), 0.61 (s, 3H).

Synthesis of compound SE-D2. To a solution of reactant SE-C2 (100 mg, 0.301 mmol) in methanol (10 mL) was added 48% hydrobromic acid (152 mg, 0.903 mmol) followed by bromine (241 mg, 0.077 mL, 1.51 mmol). The solution was heated at 25° C. for 1.5 hours then the mixture was poured into cold water (50 mL) and the resulting solid was extracted with ethyl acetate (2×50 mL). The combined organic extracts were washed with brine (50 mL), dried over magnesium sulfate and concentrated in vacuo. The crude product SE-D2 was used directly without further purification in the next step.

Example 55

Synthesis of Compound SA-115

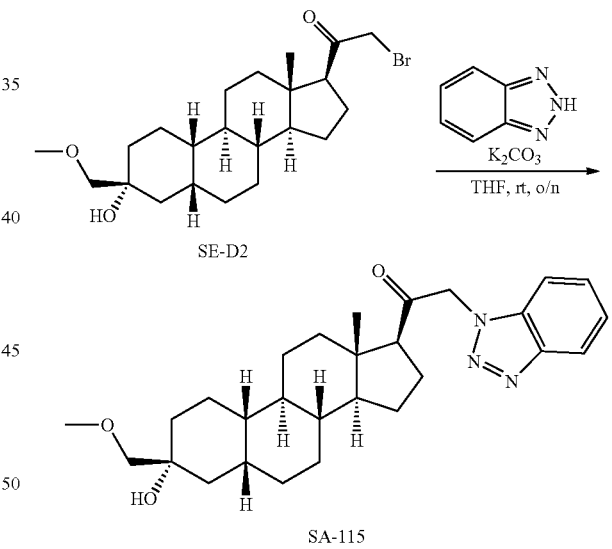

To a solution of compound SE-D2 (120 mg, 0.28 mmol) in THF (3 mL) was added K$_2$CO$_3$ (190 mg, 1.4 mmol) and 2H-benzo[d][1,2,3]triazole (167 mg, 1.4 mmol). The resulting solution was stirred at room temperature overnight, then the reaction was diluted with EtOAc (20 mL). The resulting solution was washed with brine (10 mL), dried over Na$_2$SO$_4$ and concentrated in vacuo. The residue was purified by prep-HPLC to give SA-115 (36 mg, 25%) as a white solid. 1H NMR: (500 MHz, CDCl$_3$), δ (ppm), 8.08 (d, 1H), 7.49 (t, 1H), 7.38 (t, 1H), 7.34 (d, 1H), 5.45 (AB, 1H), 5.39 (AB, 1H), 3.42 (AB, 1H), 3.40 (s, 3H), 3.39 (AB, 1H), 2.72 (t, 1H), 2.64 (s, 1H), 0.73 (s, 3H). LC-MS: rt=2.37 min; m/z=466.2 (M+H)$^+$

Example 56

Synthesis of Compound SA-116 and SA-117

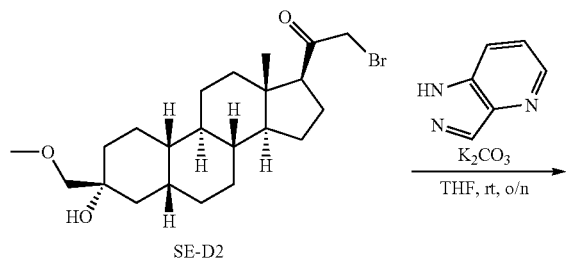
SE-D2

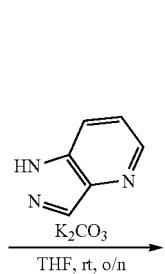

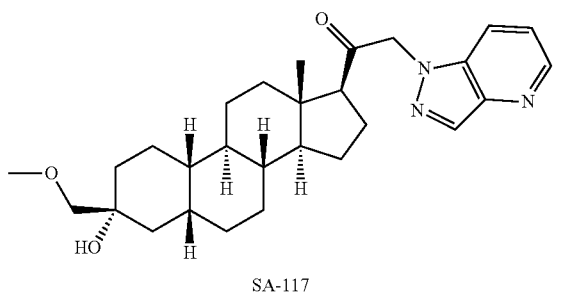
SA-116

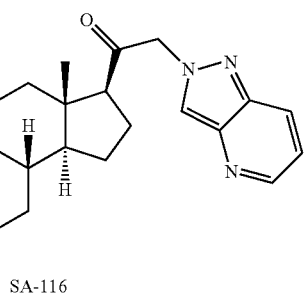
SA-117

To a solution of compound SE-D2 (120 mg, 0.28 mmol) in THF (3 mL) was added K₂CO₃ (190 mg, 1.4 mmol) and 1H-pyrazolo[4,3-b]pyridine (167 mg, 1.4 mmol). The resulting solution was stirred at room temperature overnight, the the reaction was diluted with EtOAc (20 mL). The resulting solution was washed with brine (10 mL), dried over Na₂SO₄ and concentrated in vacuo. The residue was purified by prep-HPLC to give SA-116 (18 mg, 14%), SA-117 (13 mg, 10%) as a white solid. SA-116: 1H NMR: (500 MHz, CDCl₃), δ (ppm), 8.59 (d, 1H), 8.23 (s, 1H), 8.04 (d, 1H), 7.23 (dd, 1H), 5.28 (AB, 1H), 5.21 (AB, 1H), 3.42 (AB, 1H), 3.40 (s, 3H), 3.39 (AB, 1H), 2.67 (t, 1H), 2.64 (s, 1H), 0.73 (s, 3H). LC-MS: rt=2.22 min; m/z=466.2 (M+H)⁺ SA-117: 1H NMR: (500 MHz, CDCl₃), δ (ppm), 8.60 (d, 1H), 8.28 (s, 1H), 7.58 (d, 1H), 7.29 (dd, 1H), 5.19 (AB, 1H), 5.14 (AB, 1H), 3.42 (AB, 1H), 3.40 (S, 3H), 3.39 (AB, 1H), 2.67 (t, 1H), 2.6 (s, 1H), 0.72 (s, 3H). LC-MS: rt=2.26 min; m/z=466.2 (M+H)⁺

Example 57

Synthesis of Compound SA-118 and SA-119

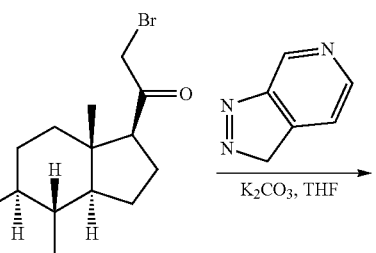
SE-D2

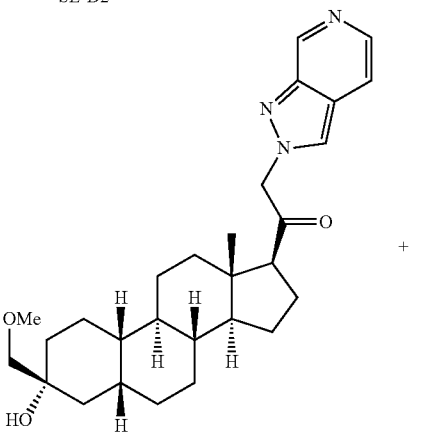
SA-118

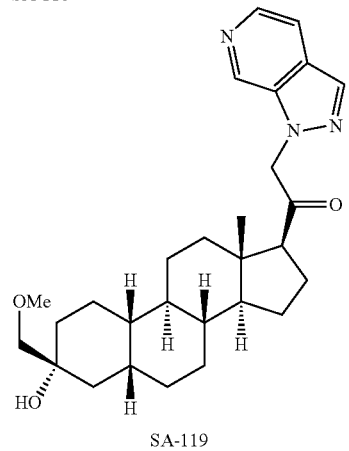
SA-119

To a suspension of K₂CO₃ (55 mg, 0.4 mmol) in THF (5 mL) was added 3H-pyrazolo[3,4-c]pyridine (47.6 mg, 0.4 mmol) and 10 (85 mg, 0.2 mmol). The mixture was stirred at RT for 15 h then was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-118 as a white solid (21 mg, 22.5%) and SA-119 as a white solid (15 mg, 16.1%). Compound SA-118: ¹H NMR (500 MHz, CDCl₃) δ (ppm): 9.25 (s, 1H), 8.16 (d, 1H), 7.98 (s, 1H), 7.52 (dd, 1H), 5.32 (AB, 1H), 5.23 (AB, 1H), 3.42 (AB, 1H), 3.39 (AB, 1H), 3.40 (s, 3H), 2.67 (t, 1H), 2.26-2.19 (m, 1H), 2.14-2.12 (m, 1H), 0.71 (s, 3H). LC-MS: rt=2.11 min, m/z=466.1 [M+H]+
Compound SA-119: ¹H NMR (500 MHz, CDCl₃) δ (ppm): 8.79 (s, 1H), 8.33 (d, 1H), 8.09 (s, 1H), 7.64 (d, 1H), 5.28 (AB, 1H), 5.23 (AB, 1H), 3.43 (AB, 1H), 3.40 (s, 3H), 3.39 (AB, 1H), 2.71-2.67 (m, 1H), 2.21-2.12 (m, 1H), 0.72 (s, 3H). LC-MS: rt=2.18 min, m/z=466.1 [M+H]+

Example 58

Synthesis of Compound SA-120, SA-121 and SA-122

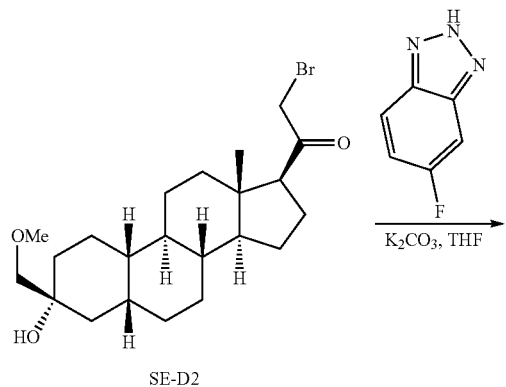

SE-D2

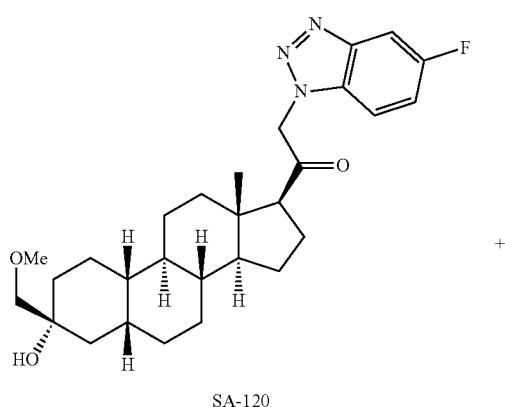

SA-120

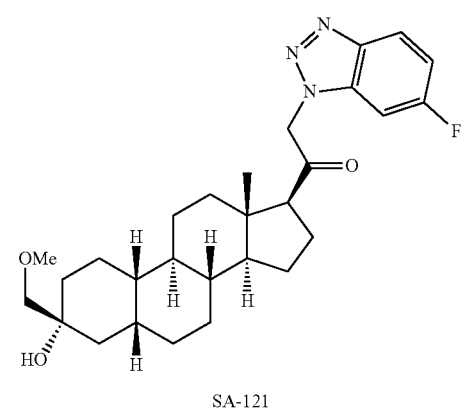

SA-121

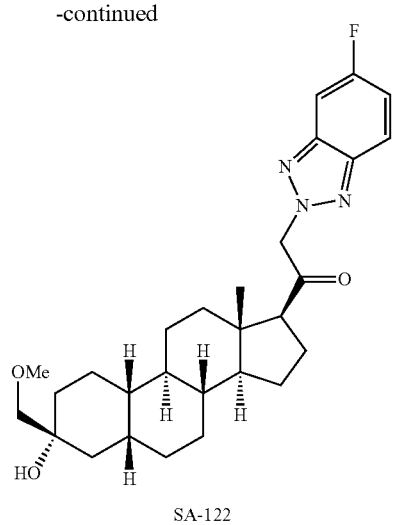

SA-122

To a suspension of K₂CO₃ (55 mg, 0.4 mmol) in THF (5 mL) was added 5-fluoro-2H-benzo[d][1,2,3]triazole (55 mg, 0.4 mmol) and 10 (85 mg, 0.2 mmol). The reaction mixture was stirred at RT for 15 h then was poured into 5 mL H₂O and extracted with EtOAc (2×10 mL). The combined organic layers were washed with brine, dried over sodium sulfate, filtered and concentrated. The residue mixture was purified by reverse-phase prep-HPLC to afford SA-120 as a white solid (6.0 mg, 6.2%) and SA-121 as a white solid (8.6 mg, 8.9%) and SA-122 as a white solid (12.6 mg, 13.0%). Compound SA-120: ¹H NMR (500 MHz, CDCl3) δ (ppm): 7.70 (dd, 1H), 7.29-7.26 (m, 2H), 5.45 (AB, 1H), 5.38 (AB, 1H), 3.42 (AB, 1H), 3.39 (AB, 1H), 3.40 (s, 3H), 2.72 (t, 1H), 2.64 (s, 1H), 2.47 (s, 3H), 2.22-2.13 (m, 2H), 0.72 (s, 3H). LC-MS: rt=2.42 min, m/z=484.2 [M+H]+ Compound SA-121: ¹H NMR (500 MHz, CDCl₃) δ (ppm): 8.04 (dd, 1H), 7.15 (td, 1H), 6.98 (dd, 1H), 5.41 (AB, 1H), 5.34 (AB, 1H), 3.42 (AB, 1H), 3.39 (AB, 1H), 3.40 (s, 3H), 2.72 (t, 1H), 2.64 (s, 1H), 2.23-2.13 (m, 2H), 0.73 (s, 3H). LC-MS: rt=2.43 min, m/z=484.2 [M+H]+ Compound SA-122: ¹H NMR (500 MHz, CDCl₃) δ (ppm): 7.86 (dd, 1H), 7.47 (dd, 1H), 7.20 (td, 1H), 5.52 (AB, 1H), 5.47 (AB, 1H), 3.42 (AB, 1H), 3.39 (AB, 1H), 3.40 (s, 3H), 2.66 (t, 1H), 2.65 (s, 1H), 2.23-2.12 (m, 2H), 0.74 (s, 3H). LC-MS: rt=2.53 min, m/z=484.2 [M+H]+

Example 59

Synthesis of Compound SA-123, SA-124 and SA-125

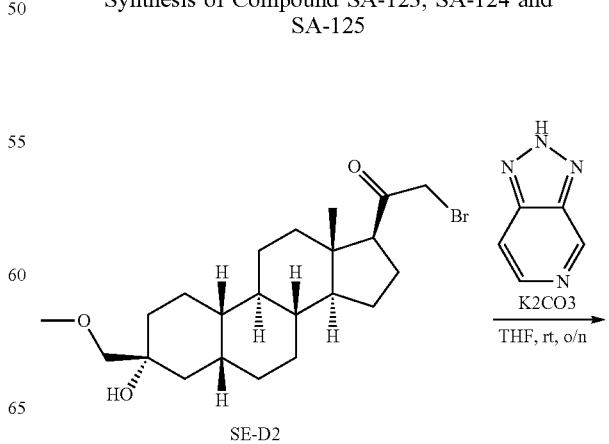

SE-D2

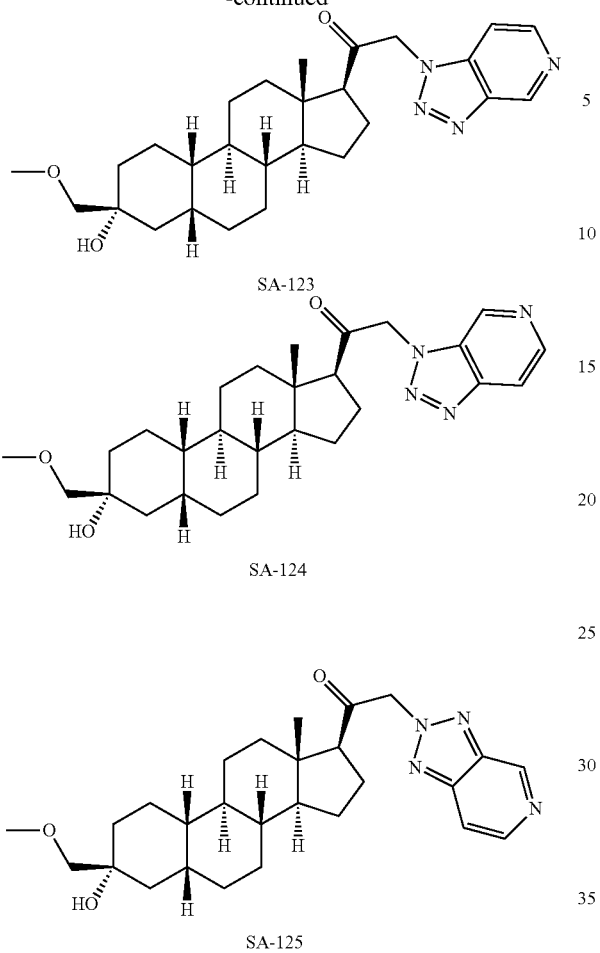

To a solution of Compound SE-D2 (160 mg, 0.38 mmol) in THF (3 mL) was added 2H-[1,2,3] triazolo[4,5-c] pyridine (230 mg, 1.9 mmol) and $K_2CO_3$ (262 mg, 1.9 mmol). The resulting solution was stirred at room temperature overnight, then LCMS showed the reaction was completed. The reaction was diluted with EtOAc (40 mL) and washed with brine (20 mL×2), dried over $Na_2SO_4$ and concentrated in vacuo. The residue was purified by Prep-HPLC to give SA-123/SA-124 (mixture, 40 mg, 23%) and SA-125 (33 mg, 19%) as a white solid. NMR showed a mixture of two compounds, further purification by Chiral-HPLC of which gave SA-123 (21 mg, 12%), SA-124 (9 mg, 5%) as a white solid. SA-123: 1H NMR: (500 MHz, $CDCl_3$), δ (ppm), 9.47 (s, 1H), 8.56 (d, 1H), 7.29 (dd, 1H), 5.48 (AB, 1H), 5.40 (AB, 1H), 3.42 (AB, 1H), 3.40 (s, 3H), 3.39 (AB, 1H), 2.74 (t, 1H), 0.71 (s, 3H). LC-MS: rt=2.253 min; m/z=467.1 (M+H)+ SA-124: 1H NMR: (500 MHz, $CDCl_3$), δ (ppm), 8.96 (s, 1H), 8.54 (d, 1H), 7.98 (dd, 1H), 5.57 (AB, 1H), 5.50 (AB, 1H), 3.42 (AB, 1H), 3.40 (s, 3H), 3.39 (AB, 1H), 2.77 (t, 1H), 0.73 (s, 3H). LC-MS: rt=2.271 min; m/z=467.1 (M+H)+ SA-125: 1H NMR: (500 MHz, $CDCl_3$), δ (ppm), 9.46 (d, 1H), 8.47 (d, 1H), 7.76 (dd, 1H), 5.62 (AB, 1H), 5.57 (AB, 1H), 3.42 (AB, 1H), 3.40 (s, 3H), 3.39 (AB, 1H), 2.70 (t, 1H), 0.76 (s, 3H). LC-MS: rt=2.271 min; m/z=467.2 (M+H)+

Example 60

Synthesis of Compound SF-D2

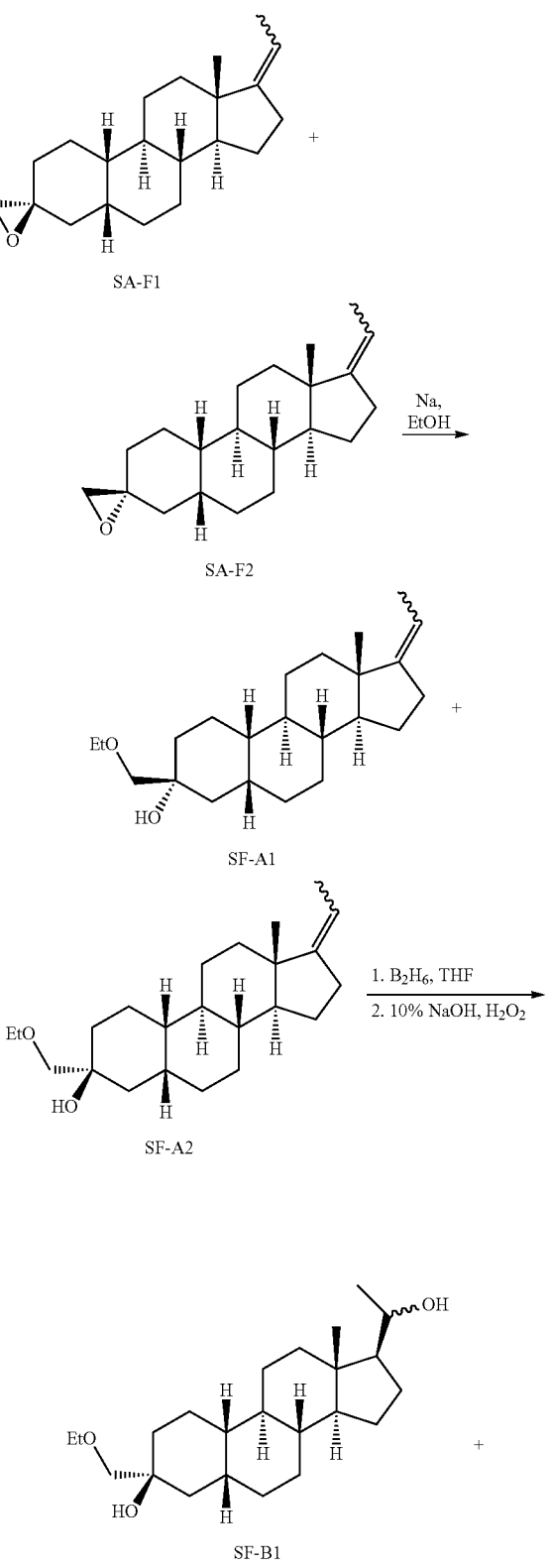

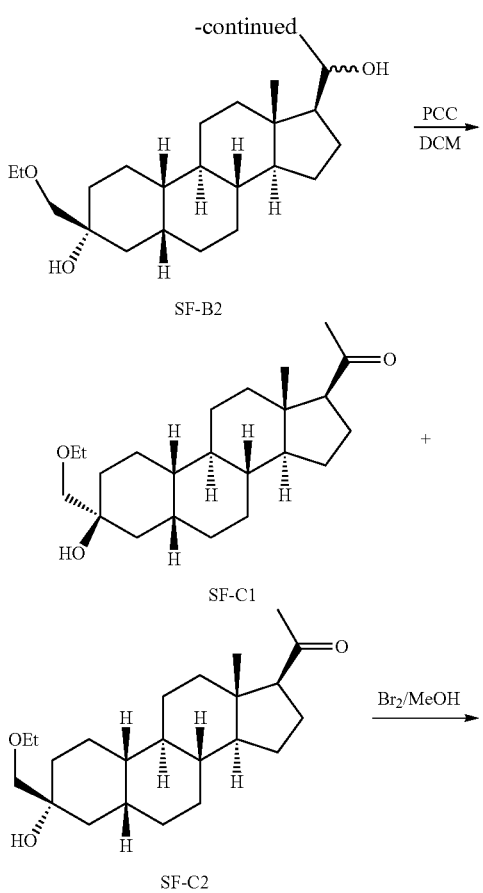

and resulting solution was washed with brine (2×100 mL), dried over magnesium sulfate and concentrated in vacuo. The crude product mixture was used directly in the next step without further purification.

Synthesis of compound SF-C. To a solution of crude reactant mixture SF-B1 and SF-B2 (4.5 g, 13.0 mmol, theoretical amount) in dichloromethane (40 mL) was added Pyridinium chlorochromate (PCC) in portions (5.7 g, 26.0 mmol). The solution was stirred at 25° C. overnight. Then the mixture was filtered through a short pad of silica gel and the silica gel was washed with dichloromethane (3×50 mL). All filtrate was combined and concentrated in vacuo. The residue was purified by flash chromatography (eluant: petroleum ether/ethyl acetate=15:1) to afford product SF-C1 (2.0 g, 5.5 mmol, Yield=42% (2 steps)) as white solid and product SF-C2 (1.8 g, 4.97 mmol, Yield=38% (2 steps)) as white solid. Compound SF-C2: $^1$H NMR (500 MHz, CDCl$_3$) δ (ppm): 3.53 (q, 2H), 3.45 (AB, 1H), 3.41 (AB, 1H), 2.54 (t, 1H), 2.16-2.12 (m, 1H), 2.11 (s, 3H), 2.02-1.98 (m, 1H), 1.2 (t, 3H), 0.61 (s, 3H).

Synthesis of compound SF-D2. To a solution of reactant SF-C2 (100 mg, 0.301 mmol) in methanol (10 mL) was added 48% hydrobromic acid (152 mg, 0.903 mmol) followed by bromine (241 mg, 0.077 mL, 1.505 mmol). The solution was heated at 25° C. for 1.5 hours. Then the mixture was poured into cooled water (50 mL). The resulting solid was extracted with ethyl acetate (2×50 mL). The combined organic extracts were washed with brine (50 mL), dried over magnesium sulfate and concentrated in vacuo. The crude product SF-D2 was used directly without further purification in the next step.

Example 61

Synthesis of Compound SA-126, SA-127 and SA-128

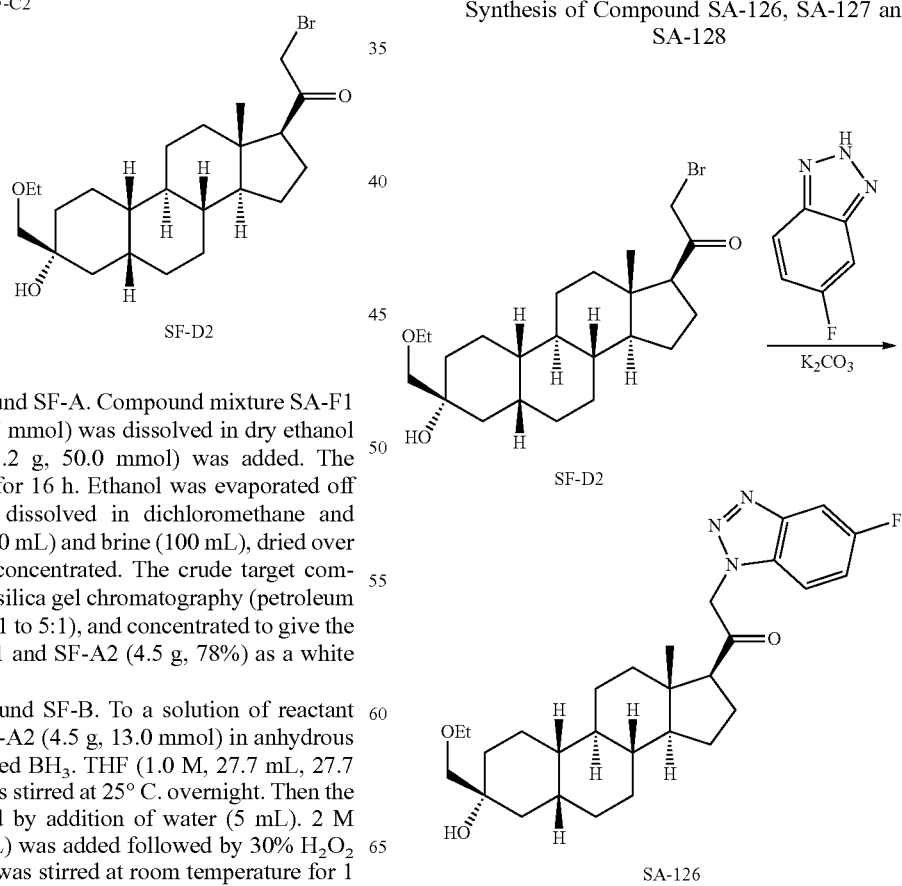

Synthesis of compound SF-A. Compound mixture SA-F1 and SA-F2 (5.0 g, 16.7 mmol) was dissolved in dry ethanol (250 mL), and Na (1.2 g, 50.0 mmol) was added. The solution was refluxed for 16 h. Ethanol was evaporated off and the residue was dissolved in dichloromethane and washed with H$_2$O (3×50 mL) and brine (100 mL), dried over MgSO$_4$, filtered, and concentrated. The crude target compound was purified by silica gel chromatography (petroleum ether/ethyl acetate=10:1 to 5:1), and concentrated to give the product mixture SF-A1 and SF-A2 (4.5 g, 78%) as a white solid.

Synthesis of compound SF-B. To a solution of reactant mixture SF-A1 and SF-A2 (4.5 g, 13.0 mmol) in anhydrous THF (30 mL) was added BH$_3$.THF (1.0 M, 27.7 mL, 27.7 mmol), the solution was stirred at 25° C. overnight. Then the reaction was quenched by addition of water (5 mL). 2 M NaOH solution (30 mL) was added followed by 30% H$_2$O$_2$ (30 mL). The mixture was stirred at room temperature for 1 hour. The mixture was diluted with ethyl acetate (200 mL)

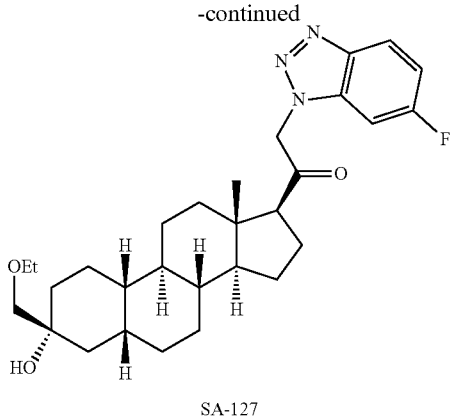

SA-127

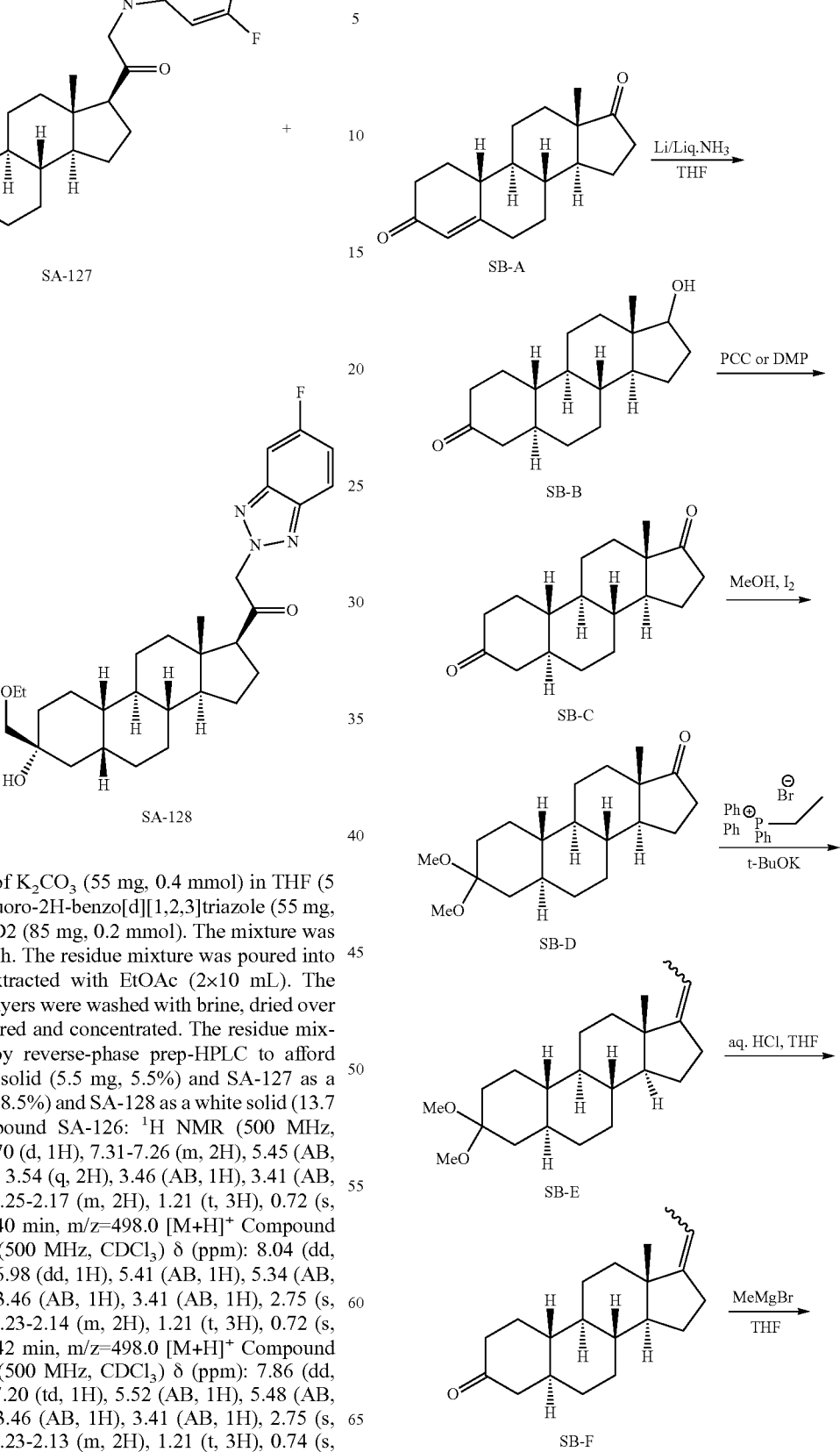

SA-128

To a suspension of $K_2CO_3$ (55 mg, 0.4 mmol) in THF (5 mL) was added 5-fluoro-2H-benzo[d][1,2,3]triazole (55 mg, 0.4 mmol) and SF-D2 (85 mg, 0.2 mmol). The mixture was stirred at RT for 15 h. The residue mixture was poured into 5 mL $H_2O$ and extracted with EtOAc (2×10 mL). The combined organic layers were washed with brine, dried over sodium sulfate, filtered and concentrated. The residue mixture was purified by reverse-phase prep-HPLC to afford SA-126 as a white solid (5.5 mg, 5.5%) and SA-127 as a white solid (8.4 mg, 8.5%) and SA-128 as a white solid (13.7 mg, 14.0%). Compound SA-126: $^1$H NMR (500 MHz, $CDCl_3$) δ (ppm): 7.70 (d, 1H), 7.31-7.26 (m, 2H), 5.45 (AB, 1H), 5.38 (AB, 1H), 3.54 (q, 2H), 3.46 (AB, 1H), 3.41 (AB, 1H), 2.73 (t, 1H), 2.25-2.17 (m, 2H), 1.21 (t, 3H), 0.72 (s, 3H). LC-MS: rt=2.40 min, m/z=498.0 [M+H]$^+$ Compound SA-127: $^1$H NMR (500 MHz, $CDCl_3$) δ (ppm): 8.04 (dd, 1H), 7.15 (td, 1H), 6.98 (dd, 1H), 5.41 (AB, 1H), 5.34 (AB, 1H), 3.54 (q, 2H), 3.46 (AB, 1H), 3.41 (AB, 1H), 2.75 (s, 1H), 2.73 (t, 1H), 2.23-2.14 (m, 2H), 1.21 (t, 3H), 0.72 (s, 3H). LC-MS: rt=2.42 min, m/z=498.0 [M+H]$^+$ Compound SA-128: $^1$H NMR (500 MHz, $CDCl_3$) δ (ppm): 7.86 (dd, 1H), 7.47 (d, 1H), 7.20 (td, 1H), 5.52 (AB, 1H), 5.48 (AB, 1H), 3.54 (q, 2H), 3.46 (AB, 1H), 3.41 (AB, 1H), 2.75 (s, 1H), 2.66 (t, 1H), 2.23-2.13 (m, 2H), 1.21 (t, 3H), 0.74 (s, 3H). LC-MS: rt=2.51 min, m/z=498.0 [M+H]$^+$ Example 62

Synthesis of SB and SB Intermediates

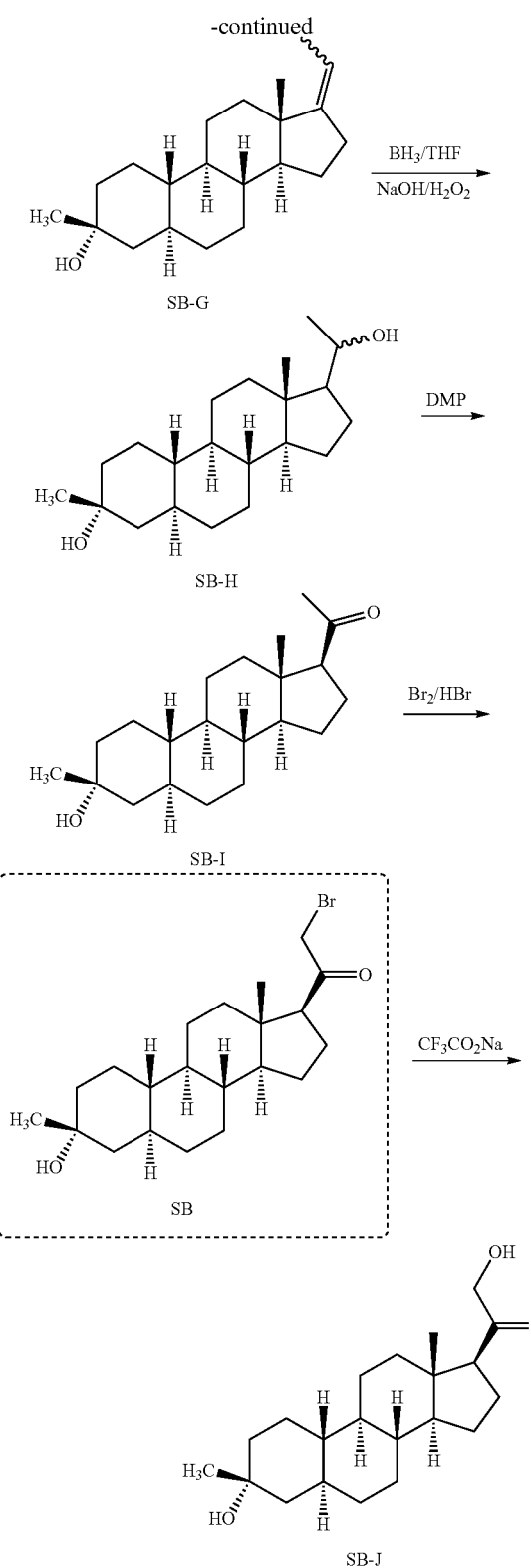

Synthesis of compounds SB-B and SB-C. Small pieces of lithium (7.63 g, 1.1 mol) were added to 2.7 L of condensed ammonia in a three neck flask at −70° C. As soon as all lithium was dissolved, the blue solution was warmed to −50° C. A solution of 19-norandrost-4-ene-3,17-dione SB-A (1, 30 g, 110 mmol) and tert-BuOH (8.14 g, 110 mmol) in 800 ml of anhydrous tetrahydrofuran was added dropwise and stirred for 90 min until the reaction mixture turned light yellow. Ammonium chloride (70 g) was added and excess ammonia was left to evaporate. The residue was extracted with 0.5N HCl (500 mL) and dichloromethane (500 mL×2). The combined organic layers were washed with saturated NaHCO$_3$ solution, dried over Na$_3$SO$_4$, filtered and concentrated to give a mixture of SB-B and SB-C (21 g, 70%) which was directly used in the next step without further purification. A solution of SB-B and SB-C (21 g, 76 mmol) in 50 mL of anhydrous dichloromethane was added to a suspension of pyridinium chlorochromate (PCC) (32.8 g, 152 mmol) in 450 mL of dichloromethane. After stirring at room temperature for 2 h, 2N NaOH solution (500 mL) was added to the dark brown reaction mixture and stirred for another 10 min. The resulting solution was extracted with dichloromethane, the combined organic layers were washed with 2N HCl, brine, dried over Na$_2$SO$_4$, filtered and concentrated. The residue was purified by chromatography on silica gel (pretroleum ether/ethyl acetate=20:1 to 10:1) to afford title compound SB-C(16.8 g, 80%) as a white solid. $^1$H NMR of SB-B (400 MHz, CDCl$_3$), δ (ppm), 3.65 (t, 1H), 0.77 (s, 3H). $^1$H NMR of SB-C (400 MHz, CDCl$_3$), δ (ppm), 0.88 (s, 3H).

Synthesis of compound SB-D. To a solution of compound SB-C (16.8 g. 61.3 mmol) in methanol (250 mL) was added iodine (1.54 g, 6.1 mmol). After stirring at 60° C. for 12 h, the solvent was removed in vacuo. The crude product was dissolved in dichloromethane (200 mL) and washed with saturated NaHCO$_3$ (150 mL), brine, dried over Na$_2$SO$_4$, filtered and concentrated. The residue was purified by chromatography on basic alumina (pretroleum ether/ethyl acetate=100:1) to give compound SB-D (14 g, 43.8 mmol, 71%). $^1$H NMR (400 MHz, CDCl$_3$), δ (ppm), 3.18 (s, 3H), 3.12 (s, 3H), 0.85 (s, 3H).

Synthesis of compound SB-E. To a suspension of t-BuOK (7.36 g, 65.7 mmol) in THF (100 mL) at 0° C. was added ethyltriphenylphosphonium bromide (26 g, 70 mmol) slowly. After stirring at 60° C. for 3 h, compound SB-D (7 g, 21.9 mmol) was added and the mixture was stirred at 60° C. for another 2 h. After cooling to room temperature, the reaction mixture was poured into saturated ammonium chloride and extracted with EtOAc (2×500 mL). The combined organic layers were washed with brine, dried over sodium sulfate, filtered and concentrate to afford the crude compound SB-E (7.36 g, 100%). The crude product was used in the next step without further purification.

Synthesis of compound SB-F. A solution of crude compound SB-E (7.36 g, 21.9 mmol) in THF (50 mL) was acidified to pH=3 by 1N aqueous HCl. After stirring at room temperature for 12 h, the reaction mixture was extracted with ethyl acetate (250 mL×3). The combined organic layers were washed with brine, dried over sodium sulfate, filtered and concentrated. The residue was purified by column chromatography (pretroleum ether/ethyl acetate=30:1 to 20:1) to afford compound SB-F (4.8 g, 16.7 mmol, 76% for two steps). $^1$H NMR (400 MHz, CDCl$_3$), δ (ppm), 5.12-5.10 (m, 1H), 1.64-1.63 (m, 3H), 0.77 (s, 3H).

Synthesis of compound SB-G. To a solution of MeMgBr (28 mmol, 1M in THF) in THF (50 mL) at 0° C. was added a solution of compound SB-F (4.8 g, 16.8 mmol) in dry THF (10 mL) via syringe pump over 30 min. After stirring at 0°

C. for 5 h, the reaction mixture was allowed to warm up and stirred at room temperature overnight. The reaction mixture was quenched with iced-cold water and extracted with ethyl acetate (150 mL×3). The combined organic layers were washed with brine, dried over sodium sulfate, filtered and concentrated. The white residue was purified by flash column chromatography (pretroleum ether/ethyl acetate=20:1 to 10:1) to give compound SB-G (2.5 g, 8.28 mmol, 49%; Rf=0.35, PE:EtOAc=10:1). $^1$H NMR (400 MHz, CDCl$_3$), δ (ppm), 5.05-5.03 (m, 1H), 1.21 (s, 3H), 0.90 (s, 3H).

Synthesis of compound SB-H. To a solution of compound SB-G (2 g, 6.62 mmol) in dry THF (50 mL) was added borane-tetrahydrofuran complex (20 mL; 1.0 M solution in THF). After stirring at room temperature for 1 hour, the reaction mixture was cooled in an ice bath then quenched slowly with 10% aqueous NaOH (10 mL) followed by 30% aqueous solution of H$_2$O$_2$ (12 mL). After stirring at room temperature for one hour, the mixture was extracted with EtOAc (3×100 mL). The combined organic layers were washed with 10% aqueous Na$_2$S$_2$O$_3$ (100 mL), brine (100 mL), dried over MgSO$_4$, filtered and concentrated to afford crude compound SB-H (2 g, 100%). The crude product was used in the next step without further purification.

Synthesis of compound SB-I. To a solution of crude compound SB-H (2 g, 6.62 mmol) in 60 mL of wet dichloromethane (dichloromethane had been shaken with several milliliters of H$_2$O then separated from the water layer) was added Dess-Martin periodinate (5.5 g, 13 mmol). After stirring at room temperature for 24 h, the reaction mixture was extracted with dichloromethane (3×100 mL). The combined organic layers were washed with 10% aqueous Na$_2$S$_2$O$_3$ (100 mL), brine (100 mL), dried over MgSO$_4$, filtered and concentrated. The residue was purified by chromatography on silica gel (pretroleum ether/ethyl acetate=10:1 to 5:1) to afford compound SB-I (1 g, 3.14 mmol, 47% for two steps) as a white solid. $^1$H NMR (400 MHz, CDCl$_3$), δ (ppm), 2.56 (t, 1H), 2.11 (s and m, 4H), 2.0 (dt, 1H), 1.8 (dm, 2H), 1.54 (m, 6H) 1.43 (m, 1H), 1.34 (m, 2H), 1.20 (m, 12H), 0.7 (m, 2H), 0.62(s, 3H).

Synthesis of compound SB. To a solution of compound SB-I (600 mg, 1.89 mmol) in MeOH (20 mL) was added 5 drops of HBr (48%) followed by bromine (302 mg, 1.89 mmol). After stirring at room temperature for 1 h, the reaction mixture was poured into ice-water then extracted with ethyl acetate (100 mL×3). The combined organic layers were washed with brine (200 mL), dried over MgSO$_4$, filtered and concentrated to give crude compound SB (600 mg).

Synthesis of compound SB-J. A solution of compound SB (600 mg, 1.5 mmol) in acetone 10 mL was treated with CF$_3$COOH (6.8 mL) and Et$_3$N (9.5 mL). After refluxed for 30 min, CF$_3$COONa salt (4.49 g, 33 mmol) was added in parts over a period of 10 hr. The reaction mixture was allowed to cool to room temperature and the solvent was removed in vaccuo. The residue was extracted with ethyl acetate, dried over MgSO$_4$, filtered and concentrated. The mixture was purified by chromatography on silica gel (pretroleum ether/ethyl acetate=10:1 to 3:1) to afford SB-J (300 mg, yield: 50% for two steps). $^1$H NMR (400 MHz, CDCl$_3$), δ (ppm), 4.23-4.13 (m, 2H), 2.48-2.44 (m, 1H), 2.24-2.17 (m, 1H), 1.20 (s, 3H), 0.64 (s, 3H).

Example 63

Synthesis of Compound SB-1 and SB-2

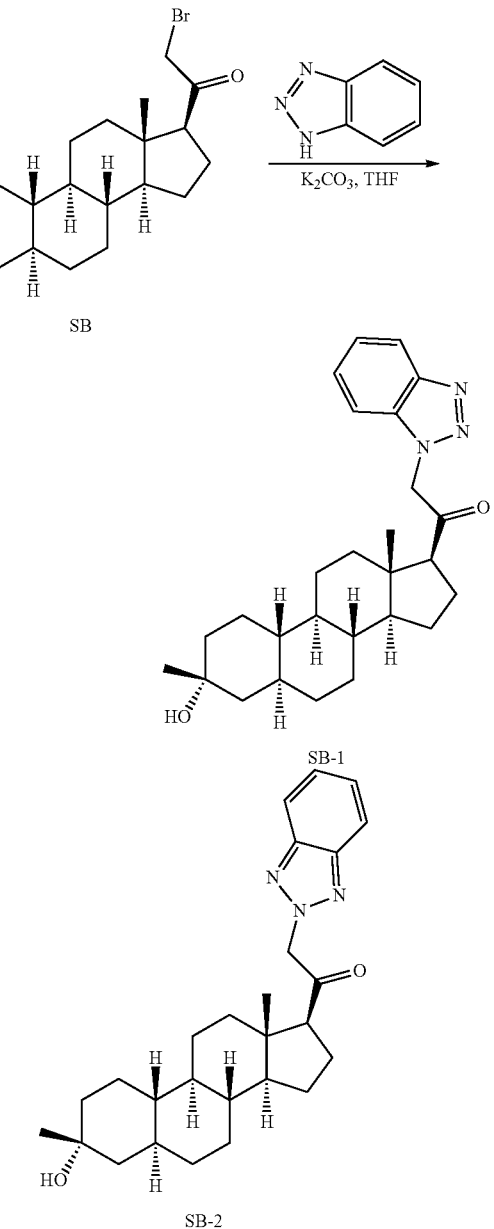

To a solution of crude compound SB (250 mg, 0.629 mmol, theoretical amount) in anhydrous THF (5 mL) was added benzotriazole (374 mg, 3.14 mmol) followed by potassium carbonate (434 mg, 3.14 mmol). The solution was heated at 60° C. overnight. Then the solution was diluted with ethyl acetate (200 mL). The resulting solution was washed with brine (2×100 mL), dried over magnesium sulfate and concentrated in vacuo. The crude product was purified by reverse phase prep-HPLC to afford fraction 1 and fraction 2. Fraction 1 is desired product SB-1 (34.0 mg, 0.0781 mmol, two steps overall yield=12.4%) isolated as a white solid. Fraction 2 was further purified by silica gel chromatography (eluant: petroleum ether/ethyl acetate=3:1)

to afford desired product SB-2 (7.5 mg, 0.0172 mmol, two steps overall yield=2.7%, more polar) and by-product (3.0 mg, 0.00689 mmol, two steps overall yield=1.1%, less polar) as white solids. Compound SB-1: $^1$H NMR (400 MHz, CDCl$_3$) δ (ppm): 8.09 (1H, d), 7.50 (1H, d), 7.39 (1H, t), 7.34 (1H, d), 5.43 (1H, AB), 5.42 (1H, AB), 2.72 (1H, t), 2.15-2.27 (2H, m), 1.87-1.96 (1H, m), 1.22 (3H, s), 0.74 (3H, s). LC-MS: rt=2.38 min, m/z=436.2 [M+H]$^+$ Compound SB-2: $^1$H NMR (400 MHz, CDCl$_3$) δ (ppm): 7.88 (2H, dd), 7.40 (2H, dd), 5.54 (1H, AB), 5.52 (1H, AB), 2.67 (1H, t), 2.12-2.28 (2H, m), 1.21 (3H, s), 0.76 (3H, s). LC-MS: rt=2.49 min, m/z=436.2 [M+H]$^+$ Example 64

Synthesis of Compound SB-4 and SB-5

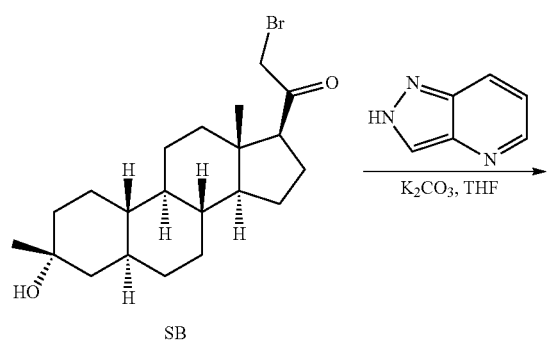

To a solution of crude compound SB (249.6 mg, 0.629 mmol, theoretical amount) in anhydrous THF (5 mL) was added 1H-pyrazolo[4,3-b]pyridine (374 mg, 3.14 mmol) followed by potassium carbonate (434 mg, 3.14 mmol). The solution was heated at 50° C. for 2 hours. Then the solution was diluted with ethyl acetate (200 mL). The resulting solution was washed with brine (2×100 mL), dried over magnesium sulfate and concentrated in vacuo. The crude product was purified by reverse phase prep-HPLC to afford product SB-4 (5.5 mg, 0.0126 mmol, Yield=2.0% (2 steps)) and product SB-5 (26.7 mg, 0.0613 mmol, Yield=9.8% (2 steps)) as white solids. Compound SB-4: $^1$H NMR (400 MHz, CDCl$_3$) δ (ppm): 8.59 (1H, d), 8.21 (1H, s), 8.04 (1H, d), 7.22 (1H, dd), 5.28 (1H, AB), 5.20 (1H, AB), 2.67 (1H, t), 2.09-2.29 (2H, m), 1.21 (3H, s), 0.73 (3H, s). LC-MS: rt=2.21 min, m/z=436.4 [M+H]$^+$ Compound SB-5: $^1$H NMR (400 MHz, CDCl$_3$) δ (ppm): 8.60 (1H, d), 8.28 (1H, s), 7.59 (1H, d), 7.30 (1H, dd), 5.19 (1H, AB), 5.14 (1H, AB), 2.67 (1H, t), 2.09-2.25 (2H, m), 1.22 (3H, s), 0.72 (3H, s). LC-MS: rt=2.26 min, m/z=436.4 [M+H]$^+$ Example 65

Synthesis of Compound SB-6, SB-7 and SB-8

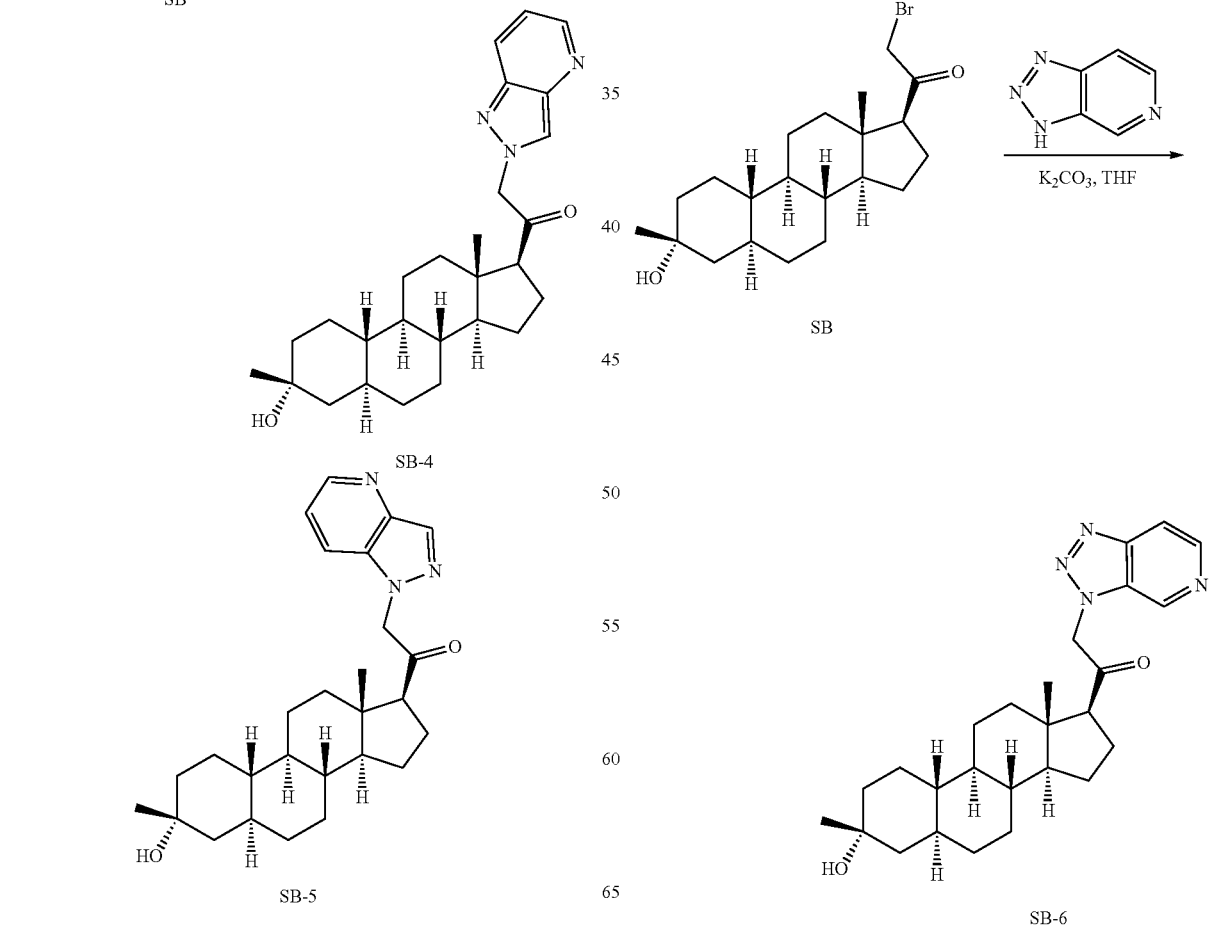

Example 66

Synthesis of Compound SB-9 and SB-10

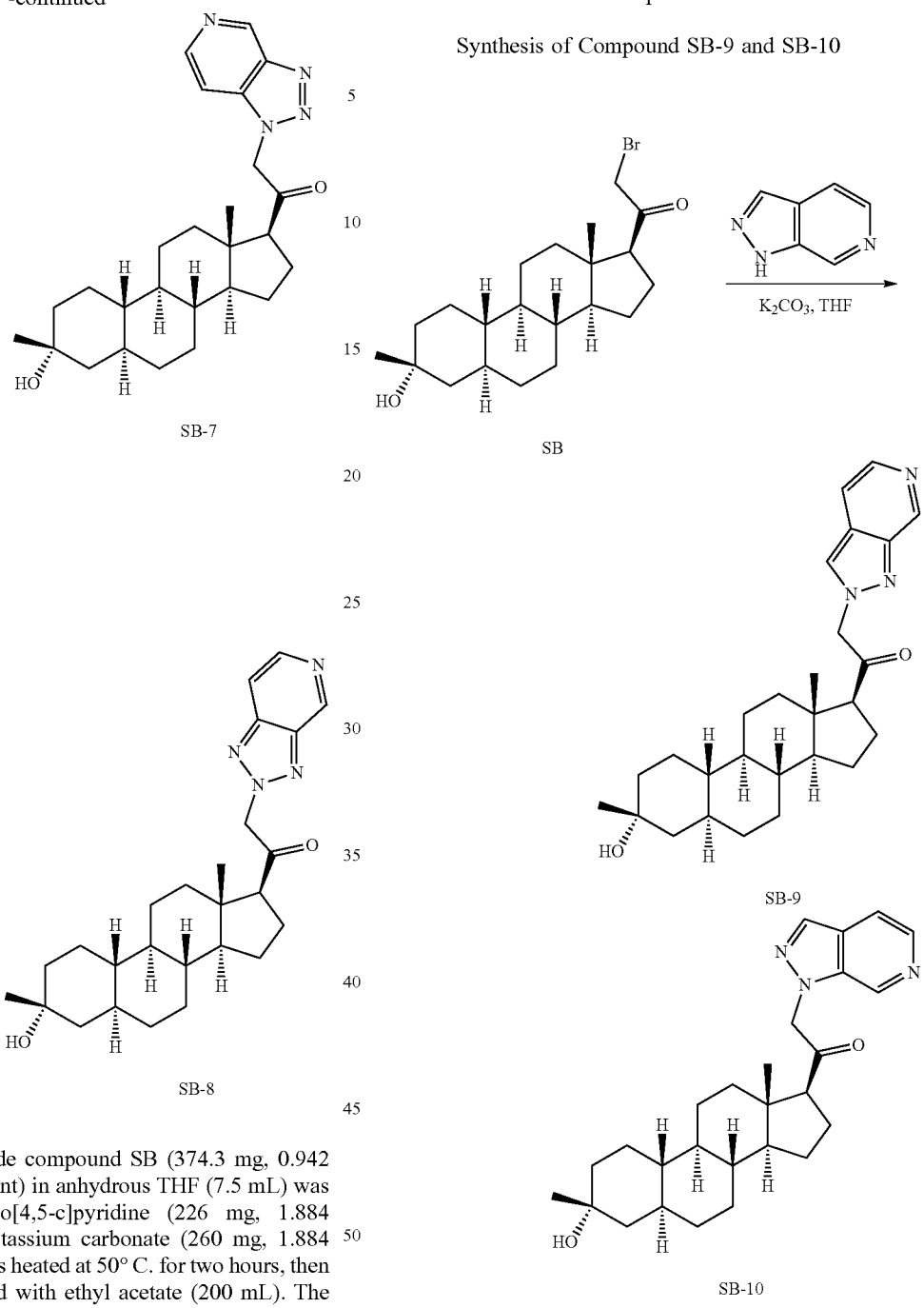

To a solution of crude compound SB (374.3 mg, 0.942 mmol, theoretical amount) in anhydrous THF (7.5 mL) was added 1H-1,2,3-triazolo[4,5-c]pyridine (226 mg, 1.884 mmol) followed by potassium carbonate (260 mg, 1.884 mmol). The solution was heated at 50° C. for two hours, then the solution was diluted with ethyl acetate (200 mL). The resulting solution was washed with brine (2×100 mL), dried over magnesium sulfate and concentrated in vacuo. The crude product was purified by reverse phase prep-HPLC to afford the desired products the SB-7 (48.9 mg, 0.112 mmol, Yield=11.9% (2 steps)) and SB-8 (42.3 mg, 0.0969 mmol, Yield=10.3% (2 steps)). All products were white solids. Compound SB-7: $^1$H NMR (400 MHz, CDCl$_3$) δ (ppm): 9.50 (1H, d), 8.58 (1H, d), 7.30 (1H, dd), 5.49 (1H, AB), 5.41 (1H, AB), 2.75 (1H, t), 1.22 (3H, s), 0.74 (3H, s). LC-MS: rt=2.23 min, m/z=437.3 [M+H]$^+$ Compound SB-8: $^1$H NMR (400 MHz, CDCl$_3$) δ (ppm): 9.46 (1H, d), 8.47 (1H, d), 7.76 (1H, dd), 5.61 (1H, AB), 5.58 (1H, AB), 2.70 (1H, t), 1.22 (3H, s), 0.76 (3H, s). LC-MS: rt=2.31 min, m/z=437.4[M+H]$^+$ To a solution of crude compound SB (249.6 mg, 0.629 mmol, theoretical amount) in anhydrous THF (5 mL) was added 1H-pyrazolo[3,4-c]pyridine (150 mg, 1.256 mmol) followed by potassium carbonate (174 mg, 1.256 mmol). The solution was heated at 50° C. for 2 hours. Then the solution was diluted with ethyl acetate (200 mL). The resulting solution was washed with brine (2×100 mL), dried over magnesium sulfate and concentrated in vacuo. The crude product was purified by reverse phase prep-HPLC to afford product SB-9 (7 mg, 0.016 mmol, Yield=2.5% (2 steps)) and product SB-10 (14.6 mg, 0.0335 mmol, Yield=5.4% (2 steps)) as white solids. Compound SB-9: $^1$H NMR (400 MHz, CDCl$_3$) δ (ppm): 9.26 (1H, s), 8.17 (1H, d), 7.99 (1H, s), 7.53 (1H, d), 5.32 (1H, AB), 5.24 (1H, AB), 2.69 (1H, t), 1.22 (3H, s), 0.73 (3H, s). LC-MS: rt=2.18 min, m/z=436.4 [M+H]+ Compound SB-10: $^1$H NMR (400 MHz, CDCl$_3$) δ (ppm): 8.80 (1H, s), 8.34 (1H, d), 8.10 (1H, s), 7.65 (1H, dd), 5.27 (1H, AB), 5.25 (1H, AB), 2.70 (1H, t), 1.22 (3H, s), 0.73 (3H, s). LC-MS: rt=2.21 min, m/z=436.3 [M+H]+

Example 67

Synthesis of Compound SB-11

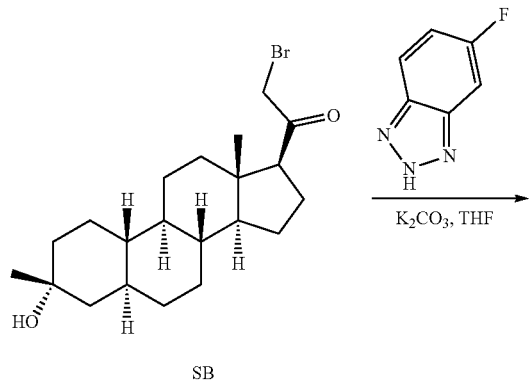

Example 68

Synthesis of compound SG

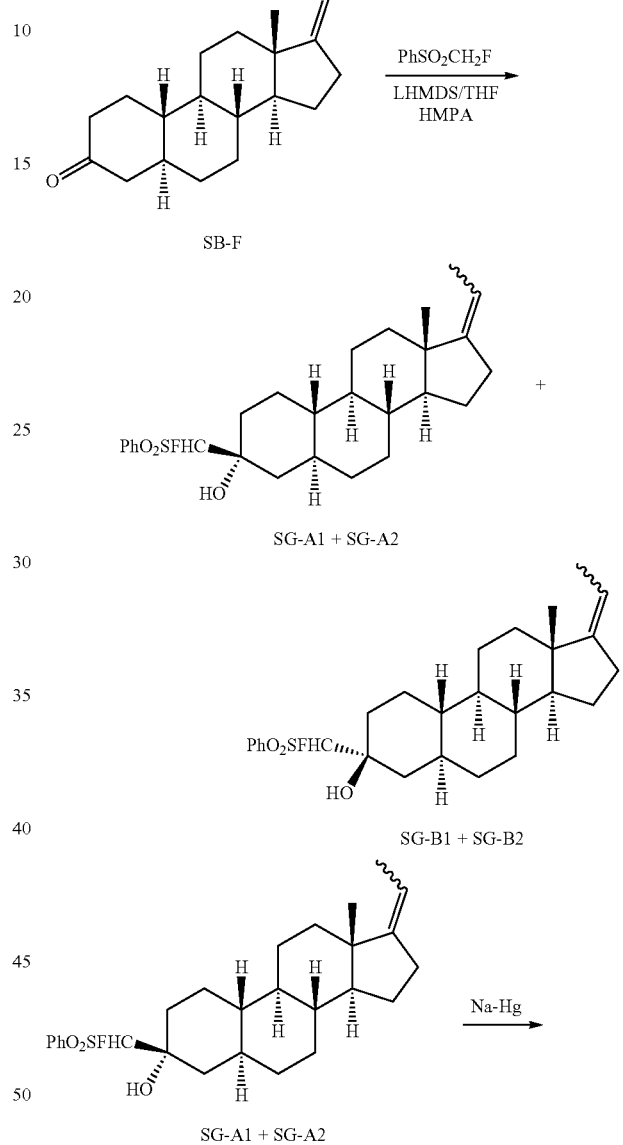

To a suspension of K$_2$CO$_3$ (67 mg, 0.50 mmol) in THF (5 mL) was added 5-fluoro-2H-benzo[d][1,2,3]triazole (68.5 mg, 0.50 mmol) and compound SB (100 mg, 0.25 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated in vacuo. The residue was purified by reverse-phase prep-HPLC to afford product SB-11 as a white solid (10.7 mg, 0.024 mmol, 9.4%). SB-11: $^1$H NMR (500 MHz, CDCl$_3$) δ (ppm): 7.86 (1H, dd), 7.46 (1H, dd), 7.20 (1H, td), 5.50 (1H, AB), 5.48 (1H, AB), 2.67 (1H, t), 1.21 (3H, s), 0.75 (3H, s). LCMS: Rt=2.47 min. m/z=454.3 [M+H]+.

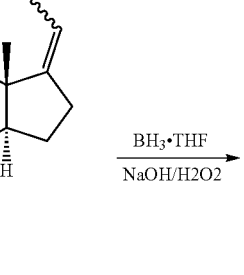

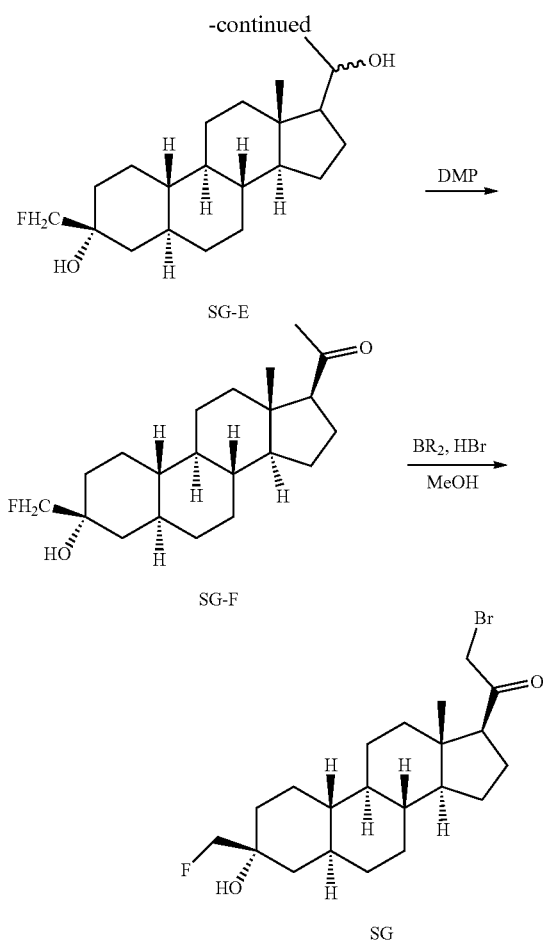

Synthesis of compounds SG-A and SC-B. To a solution of compound SB-F (1.3 g, 4.5 mmol) and PhSO₂CH₂F (790 mg, 4.5 mmol) in THF (25 mL) and HMPA (0.5 mL) at −78° C. under N₂ was added LHMDS (5.5 mL, 1M in THF) dropwise. After stirring at −78° C. for 2 h, the reaction mixture was quenched with saturated aqueous NH₄Cl solution (10 mL) and allowed to warm to room temperature then extracted with Et₂O (20 mL×3). The combined organic layers were washed with brine, dried over sodium sulfate, filtered and concentrate. The residue was purified by silica gel column chromatography (pretroleum ether/ethyl acetate=10/1) to give the mixture of compound SG-A and SG-B (1.53 g). The mixture was further purified by chiral-HPLC to afford compound SG-A1 (220 mg, t=3.41 min). ¹H NMR (500 MHz, CDCl₃), δ (ppm), 7.99-7.97 (m, 2H), 7.75-7.74 (m, 1H), 7.62-7.55 (m, 2H), 5.13-5.09 (m, 1H), 4.86-4.78 (d, 1H), 0.88 (s, 3H); SG-A2 (200 mg, t=3.66 min); ¹H NMR (500 MHz, CDCl₃), δ (ppm), 7.96-7.95 (m, 1H), 7.71-7.69 (m, 1H), 7.62-7.58 (m, 2H), 5.13-5.09 (m, 1H), 4.87-4.77 (d, 1H), 0.88 (s, 3H); SG-B1 (235 mg, t=4.9 min). ¹H NMR (500 MHz, CDCl3), δ (ppm), 7.99-7.97 (m, 1H), 7.72-7.70 (m, 1H), 7.62-7.59 (m, 2H), 5.29-5.20 (d, 1H), 4.88-4.78 (m, 1H), 0.88 (s, 3H); SG-B2 (220 mg, t=5.2 min). ¹H NMR (500 MHz, CDCl₃), δ (ppm), 7.99-7.97 (m, 2H), 7.72 (m, 1H), 7.62-7.59 (m, 2H), 5.30-5.20 (d, 1H), 5.09-5.08 (m, 1H), 0.88 (s, 3H).

Synthesis of compound SG-D. To a solution of compound SG-A (200 mg, 0.434 mmol) and anhydrous Na₂HPO₄ (100 mg) in anhydrous methanol (15 mL) at 20° C. under N₂ was added Na/Hg amalgam (400 mg). After stirring at 20° C. to 0° C. for 1 h, the methanol solution was decanted out and the solid residue was washed with Et₂O (5×3 mL). The solvent of combined organic phase was removed under vacuum, and 20 ml brine was added, followed by extracting with Et₂O. The combined ether phase was dried with MgSO₄, and the ether was removed to give the crude product, which was further purified by silica gel chromatography (PE/EA=10/1) to give product 99 mg, 69%. ¹H NMR (500 MHz, CDCl3), δ (ppm), 5.12-5.10 (m, 1H), 4.21-24.11 (d, 2H), 0.88 (s, 3H).

Synthesis of compound SG-E. To a solution of compound SG-D (95 mg, 0.296 mmol) in dry THF (5 mL) was added borane-tetrahydrofuran complex (1 mL of 1.0 M solution in THF). After stirring at room temperature for 1 hour, the reaction mixture was cooled in an ice bath then quenched slowly with 10% aqueous NaOH (1 mL) followed by 30% aqueous solution of H₂O₂ (1.2 mL). The mixture was allowed to stir at room temperature for 1 hour then extracted with EtOAc (3×10 mL). The combined organic layers were washed with 10% aqueous Na₂S₂O₃ (10 mL), brine (10 mL), dried over MgSO₄, filtered and concentrated to afford compound SG-E (120 mg crude). The crude product was used in the next step without further purification.

Synthesis of compound SG-F. To a solution of compound SG-E (120 mg crude) was dissolved in 10 mL of wet dichloromethane (dichloromethane had been shaken with several milliliters of H₂O then separated from the water layer) was added Dess-Martin periodinate (300 mg, 707 mmol). After stirring at room temperature for 24 h, the reaction mixture was extracted with dichloromethane (3×10 mL). The combined organic layers were washed with 10% aqueous Na₂S₂O₃ (10 mL), brine (10 mL), dried over MgSO₄, filtered and concentrated. The residue was purified by chromatography on silica gel (pretroleum ether/ethyl acetate=1:5) to afford compound SG-F (70 mg, 70% for two steps) as a white solid. ¹H NMR (500 MHz, CDCl₃), δ (ppm), 4.21-4.11 (d, 2H), 2.19 (s, 3H), 0.62 (s, 3H).

Synthesis of compound SG. To a solution of reactant (200 mg, 0.594 mmol) in methanol (5 mL) was added 48% hydrobromic acid (300 mg, 1.782 mmol) followed by bromine (475 mg, 0.152 mL, 2.97 mmol). The solution was heated at 25° C. for 2 hours. Then the mixture was poured into cooled water (50 mL). The resulting solid was extracted with ethyl acetate (2×100 mL). The combined organic extracts were washed with brine (100 mL), dried over magnesium sulfate and concentrated in vacuo. The crude product was used directly without further purification in the next step.

Example 69

Synthesis of Compound SB-12 and SB-13

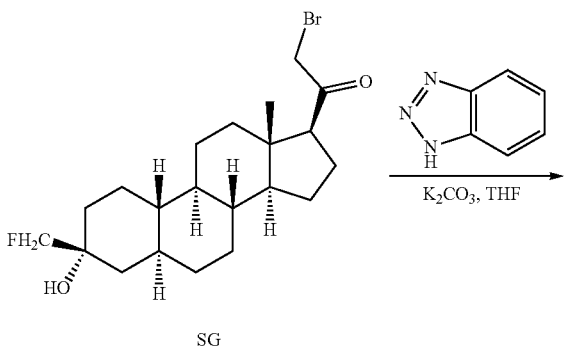

-continued

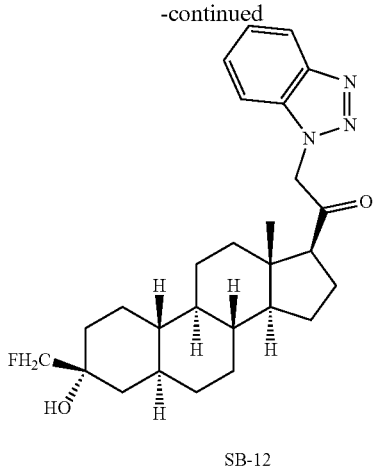

SB-12

+

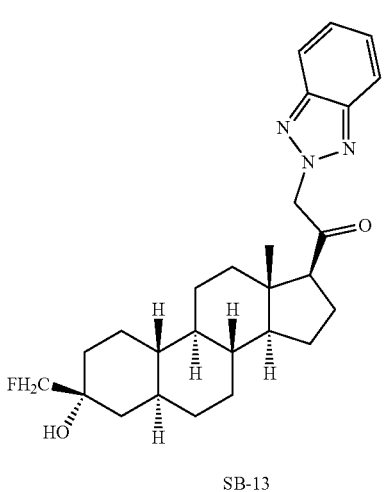

SB-13

To a solution of crude reactant SG (100 mg, 0.241 mmol) in anhydrous THF (5 mL) was added 1H-benzo[d][1,2,3]triazole (57 mg, 0.483 mmol) followed by potassium carbonate (67 mg, 0.483 mmol). The solution was heated at 60° C. for 2 h then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-12 (26 mg, 0.06 mmol, Yield=25%) and product SB-13 (18 mg, 0.04 mmol, Yield=17%) as white solid. SB-12: $^1$H NMR (500 MHz, CDCl$_3$) δ (ppm): 8.08 (1H, d), 7.49 (1H, t), 7.38 (1H, t), 7.34 (1H, d), 5.44 (1H, AB), 4.18 (2H, d), 2.72(1H, t), 0.74 (3H, s). LCMS: rt=2.30 min, m/z=454 [M+H]$^+$ SB-13: $^1$H NMR (500 MHz, CDCl$_3$) δ (ppm): 7.88 (1H, dd), 7.40 (1H, dd), 5.53 (1H, AB), 5.40 (1H, AB), 4.18 (2H, d), 2.66 (1H, t), 0.76 (3H, s). LCMS: rt=2.41 min, m/z=454 [M+H]$^+$ Example 70

Synthesis of Compound SB-14 and SB-15

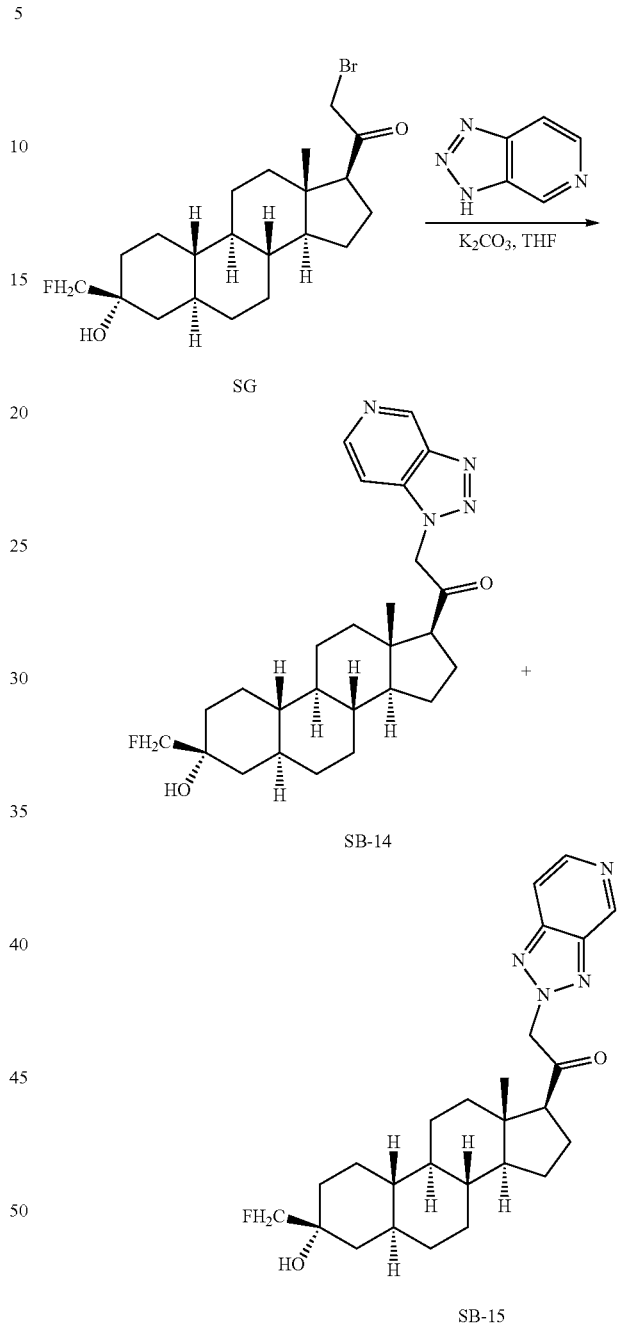

To a solution of crude reactant SG (100 mg, 0.241 mmol) in anhydrous THF (5 mL) was added 3H-[1,2,3]triazolo[4,5-c]pyridine (140 mg, 1.2 mmol) followed by potassium carbonate (170 g, 1.2 mmol). The solution was heated at 60° C. for 2 h then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-14 (20 mg, 0.04 mmol, Yield=17%) and product SB-15 (18 mg, 0.04 mmol, Yield=17%) as white solid.

SB-14: $^1$H NMR (500 MHz, CDCl$_3$) δ (ppm): 9.51 (1H, s), 8.58 (1H, d), 7.32 (1H, d), 5.50 (1H, AB), 5.42 (1H, AB), 4.18 (2H, d), 2.75 (1H, t), 0.74 (3H, s). LCMS: rt=2.18 min, m/z=455 [M+H]$^+$ SB-15: $^1$H NMR (500 MHz, CDCl$_3$) δ (ppm): 9.46 (1H, s), 8.47 (1H, d), 7.76 (1H, d), 5.62(1H, AB), 5.60 (1H, AB), 4.18 (2H, d), 2.70 (1H, t), 0.77(3H, s). LCMS: rt=2.41 min, m/z=455 [M+H]$^+$ Example 71

Synthesis of Compound SB-16 and SB-17

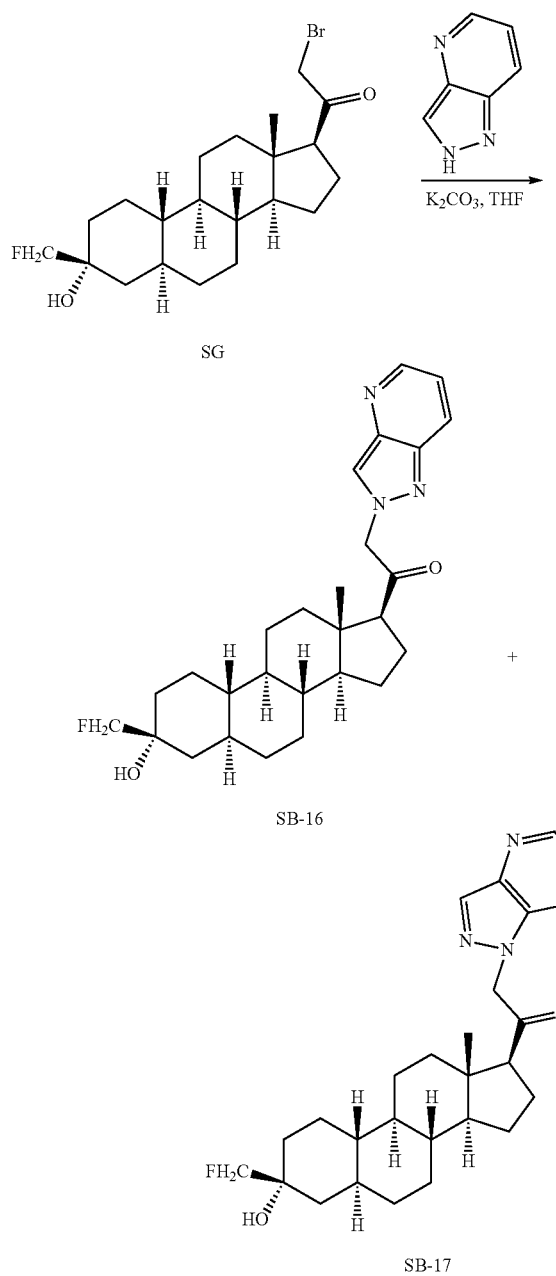

To a solution of crude reactant SG (100 mg, 0.241 mmol) in anhydrous THF (5 mL) was added 2H-pyrazolo[4,3-b] pyridine (140 mg, 1.2 mmol) followed by potassium carbonate (170 g, 1.2 mmol). The solution was heated at 60° C. for 2 h then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-16 (18 mg, 0.04 mmol, Yield=17%) and SB-17 (40 mg, 0.09 mmol, Yield=38%) as white solid. SB-16: $^1$H NMR (500 MHz, CDCl$_3$) δ (ppm): 8.58 (1H, dd), 8.28 (1H, s), 8.04 (1H, d), 7.22(1H, dd), 5.28(1H, AB), 5.20 (1H, AB), 4.17(2H, d), 2.67 (1H, t), 0.73 (3H, s). LCMS: rt=2.09 min, m/z=454 [M+H]$^+$ SB-17: $^1$H NMR (400 MHz, CDCl$_3$) δ (ppm): 8.60 (1H, dd), 8.22 (1H, s), 7.59 (1H, d), 7.30 (1H, dd), 5.20 (1H, AB), 5.13 (1H, AB), 4.18 (2H, d), 2.68(1H, t), 0.73(3H, s). LCMS: rt=2.13 min, m/z=454 [M+H]$^+$ Example 72

Synthesis of Compound SB-18 and SB-19

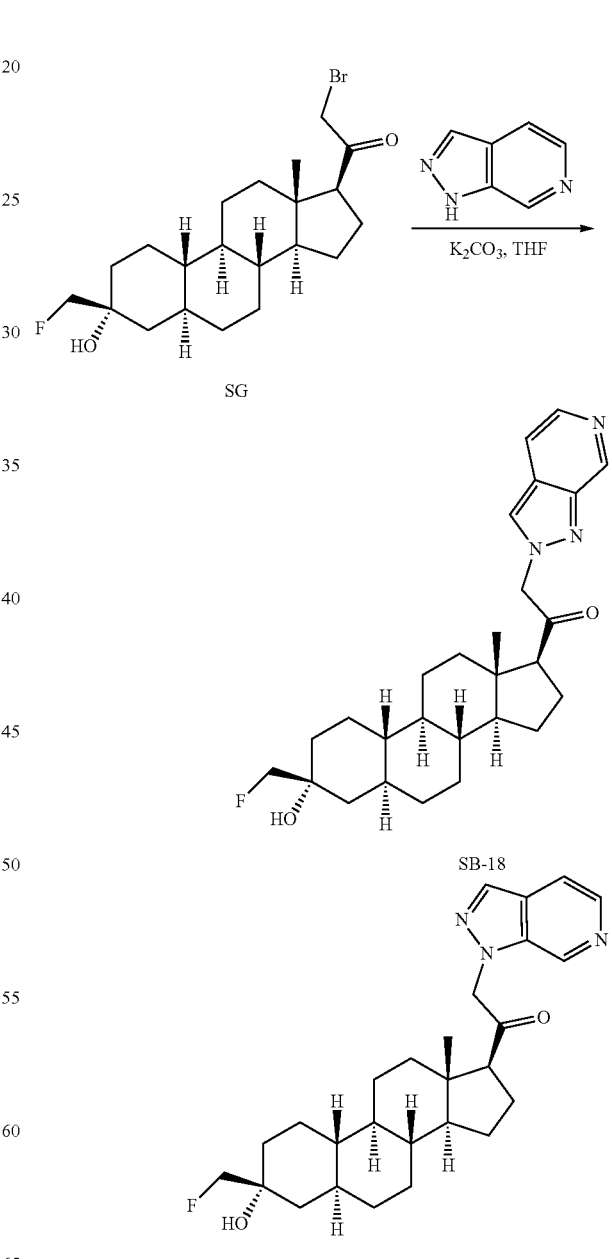

To a solution of crude reactant SG (246.9 mg, 0.595 mmol, theoretical amount) in anhydrous THF (5 mL) was added 1H-pyrazolo[3,4-c]pyridine (142 mg, 1.188 mmol) followed by potassium carbonate (164 mg, 1.188 mmol). The solution was heated at 50° C. for 2 hours. Then the solution was diluted with ethyl acetate (200 mL). The resulting solution was washed with brine (2×100 mL), dried over magnesium sulfate and concentrated in vacuo. The crude product was purified by reverse phase prep-HPLC to afford fraction 1 and 2. Fraction 1 was pure product SB-18 (11.5 mg, 0.0254 mmol, Yield=4.3% (2 steps)). But fraction 2 was impure and crude product was further purified by silica gel chromatography (eluant: petroleum ether/ethyl acetate=1:1) to afford pure product SB-19 (13.9 mg, 0.0306 mmol, Yield=5.2% (2 steps)). Both products were white solid. SB-18: $^1$H NMR (400 MHz, CDCl$_3$) δ (ppm): 9.26 (1H, s), 8.17 (1H, d), 7.98 (1H, s), 7.53 (1H, dd), 5.32 (1H, AB), 5.23 (1H, AB), 4.17 (2H, d), 2.69 (1H, t), 0.73 (3H, s). LCMS: rt=2.10 min, m/z=454.1 [M+H]$^+$ SB-19: $^1$H NMR (400 MHz, CDCl$_3$) δ (ppm): 8.80 (1H, s), 8.34 (1H, d), 8.10 (1H, s), 7.64 (1H, d), 5.27 (1H, AB), 5.25 (1H, AB), 4.18 (1H, d), 2.70 (1H, t), 0.74 (3H, s). LCMS: rt=2.26 min, m/z=454.2 [M+H]$^+$ Example 73

Synthesis of Compound SG-20

To a suspension of K$_2$CO$_3$ (63 mg, 0.47 mmol) in THF (10 mL) was added 6-fluoro-2H-indazole (63.9 mg, 0.47 mmol) and compound SG (100 mg, 0.24 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated in vacuum. The residue was purified by reverse-phase prep-HPLC to afford SB-20 as a white solid (28.7 mg, 0.06 mmol, 26.5%). SG-20: $^1$H NMR (400 MHz, CDCl$_3$) δ (ppm): 7.94 (1H, d), 7.63 (1H, dd), 7.27 (1H, dd), 6.89 (1H, td), 5.19 (1H, AB), 5.14 (1H, AB), 4.17 (2H, d), 2.65 (1H, t), 0.72 (3H, s). LCMS: Rt=2.33 min. m/z=471.0 [M+H]$^+$.

Example 74

Synthesis of Compound SG-21, SG-22 and SG-23

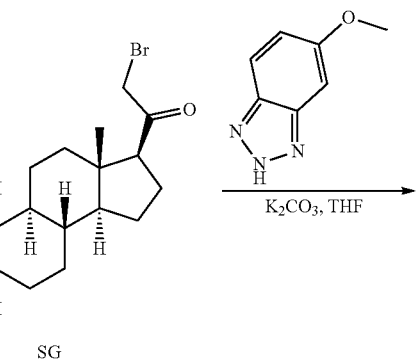

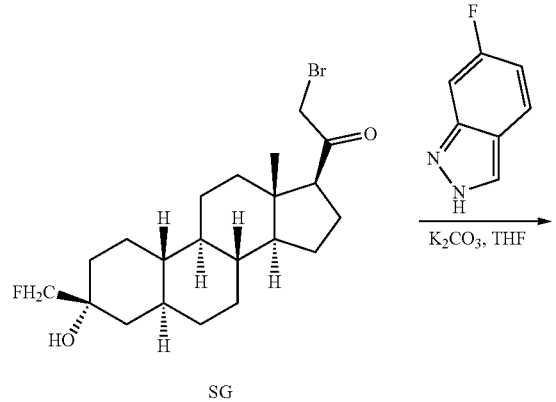

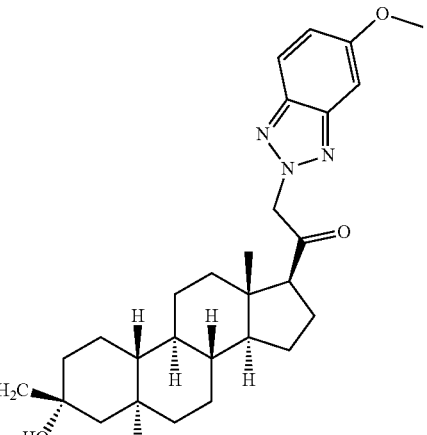

204

Example 75

Synthesis of Compound SG-24 and SG-25

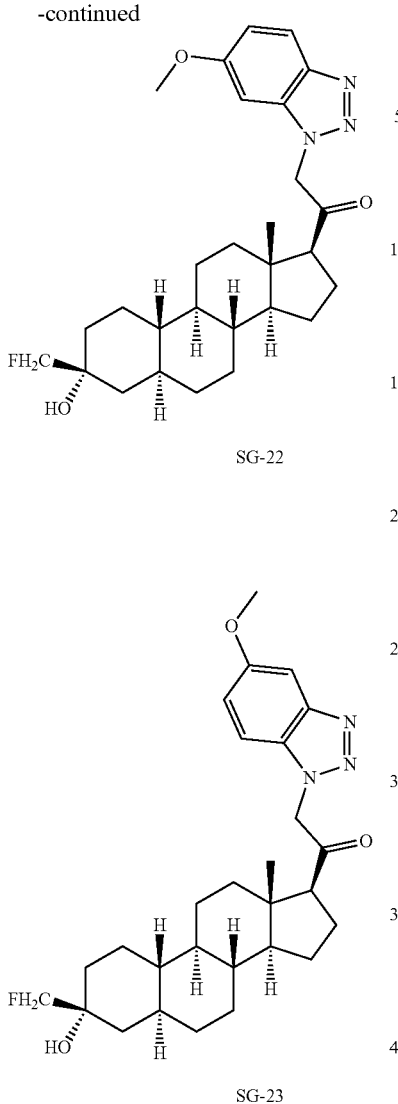

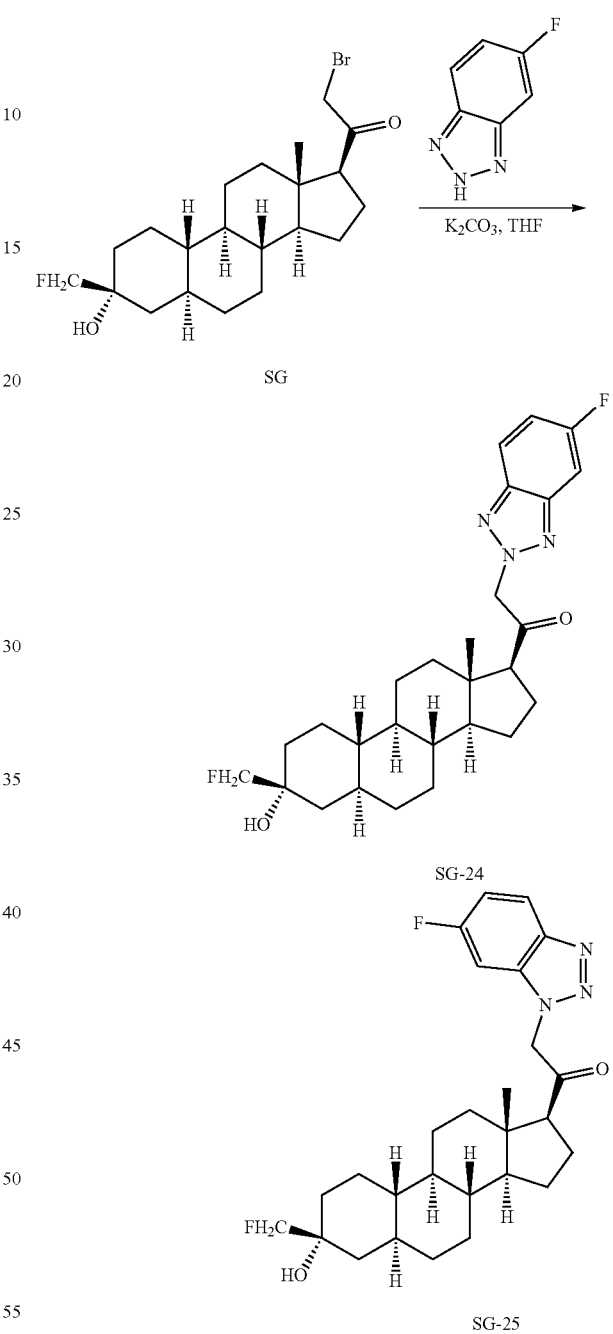

To a suspension of K₂CO₃ (63 mg, 0.47 mmol) in THF (10 mL) was added 5-methoxy-2H-benzo[d][1,2,3]triazole (70.1 mg, 0.47 mmol) and compound SG (100 mg, 0.24 mmol). After stirring at room temperature for 15 h, the reaction mixture was poured into 5 mL H₂O and extracted with EtOAc (2×10 mL). The combined organic layers were washed with brine(2×10 mL), dried over sodium sulfate, filtered and concentrated in vacuum. The residue was purified by reverse-phase prep-HPLC to afford SG-21 as a white solid (12.8 mg, 0.026 mmol, 11.5%), SG-22 as a white solid (25.4 mg, 0.053 mmol, 22.1%) and SG-23 as a white solid (14.5 mg, 0.029 mmol, 12.5%). SG-21: 1H NMR (500 MHz, CDCl₃) δ (ppm): 7.73 (d), 7.08-7.05 (m, 2H), 5.50 (AB), 5.43 (AB), 4.17 (d), 3.88 (3H, s), 2.65 (t), 0.75 (s, 3H). LCMS: Rt=2.34 min. m/z=484.3 [M+H]⁺. SG-22: 1H NMR (500 MHz, CDCl₃) δ (ppm): 7.92 (1H, d), 7.01 (1H, dd), 6.61 (1H, d), 5.35 (1H, AB), 5.30 (1H, AB), 4.17 (2H, d), 3.89 (3H, s), 2.70 (1H, t), 0.74 (3H, s). LCMS: Rt=2.36 min. m/z=484.1 [M+H]⁺. SG-23: 1H NMR (500 MHz, CDCl₃) δ (ppm): 7.39 (1H, d), 7.21 (1H, d), 7.15 (1H, dd), 6.61 (1H, d), 5.37 (1H, AB), 5.35 (1H, AB), 4.17 (2H, d), 3.89 (3H, s), 2.69 (1H, t), 0.73 (3H, s). LCMS: Rt=2.36 min. m/z=484.2 [M+H]⁺.

To a suspension of K₂CO₃ (63 mg, 0.47 mmol) in THF (10 mL) was added 5-fluoro-2H-benzo[d][1,2,3]triazole (64.4 mg, 0.47 mmol) and compound SG (100 mg, 0.24 mmol). After stirring at room temperature for 15 h, the reaction mixture was poured into 5 mL H₂O and extracted with EtOAc (2×10 mL). The combined organic layers were washed with brine (2×10 mL), dried over sodium sulfate, filtered and concentrated in vacuum. The residue was purified by reverse-phase prep-HPLC to afford SG-24 as a white solid (25.6 mg, 0.054 mmol, 22.5%) and SG-25 as a white solid (11.9 mg, 0.025 mmol, 10.4%). SG-24: ¹H NMR (400 MHz, CDCl₃), δ (ppm), 7.85 (1H, dd), 7.46 (1H, dd), 7.19 (1H, td), 5.50 (1H, AB), 5.48 (1H, AB), 4.17 (2H, d), 2.66 (1H, t), 0.73 (3H, s). LCMS: Rt=2.39 min. m/z=472.3 [M+H]⁺. SG-25: ¹H NMR (400 MHz, CDCl₃) δ (ppm): 8.04 (1H, dd), 8.15 (1H, td), 6.98 (1H, dd), 5.40 (1H, AB), 5.36 (1H, AB), 4.18 (2H, d), 2.72 (1H, t), 0.74 (3H, s). LCMS: Rt=2.30 min. m/z=472.3 [M+H]⁺.

Example 76

Synthesis of Compound SB-26

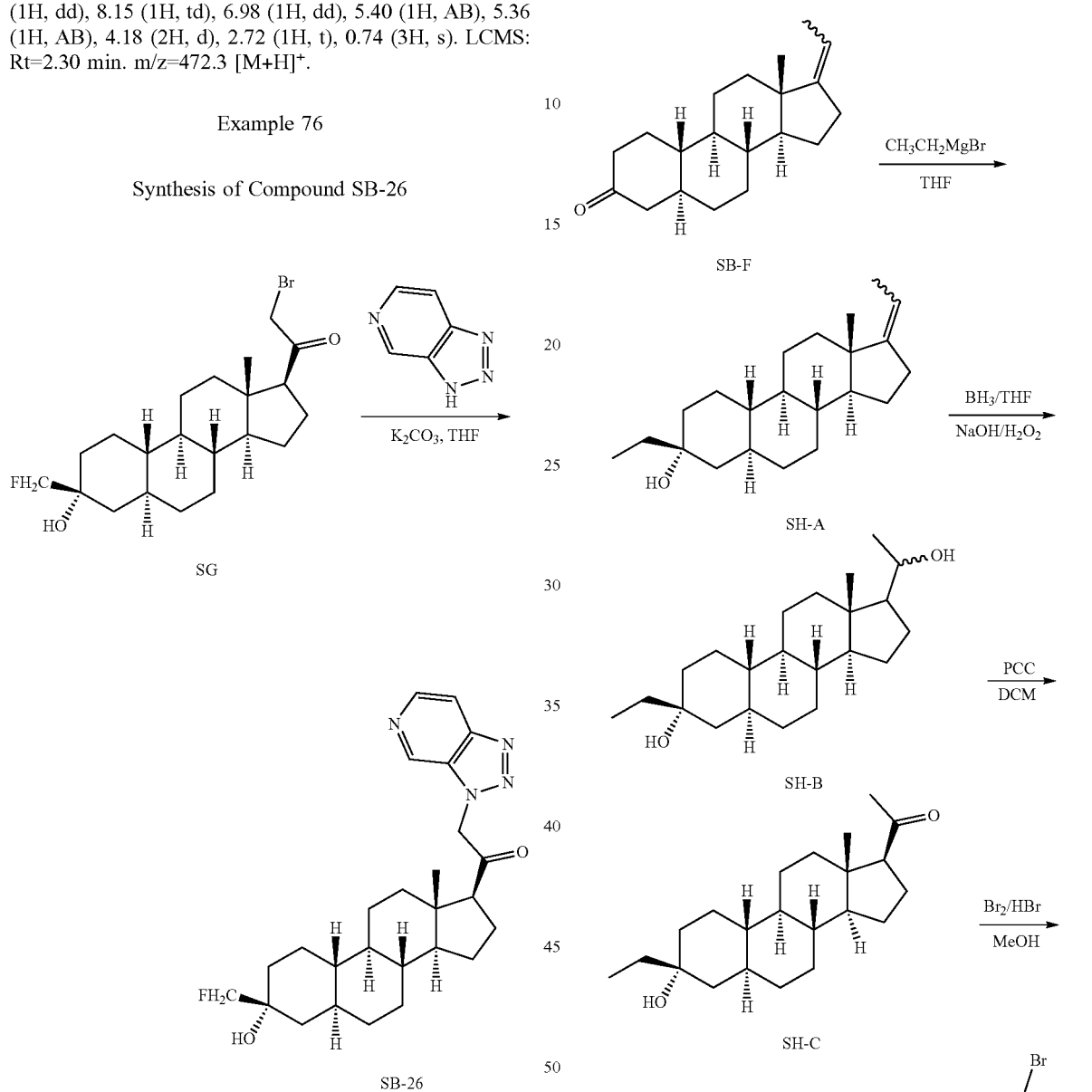

To a suspension of K₂CO₃ (63 mg, 0.47 mmol) in THF (10 mL) was added 3H-[1,2,3]triazolo[4,5-c]pyridine (56.4 mg, 0.47 mmol) and compound SG (100 mg, 0.24 mmol). After stirring at room temperature for 15 h, the reaction mixture was poured into 5 mL H₂O and extracted with EtOAc (2×10 mL). The combined organic layers were washed with brine(2×10 mL), dried over sodium sulfate, filtered and concentrated in vacuum. The residue was purified by reverse-phase prep-HPLC to afford product SB-26 as a white solid (24.5 mg, 0.054 mmol, 22.5%). SB-26: ¹H NMR (400 MHz, CDCl₃), δ (ppm), 8.96 (1H, d), 8.55 (1H, d), 7.98 (1H, dd), 5.55 (1H, AB), 5.52 (1H, AB), 4.17 (d, 2H), 2.77 (t), 0.75 (s, 3H). LCMS: Rt=2.24 min. m/z=455.1 [M+H]⁺.

Example 77

Synthesis of Compound SH

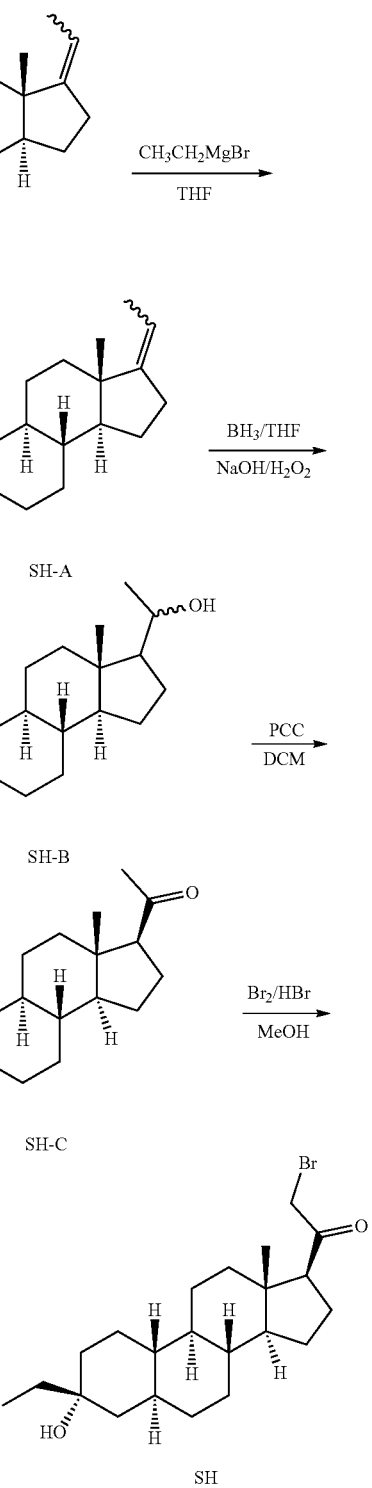

Synthesis of compound SH-A. To a solution of reactant SB-F (4.4 g, 15.38 mmol) in dry THF (50 mL) was added ethylmagnesium bromide (3M in THF, 51.28 mL) dropwise at 0° C. The solution was then slowly warmed and stirred at ambient temperature for 15 h. Sat. NH₄Cl solution (20 mL) was added to quench the reaction and the resulting solution was extracted with ethyl acetate (3×100 mL). The extracts were washed with brine, dried over Na₂SO₄ and concentrated in vacuo. The residue was purified by flash chromatography (eluant:petroleum ether:ethyl acetate=10:1) to afford product 8 (3.15 g, 10.00 mmol, 64.8%) as a white solid.

Synthesis of compound SH-B. To a solution of reactant SH-A (500 mg, 1.58 mmol) in anhydrous THF (10 mL) was added BH₃·THF (1.0 M, 7.23 mL, 7.23 mmol) at room temperature, and the solution was stirred at 25° C. overnight. Then the reaction was quenched by addition of water (5 mL), 2 M NaOH solution (10 mL) was added followed by 30% H₂O₂ (10 mL). The resulting mixture was stirred at room temperature for 1 hour. Then the mixture was diluted with ethyl acetate (200 mL) and resulting solution was washed with brine (2×100 mL), dried over magnesium sulfate and concentrated in vacuo. The crude product SH-B was used directly in the next step without further purification.

Synthesis of compound SH-C. To a solution of reactant SH-B (6.53 g, 19.67 mmol) in anhydrous DCM (100 mL) cooled in an ice-water cooling bath was added pyridinium chlorochromate (8.48 g, 39.34 mol) in portions. The mixture was stirred at ambient temperature overnight. The solution was then diluted with DCM (50 mL) and filtered. The combined organic solutions were washed with brine (100 mL), dried over Na₂SO₄ and concentrated in vacuo. The residue was purified by flash chromatography (eluant: petroleum ether:elthyl acetate=10:1) to afford product SH-B (2.5 g, 7.53 mmol, yield 39%) as a white solid. SH-B: ¹HNMR (500 MHz, CDCl₃) δ (ppm): 2.54 (1H, t), 2.11 (3H, s), 1.42-1.45 (2H, q), 0.91 (3H, t), 0.62 (3H, s).

Synthesis of compound SH. To a solution of reactant SH-C (80 mg, 0.24 mmol) in methanol (5 mL) was added 48% hydrobromic acid (148 mg, 0.884 mmol) followed by bromine (241 mg, 0.077 mL, 1.505 mmol). The solution was heated at 25° C. for 1.5 hours, then the mixture was poured into cooled water (50 mL). The resulting solid was extracted with ethyl acetate (2×50 mL). The combined organic extracts were washed with brine (20 mL), dried over magnesium sulfate and concentrated in vacuo. The crude product SH was used directly without further purification in the next step.

Example 79

Synthesis of Compound SB-29 and SB-30

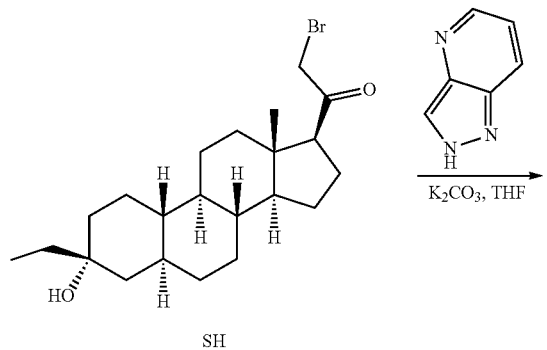

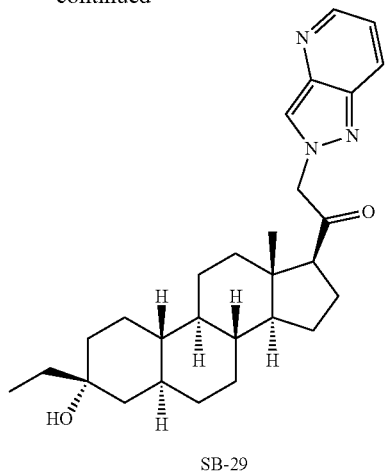

SB-29

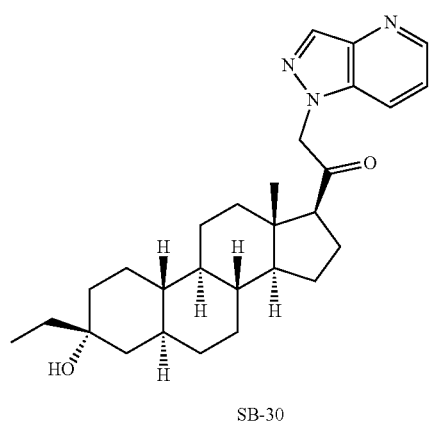

SB-30

To a solution of crude reactant SH (100 mg, 0.241 mmol) in anhydrous THF (5 mL) was added 2H-pyrazolo[4,3-b]pyridine (142 mg, 1.2 mmol) followed by potassium carbonate (170 mg, 1.2 mmol) and the solution was heated at 60° C. for 2 h. Then the reaction mixture was diluted with ethyl acetate (100 mL). The resulting solution was washed with brine (2×50 mL), dried over magnesium sulfate and concentrated in vacuo. The crude product was purified by reverse phase prep-HPLC to afford product SB-29 (7 mg, 0.015 mmol, Yield=6.6%) and SB-30 (9 mg, 0.02 mmol, Yield=8.3%) as white solid. SB-29: ¹H NMR (500 MHz, CDCl₃) δ (ppm): 8.58 (1H, s), 8.21 (1H, s), 8.04 (1H, d), 7.22 (1H, dd), 5.26 (1H, AB), 5.22 (1H, AB), 2.67 (1H, t), 0.73 (3H, s). LCMS: rt=2.40 min, m/z=450.2 [M+H]⁺ SB-30: ¹HNMR (500 MHz, CDCl₃) δ (ppm): 8.60 (1H, dd), 8.28 (1H, s), 7.59 (1H, d), 7.30 (1H, dd), 5.17 (1H, AB), 5.15(1H, AB), 2.67 (1H, t), 0.73(3H, s). LCMS: rt=2.43 min, m/z=450.2 [M+H]⁺

Example 80

Synthesis of Compound SB-31 and SB-32

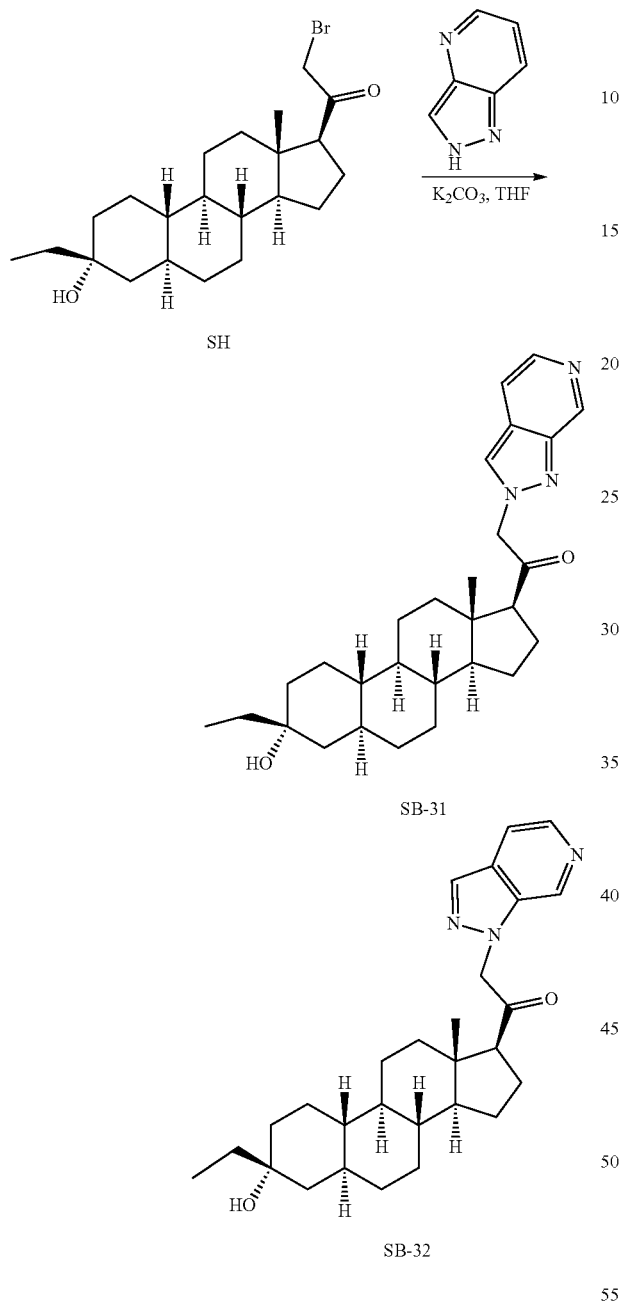

Example 81

Synthesis of Compound SB-33 and SB-34

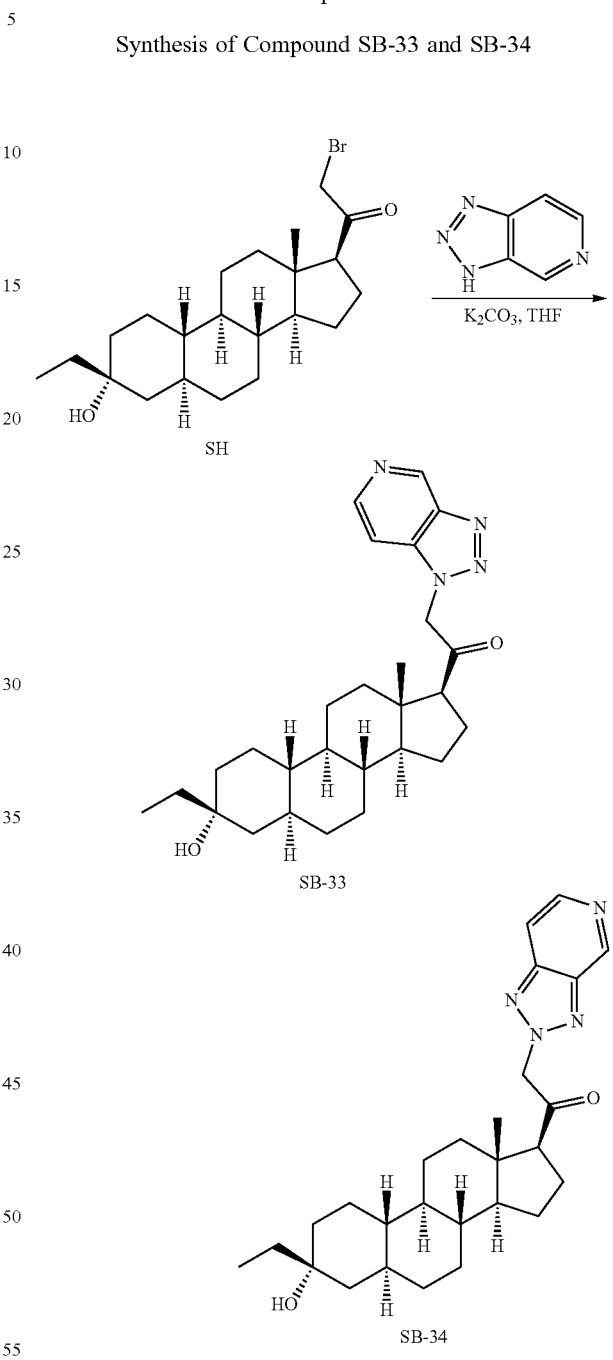

To a solution of crude reactant SH (100 mg, 0.241 mmol) in anhydrous THF (5 mL) was added 2H-pyrazolo[3,4-c]pyridine (143 mg, 1.2 mmol) followed by potassium carbonate (170 g, 1.2 mmol). The solution was heated at 60° C. for 2 h, then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-32 (11 mg, 0.09 mmol, Yield=8.3%) as white solid. SB-32: $^1$H NMR (500 MHz, CDCl3) δ (ppm): 8.80 (1H, s), 8.33(1H, d), 8.10(1H, s), 7.67(1H, d), 5.27(1H, AB), 5.25(1H, AB), 2.70(1H, t), 1.45-1.51(2H,q), 0.91 (3H, t), 0.73 (3H, s). LCMS: rt=2.46 min, m/z=450 [M+H]$^+$ To a solution of crude reactant SH (100 mg, 0.241 mmol) in anhydrous THF (5 mL) was added 3H-[1,2,3]triazolo[4,5-c]pyridine (143 mg, 1.2 mmol) followed by potassium carbonate (170 g, 1.2 mmol). The solution was heated a 60° C. for 2 h, then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-33 (7 mg, 0.09 mmol, Yield=8.3%) as white solid. SB-34: $^1$H NMR (500 MHz, CDCl$_3$) δ (ppm): 9.46

(1H, s), 8.47(1H, d), 7.76(1H, d), 5.61(1H, AB), 5.58(1H, AB), 2.70(1H, t), 1.27-1.42(2H, q), 0.91 (3H, t), 0.73 (3H, s). LCMS: rt=2.50 min, m/z=451 [M+H]+

Example 82

Synthesis of Compound SB-35 and SB-36

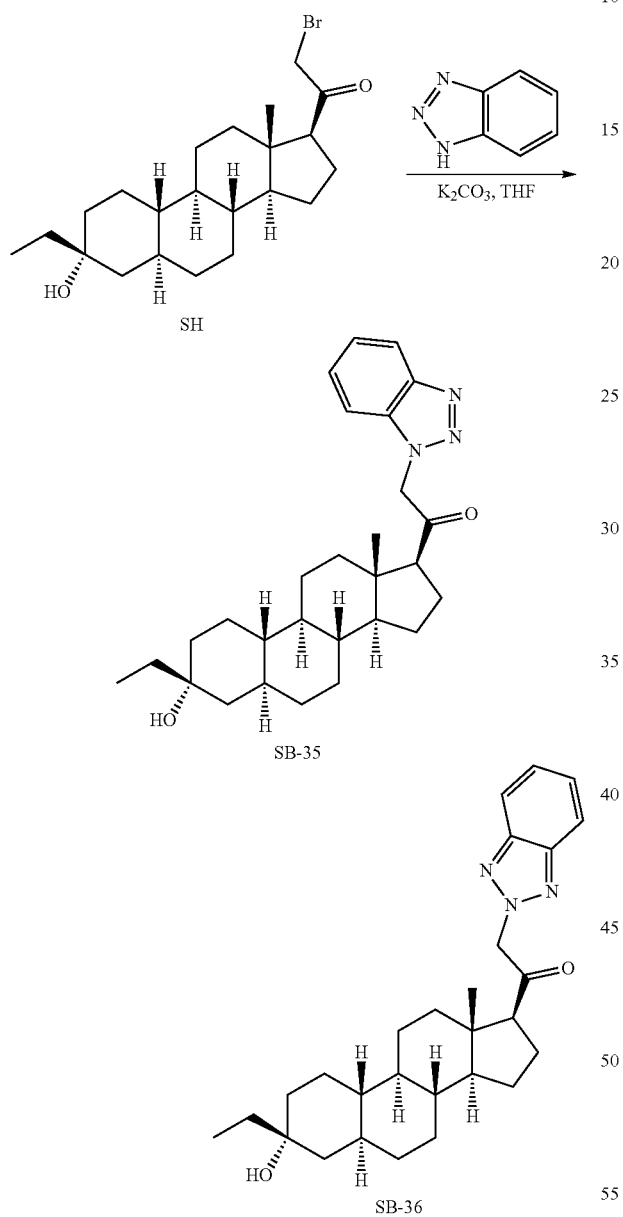

To a solution of crude reactant SH (100 mg, 0.241 mmol) in anhydrous THF (5 mL) was added 1H-benzo[d][1,2,3]triazole (143 mg, 1.2 mmol) followed by potassium carbonate (170 g, 1.2 mmol). The solution was heated at 60° C. for 2 h, then the solution was cooled to room temperature and diluted with ethyl acetate (100 mL). The resulting solution was washed with brine (2×50 mL), dried over magnesium sulfate and concentrated in vacuo. The crude product was purified by reverse phase prep-HPLC to afford product SB-35 (15.4 mg, 0.18 mmol, Yield=16.7%) and SB-36 (8 mg, 0.09 mmol, Yield=8.3%) as white solid. SB-35: ¹H NMR (400 MHz, CDCl₃) δ (ppm): 8.09(1H, d), 7.49(1H, t), 7.38(1H, t), 7.34(1H, t), 5.42(1H, AB), 5.41(1H, AB), 2.72 (1H, t), 1.45(2H, q), 0.91 (3H, t), 0.74 (3H, s). LCMS: rt=2.44 min, m/z=450 [M+H]+ SB-36: ¹H NMR (400 MHz, CDCl₃) δ (ppm): 7.88(2H, dd), 7.40(2H, dd), 5.53(1H, AB), 5.51(1H, AB), 2.67(1H, t), 1.42-1.46(2H, q), 0.91 (3H, t), 0.73 (3H, s). LCMS: rt=2.64 min, m/z=450 [M+H]+

Example 83

Synthesis of Compound SB-37, SB-38 and SB-39

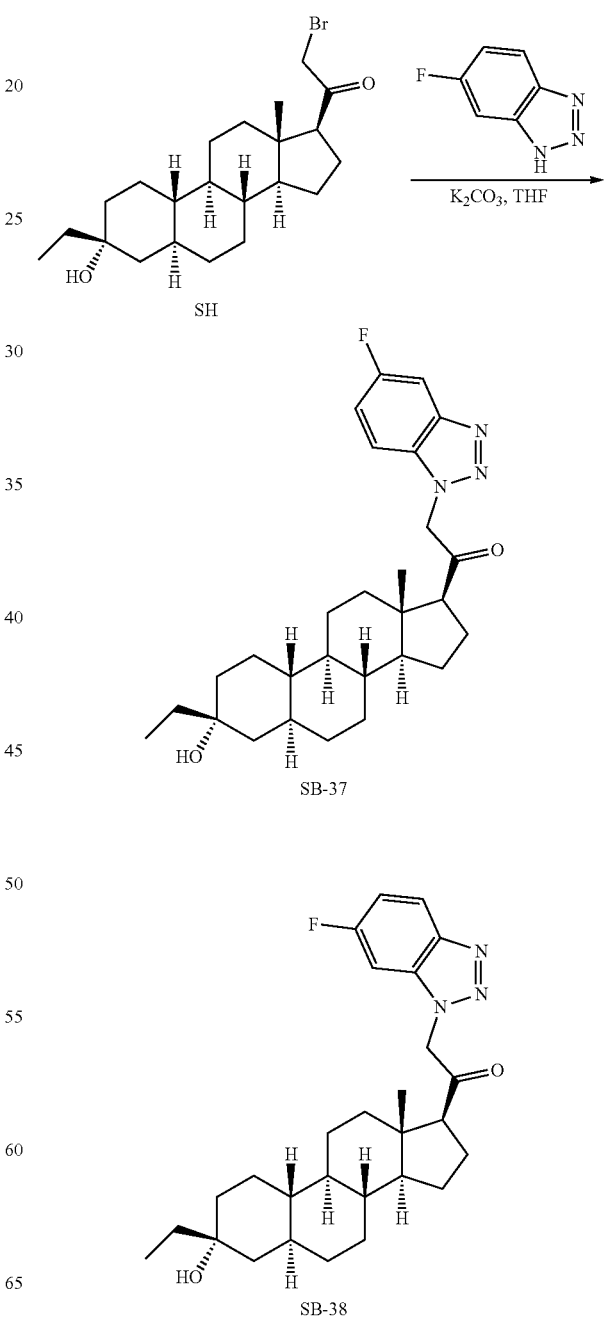

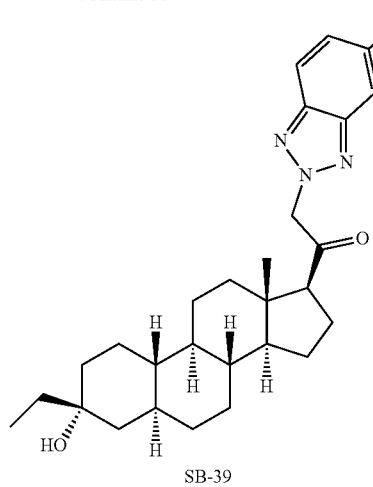

To a suspension of K$_2$CO$_3$ (67 mg, 0.50 mmol) in THF (5 mL) was added 5-fluoro-2H-benzo[d][1,2,3]triazole (68.5 mg, 0.50 mmol) and compound SH (100 mg, 0.24 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated in vacuum. The residue was purified by reverse-phase prep-HPLC to afford SB-37 as a white solid (3.2 mg, 0.007 mmol, 2.9%), SB-38 as a white solid (4.5 mg, 0.010 mmol, 4.0%) and SB-39 as a white solid (10.9 mg, 0.022 mmol, 9.3%). SB-37: $^1$H NMR (500 MHz, CDCl$_3$) δ (ppm): 7.70 (1H, d), 7.31-7.28 (2H, m), 5.43 (1H, AB), 5.38 (1H, AB), 2.72 (1H, t), 0.91(t), 0.73 (3H, s). LCMS: Rt=2.43 min. m/z=468.3 [M+H]$^+$. SB-38: $^1$H NMR (500 MHz, CDCl$_3$) δ (ppm): 8.04 (1H, dd), 7.15 (1H, td), 6.99 (1H, dd), 5.40 (1H, AB), 5.36 (1H, AB), 2.72 (1H, t), 0.91(t), 0.74 (3H, s). LCMS: Rt=2.46 min. m/z=468.3 [M+H]$^+$. SB-39: $^1$H NMR (400 MHz, CDCl$_3$) δ (ppm): 7.85 (1H, dd), 7.46 (1H, dd), 7.20 (1H, td), 5.50 (1H, AB), 5.48 (1H, AB), 2.66 (1H, t), 0.91(t), 0.74 (3H, s). LCMS: Rt=2.53 min. m/z=468.3 [M+H]$^+$.

Example 84

Synthesis of Compound SI

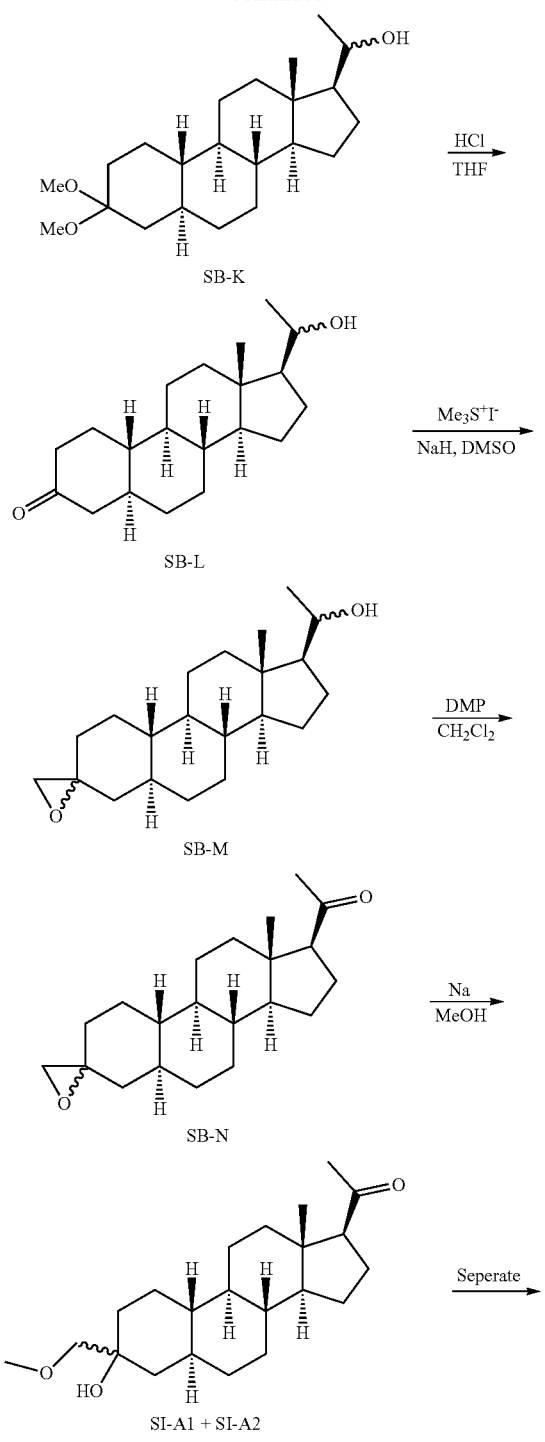

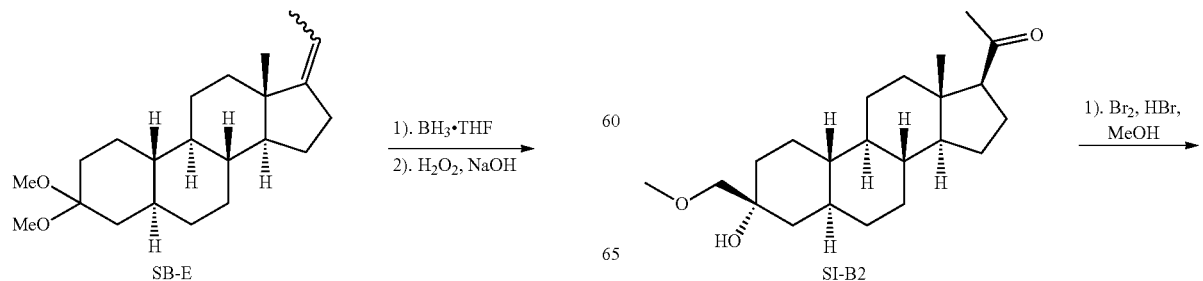

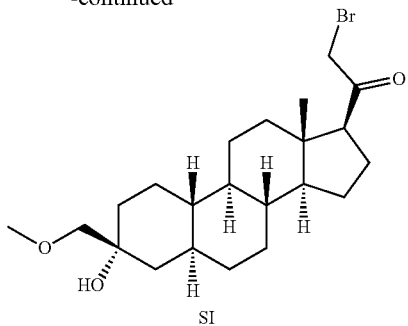

SI

Synthesis of compound SB-K. To a solution of compound SB-E (5 g, 15 mmol) in dry THF (20 mL) was added borane-tetrahydrofuran complex (30 mL of 1.0 M solution in THF) and the reaction mixture was stirred at ambient temperature for 1 hour then 10% aqueous NaOH (56 mL) was slowly added. The mixture was cooled in ice and 30% aqueous solution of $H_2O_2$ (67 mL) was slowly added. The mixture was stirred at ambient temperature for 1 hour and then extracted with EtOAc (3×100 mL). The combined EtOAc extracts were washed with 10% aqueous $Na_2S_2O_3$ (100 mL), brine (100 mL), dried over $MgSO_4$. Filtration and removal of the solvent gave the crude product 3.2 g for next step reaction.

Synthesis of compound SB-L. To a solution of compound SB-K (3.2 g, 9 mmol) in THF (40 mL) was added 2M HCl (3 mL). The reaction solution was stirred at RT for 12 h then the solvent was removed under reduced pressure. The crude target compound was purified by silica gel chromatography (eluant: petroleum ether/ethyl acetate=10:1 to 5:1) to give 2.2 g of the product as a white solid, yield: 81.40%.

Synthesis of compound SB-M. To a stirred solution of trimethylsufonium iodide (6.43 g, 31.5 mmol) in 100 mL of DMSO was added 60 wt % NaH (1.26 g, 31.5 mmol). After stirring at room temperature (15° C.) for 1 h, a solution of compound SB-L (2.2 g, 7.2 mmol) in 20 mL of DMSO was added dropwise. After 2.5 h, the reaction mixture was poured into ice-cold water and extracted with ether (100 mL×3). The combined ether layers were then washed with brine (100 mL×3), dried ($MgSO_4$), filtered, and concentrated to give the crude product 1.6 g for next step reaction.

Synthesis of compound SB-N. Compound SB-M (1.6 g, 5 mmol) was dissolved in 60 mL of $H_2O$ saturated $CH_2Cl_2$. (Using a separatory funnel, the $CH_2Cl_2$ had been shaken with several milliliters of $H_2O$ and then separated from the water layer). DMP was added (4.2 g, 10 mmol), and the resultant reaction mixture was vigorously stirred for 24 h. The reaction solution was diluted with DCM (100 mL), washed with 10% aqueous $Na_2S_2O_3$ (100 mL), brine (100 mL), dried over $MgSO_4$, filtered, and concentrated. The residue was purified by chromatography on silica gel (eluant: petroleum ether/ethyl acetate=20:1 to 10:1) to afford title compound (1.2 g, 3.79 mmol, 75%) as a white solid. $H^1$ NMR (400 MHz, $CDCl_3$) δ (ppm): 2.63 (s, 1H), 2.59 (s, 1H), 2.12 (s, 3H), 0.63 (s, 3H).

Synthesis of SI-A1 and SI-A2. Compound SB-N (1.2 g, 3.8 mmol) was dissolved in dry methanol (250 mL), and Na (262 mg, 11.4 mmol) was added. The solution was refluxed for 16 h. Methanol was evaporated off and the residue was dissolved in dichloromethane and washed with $H_2O$ (3×50 mL) and brine (100 mL), dried over $MgSO_4$, filtered, and concentrated. The crude target compound was purified by silica gel chromatography (eluant: petroleum ether/ethyl acetate=10:1 to 5:1) to give SI-A1 (300 mg, 25%), SI-A2 (300 mg, 25%) as a white solid. SI-A1, 1H NMR (400 MHz, $CDCl_3$) δ (ppm): 3.39 (s, 3H), 3.19 (s, 2H), 2.54 (t, 1H), 2.11(s, 3H), 0.61 (s, 3H). SI-A2, 1H NMR (400 MHz, $CDCl_3$) δ (ppm): 3.39 (s, 5H), 3.37 (s, 2H), 2.52 (t, 1H), 2.11 (s, 3H), 0.62 (s, 3H).

Synthesis of compound SI. A solution of SI-B2 (50 mg, 0.14 mmol) in MeOH and was treated with 2 drops of HBr(48%) followed by bromine (6 drops). The mixture was stirred at rt for 1 h and was poured into ice-water. The mixture was extracted with EA (50 mL) and dried over sodium sulfate filtration.

Example 85

Synthesis of Compound SB-40 and SB-41

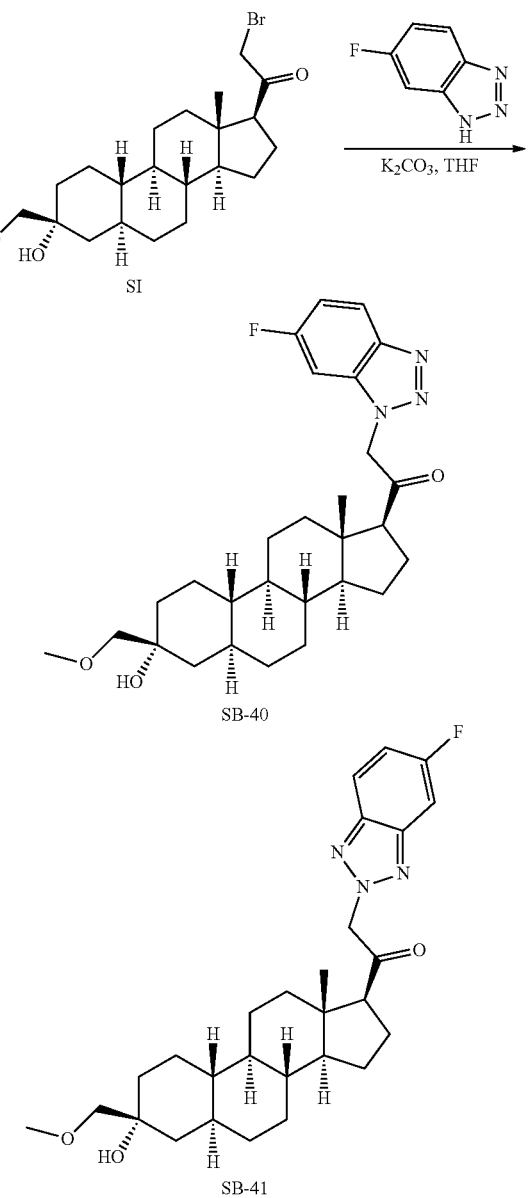

To a suspension of $K_2CO_3$ (67 mg, 0.50 mmol) in THF (5 mL) was added 5-fluoro-2H-benzo[d][1,2,3]triazole (68.5 mg, 0.50 mmol) and compound SI (100 mg, 0.23 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated in vacuo. The residue was purified by reverse-phase prep-HPLC to afford SB-40 as a white solid (12.3 mg, 0.025 mmol, 11.1%) and SB-41 as a white solid (16.2 mg, 0.033 mmol, 14.6%). SB-40: $^1$H NMR (500 MHz, CDCl$_3$) δ (ppm): 8.04 (1H, dd), 7.15 (1H, td), 6.98 (1H, dd), 5.40 (1H, AB), 5.35 (1H, AB), 3.39 (s, 3H), 3.20 (s, 2H), 2.73 (1H, t), 0.73 (3H, s). LCMS: Rt=2.33 min. m/z=484.3 [M+H]$^+$. SB-41: $^1$H NMR (500 MHz, CDCl$_3$) δ (ppm): 7.85 (1H, dd), 7.46 (1H, dd), 7.20 (1H, td), 5.50 (1H, AB), 5.48 (1H, AB), 3.39 (s, 3H), 3.20 (s, 2H), 2.67 (1H, t), 0.75 (3H, s). LCMS: Rt=2.42 min. m/z=484.3 [M+H]$^+$.

Example 86

Synthesis of Compound SB-42, SB-43 and SB-44

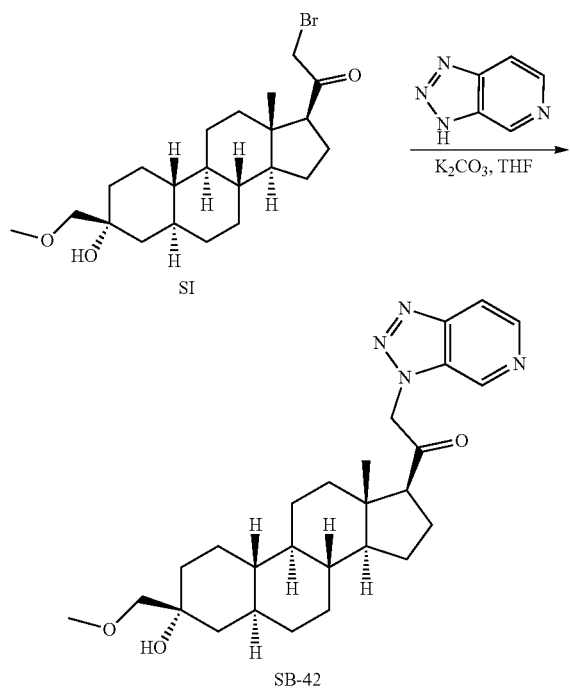

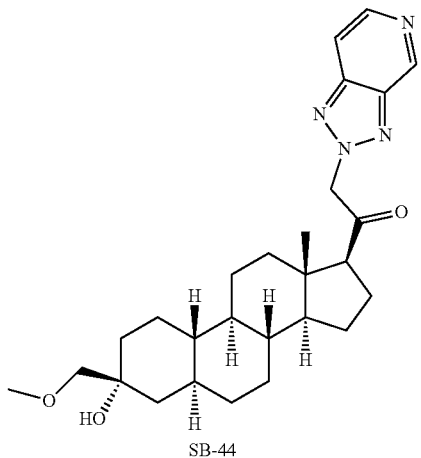

To a solution of crude reactant SI (367.9 mg, 0.861 mmol, theoretical amount) in anhydrous THF (7.5 mL) was added 1H-1,2,3-triazolo[4,5-c]pyridine (206.8 mg, 1.722 mmol) followed by potassium carbonate (238 mg, 1.722 mmol). The solution was heated at 50° C. for two hours, then the solution was diluted with ethyl acetate (200 mL). The resulting solution was washed with brine (2×100 mL), dried over magnesium sulfate and concentrated in vacuo. The crude product was purified by reverse phase prep-HPLC to afford fraction 1, 2, and 3. Fraction 1 was not desired product listed first based on the data of 1H NMR and NOESY but a by-product with unknown structure. Fraction 2 was desired product SB-43 (30 mg, 0.0643 mmol, Yield=7.5% (2 steps)). Fraction 3 was desired product SB-44 (39.3 mg, 0.0842 mmol, Yield=9.8% (2 steps)). All products were white solids. Compound SB-43: $^1$H NMR (400 MHz, CDCl$_3$) δ (ppm): 9.50 (1H, s), 8.58 (1H, d), 7.30 (1H, dd), 5.49 (1H, AB), 5.42 (1H, AB), 3.40 (3H, s), 3.20 (2H, s), 2.76 (1H, t), 0.73 (3H, s). LC-MS: rt=2.14 min, m/z=467.2 [M+H]$^+$
Compound SB-44: $^1$H NMR (400 MHz, CDCl$_3$) δ (ppm): 9.46 (1H, s), 8.47 (1H, d), 7.76 (1H, dd), 5.61 (1H, AB), 5.58 (1H, AB), 3.40 (3H, s), 3.20 (2H, s), 2.71 (1H, t), 0.76 (3H, s). LC-MS: rt=2.22 min, m/z=467.3 [M+H]$^+$ Example 87

Synthesis of Compound SB-45 and SB-46

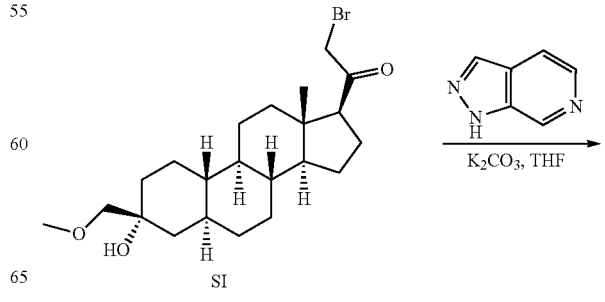

-continued

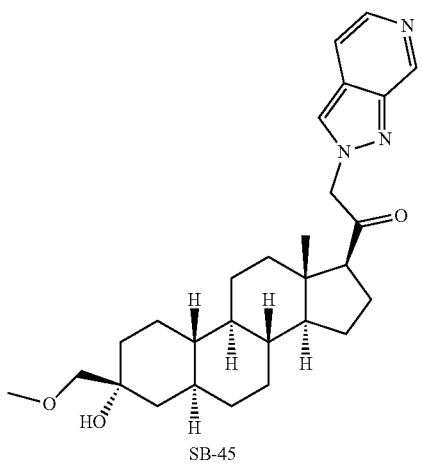

SB-45

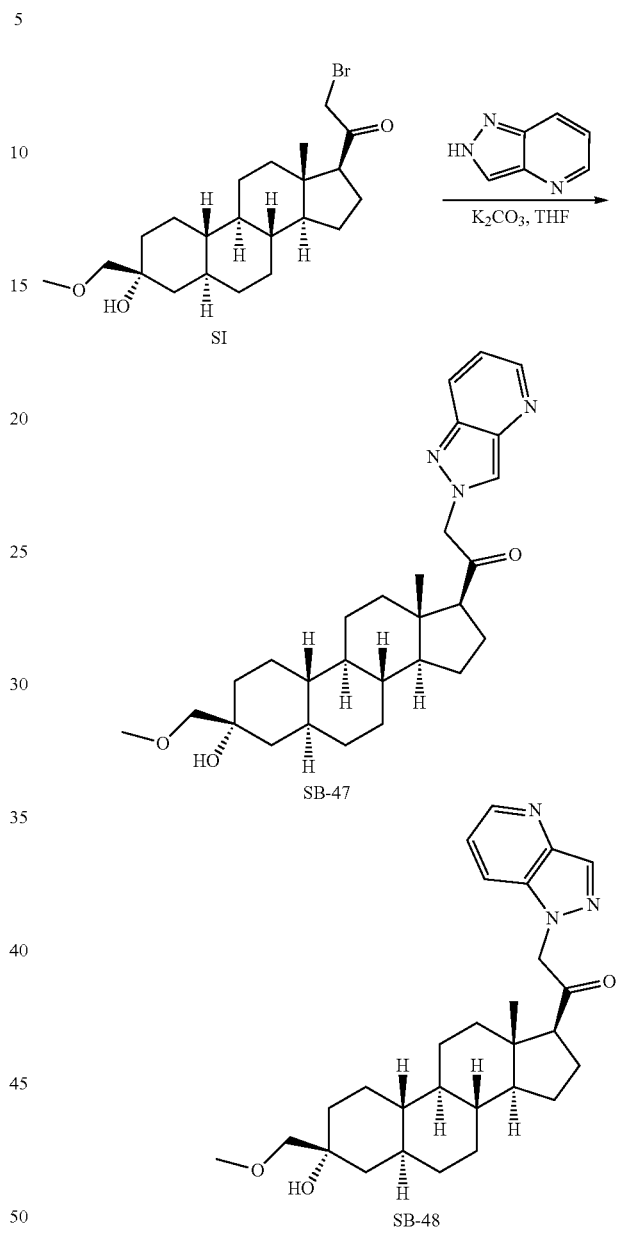

Example 88

Synthesis of Compound SB-47 and SB-48

To a solution of crude reactant SI (245.3 mg, 0.573 mmol, theoretical amount) in anhydrous THF (5 mL) was added 1H-pyrazolo[3,4-c]pyridine (137 mg, 1.148 mmol) followed by potassium carbonate (159 mg, 1.148 mmol). The solution was heated at 50° C. for 2 hours, then the solution was diluted with ethyl acetate (200 mL). The resulting solution was washed with brine (2×100 mL), dried over magnesium sulfate and concentrated in vacuo. The crude product was purified by reverse phase prep-HPLC to afford product SB-45 (5 mg, 0.011 mmol, Yield=1.9% (2 steps)) and product SB-46 (21.7 mg, 0.0466 mmol, Yield=8.2% (2 steps)) as a white solid. Compound SB-45: $^1$H NMR (400 MHz, CDCl$_3$) δ (ppm): 9.26 (1H, s), 8.17 (1H, d), 7.99 (1H, s), 7.53 (1H, d), 5.32 (1H, AB), 5.24 (1H, AB), 3.39 (3H, s), 3.20 (2H, s), 2.69 (1H, t), 0.72 (3H, s). LC-MS: rt=2.22 min, m/z=466.2 [M+H]$^+$ Compound SB-46: $^1$H NMR (400 MHz, CDCl$_3$) δ (ppm): 8.80 (1H, s), 8.34 (1H, d), 8.10 (1H, s), 7.65 (1H, dd), 5.27 (1H, AB), 5.25 (1H, AB), 3.40 (3H, s), 3.20 (2H, s), 2.70 (1H, t), 0.73 (3H, s). LC-MS: rt=2.29 min, m/z=466.2 [M+H]$^+$ To a solution of crude reactant SI (245.3 mg, 0.574 mmol, theoretical amount) in anhydrous THF (5 mL) was added 1H-pyrazolo[4,3-b]pyridine (137 mg, 1.148 mmol) followed by potassium carbonate (159 mg, 1.148 mmol). The solution was heated at room temperature overnight, then the solution was diluted with ethyl acetate (200 mL). The resulting solution was washed with brine (2×100 mL), dried over magnesium sulfate and concentrated in vacuo. The crude product was purified by reverse phase prep-HPLC to afford product SB-47 (18.3 mg, 0.0393 mmol, Yield=6.8% (2 steps)) and product SB-48 (57.1 mg, 0.213 mmol, Yield=21% (2 steps)) as a pale yellow solid. Compound SB-47: $^1$H NMR (400 MHz, CDCl$_3$) δ (ppm): 8.59 (1H, d), 8.21 (1H, s), 8.04 (1H, d), 7.22 (1H, dd), 5.27 (1H, AB), 5.21 (1H, AB), 3.39 (3H, s), 3.19 (2H, s), 2.67 (1H, t), 0.73 (3H, s). LC-MS: rt=2.15 min, m/z=466.4 [M+H]+ Compound SB-48: ¹H NMR (400 MHz, CDCl₃) δ (ppm): 8.60 (1H, dd), 8.28 (1H, s), 7.59 (1H, t), 7.31 (1H, dd), 5.18 (1H, t), 5.15 (1H, AB), 3.39 (3H, s), 3.19 (2H, s), 2.68 (1H, t), 0.72 (3H, s). LC-MS: rt=2.19 min, m/z=466.4 [M+H]+

Example 89

Synthesis of Compound SB-49, SB-50 and SB-51

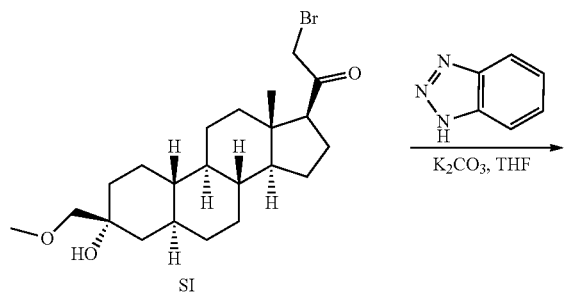

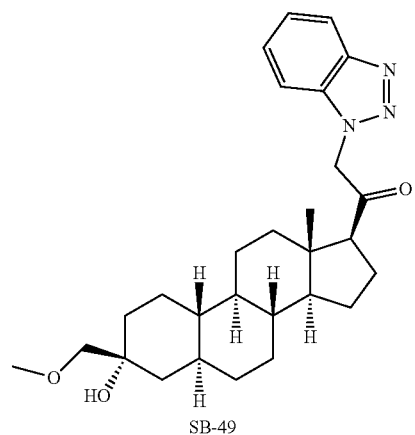

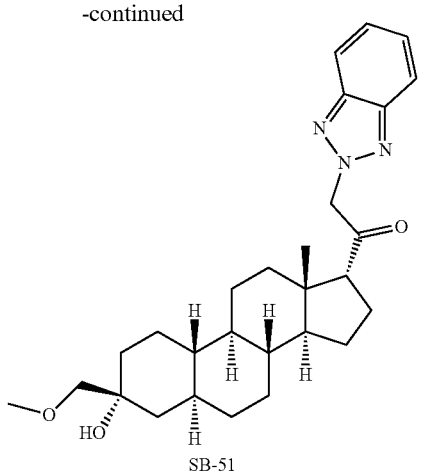

To a solution of crude reactant SI (245.3 mg, 0.574 mmol, theoretical amount) in anhydrous THF (5 mL) was added benzotriazole (342 mg, 2.87 mmol) followed by potassium carbonate (397 mg, 2.87 mmol). The solution was heated at 60° C. overnight. Then the solution was diluted with ethyl acetate (200 mL). The resulting solution was washed with brine (2×100 mL), dried over magnesium sulfate and concentrated in vacuo. The crude product was purified by reverse phase prep-HPLC to afford fraction 1 and fraction 2. Fraction 1 was desired product SB-49 (35.9 mg, 0.0771 mmol, two steps overall yield=13.4%) as white solid. Fraction 2 was additionally purified by chiral prep-HPLC to afford desired product SB-50 (5.9 mg, 0.0127 mmol, two steps overall yield=2.2%) and by product SB-51 (4.0 mg, 0.00859 mmol, two steps overall yield=1.5%) as white solid. Compound SB-49: ¹H NMR (500 MHz, CDCl₃) δ (ppm): 8.08 (1H, d), 7.49 (1H, d), 7.38 (1H, d), 7.34 (1H, d), 5.43 (1H, AB), 5.40 (1H, AB), 3.39 (3H, s), 3.19 (2H, s), 2.72 (1H, t), 0.74 (3H, s). LC-MS: rt=2.37 min, m/z=466.3 [M+H]+ Compound SB-50: ¹H NMR (400 MHz, CDCl₃) δ (ppm): 7.88 (2H, dd), 7.39 (2H, dd), 5.54 (1H, AB), 5.51 (1H, AB), 3.39 (3H, s), 3.19 (2H, s), 2.67 (1H, t), 0.75 (3H, s). LC-MS: rt=2.50 min, m/z=466.2 [M+H]+ Compound SB-51: ¹H NMR (400 MHz, CDCl₃) δ (ppm): 7.89 (2H, dd), 7.40 (2H, dd), 5.56 (1H, AB), 5.48 (1H, AB), 3.38 (3H, s), 3.18 (2H, s), 2.74 (1H, dd), 0.92 (3H, s). LC-MS: rt=2.48 min, m/z=466.2 [M+H]+

Example 90

Synthesis of Compound SJ

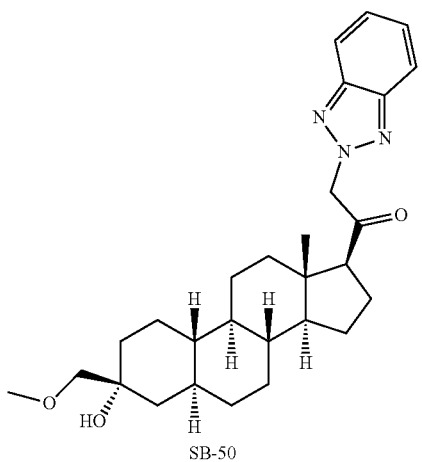

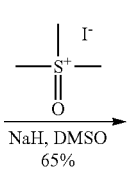

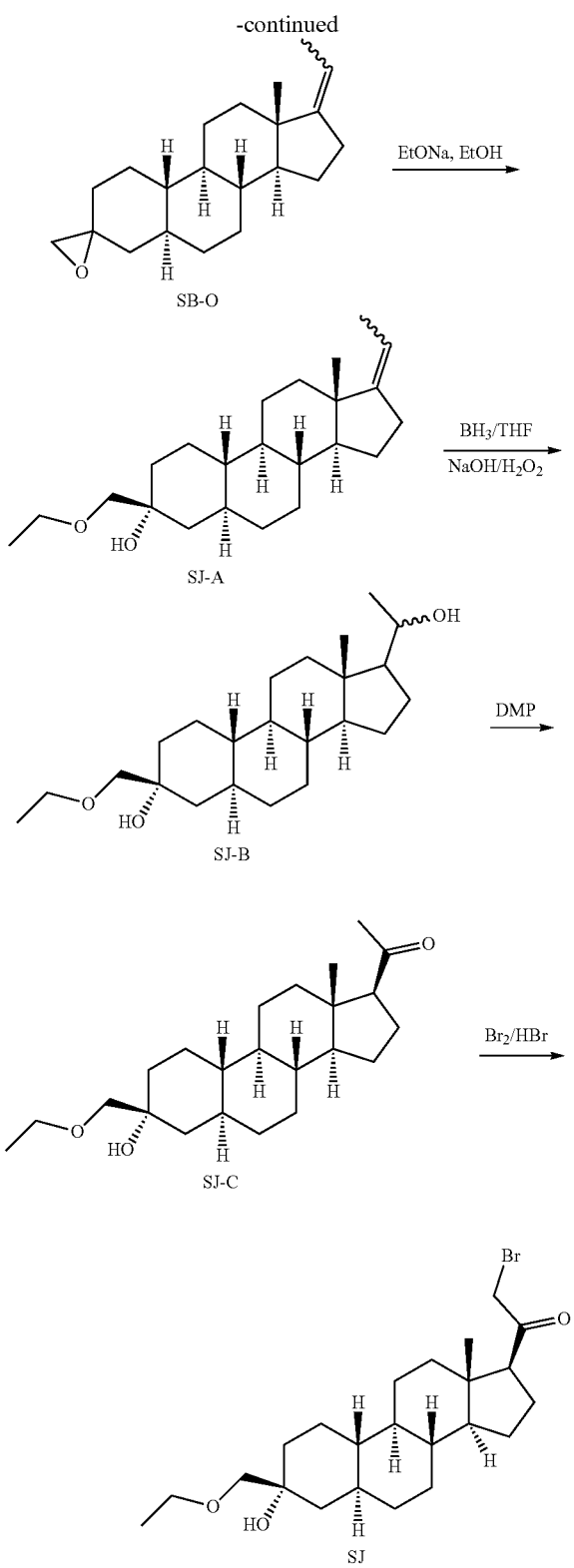

Synthesis of compound SB-O. To a stirred solution of trimethylsulfonium iodide (8.1 g, 36.9 mmol) in 100 mL of DMSO was added NaH (60%; 1.26 g, 31.5 mmol). After stirring at room temperature for 1 h, a suspension of compound SB-F (2.2 g, 7.2 mmol) in DMSO (20 mL) was added dropwise. The mixture was stirred for another 2.5 h, then poured into ice-cold water and extracted with ether (100 mL×3). The combined ether layers were then washed with brine (100 mL×3), dried over MgSO$_4$, filtered, and concentrated to give the crude product SB-O (2.2 g). The crude product was used in the next step without further purification.

Synthesis of compound SJ-A. Compound SB-O (2.2 g, 7.3 mmol) was dissolved in dry methanol (250 mL), and Na (672 mg, 29.2 mmol) was added. The solution was stirred reflux for 6 h. Methanol was evaporated off and the residue was dissolved in dichloromethane and washed with H$_2$O (3×50 mL) and brine (100 mL), dried over MgSO$_4$, filtered, and concentrated. The crude target compound was purified by via silica gel chromatography (pretroleum ether/ethyl acetate=10:1 to 5:1),and concentrated to give SJ-A (1.8 g, 82%) as a white solid. $^1$H NMR (500 MHz, CDCl$_3$), δ (ppm), 5.03-5.01 (m, 1H), 3.43 (q, 2H), 3.13 (s, 2H), 0.80 (s, 3H).

Synthesis of compound SJ-B. To a solution of compound SJ-A (1.8 g, 5.2 mmol) in dry THF (50 mL) was added borane-tetrahydrofuran complex (20 mL of 1.0 M solution in THF). After stirring at room temperature for 1 hour, the reaction mixture was cooled in an ice bath then quenched slowly with 10% aqueous NaOH (10 mL) followed 30% aqueous solution of H$_2$O$_2$ (12 mL). The mixture was allowed to stir at room temperature for 1 hour then extracted with EtOAc (3×100 mL). The combined organic layers were washed with 10% aqueous Na$_2$S$_2$O$_3$ (100 mL), brine (100 mL), dried over MgSO$_4$, filtered and concentrated to afford crude compound SJ-B (1.8 g, 100%). The crude product was used in the next step without further purification.

Synthesis of SJ-C. To a solution of crude compound SJ-B (1.8 g, 5.2 mmol) was dissolved in 60 mL of H$_2$O saturated dichloromethane (dichloromethane had been shaken with several milliliters of H$_2$O then separated from the water layer) was added Dess-Martin periodinate (4.4 g, 10.4 mmol). After stirring at room temperature for 24 h, the reaction mixture was extracted with dichloromethane (3×100 mL). The combined organic layers were washed with 10% aqueous Na$_2$S$_2$O$_3$ (100 mL), brine (100 mL), dried over MgSO$_4$, filtered and concentrated. The residue was purified by chromatography on silica gel (pretroleum ether/ethyl acetate=10:1 to 5:1) to afford SJ-C (1 g, 2.8 mmol, 56% for two steps) as a white solid. $^1$H NMR (400 MHz, CDCl$_3$), δ (ppm), 3.52 (q, 2H), 3.21 (s, 2H), 2.54 (t, 2H), 2.11 (s, 3H), 1.20 (t, 3H), 0.61 (s, 3H). LCMS: Rt=7.25 min. m/z=345.1 [M-17]$^+$.

Synthesis of compound SJ. To a solution of compound SJ-C (600 mg, 1.65 mmol) in MeOH (20 mL) was added 5 drops of HBr (48%) followed by bromine (264 mg, 1.65 mmol). After stirring at room temperature for 1 h, the reaction mixture was poured into ice-water then extracted with ethyl acetate (100 mL×3). The combined organic layers were washed with brine (200 mL), dried over MgSO$_4$, filtered and concentrated to give crude compound SJ (600 mg, 100%). The crude product was used in the next step without further purification. LCMS: Rt=7.25 min. m/z=463.1 [M+Na]$^+$.

Example 91

Synthesis of Compound SB-52 and SB-53

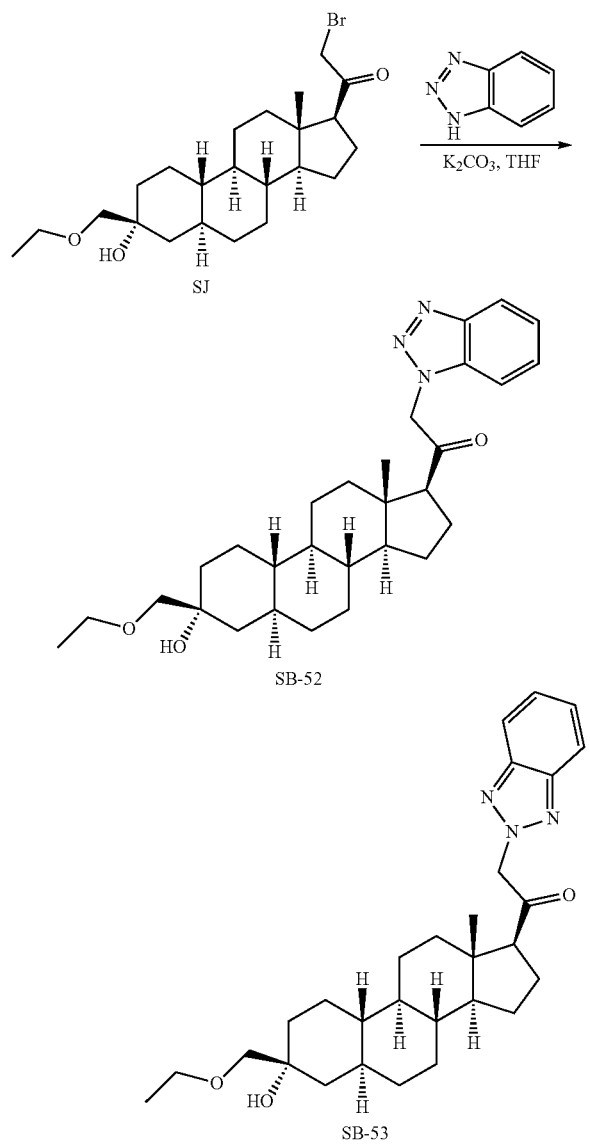

To a suspension of K₂CO₃ (63 mg, 0.46 mmol) in THF (10 mL) was added 1H-Benzotriazole (55 mg, 0.46 mmol) and compound SJ (100 mg, 0.23 mmol). After stirring at room temperature for 15 h, the reaction mixture was poured into 5 mL H₂O and extracted with EtOAc (2×10 mL). The combined organic layers were washed with brine (2×10 mL), dried over sodium sulfate, filtered and concentrated under vacuum. The residue was purified by reverse-phase prep-HPLC to afford SB-52 as a white solid (21.8 mg, 0.045 mmol, 19.6%) and SB-53 as a white solid (9.7 mg, 0.020 mmol, 8.7%). SB-52: ¹H NMR (500 MHz, CDCl₃) δ (ppm): 8.08 (d, 1H), 7.49 (d, 1H), 7.38 (d, 1H), 7.34 (d, 1H), 5.44 (AB, 1H), 5.40 (AB, 1H), 3.53 (q, 2H), 3.22 (s, 2H), 2.72 (t, 1H), 1.21 (t, 3H), 0.74 (s, 3H). LCMS: Rt=2.43 min. m/z=480.4 [M+H]⁺. SB-53: ¹H NMR (500 MHz, CDCl₃) δ (ppm): 7.88 (dd, 2H), 7.39 (dd, 2H), 5.55 (AB, 1H), 5.49 (AB, 1H), 3.53 (q, 2H), 3.22 (s, 2H), 2.37 (t, 1H), 1.20 (t, 3H), 0.76 (s, 3H). LCMS: Rt=2.55 min. m/z=480.4 [M+H]⁺.

Example 92

Synthesis of Compound SB-54 and SB-55

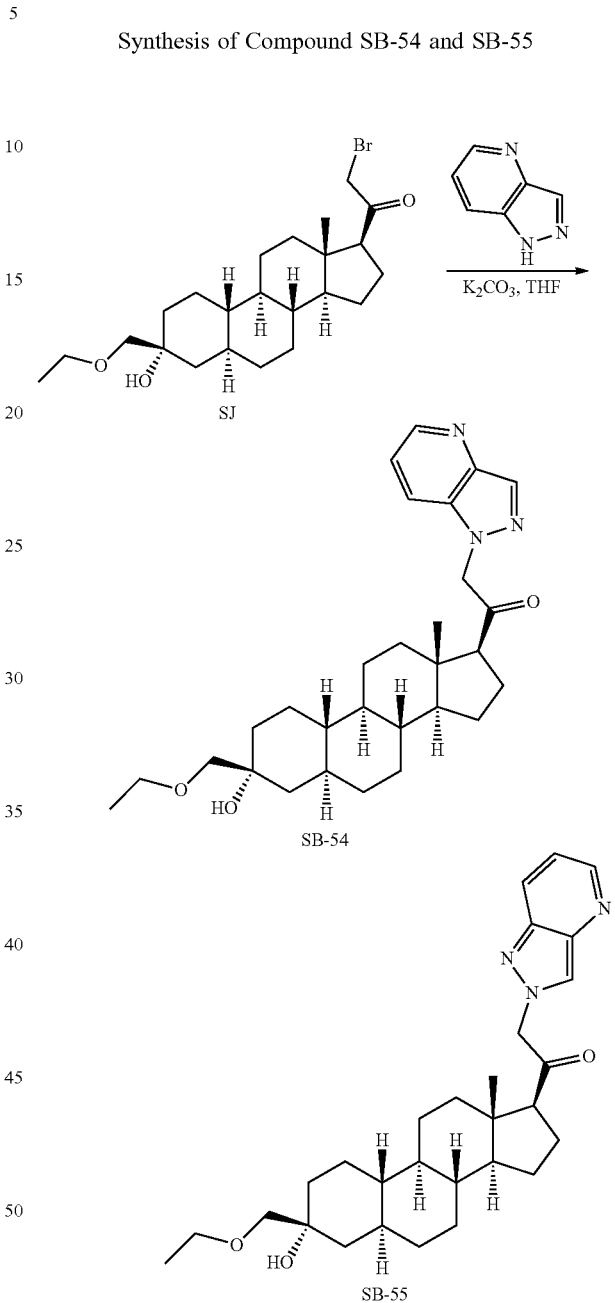

To a suspension of K₂CO₃ (63 mg, 0.46 mmol) in THF (10 mL) was added 1H-pyrazolo[4,3-b]pyridine (55 mg, 0.46 mmol) and compound SJ (100 mg, 0.23 mmol). After stirring at room temperature for 15 h, the reaction mixture was poured into 5 mL H₂O and extracted with EtOAc (2×10 mL). The combined organic layers were washed with brine (2×10 mL), dried over sodium sulfate, filtered and concentrated under vacuum. The residue was purified by reverse-phase prep-HPLC to afford SB-54 as a white solid (23.1 mg, 0.048 mmol, 20.1%) and SB-55 as a white solid (8.1 mg, 0.017 mmol, 7.3%). SB-54: ¹H NMR (400 MHz, CDCl₃) δ (ppm): 8.60 (1H, dd), 8.28 (1H, s), 7.59 (1H, t), 7.31 (1H, dd), 5.17 (1H, t), 5.15 (1H, AB), 3.53 (2H, q), 3.22 (2H, s), 2.68 (1H, t), 1.21 (3H, t), 0.72 (3H, s). LCMS: Rt=2.32 min. m/z=480.4 [M+H]$^+$. SB-55: $^1$H NMR (400 MHz, CDCl$_3$) δ (ppm): 8.58 (1H, d), 8.21 (1H, s), 8.04 (1H, d), 7.22 (1H, dd), 5.27 (1H, AB), 5.21 (1H, AB), 3.53 (2H, q), 3.22 (2H, s), 2.67 (1H, t), 1.21 (3H, t), 0.73 (3H, s). LCMS: Rt=2.27 min. m/z=480.4 [M+H]$^+$.

Example 93

Synthesis of Compound SB-56 and SB-57

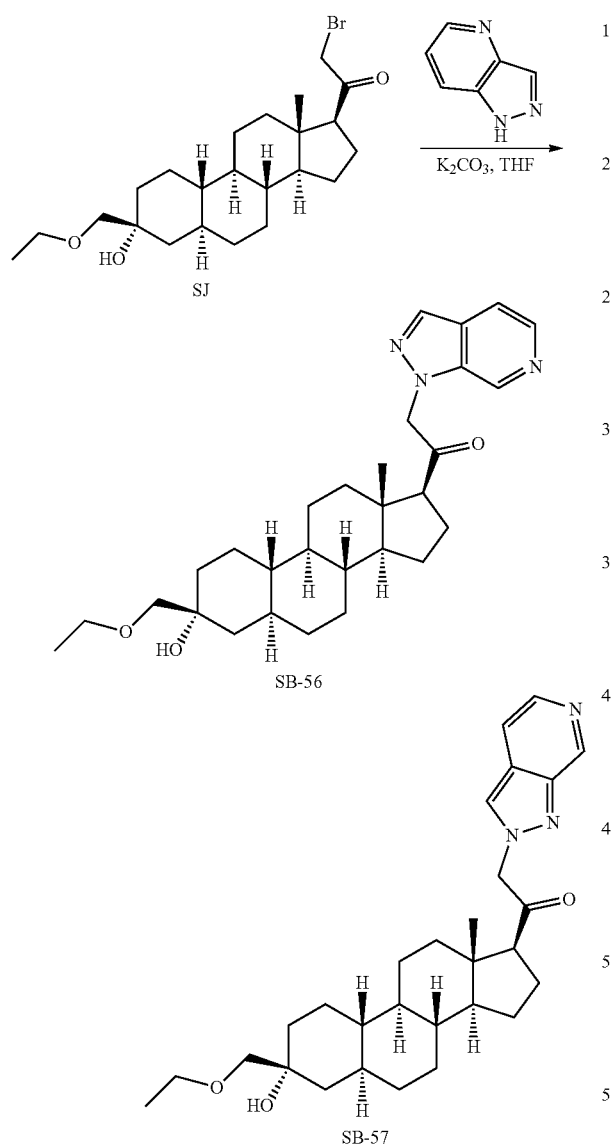

To a suspension of K$_2$CO$_3$ (63 mg, 0.46 mmol) in THF (10 mL) was added 1H-pyrazolo[4,3-b]pyridine (55 mg, 0.46 mmol) and compound SJ (100 mg, 0.23 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated under vacuum. The residue was purified by reverse-phase prep-HPLC to afford SB-56 as a white solid (10.8 mg, 0.023 mmol, 10.0%) and SB-57 as a white solid (28.1 mg, 0.059 mmol, 25.5%). SB-56: $^1$H NMR (400 MHz, CDCl$_3$) δ (ppm): 8.80 (1H, s), 8.34 (1H, d), 8.10 (1H, s), 7.64 (1H, dd), 5.27 (1H, AB), 5.25 (1H, AB), 3.53 (2H, q), 3.22 (2H, s), 2.70 (1H, t), 1.21 (3H, t), 0.73 (3H, s). LCMS: Rt=2.43 min. m/z=480.2 [M+H]$^+$. SB-57: $^1$H NMR (400 MHz, CDCl$_3$) δ (ppm): 9.26 (1H, s), 8.17 (1H, d), 7.98 (1H, s), 7.53 (1H, d), 5.32 (1H, AB), 3.53 (2H, q), 3.22 (2H, s), 2.68 (1H, t), 1.21 (3H, t), 0.72(3H, s). LCMS: Rt=2.23 min. m/z=480.3 [M+H]$^+$.

Example 94

Synthesis of Compound SB-58 and SB-59

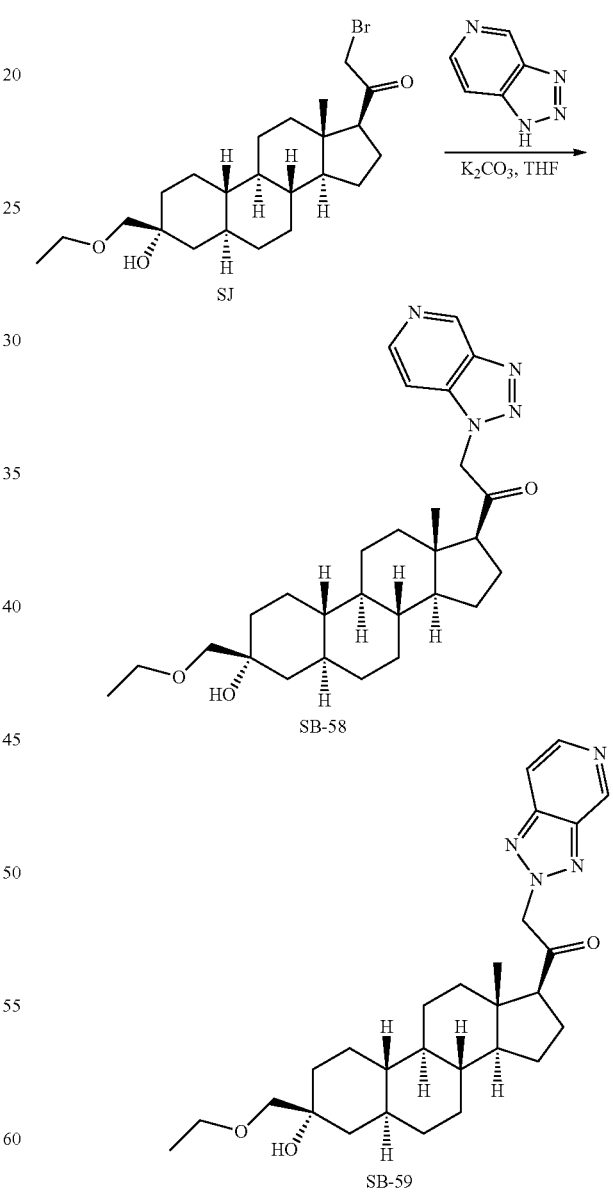

To a suspension of K$_2$CO$_3$ (63 mg, 0.46 mmol) in THF (10 mL) was added 1H-[1,2,3]triazolo[4,5-c]pyridine (55 mg, 0.46 mmol) and compound SJ (100 mg, 0.23 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated under vacuum. The residue was purified by reverse-phase prep-HPLC to afford compound SB-58 as a white solid (11.3 mg, 0.024 mmol, 10.2%) and SB-59 as a white solid (20.1 mg, 0.042 mmol, 18.2%). SB-58: $^1$H NMR (400 MHz, CDCl$_3$) δ (ppm): 9.50 (1H, s), 8.58 (1H, d), 7.29 (1H, dd), 5.48 (1H, AB), 5.42 (1H, AB), 3.53 (2H, q), 3.22 (2H, s), 2.68 (1H, t), 1.14 (3H, t), 0.67 (3H, s). LCMS: Rt=2.37 min. m/z=481.2 [M+H]$^+$. SB-59: $^1$H NMR (500 MHz, CDCl$_3$) δ (ppm): 9.46 (1H, d), 8.47 (1H, d), 7.76 (1H, dd), 5.60 (1H, AB), 5.58 (1H, AB), 3.53 (2H, q), 3.22 (2H, s), 2.70 (1H, t), 1.21 (3H, t), 0.76(3H, s). LCMS: Rt=2.28 min. m/z=481.1 [M+H]$^+$.

Example 95

Synthesis of Compound SB-60

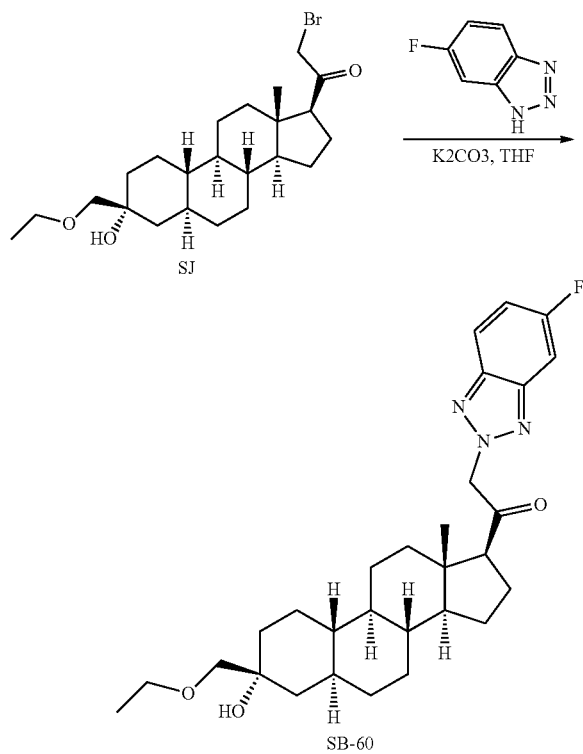

To a suspension of K$_2$CO$_3$ (67 mg, 0.50 mmol) in THF (5 mL) was added 5-fluoro-2H-benzo[d][1,2,3]triazole (68.5 mg, 0.50 mmol) and compound SJ (100 mg, 0.25 mmol). After stirring at room temperature for 15 h, the reaction mixture was poured into 5 mL H$_2$O and extracted with EtOAc (2×10 mL). The combined organic layers were washed with brine (2×10 mL), dried over sodium sulfate, filtered and concentrated in vacuum. The residue was purified by reverse-phase prep-HPLC to afford SB-60 as a white solid (5.9 mg, 0.012 mmol, 4.8%). SB-60: $^1$H NMR (500 MHz, CDCl$_3$) δ (ppm): 7.86 (1H, dd), 7.46 (1H, dd), 7.20 (1H, td), 5.50 (1H, AB), 5.48 (1H, AB), 3.53 (q), 3.22 (s, 2H), 2.67 (t), 1.21 (t), 0.75 (s, 3H). LCMS: Rt=2.51 min. m/z=498.3 [M+H]$^+$.

Assay Methods

Compounds provided herein can be evaluated using various in vitro and in vivo assays; examples of which are described below.

Steroid Inhibition of TBPS Binding

TBPS binding assays using rat brain cortical membranes in the presence of 5 μM GABA has been described (Gee et al, J. Pharmacol. Exp. Ther. 1987, 241, 346-353; Hawkinson et al, Mol. Pharmacol. 1994, 46, 977-985; Lewin, A. H et al., Mol. Pharmacol. 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na-K phosphate pH 7.4 buffer and centrifuged at 10,000×g for 10 min at 4° C. This washing procedure is repeated twice and the pellets are resuspended in 10 volumes of buffer. Aliquots (100 μL) of the membrane suspensions are incubated with 3 nM [$^{35}$S]-TBPS and 5 μL aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (Imax) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures.

Patch Clamp Electrophysiology of Recombinant α$_1$β$_2$γ$_2$ and α$_4$β$_3$δ GABA$_A$ Receptors Cellular electrophysiology is used to measure the pharmacological properties of our GABA$_A$ receptor modulators in heterologous cell systems. Each compound is tested for its ability to affect GABA mediated currents at a submaximal agonist dose (GABA EC$_{20}$=2 μM). LTK cells are stably transfected with the α$_1$β$_2$γ$_2$ subunits of the GABA receptor and CHO cells are transiently transfected with the α$_4$β$_3$δ subunits via the Lipofecatamine method. Cells were passaged at a confluence of about 50-80% and then seeded onto 35 mm sterile culture dishes containing 2 ml culture complete medium without antibiotics or antimycotics. Confluent clusters of cells are electrically coupled (Pritchett et al., 1988). Because responses in distant cells are not adequately voltage clamped and because of uncertainties about the extent of coupling (Verdoorn et al., 1990), cells were cultivated at a density that enables the recording of single cells (without visible connections to other cells).

Whole cell currents were measured with HEKA EPC-10 amplifiers using PatchMaster software or by using the high throughput QPatch platform (Sophion). Bath solution for all experiments contained (in mM): NaCl 137 mM, KCl 4 mM, $CaCl_2$ 1.8 mM, $MgCl_2$ 1 mM, HEPES 10 mM, D-Glucose 10 mM, pH (NaOH) 7.4. In some cases 0.005% cremophor was also added. Intracellular (pipette) solution contained: KCl 130 mM, $MgCl_2$ 1 mM, Mg-ATP 5 mM, HEPES 10 mM, EGTA 5 mM, pH 7.2. During experiments, cells and solutions were maintained at room temperature (19° C.-30° C.). For manual patch clamp recordings, cell culture dishes were placed on the dish holder of the microscope and continuously perfused (1 ml/min) with bath solution. After formation of a Gigaohm seal between the patch electrodes and the cell (pipette resistance range: 2.5 MΩ-6.0 MΩ; seal resistance range: >1 GΩ) the cell membrane across the pipette tip was ruptured to assure electrical access to the cell interior (whole-cell patch-configuration). For experiments using the QPatch system, cells were transferred as suspension to the QPatch system in the bath solution and automated whole cell recordings were performed.

Cells were voltage clamped at a holding potential of −80 mV. For the analysis of test articles, GABA receptors were stimulated by 2 μM GABA after sequential pre-incubation of increasing concentrations of the test article. Pre-incubation duration was 30 s and the duration of the GABA stimulus was 2 s. Test articles were dissolved in DMSO to form stock solutions (10 mM). Test articles were diluted to 0.01, 0.1, 1, and 10 μM in bath solution. All concentrations of test articles were tested on each cell. The relative percentage potentiation was defined as the peak amplitude in response to GABA $EC_{20}$ in the presence of the test article divided by the peak amplitude in response to GABA $EC_{20}$ alone, multiplied by 100.

TABLE 1

TBPS binding evaluation of the exemplary compounds

| Entry | Compound | TBPS IC50 (nM) |
|---|---|---|
| 1. | SA-1 | B |
| 2. | SA-2 | A |
| 3. | SA-4 | A |
| 4. | SA-3 | B |
| 5. | SA-7 | B |
| 6. | SA-8 | B |
| 7. | SA-6 | B |
| 8. | SA-5 | B |
| 9. | SA-16 | B |
| 10. | SA-17 | B |
| 11. | SA-18 | B |
| 12. | SA-19 | B |
| 13. | SA-21 | B |
| 14. | SA-23 | B |
| 15. | SA-11 | A |
| 16. | SA-12 | B |
| 17. | SA-20 | B |
| 18. | SA-22 | B |
| 19. | SA-13 | B |
| 20. | SA-14 | A |
| 21. | SA-15 | A |
| 22. | SA-10 | B |
| 23. | SA-54 | B |
| 24. | SA-40 | B |
| 25. | SA-39 | A |
| 26. | SB-49 | B |
| 27. | SB-50 | B |
| 28. | SA-55 | A |
| 29. | SA-83 | C |

TABLE 1-continued

TBPS binding evaluation of the exemplary compounds

| Entry | Compound | TBPS IC50 (nM) |
|---|---|---|
| 30. | SA-84 | C |
| 31. | SA-56 | B |
| 32. | SA-57 | A |
| 33. | SA-58 | A |
| 34. | SB-1 | C |
| 35. | SB-2 | C |
| 36. | SB-12 | D |
| 37. | SB-13 | C |
| 38. | SB-14 | E |
| 39. | SB-15 | B |
| 40. | SA-91 | D |
| 41. | SB-17 | E |
| 42. | SB-45 | B |
| 43. | SB-46 | C |
| 44. | SB-53 | E |
| 45. | SB-56 | E |
| 46. | SB-35 | E |
| 47. | SA-31 | E |
| 48. | SA-100 | D |
| 49. | SG-21 | D |
| 50. | SG-23 | D |
| 51. | SB-26 | E |
| 52. | SA-70 | C |
| 53. | SA-71 | C |
| 54. | SG-25 | E |
| 55. | SB-41 | E |
| 56. | SB-39 | D |
| 57. | SA-102 | E |
| 58. | SA-103 | E |
| 59. | SA-120 | E |
| 60. | SA-121 | E |
| 61. | SB-60 | E |
| 62. | SB-37 | E |
| 63. | SB-38 | E |
| 64. | SA-53 | B |
| 65. | SA-87 | D |
| 66. | SA-88 | D |
| 67. | SB-40 | D |
| 68. | SA-126 | D |
| 69. | SA-127 | D |
| 70. | SA-128 | C |
| 71. | SA-107 | E |
| 72. | SA-108 | E |
| 73. | SA-105 | B |
| 74. | SA-106 | D |

For Table 1, "A" indicates an $IC_{50}$<10 nM, "B" indicates an $IC_{50}$ of 10 nM to 50 nM, "C" indicates an $IC_{50}$ of 50 nM to 100 nM, "D" indicates an $IC_{50}$ of 100 nM to 500 nM, and "E" indicates $IC_{50}$>500 nM.

TABLE 2

Biochemical evaluation of the exemplary compounds over GABA alpha-1.

| Entry | Compound | GABAa alpha1 (α1β2γ2)$EC_{50}$ (nM) | GABAa alpha1 (α1β2γ2) Emax (%) |
|---|---|---|---|
| 1. | SA-1 | C | b |
| 2. | SA-2 | C | a |
| 3. | SA-4 | D | b |
| 4. | SA-3 | D | b |
| 5. | SA-8 | D | a |
| 6. | SA-6 | E | b |
| 7. | SA-5 | D | b |
| 8. | SA-18 | E | b |
| 9. | SA-19 | E | b |

The biochemical evaluation of the exemplary compounds over GABA alpha-1 are shown in Table 2. For Table 2, column "GABAa alpha1 (α1β2γ2)EC50 (nM)": "A" indicates an EC50<100 nM, "B" indicates an EC50 of 100 nM to less than or equal to 500 nM, "C" indicates an EC50 of >500 nM to less than or equal to 1000 nM, "D" indicates an EC50 of >1000 nM to less than or equal to 2000 nM, and "E" indicates EC50>2000 nM. Column "GABAa alpha1 ($\alpha1\beta2\gamma2$)Emax (%)": "a" indicates Emax of 0-500%; "b" indicates Emax of 500-1000%; "c" indicates Emax of >1000%.

TABLE 3

Biochemical evaluation of the exemplary compounds over GABA alpha-1.

| Entry | | $\alpha1\beta2\gamma2$ GABA Qpatch in Ltk (Efficacy at 10 μm) | $\alpha4\beta3\delta$ GABA Manual Patch in CHO (Efficacy at 10 μM) |
|---|---|---|---|
| 1. | SA-1 | C | D |
| 2. | SA-2 | B | C |
| 3. | SA-4 | C | B |
| 4. | SA-3 | C | D |
| 5. | SA-7 | B | B |
| 6. | SA-8 | B | D |
| 7. | SA-6 | C | B |
| 8. | SA-5 | C | D |
| 9. | SA-16 | C | B |
| 10. | SA-17 | B | D |
| 11. | SA-18 | C | C |
| 12. | SA-19 | B | D |
| 13. | SA-9 | B | D |
| 14. | SA-20 | C | C |
| 15. | SA-21 | B | D |
| 16. | SA-22 | C | B |
| 17. | SA-23 | C | D |
| 18. | SA-11 | C | B |
| 19. | SA-12 | B | D |
| 20. | SA-13 | C | D |
| 21. | SA-14 | C | B |
| 22. | SA-15 | C | D |
| 23. | SA-10 | C | D |
| 24. | SA-54 | C | D |
| 25. | SA-40 | B | D |
| 26. | SA-39 | B | D |
| 27. | SA-41 | C | B |
| 28. | SB-49 | B | D |
| 29. | SB-50 | A | B |
| 30. | SA-55 | B | D |
| 31. | SA-83 | B | B |
| 32. | SA-84 | B | D |
| 33. | SA-56 | B | D |
| 34. | SA-57 | C | B |
| 35. | SA-58 | C | D |
| 36. | SB-1 | B | D |
| 37. | SB-2 | C | D |
| 38. | SB-12 | B | D |
| 39. | SB-13 | B | D |
| 40. | SB-14 | A | D |
| 41. | SB-15 | B | B |
| 42. | SB-4 | C | C |
| 43. | SB-5 | B | D |
| 44. | SA-42 | B | D |
| 45. | SA-43 | B | D |
| 46. | SA-44 | B | B |
| 47. | SA-45 | C | D |
| 48. | SA-46 | C | D |
| 49. | SA-79 | C | D |
| 50. | SA-80 | C | C |
| 51. | SA-90 | A | D |
| 52. | SA-92 | B | D |
| 53. | SB-16 | B | D |
| 54. | SB-17 | A | D |
| 55. | SB-43 | B | D |
| 56. | SB-44 | C | D |
| 57. | SA-82 | C | B |
| 58. | SA-81 | C | D |
| 59. | SA-115 | C | D |
| 60. | SA-116 | C | D |
| 61. | SA-117 | C | D |
| 62. | SB-7 | B | D |
| 63. | SB-8 | C | B |

TABLE 3-continued

Biochemical evaluation of the exemplary compounds over GABA alpha-1.

| Entry | | $\alpha1\beta2\gamma2$ GABA Qpatch in Ltk (Efficacy at 10 μm) | $\alpha4\beta3\delta$ GABA Manual Patch in CHO (Efficacy at 10 μM) |
|---|---|---|---|
| 64. | SA-47 | C | D |
| 65. | SA-48 | C | D |
| 66. | SA-49 | C | C |
| 67. | SA-93 | C | D |
| 68. | SA-94 | B | D |
| 69. | SA-37 | C | D |
| 70. | SA-38 | C | D |
| 71. | SB-9 | C | B |
| 72. | SB-10 | B | D |
| 73. | SB-45 | B | B |
| 74. | SB-46 | B | D |
| 75. | SB-52 | B | D |
| 76. | SB-53 | A | D |
| 77. | SB-47 | C | D |
| 78. | SB-48 | C | D |
| 79. | SB-29 | B | D |
| 80. | SB-30 | B | D |
| 81. | SA-110 | C | D |
| 82. | SA-111 | C | D |
| 83. | SB-32 | B | D |
| 84. | SB-34 | C | D |
| 85. | SB-36 | B | D |
| 86. | SB-54 | B | D |
| 87. | SB-56 | A | D |
| 88. | SB-55 | A | D |
| 89. | SB-35 | A | D |
| 90. | SB-18 | C | D |
| 91. | SB-19 | B | D |
| 92. | SA-118 | C | D |
| 93. | SA-119 | C | D |
| 94. | SA-112 | B | D |
| 95. | SA-113 | B | D |
| 96. | SA-114 | C | D |
| 97. | SA-58 | B | D |
| 98. | SA-96 | B | D |
| 99. | SA-97 | C | D |
| 100. | SA-123 | B | D |
| 101. | SA-124 | B | D |
| 102. | SA-125 | C | B |
| 103. | SA-24 | B | B |
| 104. | SA-25 | C | D |
| 105. | SA-26 | C | B |
| 106. | SA-27 | C | D |
| 107. | SB-57 | B | D |
| 108. | SA-28 | B | B |
| 109. | SA-29 | B | D |
| 110. | SA-30 | C | C |
| 111. | SA-99 | C | D |
| 112. | SA-85 | C | D |
| 113. | SA-86 | B | D |
| 114. | SA-62 | B | D |
| 115. | SA-61 | B | D |
| 116. | SA-63 | B | B |
| 117. | SA-32 | C | C |
| 118. | SA-33 | B | D |
| 119. | SG-21 | A | D |
| 120. | SB-59 | B | D |
| 121. | SG-20 | B | B |
| 122. | SA-35 | B | C |
| 123. | SA-36 | C | D |
| 124. | SA-73 | B | D |
| 125. | SA-74 | B | D |
| 126. | SA-75 | B | D |
| 127. | SG-22 | B | D |
| 128. | SG-23 | A | D |
| 129. | SB-26 | A | D |
| 130. | SA-76 | C | D |
| 131. | SA-77 | C | D |
| 132. | SA-78 | B | B |
| 133. | SA-64 | B | D |
| 134. | SA-65 | C | D |
| 135. | SA-66 | C | C |
| 136. | SA-67 | C | D |
| 137. | SA-69 | B | B |

TABLE 3-continued

Biochemical evaluation of the exemplary compounds over GABA alpha-1.

| Entry | | α1β2γ2 GABA Qpatch in Ltk (Efficacy at 10 μm) | α4β3δ GABA Manual Patch in CHO (Efficacy at 10 μM) |
|---|---|---|---|
| 138. | SB-11 | B | D |
| 139. | SG-24 | B | D |
| 140. | SA-72 | C | D |
| 141. | SB-41 | A | D |
| 142. | SB-39 | A | D |
| 143. | SA-51 | C | D |
| 144. | SA-104 | B | D |
| 145. | SA-122 | B | D |
| 146. | SB-60 | A | D |
| 147. | SA-89 | B | D |
| 148. | SA-105 | C | D |

For Table 3: The biochemical evaluation of the exemplary compounds over GABA alpha-1 and alpha 4 are shown in Table 3. For Table 3. GABAA receptors α1β2γ2 and α4β3δ % efficacy measured at 10 μM of compound: "A" indicates an efficacy value of 10-100%, "B" indicates an efficacy value of >100-500%, "C" indicates an efficacy value of >500%; "D" indicates data not determined or not available.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method of treating a sleep disorder or a mood disorder in a human subject in need thereof, comprising administering to the human subject a therapeutically effective amount of (a) a compound of Formula (I) or a pharmaceutically acceptable salt thereof or (b) a pharmaceutical composition comprising a compound of Formula (I) or a pharmaceutically acceptable salt thereof, and a pharmaceutically acceptable excipient:

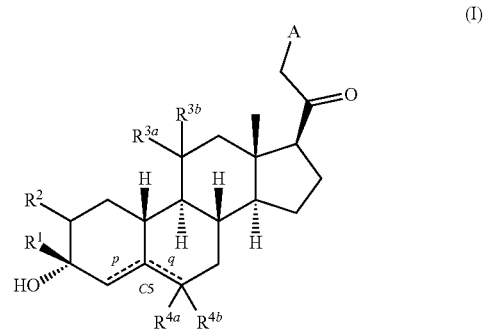

wherein:
===== represents a single or double bond as valency permits;
A is of Formula (A-1) or Formula (A-2):

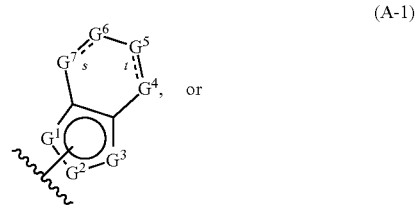

(A-2)

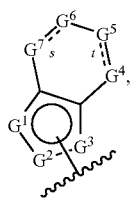

wherein the point of attachment is at $G^1$ or $G^2$ in Formula (A-1) and the point of attachment is at $G^2$ or $G^3$ in Formula (A-2);

$G^1$ is N, $NR^{N1}$, O, S, C, or C—$R^{G1}$ as valency permits;

$G^2$ is N, $NR^{N2}$, O, S, C, —C=N—, or C—$R^{G2}$ as valency permits;

$G^3$ is N, $NR^{N3}$, O, S, C, or C—$R^{G3}$ as valency permits;

$G^4$ is N, $NR^{N4}$, C—$R^{G4}$, or C—$(R^{G4})_2$ as valency permits;

$G^5$ is N, $NR^{N5}$, C—$R^{G5}$, or C—$(R^{G5})_2$ as valency permits;

$G^6$ is N, $NR^{N6}$, C—$R^{G6}$, or C—$(R^{G6})_2$ as valency permits;

$G^7$ is N, $NR^{N7}$, C—$R^{G7}$, or C—$(R^{G7})_2$ as valency permits;

each instance of $R^{G1}$, $R^{G2}$, $R^{G3}$, $R^{G4}$, $R^{G5}$, $R^{G6}$, and $R^{G7}$ is, independently, hydrogen, halogen, —$NO_2$, —CN, —$OR^{GA}$, —$N(R^{GA})_2$, —C(=O)$R^{GA}$, —C(=O)$OR^{GA}$, —OC(=O)$R^{GA}$, —OC(=O)$OR^{GA}$, —C(=O)N($R^{GA}$)$_2$, —N($R^{GA}$)C(=O)$R^{GA}$, —OC(=O)N($R^{GA}$)$_2$, —N($R^{GA}$)C(=O)$OR^{GA}$, —S(=O)$_2R^{GA}$, —S(=O)$_2OR^{GA}$, —OS(=O)$_2R^{GA}$, —S(=O)$_2$N($R^{GA}$)$_2$, —N($R^{GA}$)S(=O)$_2R^{GA}$, —S(=O)$R^{GA}$, —S(=O)$OR^{GA}$, —OS(=O)$R^{GA}$, —S(=O)N($R^{GA}$)$_2$, —N($R^{GA}$)S(=O)$R^{GA}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, or substituted or unsubstituted heteroaryl;

each instance of $R^{N1}$, $R^{N2}$, $R^{N3}$, $R^{N4}$, $R^{N5}$, $R^{N6}$, and $R^{N7}$ is independently hydrogen, substituted or unsubstituted $C_{1-6}$ alkyl, or a nitrogen protecting group;

each instance of $R^{GA}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3- to 6-membered heterocylyl, substituted or unsubstituted aryl, substituted or unsubstituted heteroaryl, an oxygen protecting group when attached to oxygen, a nitrogen protecting group when attached to nitrogen, or two $R^{GA}$ groups are taken with the intervening atoms to form a substituted or unsubstituted carbocyclic or heterocyclic ring;

$R^1$ is substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl;

$R^2$ is hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, or —$OR^{A2}$, wherein $R^{A2}$ is hydrogen or substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl; and $R^{3a}$ is hydrogen or —$OR^{A3}$, wherein $R^{A3}$ is hydrogen, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{3-6}$ carbocylyl, and $R^{3b}$ is hydrogen; or $R^{3a}$ and $R^{3b}$ are joined to form an oxo (=O) group;

each of $R^{4a}$ or $R^{4b}$ is independently hydrogen, substituted or unsubstituted $C_{1-6}$ alkyl, or halogen;

provided when bond p is a double bond, then bond q is a single bond, provided when bond q is a double bond, then bond p is a single bond and $R^{4b}$ is absent; and provided when both bonds p and q are single bonds, then the hydrogen at C5 is in the alpha or beta configuration.

2. The method of claim 1, wherein the compound is of Formula (II):

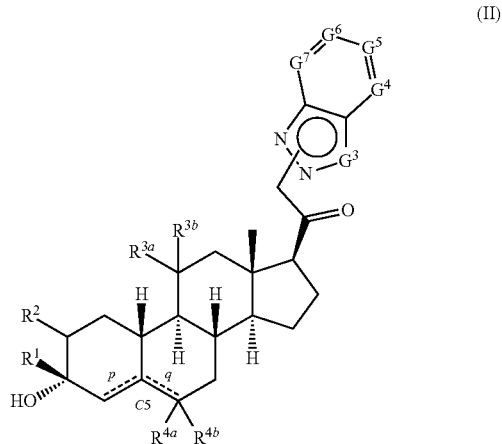

(II)

or a pharmaceutically acceptable salt thereof.

3. The method of claim 1, wherein the compound is of Formula (II-a):

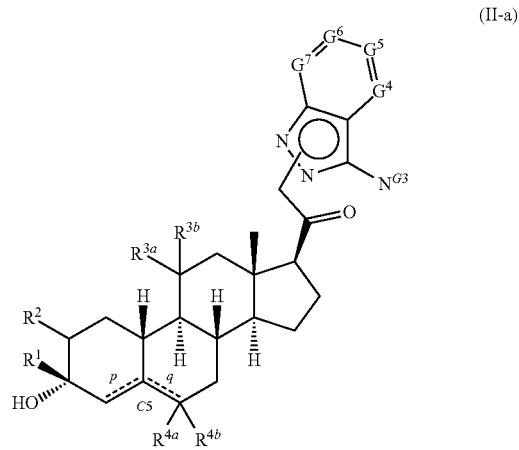

(II-a)

or a pharmaceutically acceptable salt thereof.

4. The method of claim 1, wherein the compound is one of the following formulae:

(II-a1)
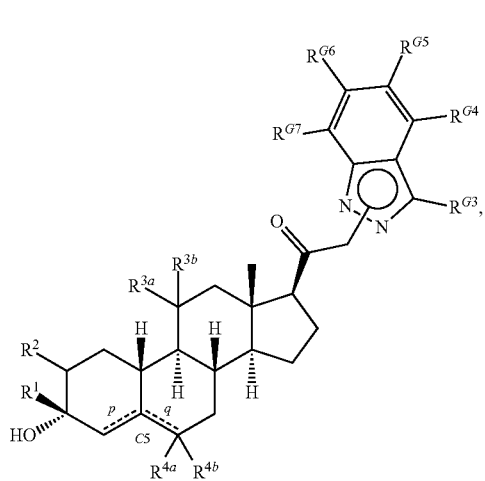
(II-a2)
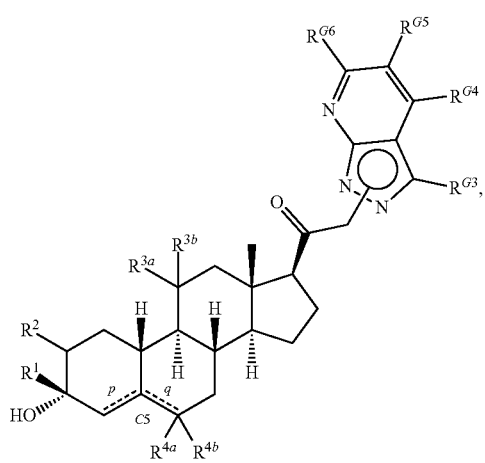
(II-a3)
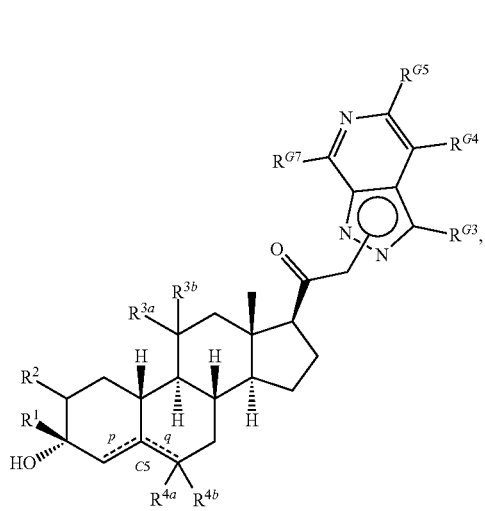
(II-a4)
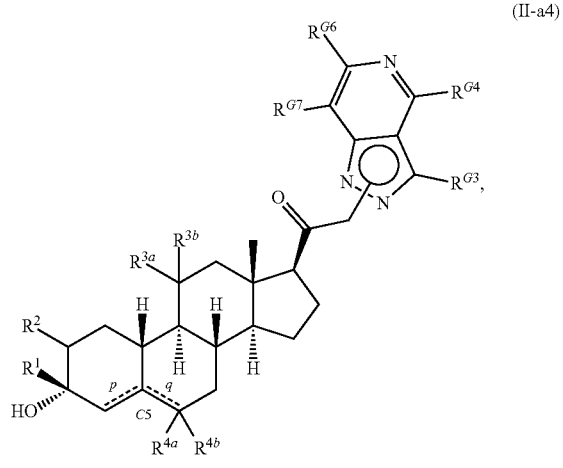
(II-a5)
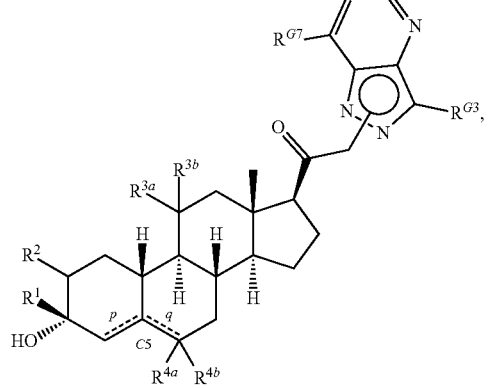
or a pharmaceutically acceptable salt thereof.
5. The method of claim 1, wherein the compound is of one of the following formulae:
(II-a1-i)
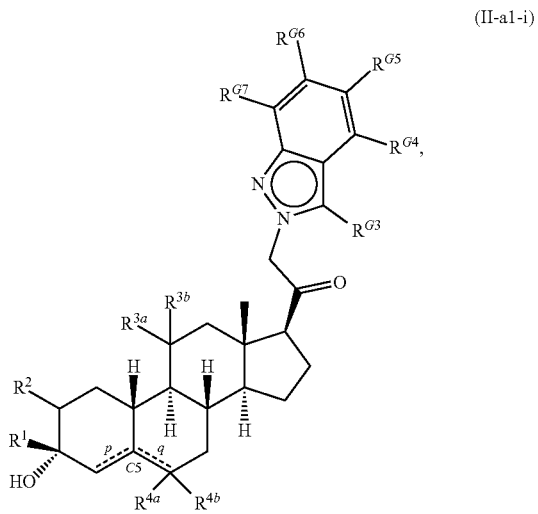

-continued
(II-a1-ii)
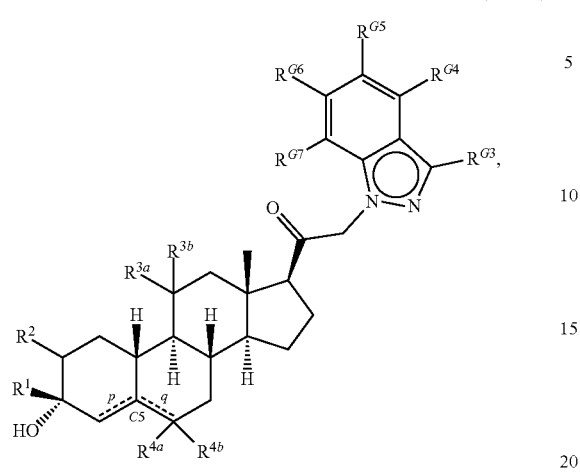
(II-a2-i)
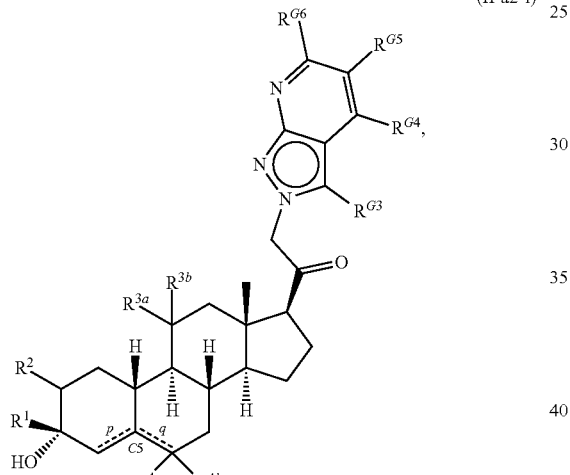
(II-a2-ii)
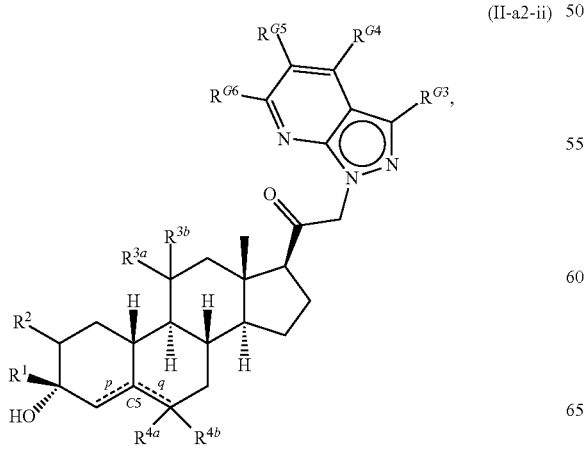
(II-a3-i)
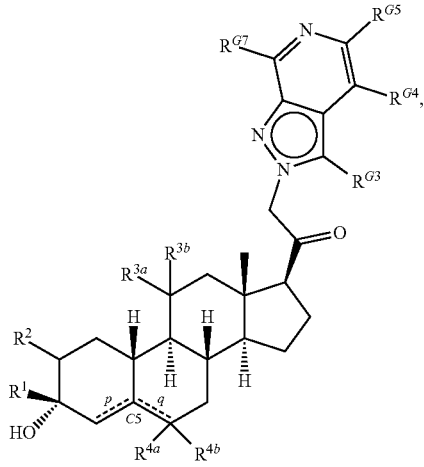
(II-a3-ii)
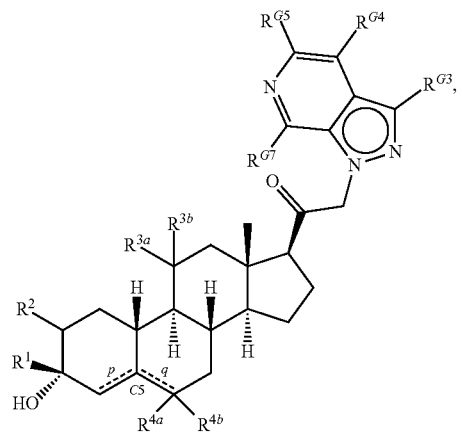
(II-a4-i)
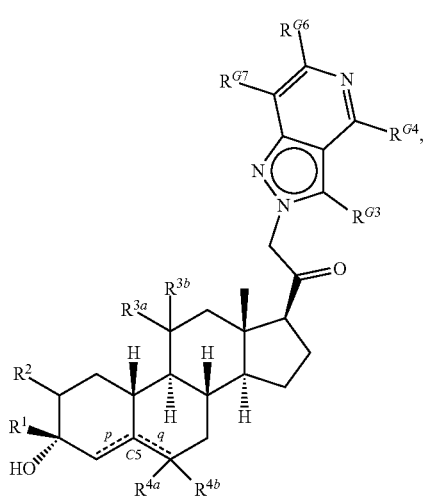

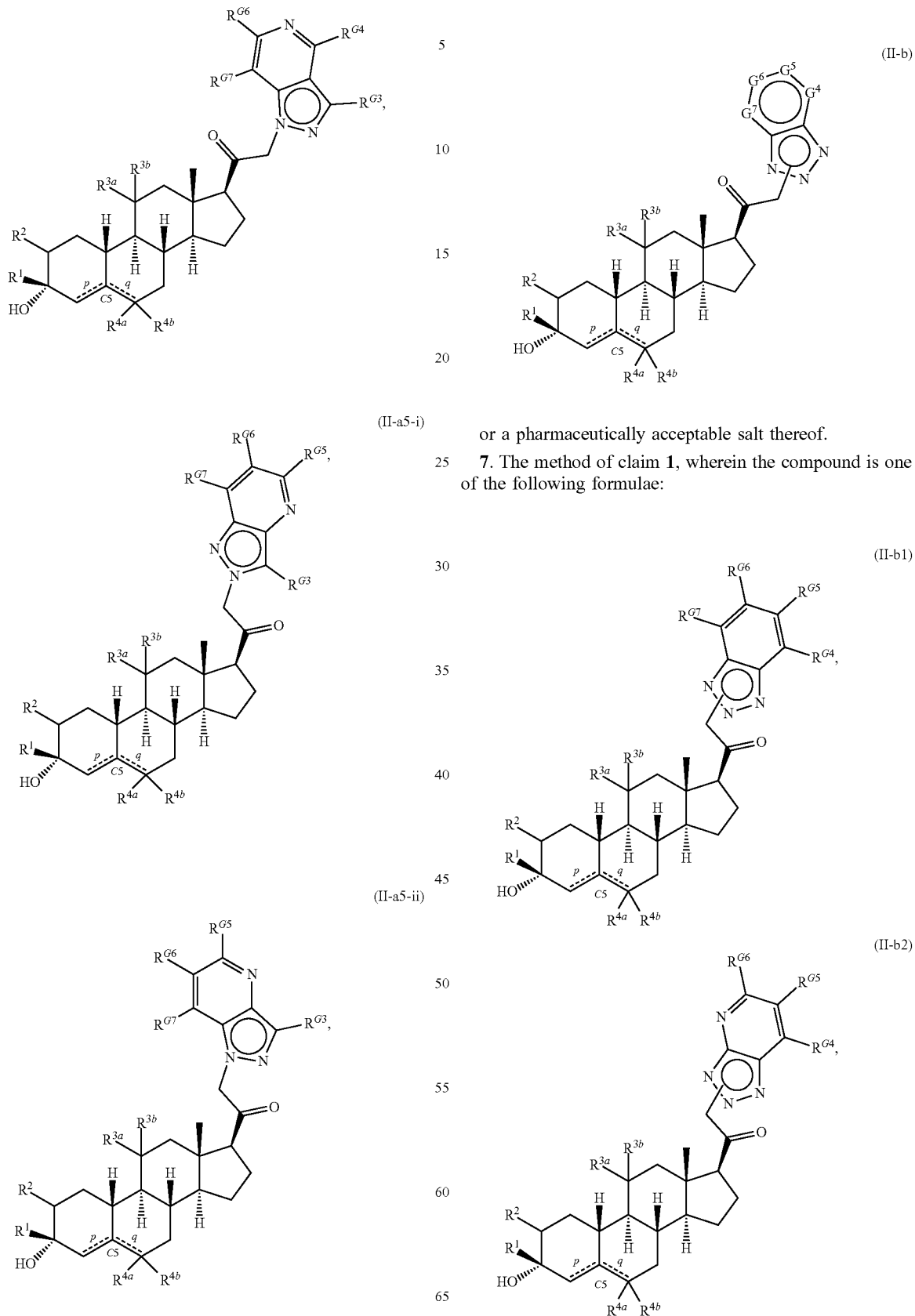
6. The method of claim 1, wherein the compound is of Formula (II-b):
or a pharmaceutically acceptable salt thereof.
7. The method of claim 1, wherein the compound is one of the following formulae:
or a pharmaceutically acceptable salt thereof.

-continued
(II-b3)
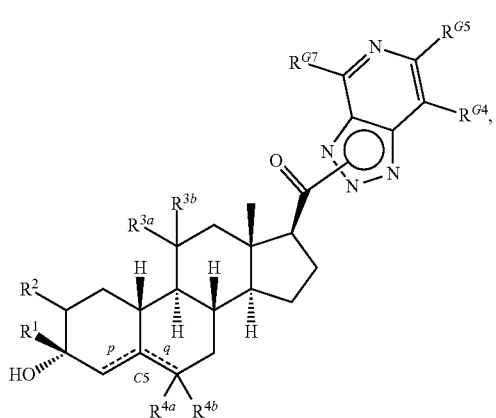
(II-b4)
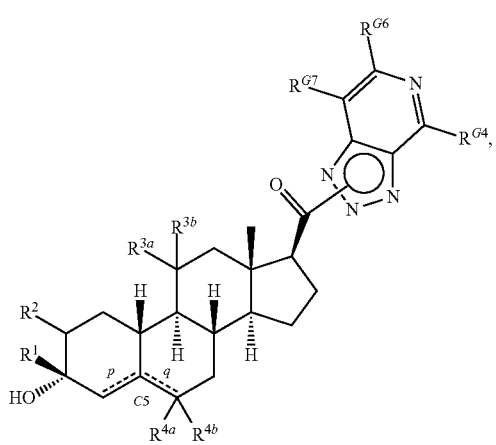
(II-b5)
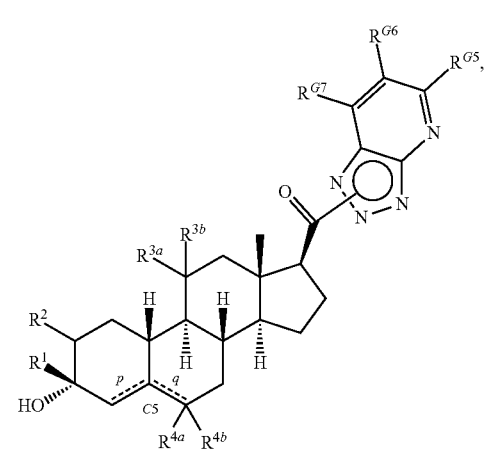
or a pharmaceutically acceptable salt thereof.
8. The method of claim 1, wherein the compound is one of the following formulae:
(II-b1-i)
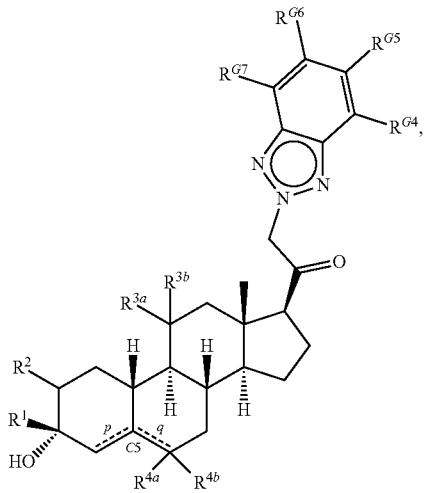
(II-b1-ii)
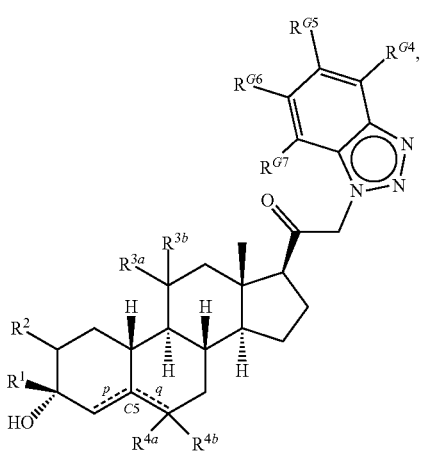
(II-b2-i)
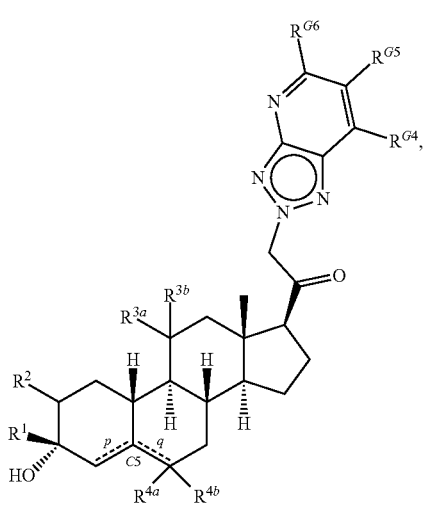

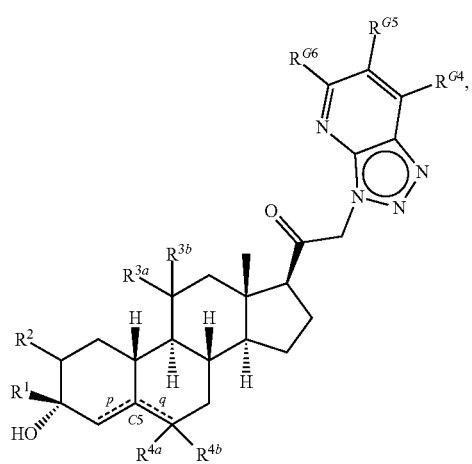
(II-b2-ii)
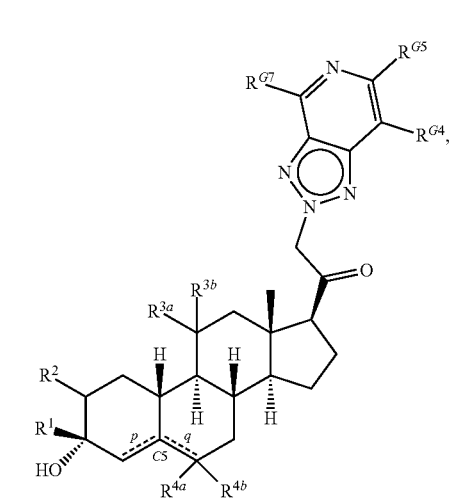
(II-b3-i)
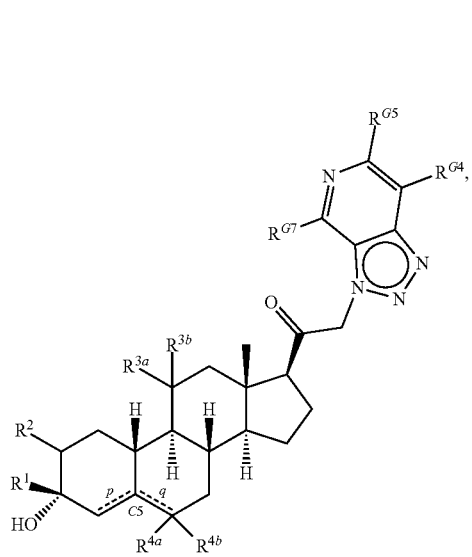
(II-b3-ii)
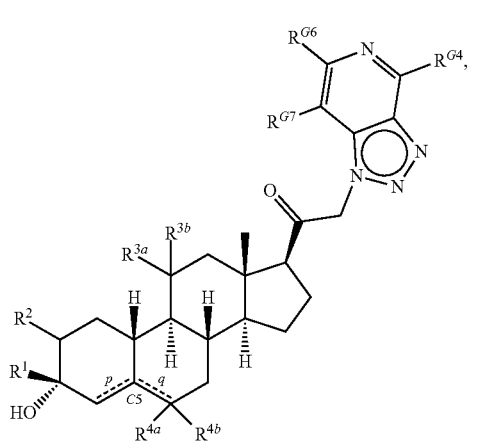
(II-b4-i)
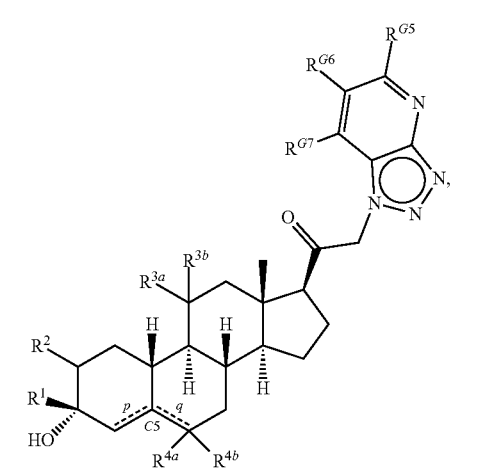
(II-b5-i)
or a pharmaceutically acceptable salt thereof.
9. The method of claim 1, wherein the compound is of Formula (III):
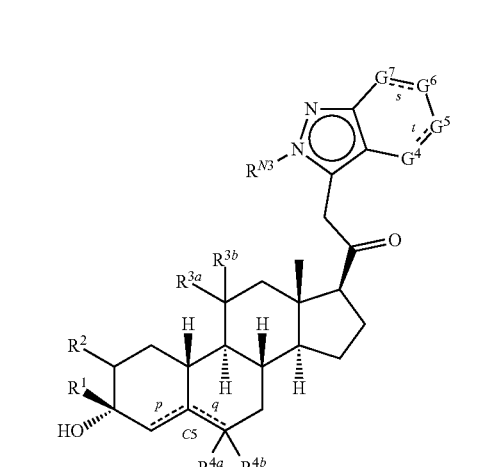
(III)
or a pharmaceutically acceptable salt thereof.
10. The method of claim 1, wherein the compound is of Formula (III-a):

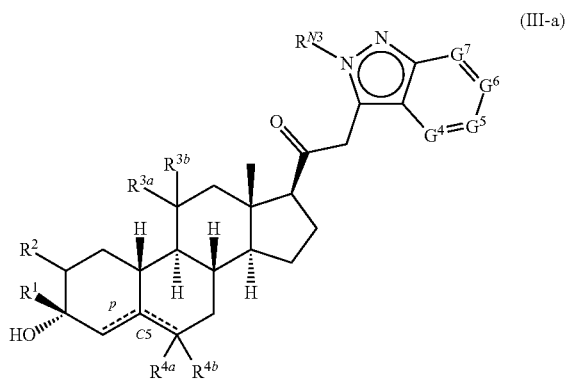

or a pharmaceutically acceptable salt thereof.

11. The method of claim 1, wherein the compound is of Formula (III-b):

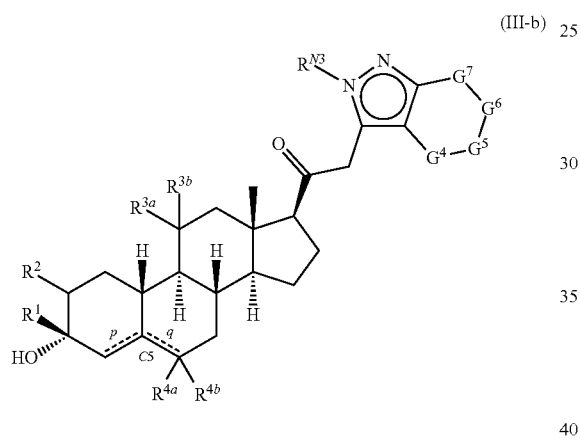

or a pharmaceutically acceptable salt thereof.

12. The method of claim 1, wherein the compound is of Formula (III-b1):

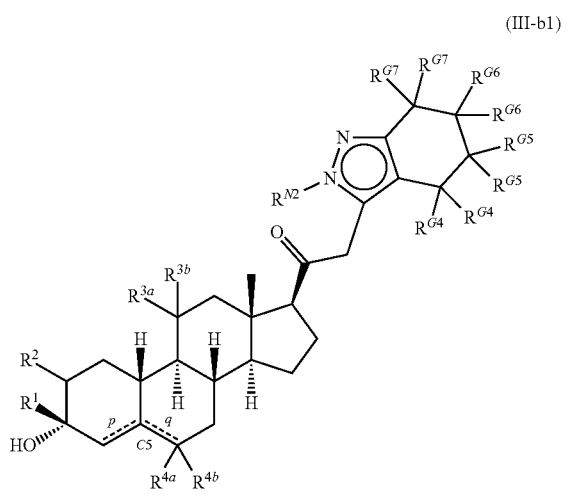

or a pharmaceutically acceptable salt thereof.

13. The method of claim 1, wherein the compound is of Formula (IV):

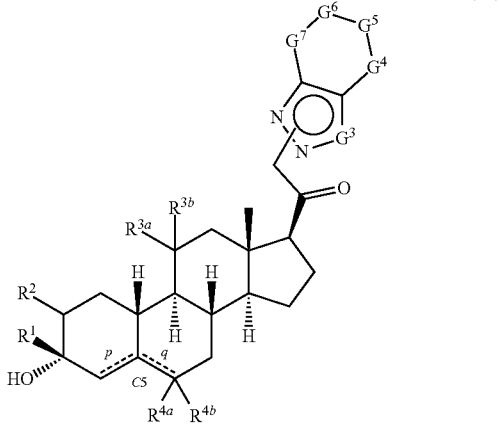

or a pharmaceutically acceptable salt thereof.

14. The method of claim 1, wherein the compound is of Formula (IV-a):

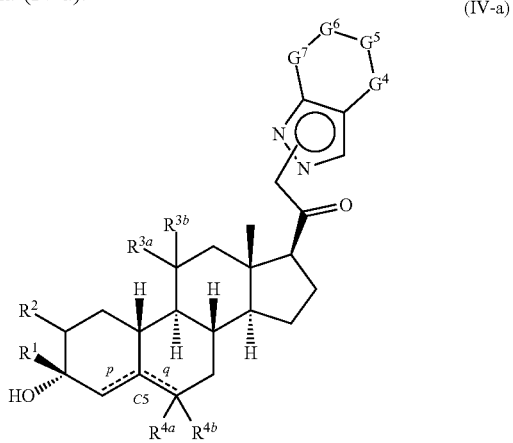

or a pharmaceutically acceptable salt thereof.

15. The method of claim 1, wherein the compound is of Formula (IV-a1):

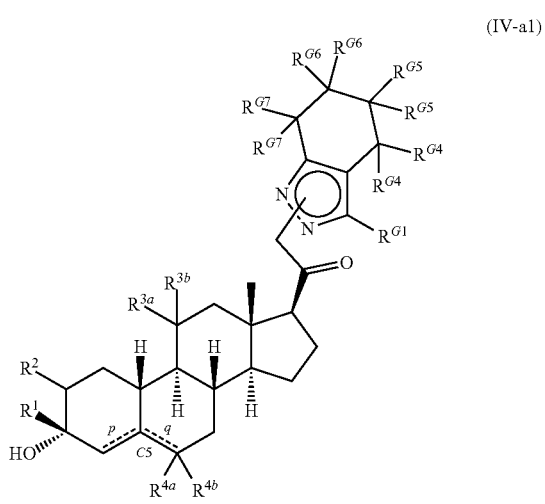

or a pharmaceutically acceptable salt thereof.

16. The method of claim 1, wherein the compound is of one of the following formulae:
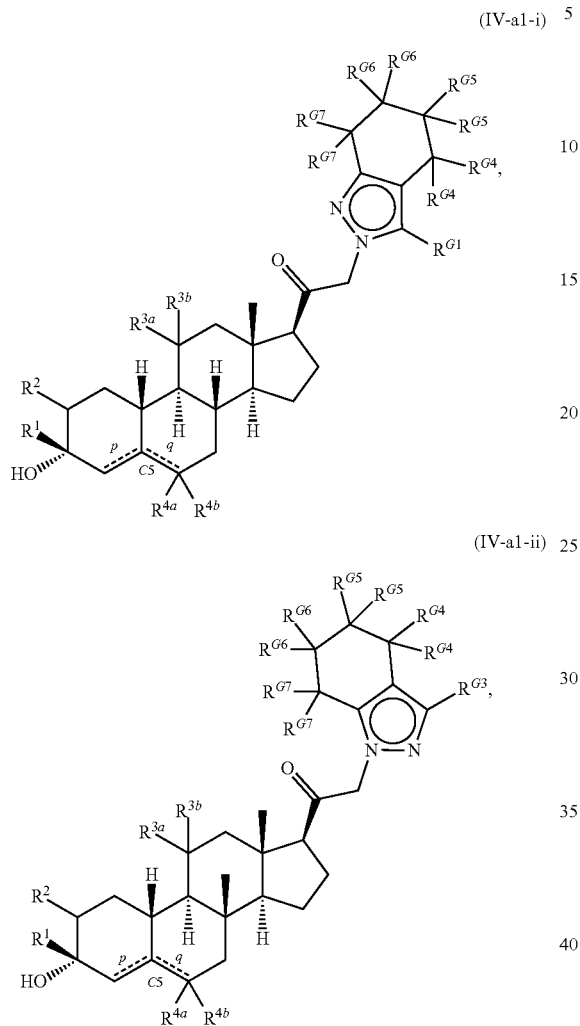
(IV-a1-i)
(IV-a1-ii)
or a pharmaceutically acceptable salt thereof.
17. The method of claim 1, wherein the compound is selected from the group consisting of:
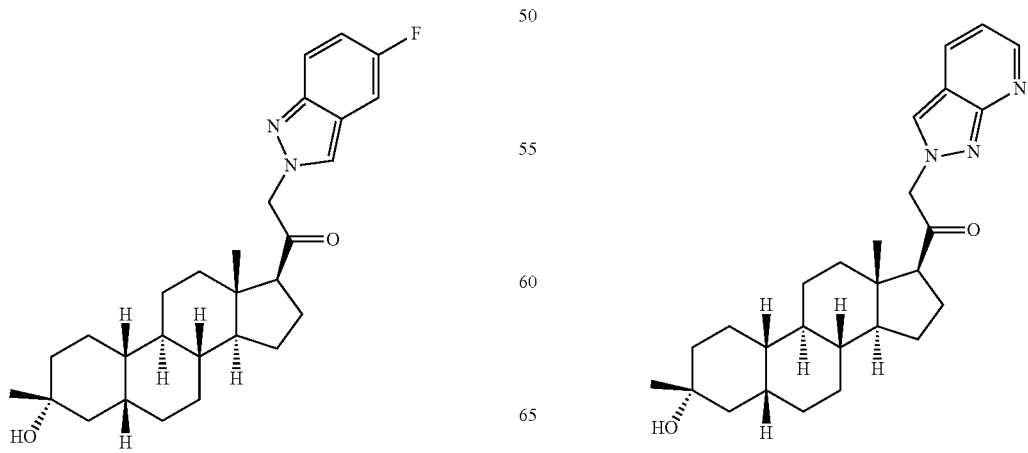
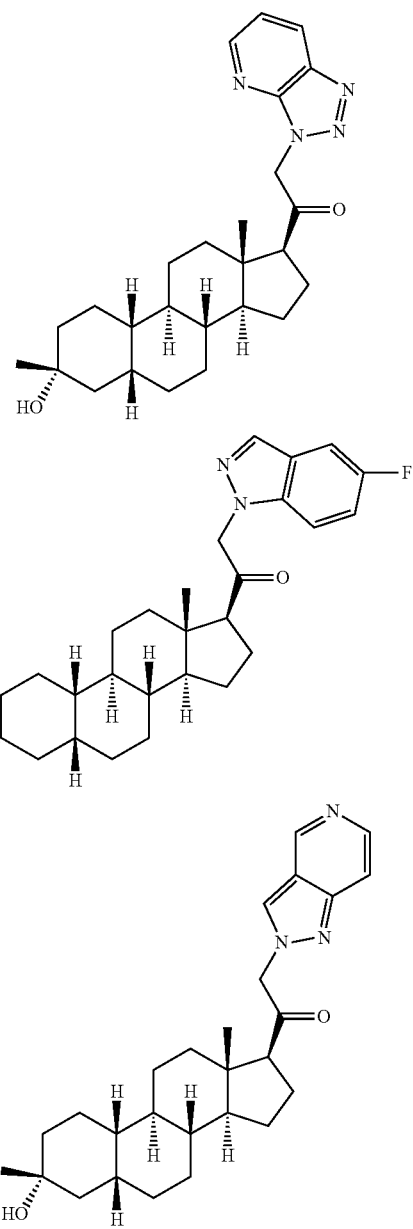

253
-continued
254
-continued
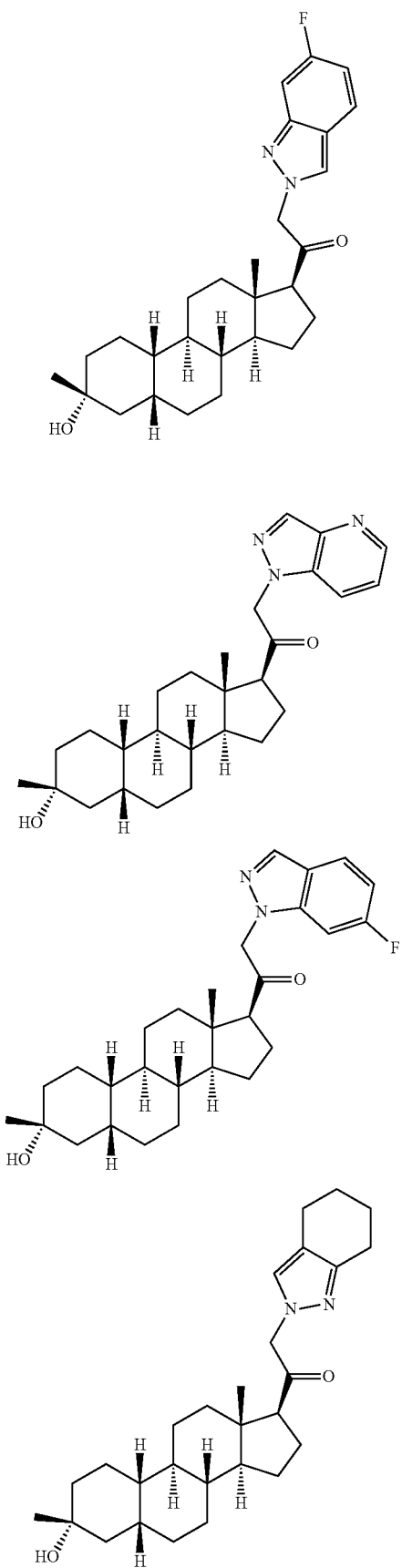
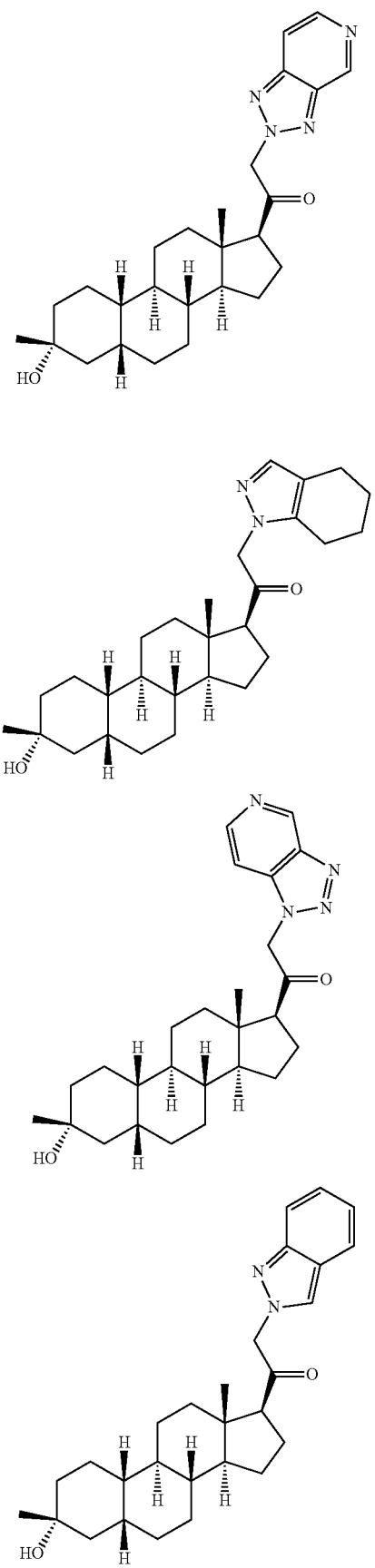

255
-continued
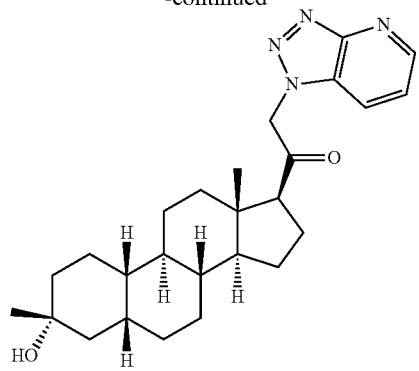
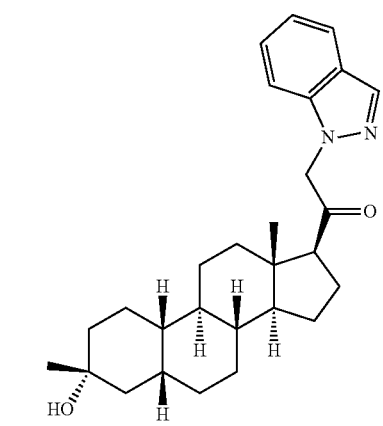
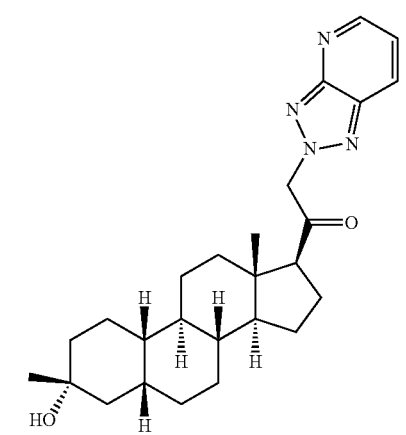
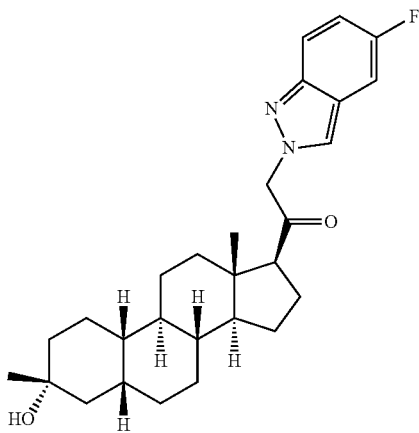
256
-continued
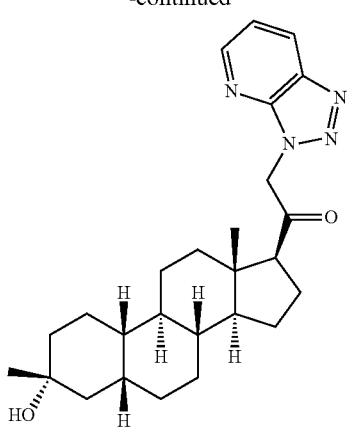
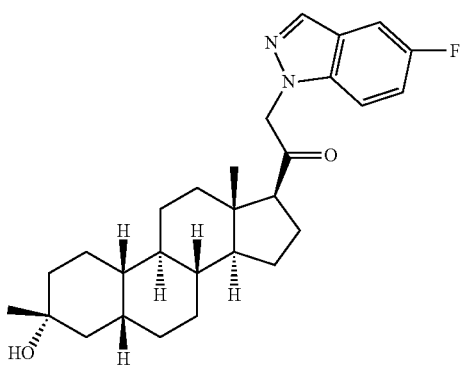
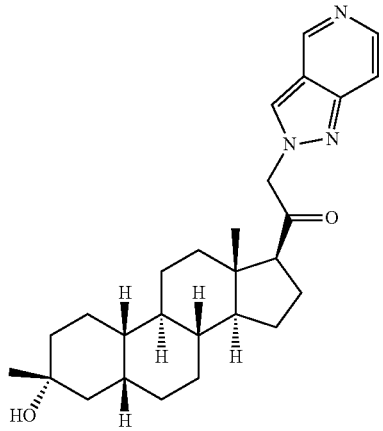
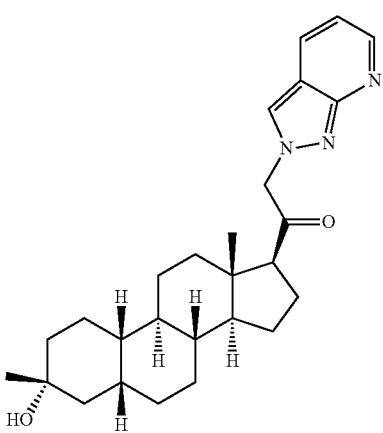

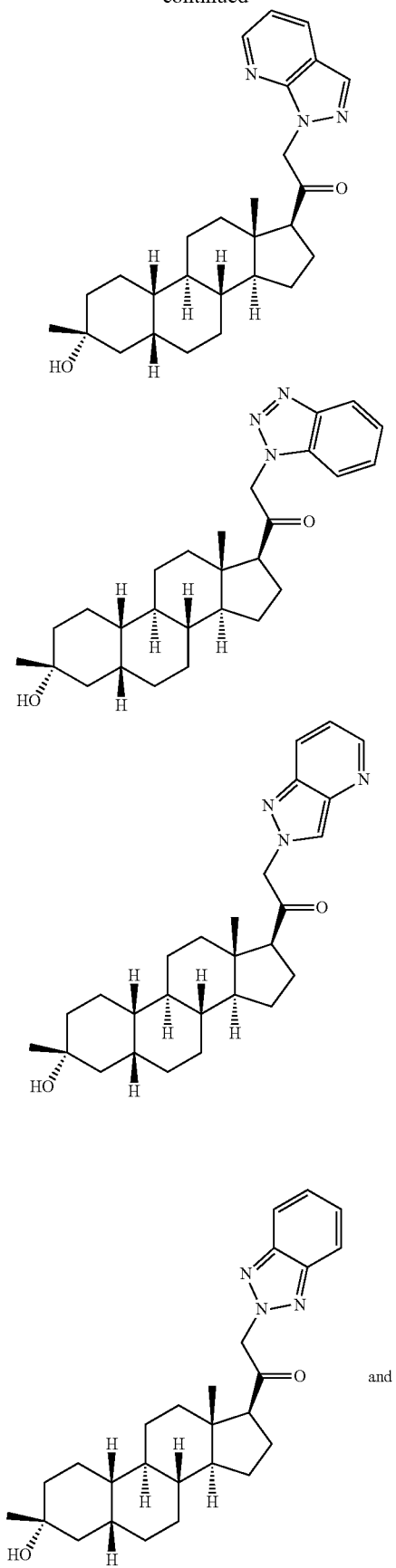
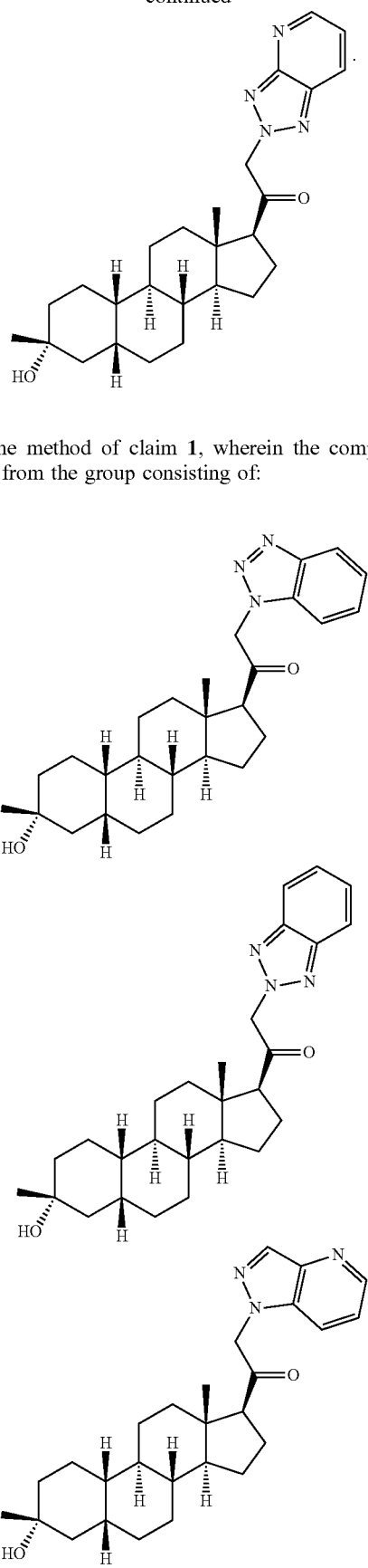
18. The method of claim 1, wherein the compound is selected from the group consisting of:
and 259
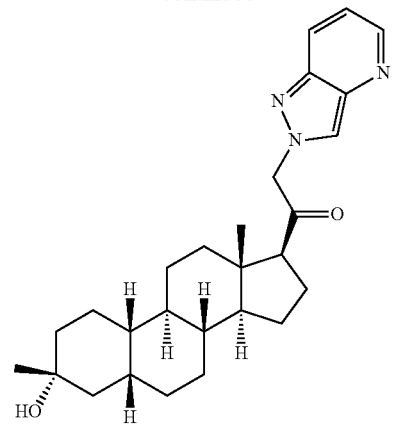
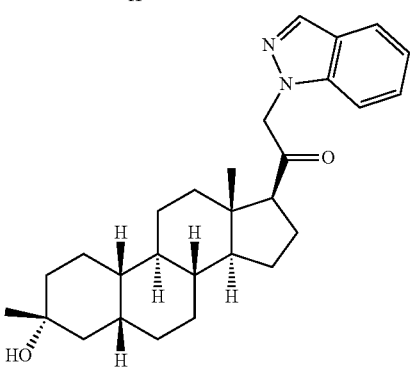
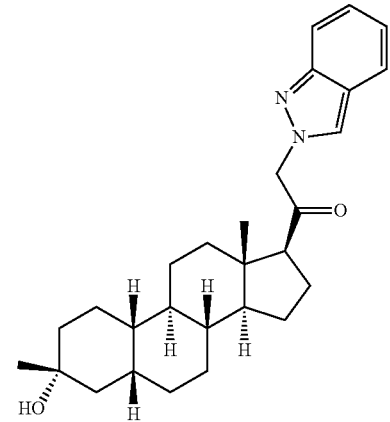
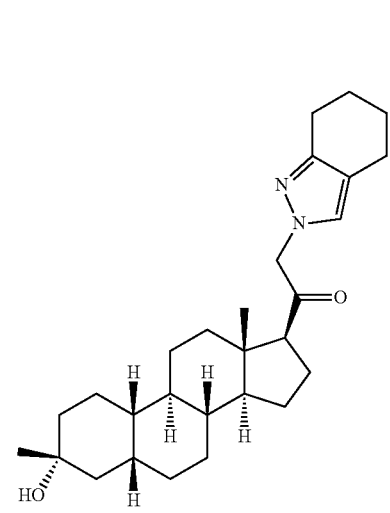
260
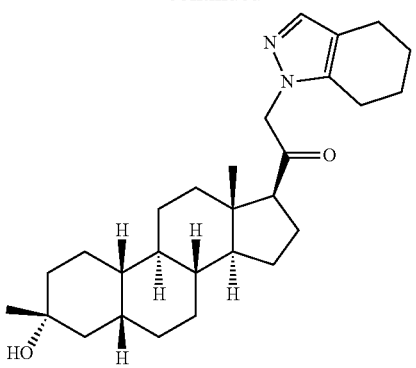
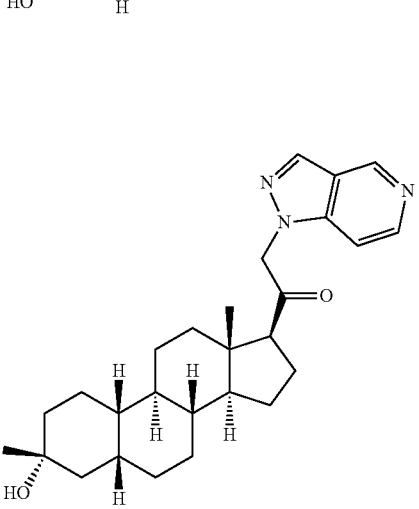
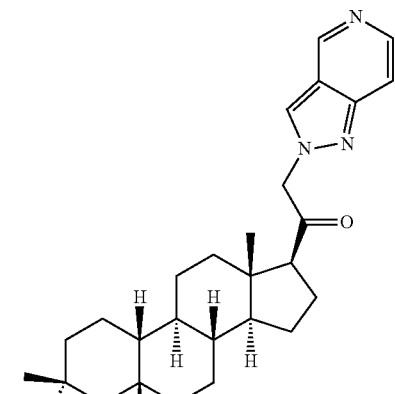
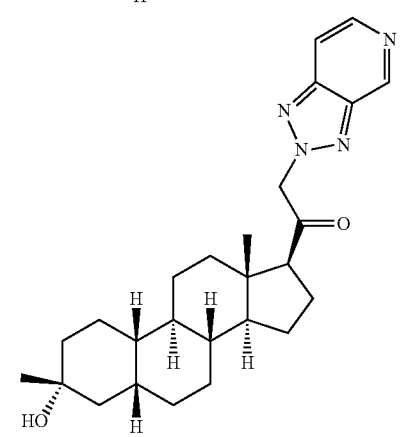

-continued
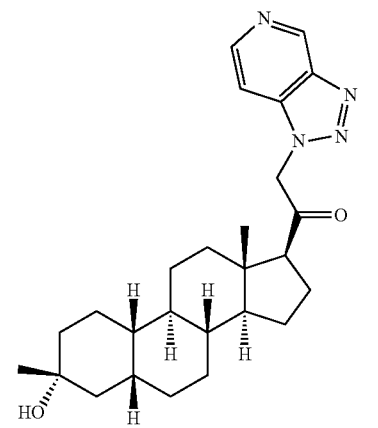
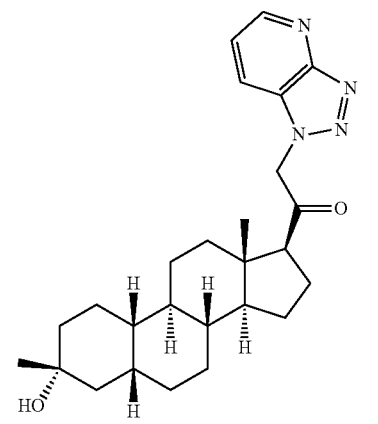
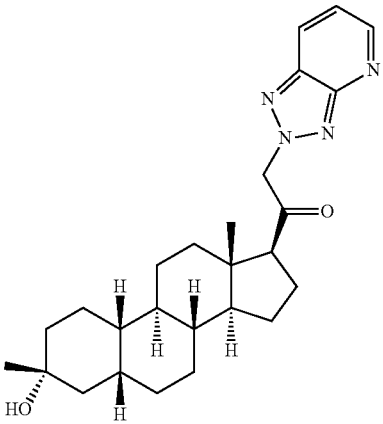
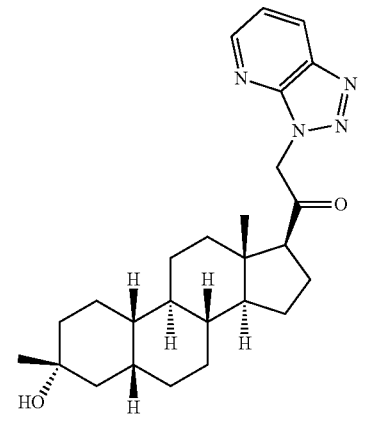
-continued
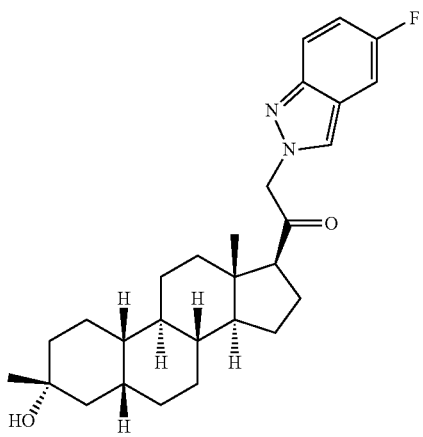
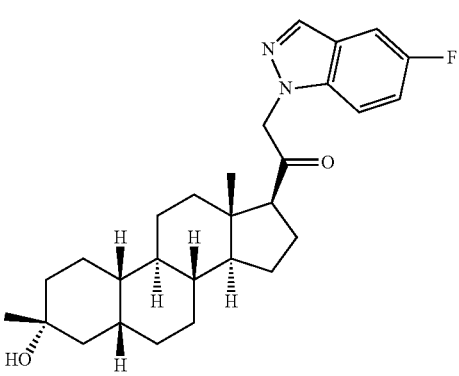
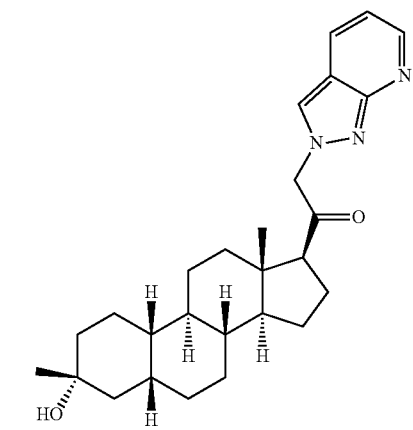
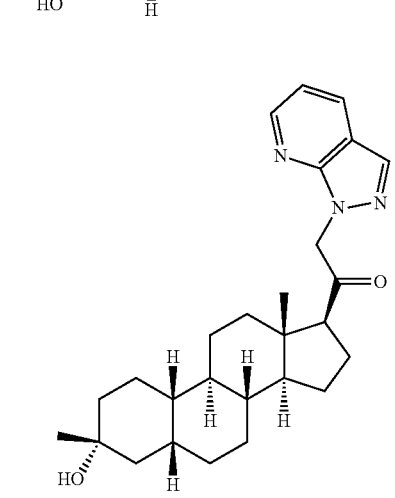

263
-continued
264
-continued
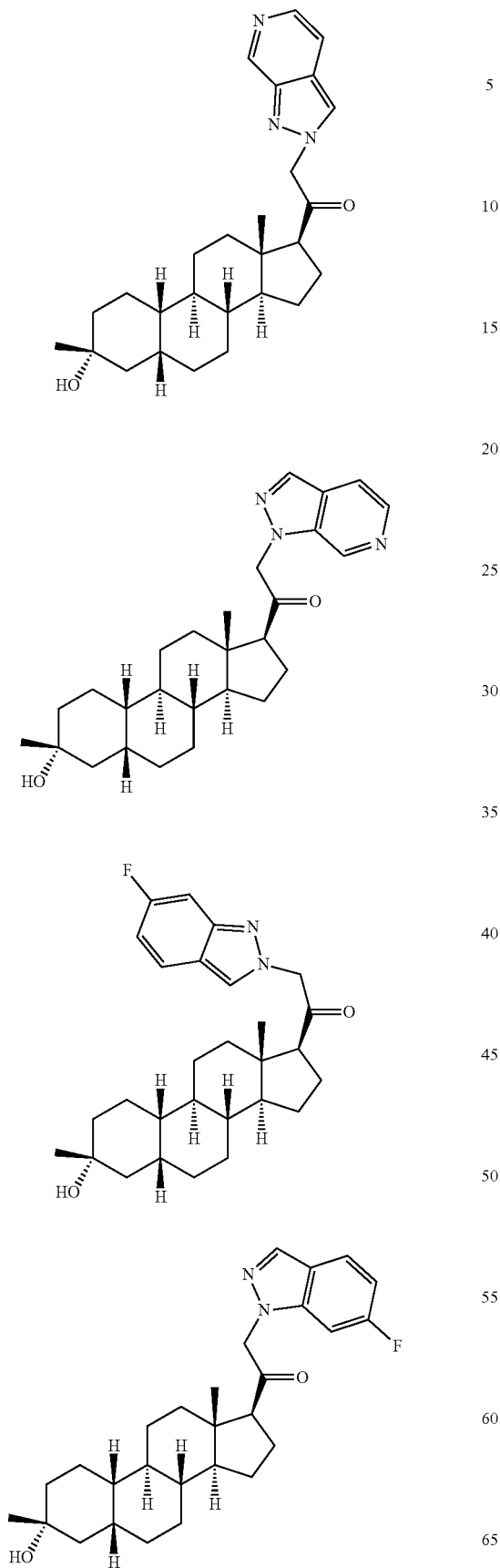
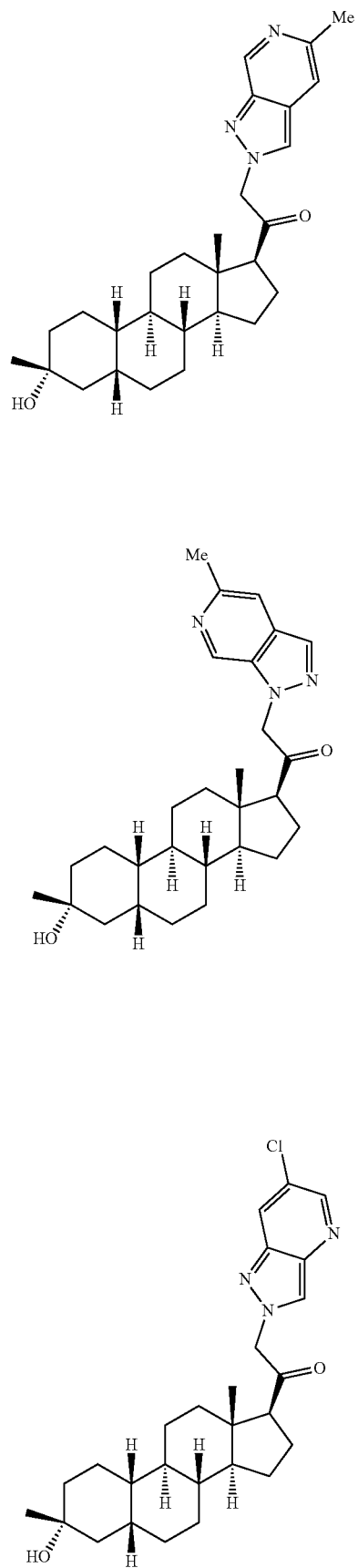

265
-continued
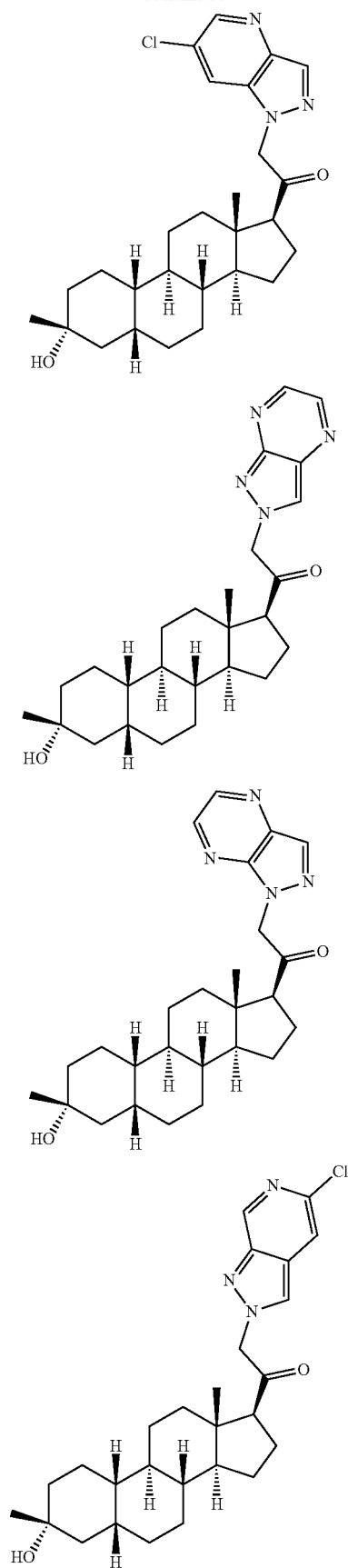
266
-continued
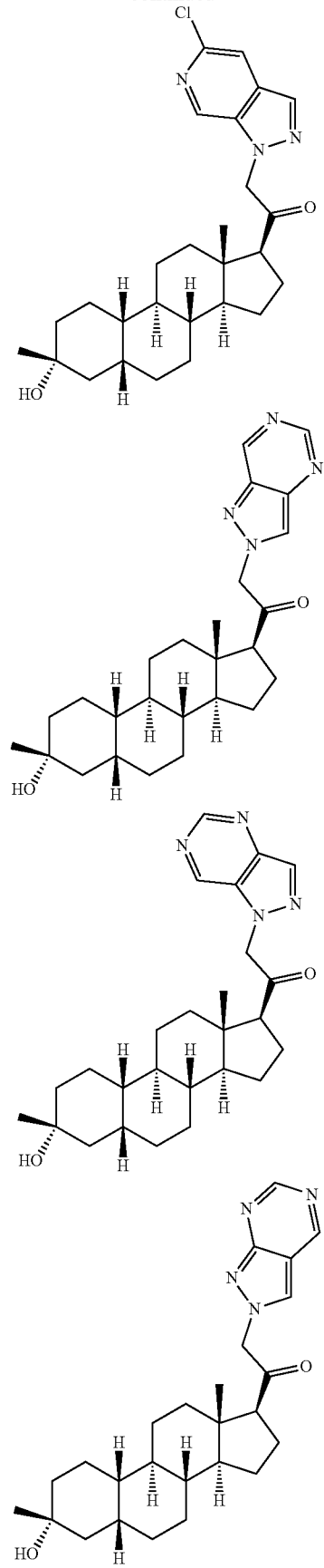

267
-continued
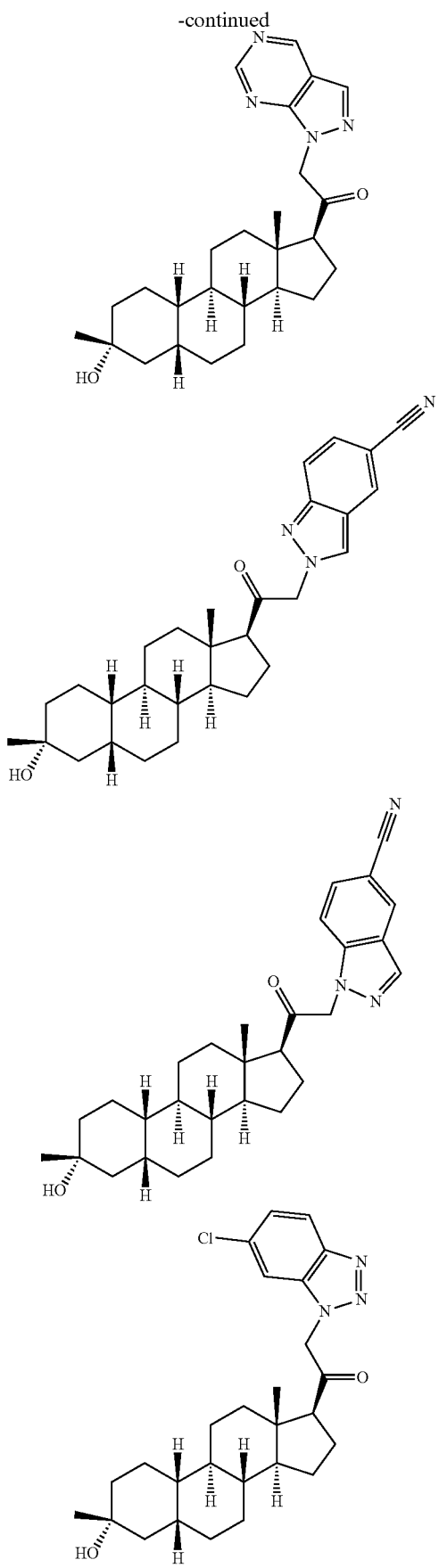
268
-continued
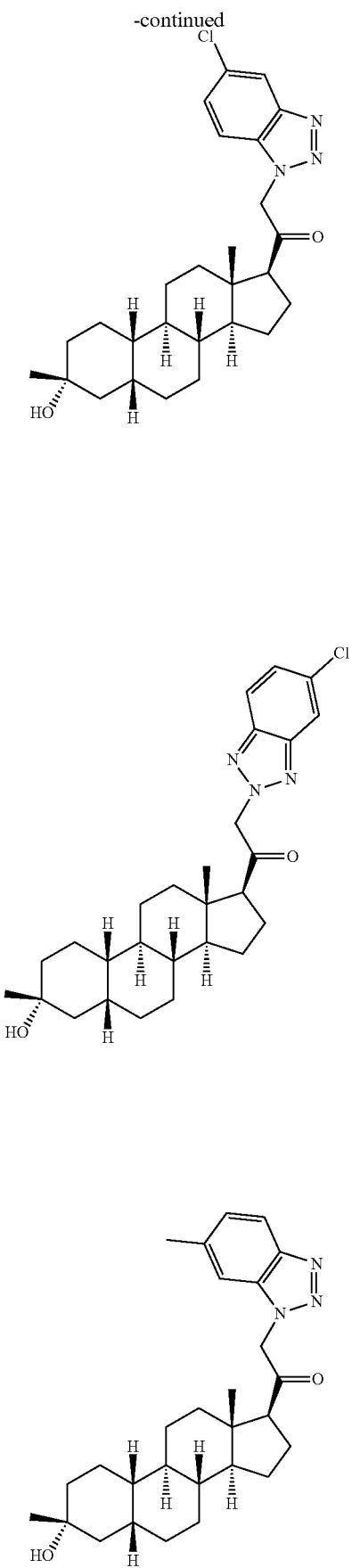

269
-continued
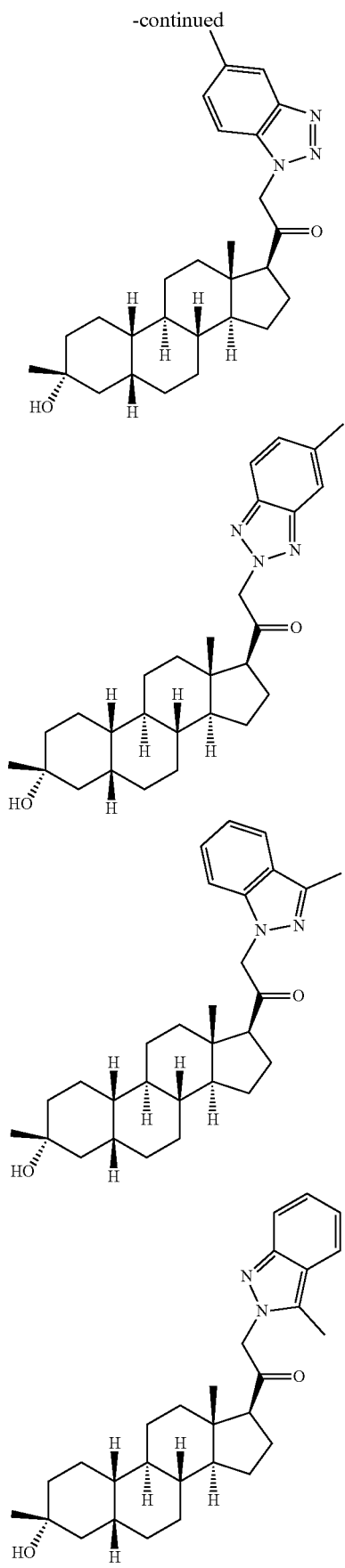
270
-continued
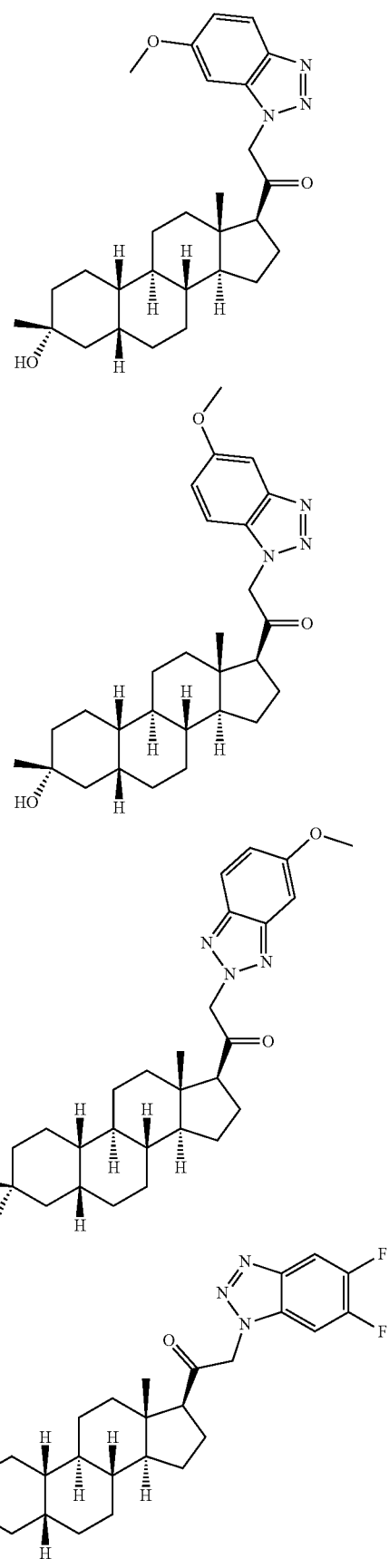

271
-continued
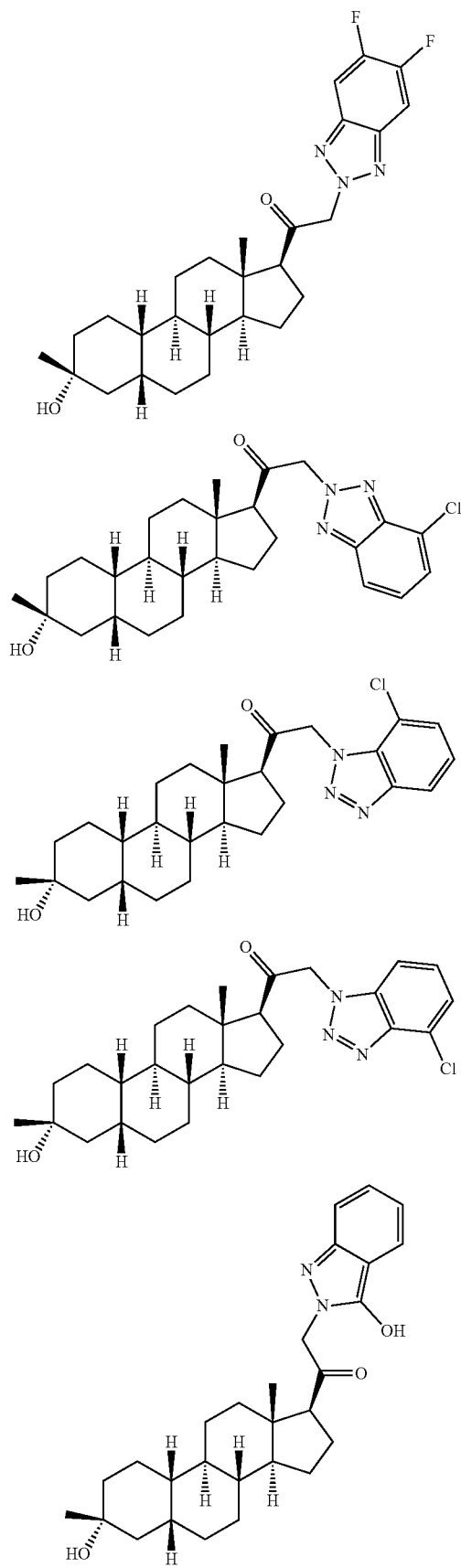
272
-continued
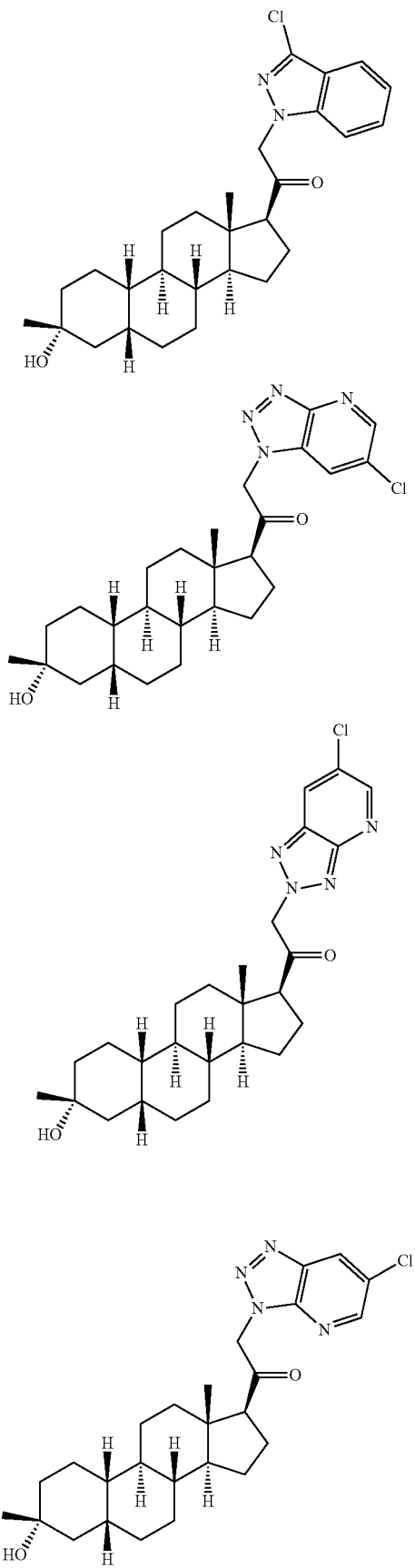

273
-continued
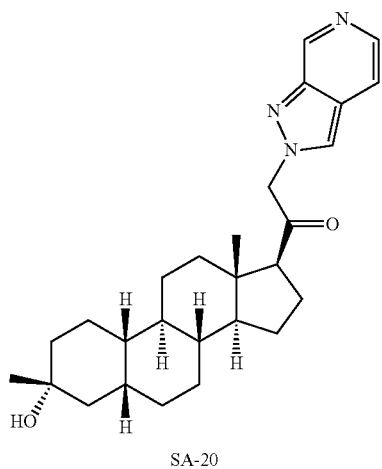
SA-20
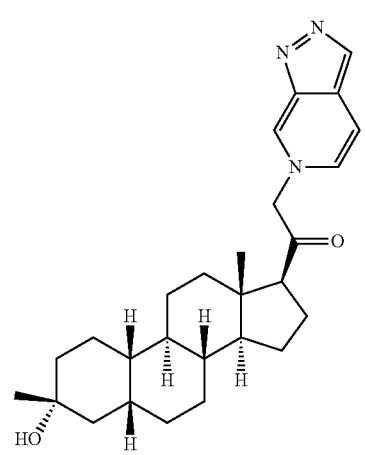
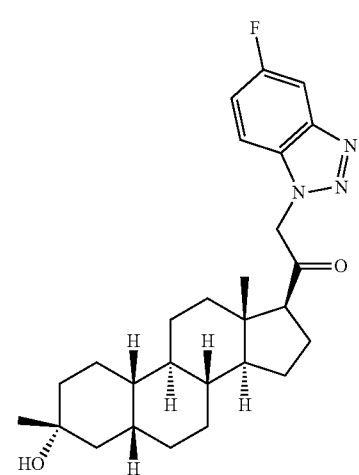
274
-continued
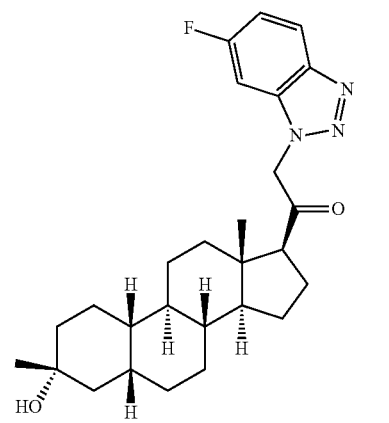
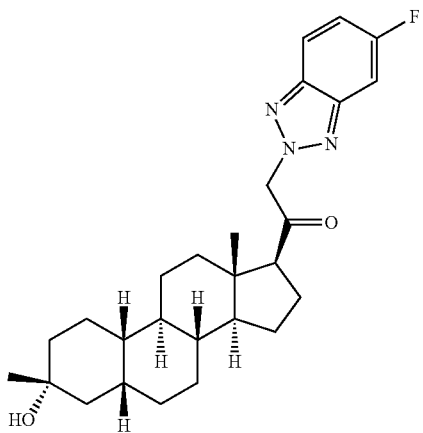
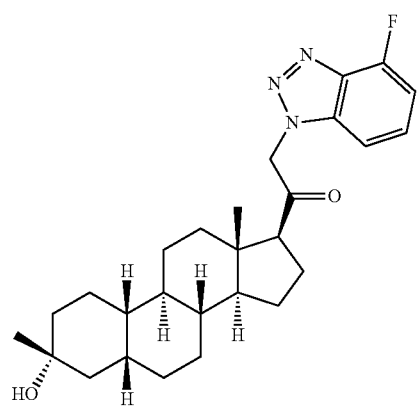
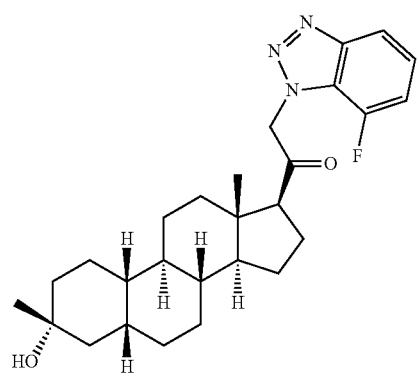

275
-continued
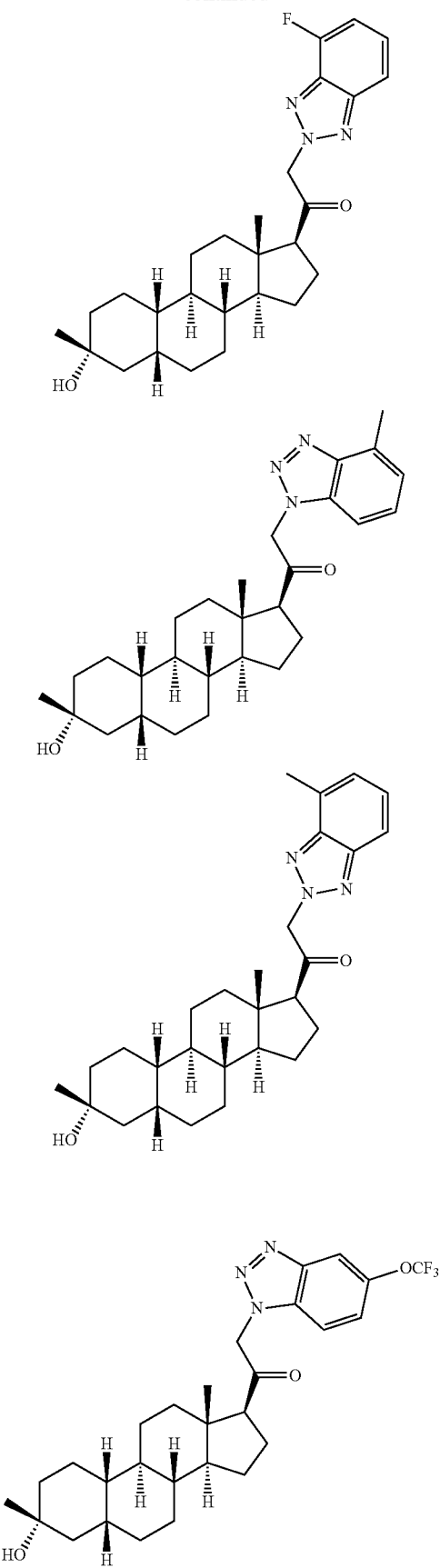
276
-continued
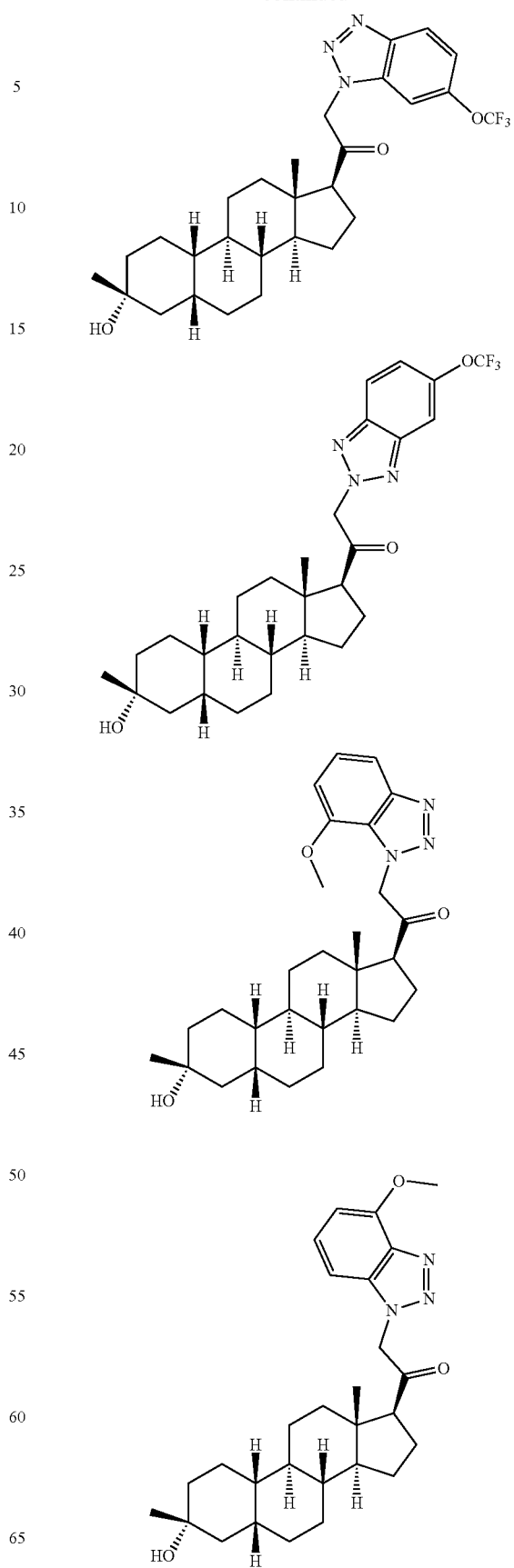

277
-continued
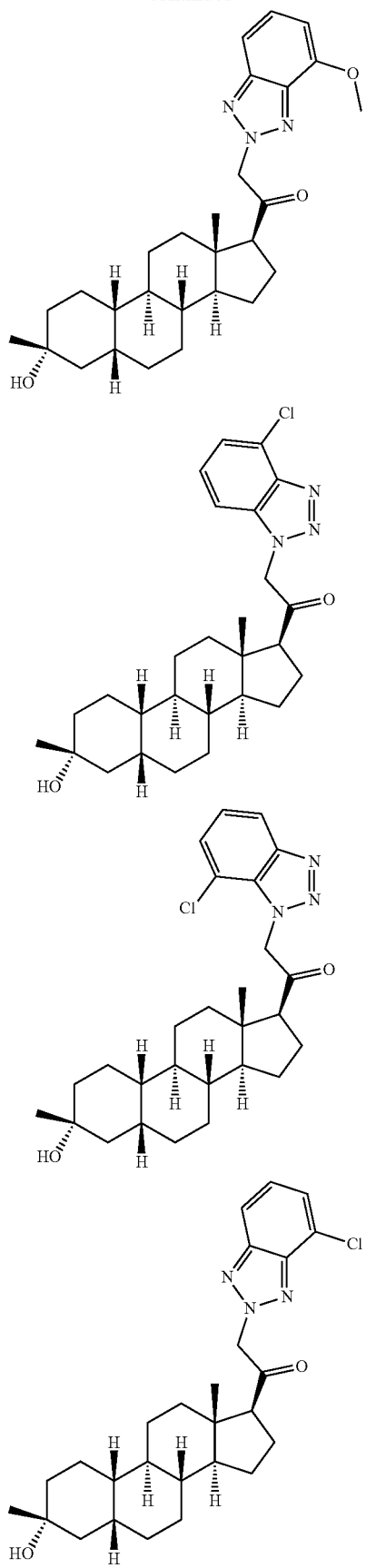
278
-continued
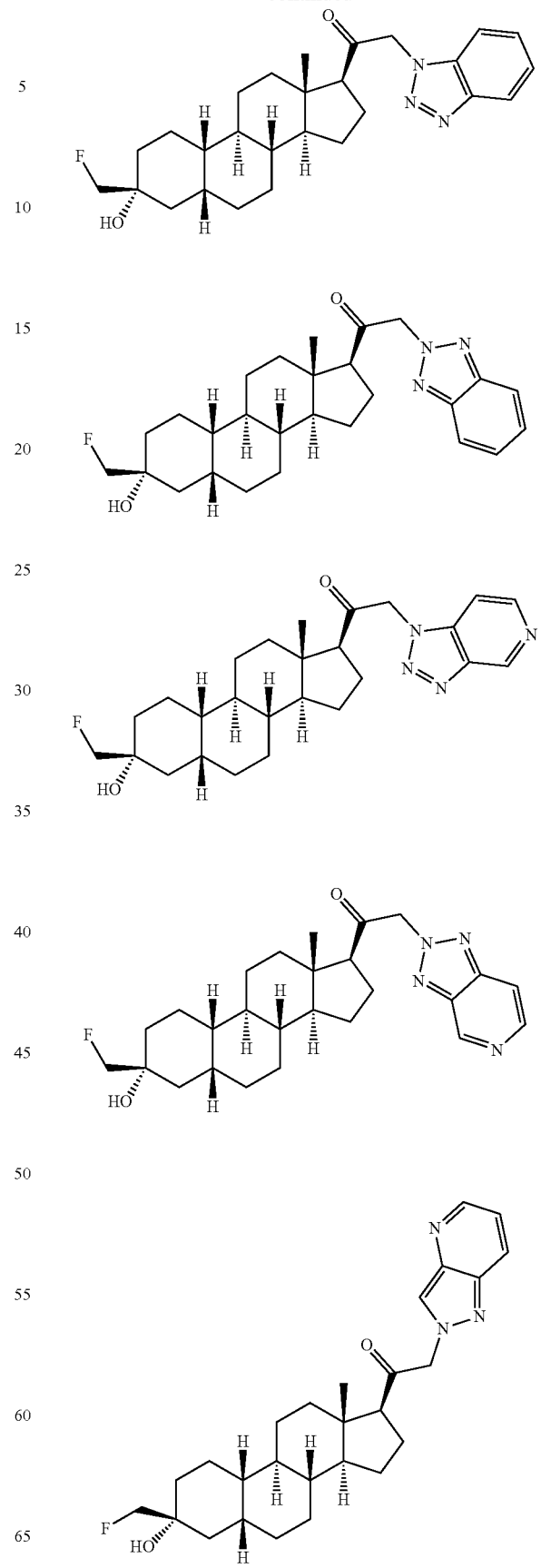

279
-continued
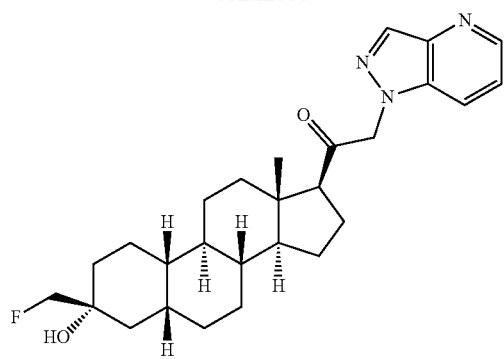
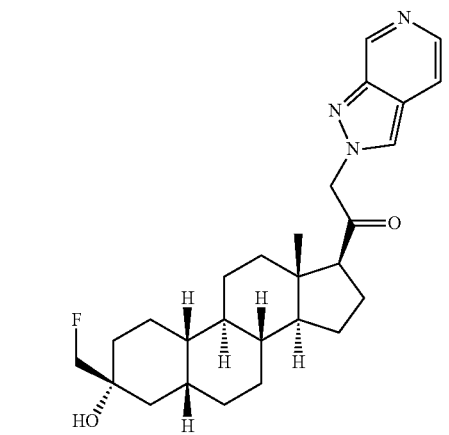
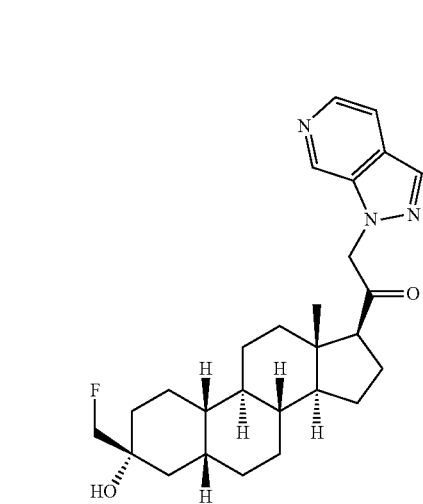
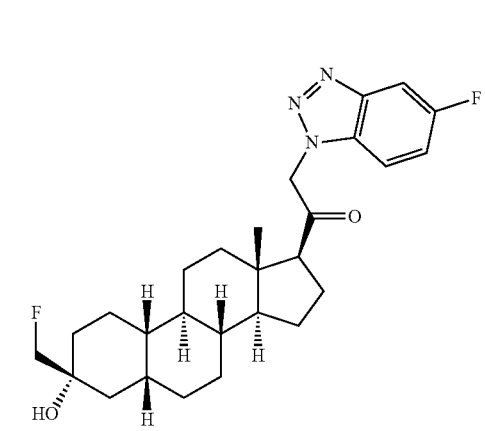
280
-continued
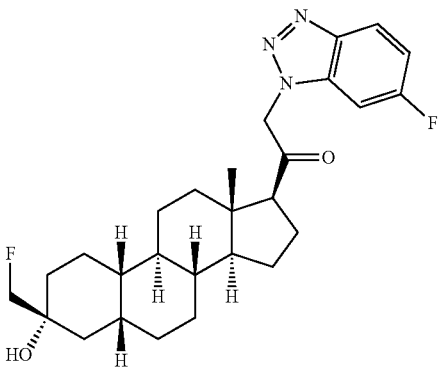
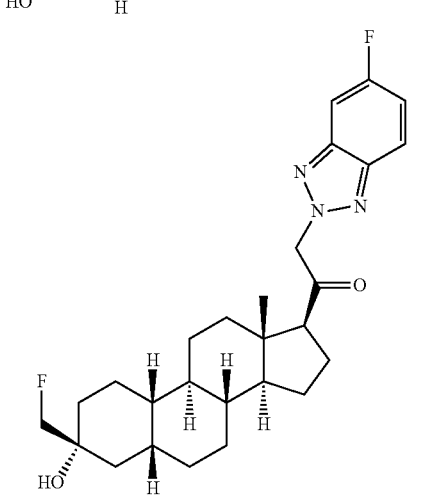

281
-continued
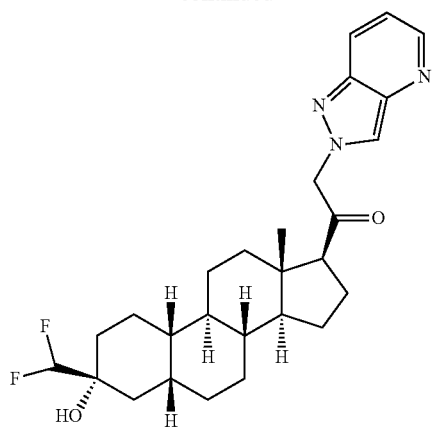
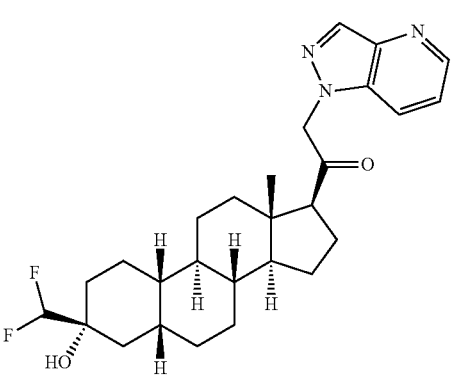
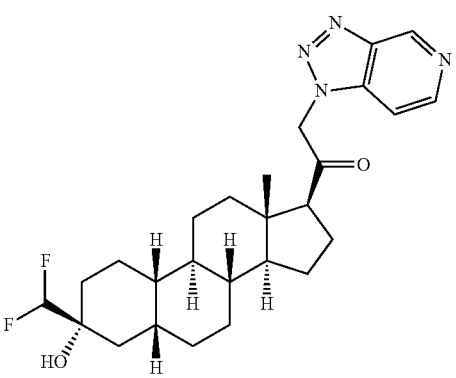
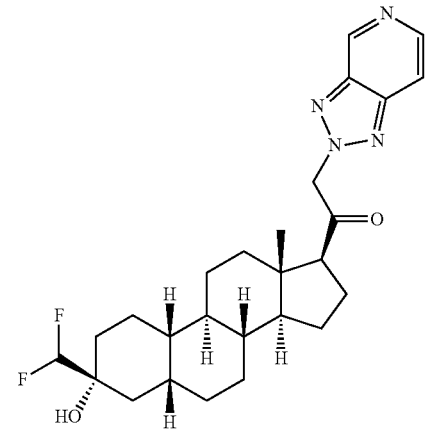
282
-continued
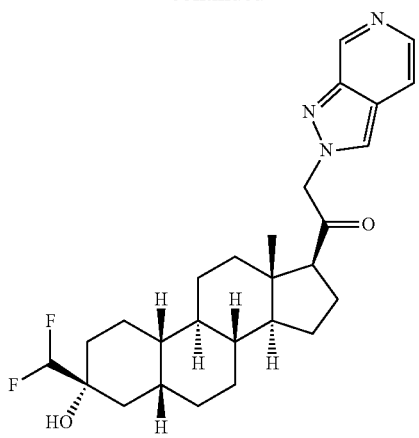
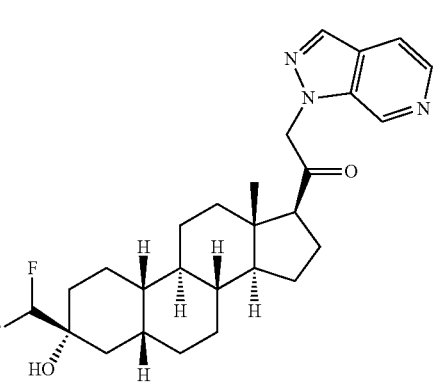
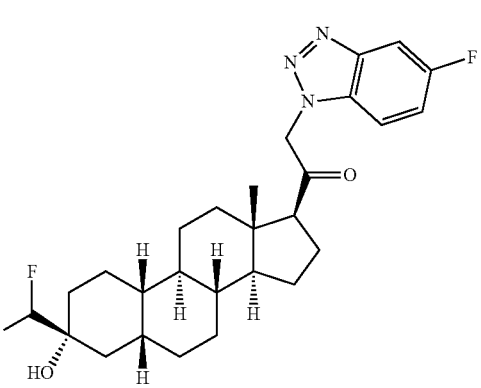
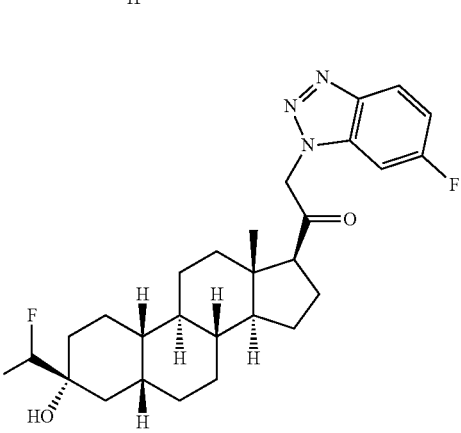

283
-continued
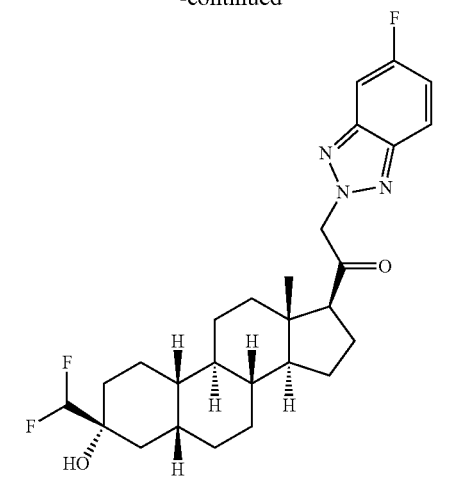
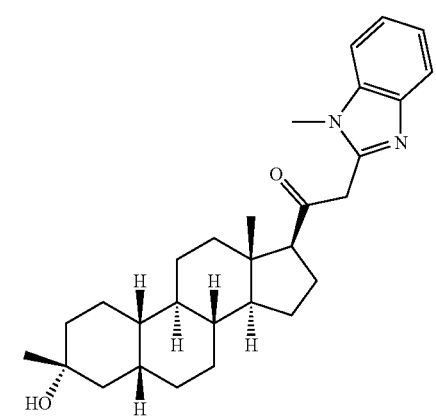
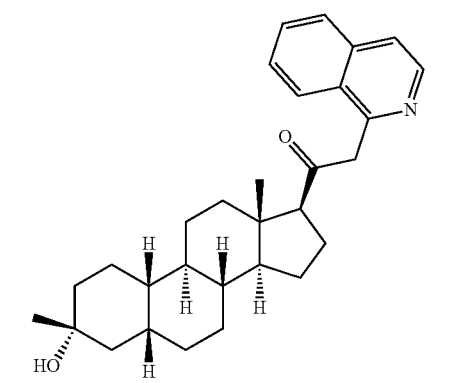
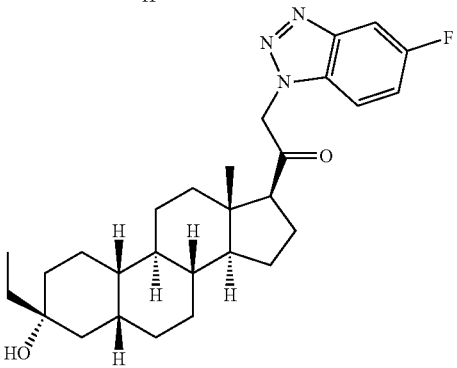
284
-continued
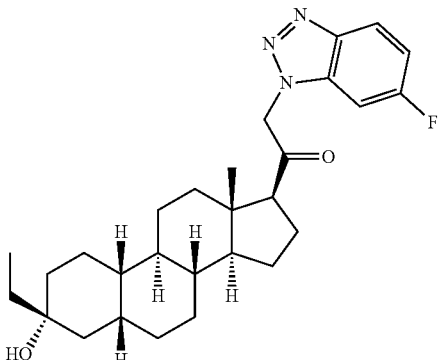
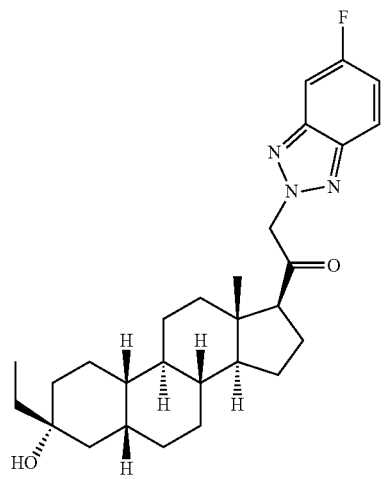
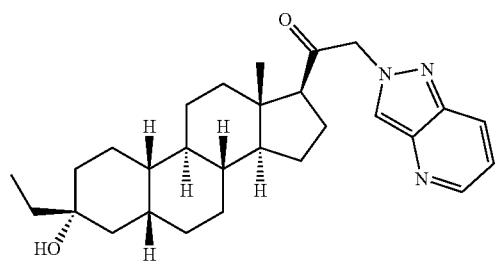
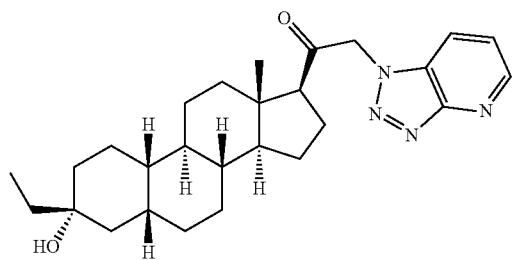
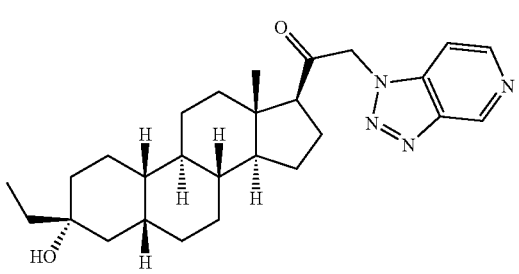

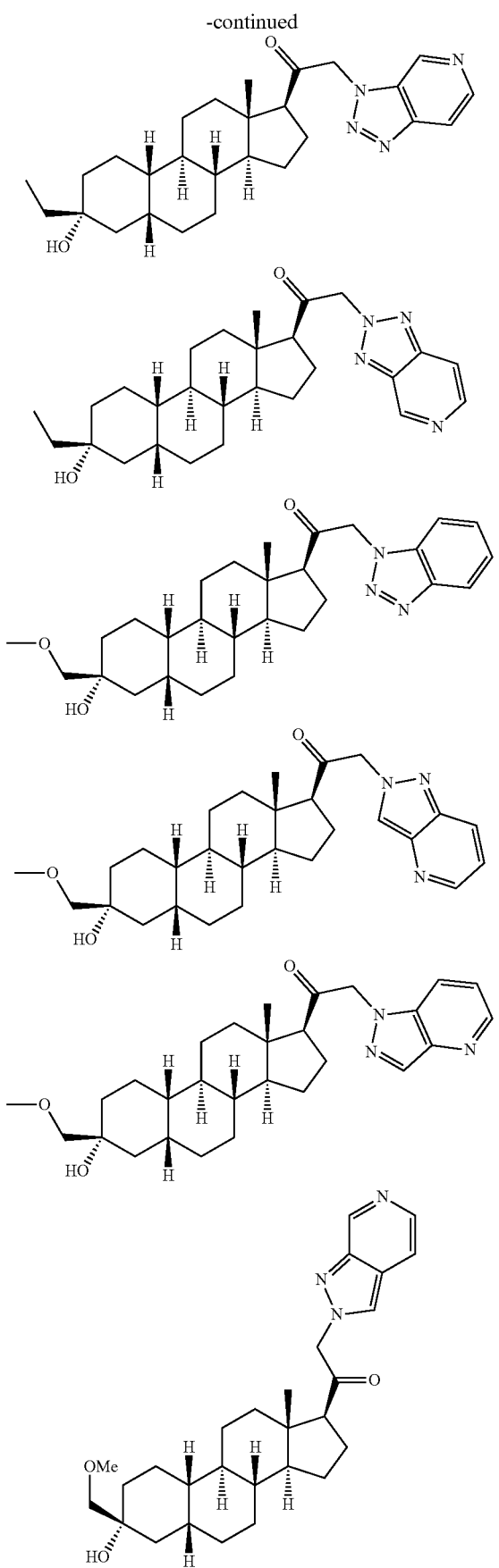
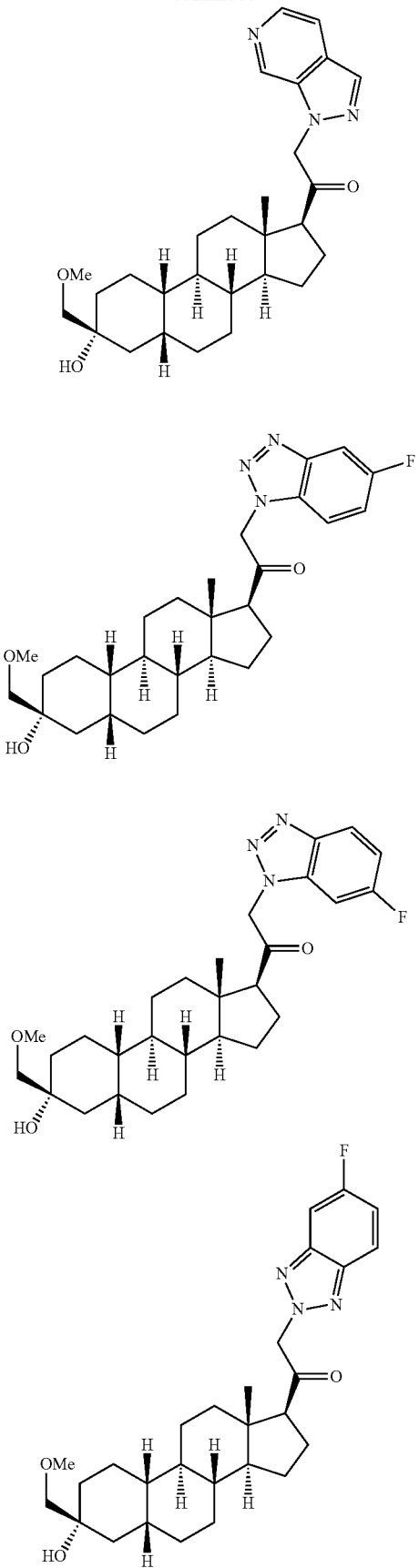

287
-continued
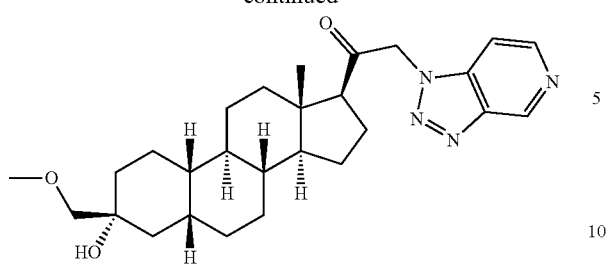
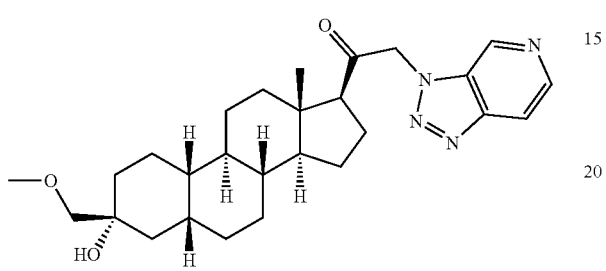
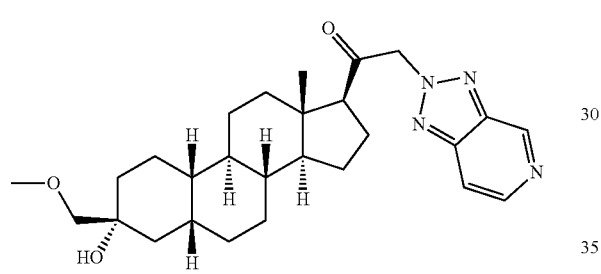
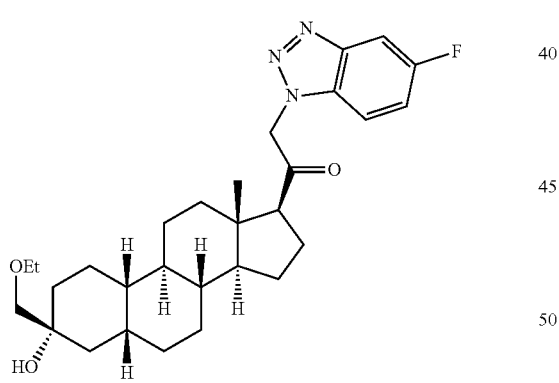
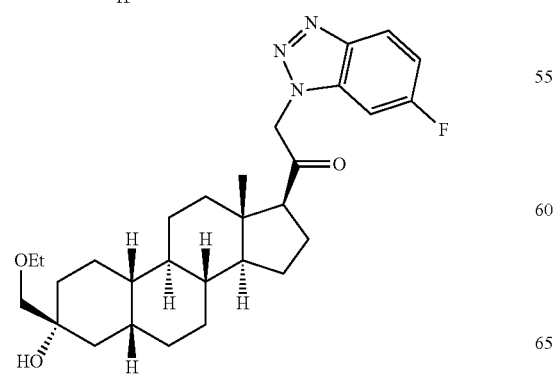
288
-continued
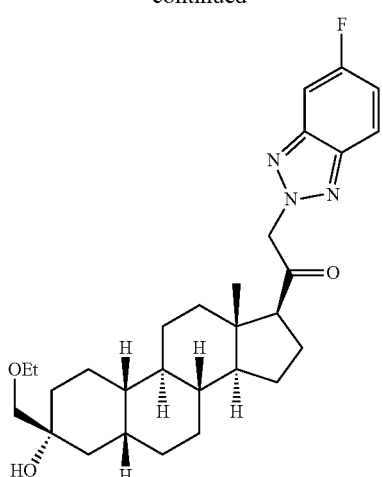
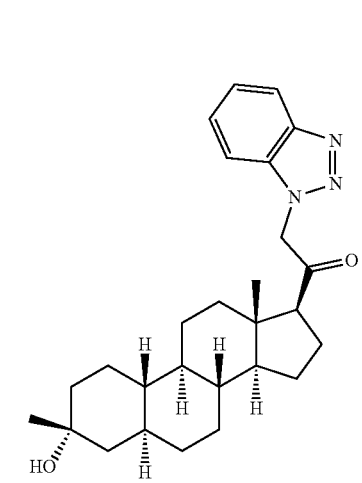
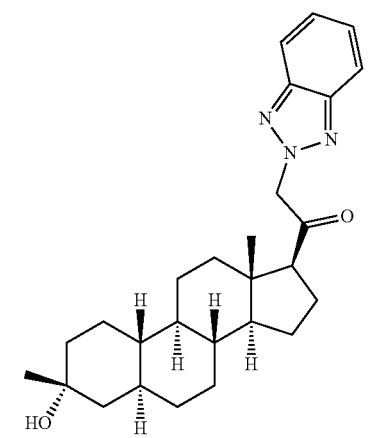

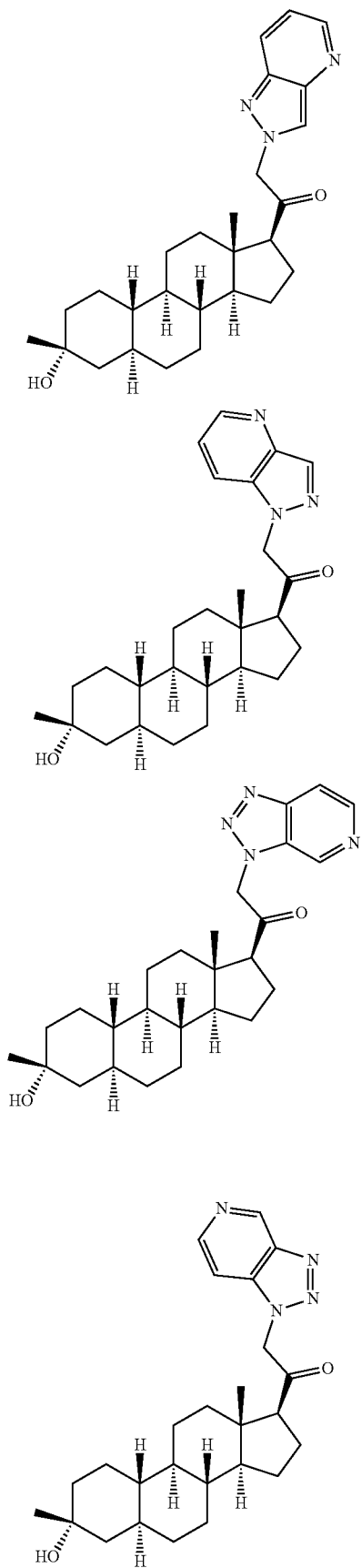
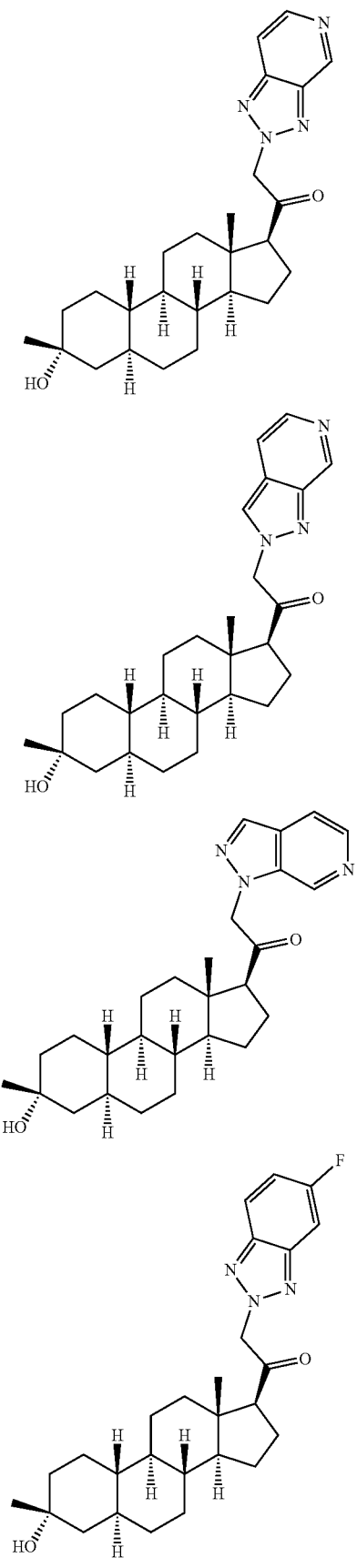

291
-continued
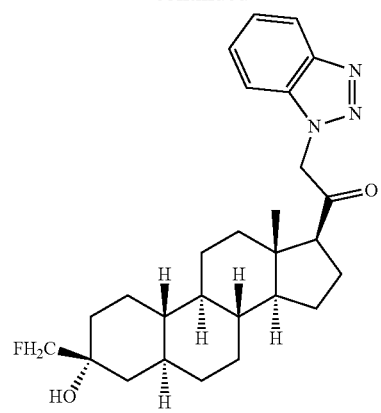
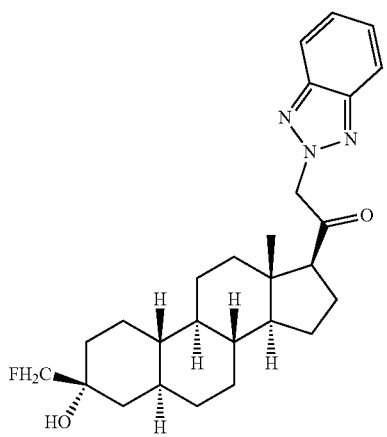
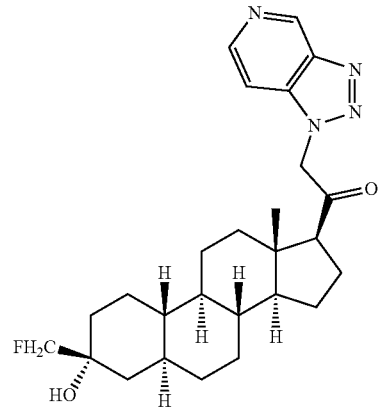
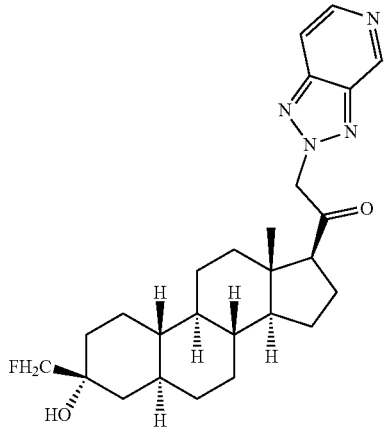
292
-continued
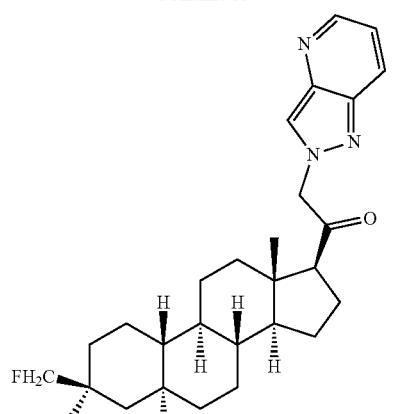
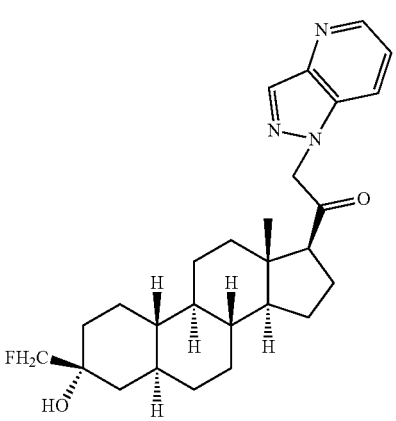
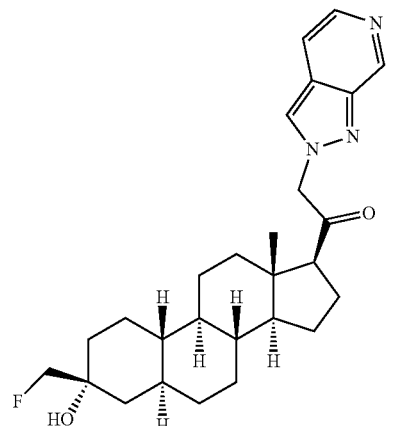
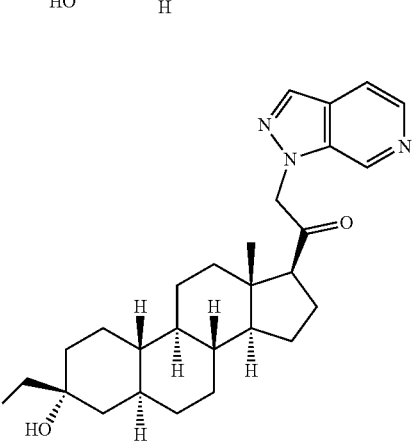

293
-continued
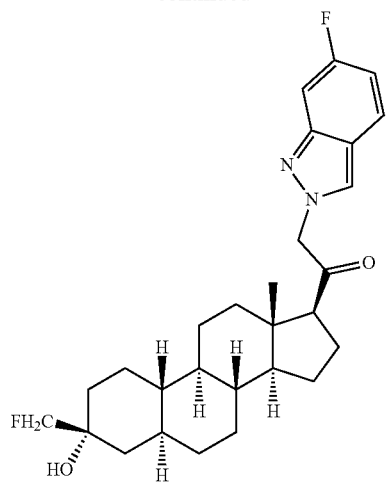
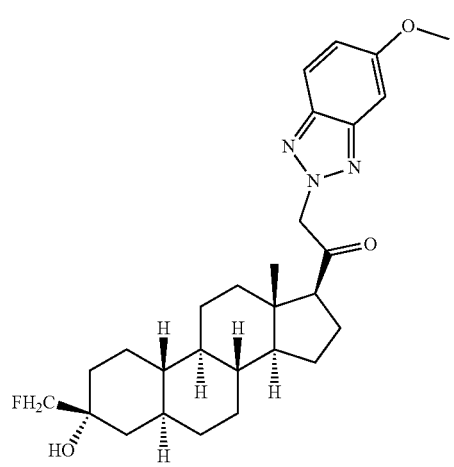
294
-continued
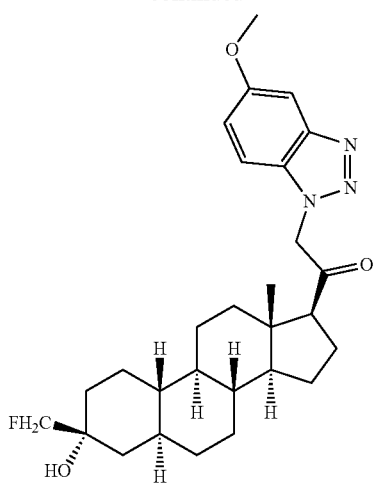
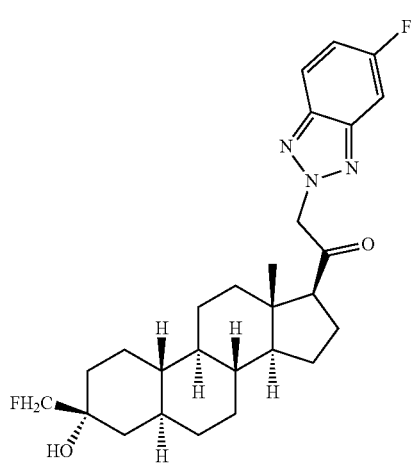
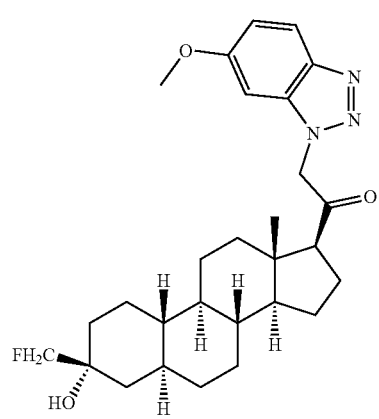
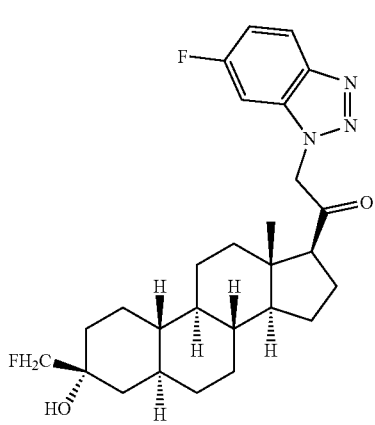

295
-continued
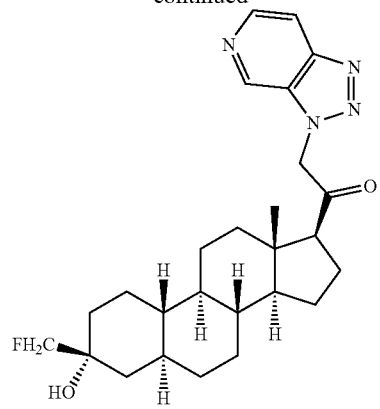
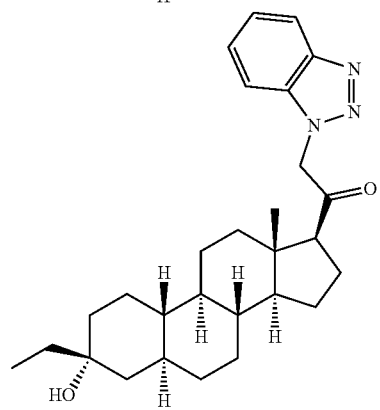
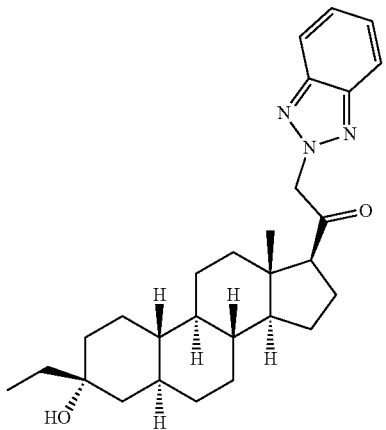
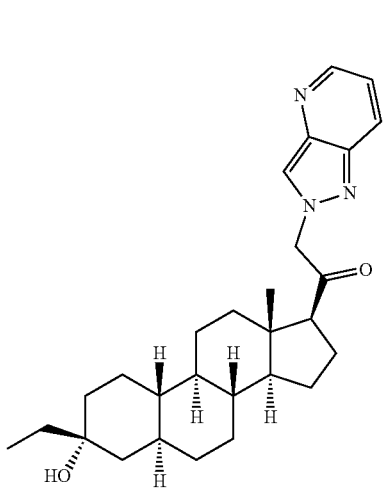
296
-continued
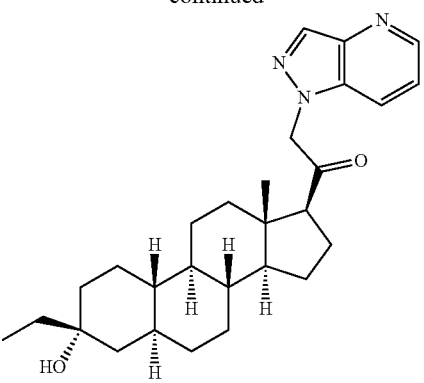
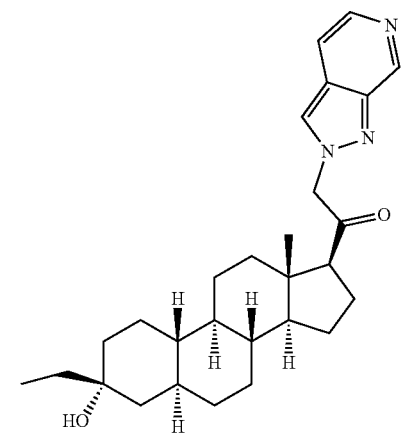
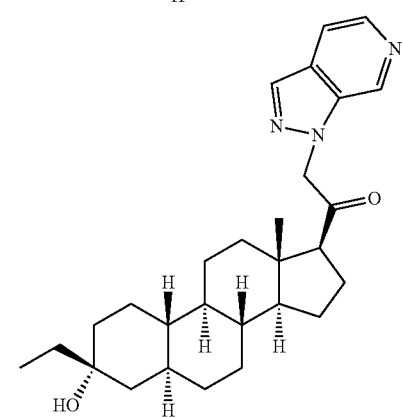
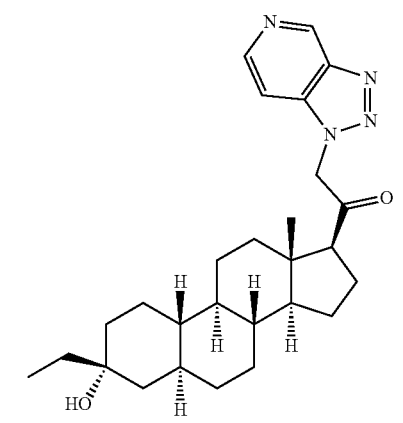

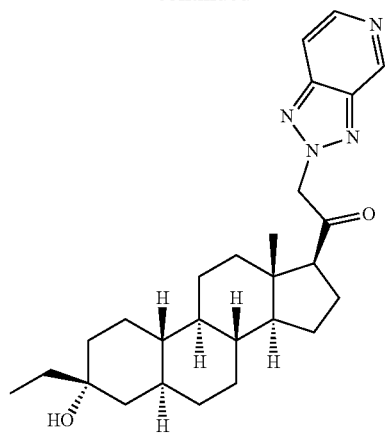
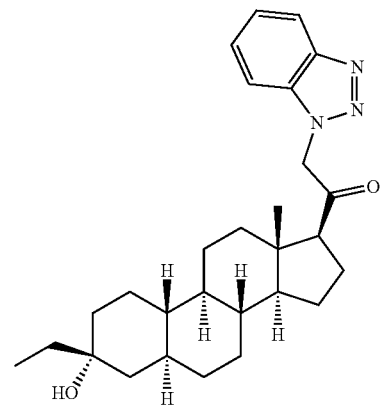
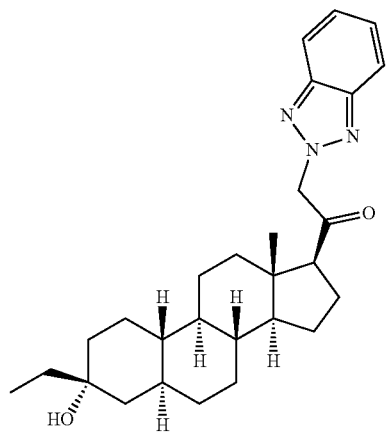
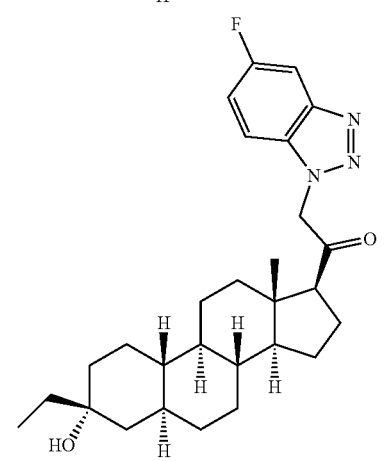
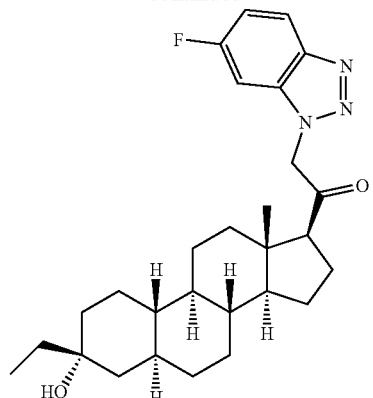
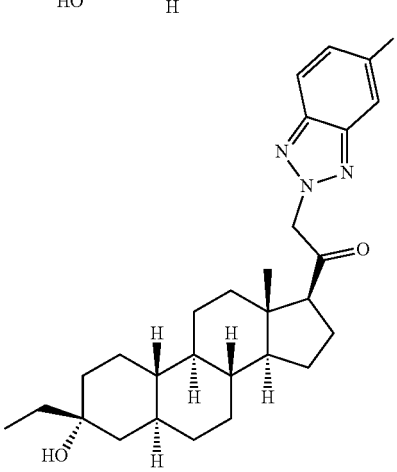
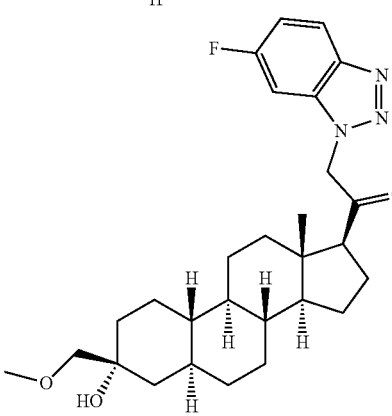
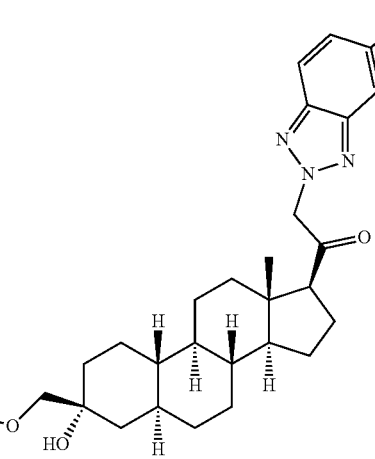

299 -continued
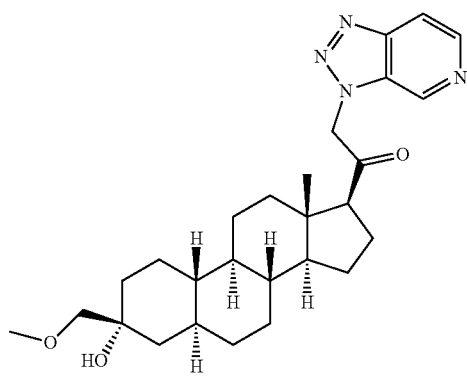
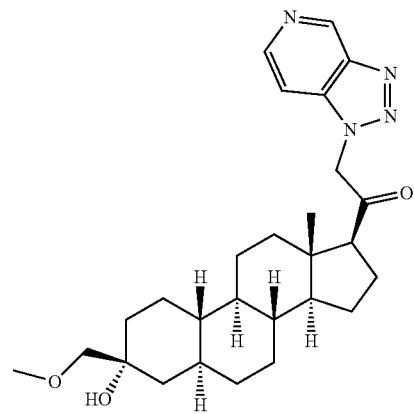
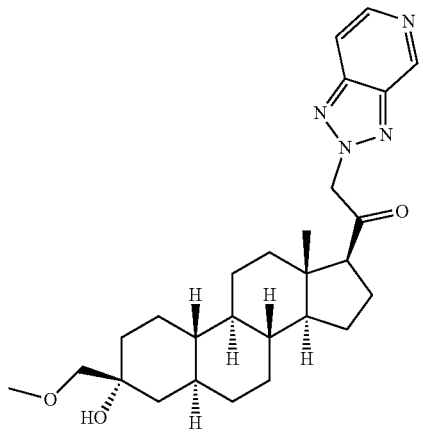
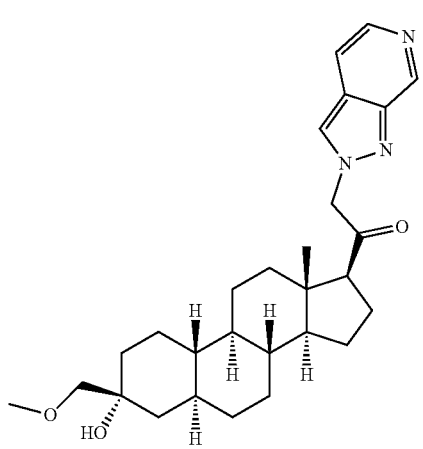
300 -continued
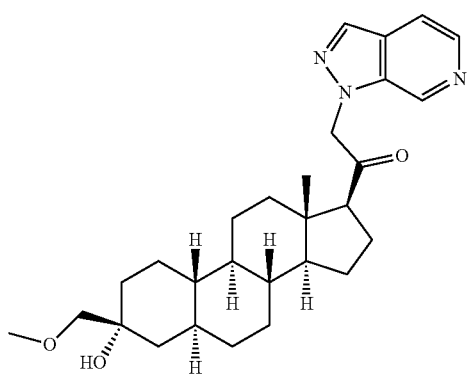
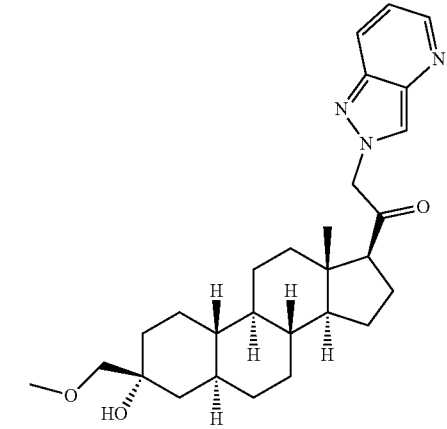
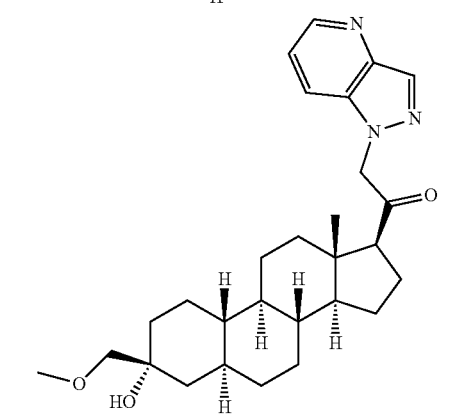
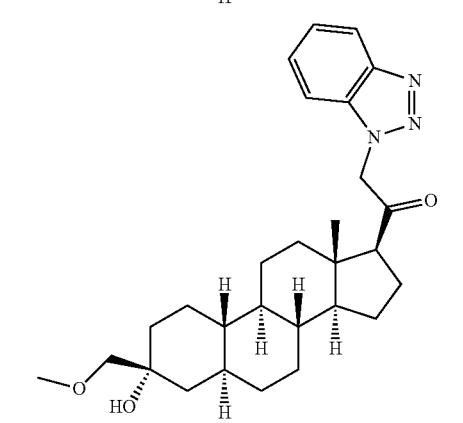

301
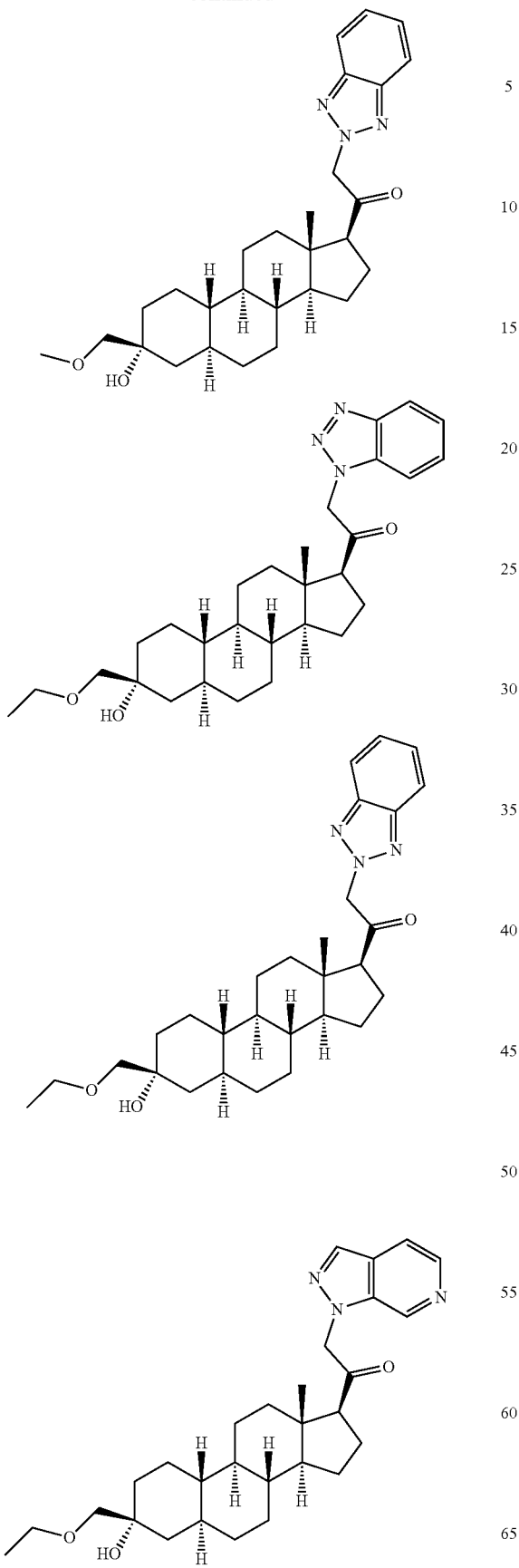
302
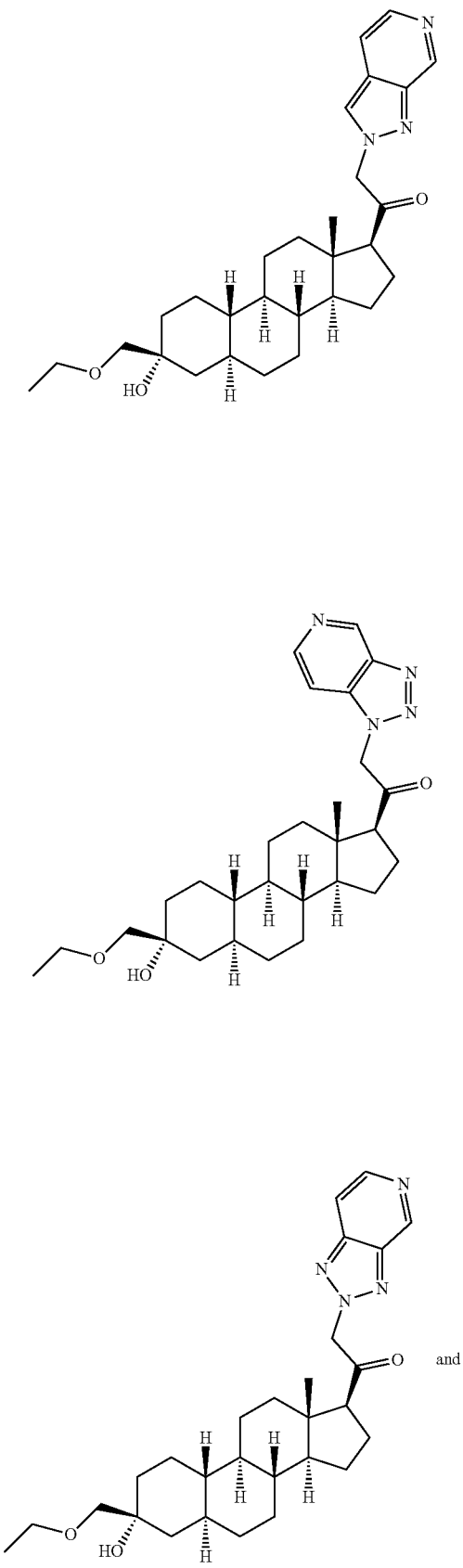
and

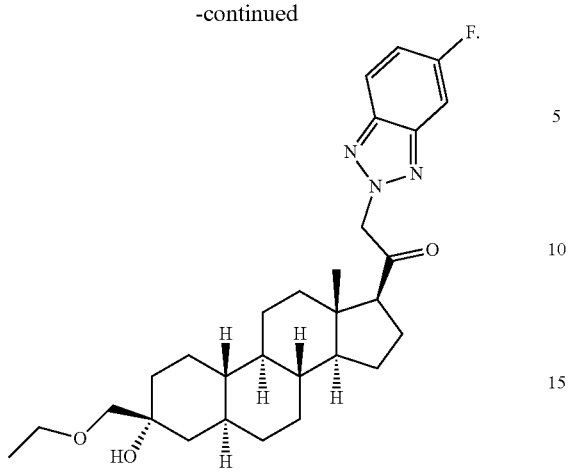

19. The method of claim 1, wherein the method is a method of treating a sleep disorder.

20. The method of claim 19, wherein the sleep disorder is insomnia.

21. The method of claim 1, wherein the method is a method of treating a mood disorder.

22. The method of claim 1, wherein the mood disorder is depression.

23. The method of claim 22, wherein the depression is postnatal depression.

24. The method of claim 23, wherein the compound or pharmaceutical composition is administered orally.

* * * * *